US009388147B2

(12) United States Patent
Martinborough et al.

(10) Patent No.: US 9,388,147 B2
(45) Date of Patent: Jul. 12, 2016

(54) SELECTIVE SPHINGOSINE 1 PHOSPHATE RECEPTOR MODULATORS AND METHODS OF CHIRAL SYNTHESIS

(71) Applicant: Receptos, Inc., San Diego, CA (US)

(72) Inventors: Esther Martinborough, San Diego, CA (US); Marcus F. Boehm, San Diego, CA (US); Adam Richard Yeager, La Mesa, CA (US); Junko Tamiya, Carlsbad, CA (US); Liming Huang, San Diego, CA (US); Enugurthi Brahmachary, San Diego, CA (US); Manisha Moorjani, San Diego, CA (US); Gregg Alan Timony, San Diego, CA (US); Jennifer L. Brooks, Encinitas, CA (US); Robert Peach, San Diego, CA (US); Fiona Lorraine Scott, San Diego, CA (US); Michael Allen Hanson, San Marcos, CA (US)

(73) Assignee: Celgene International II Sárl, Couvet (CH)

( * ) Notice: Subject to any disclaimer, the term of this patent is extended or adjusted under 35 U.S.C. 154(b) by 0 days.

(21) Appl. No.: 14/632,675

(22) Filed: Feb. 26, 2015

(65) Prior Publication Data

US 2015/0299149 A1 Oct. 22, 2015

Related U.S. Application Data

(62) Division of application No. 13/740,661, filed on Jan. 14, 2013, now abandoned, which is a division of application No. 12/946,819, filed on Nov. 15, 2010, now Pat. No. 8,362,048.

(60) Provisional application No. 61/261,301, filed on Nov. 13, 2009, provisional application No. 61/262,474, filed on Nov. 18, 2009.

(51) Int. Cl.
| | |
|---|---|
| C07D 271/06 | (2006.01) |
| C07D 413/12 | (2006.01) |
| C07D 417/12 | (2006.01) |
| C07D 413/10 | (2006.01) |
| C07D 413/14 | (2006.01) |
| A61K 31/4245 | (2006.01) |
| A61K 31/427 | (2006.01) |
| A61K 31/454 | (2006.01) |
| A61K 31/496 | (2006.01) |
| A61K 31/5377 | (2006.01) |
| A61K 45/06 | (2006.01) |
| C07C 245/14 | (2006.01) |
| C07C 255/58 | (2006.01) |
| C07C 311/13 | (2006.01) |

(52) U.S. Cl.
CPC ............ *C07D 271/06* (2013.01); *A61K 31/427* (2013.01); *A61K 31/4245* (2013.01); *A61K 31/454* (2013.01); *A61K 31/496* (2013.01); *A61K 31/5377* (2013.01); *A61K 45/06* (2013.01); *C07C 245/14* (2013.01); *C07C 255/58* (2013.01); *C07C 311/13* (2013.01); *C07D 413/10* (2013.01); *C07D 413/12* (2013.01); *C07D 413/14* (2013.01); *C07D 417/12* (2013.01)

(58) Field of Classification Search
CPC .. C07D 271/06; C07D 413/10; C07D 413/12; C07D 417/12
See application file for complete search history.

(56) References Cited

U.S. PATENT DOCUMENTS

| | | | |
|---|---|---|---|
| 5,039,802 | A | 8/1991 | Blacklock et al. |
| 5,180,741 | A | 1/1993 | Babin et al. |
| 6,511,975 | B1 | 1/2003 | Nishi et al. |
| 6,992,096 | B2 | 1/2006 | Karp et al. |
| 7,220,734 | B2 | 5/2007 | Doherty et al. |
| 7,605,171 | B2 | 10/2009 | Colandrea et al. |
| 7,834,039 | B2 | 11/2010 | Hobson et al. |
| 7,902,336 | B2 | 3/2011 | Gabriele et al. |
| 8,264,426 | B2 | 9/2012 | Chung |
| 8,357,706 | B2 | 1/2013 | Martinborough et al. |
| 8,362,048 | B2 | 1/2013 | Martinborough et al. |
| 8,466,183 | B2 | 6/2013 | Roberts et al. |
| 8,481,573 | B2 | 7/2013 | Roberts et al. |
| 8,507,538 | B2 | 8/2013 | Boehm et al. |
| 2004/0058894 | A1 | 3/2004 | Doherty et al. |
| 2006/0161005 | A1 | 7/2006 | Doherty et al. |

(Continued)

FOREIGN PATENT DOCUMENTS

| | | |
|---|---|---|
| CN | 1802360 A | 7/2006 |
| EP | 0 508 425 A1 | 10/1992 |

(Continued)

OTHER PUBLICATIONS

Mathre et al. J. Org. Chem. (1993), 58(10), p. 2880-2888.*

(Continued)

*Primary Examiner* — Yong Chu
(74) *Attorney, Agent, or Firm* — Seed IP Law Group PLLC

(57) ABSTRACT

Compounds that selectively modulate the sphingosine 1 phosphate receptor are provided including compounds which modulate subtype 1 of the S1P receptor. Methods of chiral synthesis of such compounds are provided. Uses, methods of treatment or prevention and methods of preparing inventive compositions including inventive compounds are provided in connection with the treatment or prevention of diseases, malconditions, and disorders for which modulation of the sphingosine 1 phosphate receptor is medically indicated.

36 Claims, No Drawings

(56) References Cited

U.S. PATENT DOCUMENTS

| | | | |
|---|---|---|---|
| 2006/0173183 A1 | 8/2006 | Powers et al. |
| 2007/0066647 A1 | 3/2007 | Akerman et al. |
| 2007/0293545 A1 | 12/2007 | Edwards et al. |
| 2008/0009534 A1 | 1/2008 | Cheng et al. |
| 2008/0249093 A1 | 10/2008 | Colandrea et al. |
| 2008/0280876 A1 | 11/2008 | Hobson et al. |
| 2009/0163482 A1 | 6/2009 | McHardy et al. |
| 2009/0298894 A1 | 12/2009 | Ohmori et al. |
| 2010/0010001 A1 | 1/2010 | Roberts et al. |
| 2011/0172202 A1 | 7/2011 | Martinborough et al. |
| 2011/0178056 A1 | 7/2011 | Martinborough et al. |
| 2011/0183953 A1 | 7/2011 | Boehm et al. |
| 2013/0196966 A1 | 8/2013 | Martinborough et al. |
| 2013/0231326 A1 | 9/2013 | Martinborough et al. |
| 2014/0039183 A1 | 2/2014 | Boehm et al. |
| 2015/0252037 A1 | 9/2015 | Boehm et al. |
| 2015/0299150 A1 | 10/2015 | Martinborough et al. |
| 2015/0299179 A1 | 10/2015 | Boehm et al. |

FOREIGN PATENT DOCUMENTS

| | | |
|---|---|---|
| GB | 1 479 544 A | 2/1975 |
| GB | 2 290 790 A | 1/1996 |
| JP | 50-108250 A | 8/1975 |
| JP | 4-224556 A | 8/1992 |
| JP | 6-505025 A | 6/1994 |
| JP | 2006-511579 A | 4/2006 |
| JP | 2007-34288 A | 2/2007 |
| JP | 2007-515432 A | 6/2007 |
| JP | 2009-523412 A | 6/2009 |
| JP | 2009-539762 A | 11/2009 |
| JP | 2011-523412 A | 8/2011 |
| JP | 2013-510884 A | 3/2013 |
| WO | 2004/058149 A2 | 7/2004 |
| WO | 2005/032465 A2 | 4/2005 |
| WO | 2005/058848 A1 | 6/2005 |
| WO | 2006/120577 A1 | 11/2006 |
| WO | 2008/064320 A2 | 5/2008 |
| WO | 2008/074821 A1 | 6/2008 |
| WO | 2008/076356 A1 | 6/2008 |
| WO | 2008/106204 A1 | 9/2008 |
| WO | 2009/131090 A1 | 10/2009 |
| WO | 2009/151529 A1 | 12/2009 |
| WO | 2010/146105 A1 | 12/2010 |
| WO | 2010/148650 A1 | 12/2010 |
| WO | 2011/005290 A1 | 1/2011 |
| WO | 2011/060389 A1 | 5/2011 |
| WO | 2011/060391 A1 | 5/2011 |
| WO | 2011/060392 A1 | 5/2011 |
| WO | 2013/055907 A1 | 4/2013 |

OTHER PUBLICATIONS

Tanuwidjaja et al. J. Org. Chem. (2007), 72(2), p. 626-629.*

Aldrich, "ChemFiles—Products for Suzuki Coupling," vol. 2, No. 1, 2002, 14 pages.

Buzard et al., "Recent progress in the development of selective S1P1 receptor agonists for the treatment of inflammatory and autoimmune disorders," Expert Opin. Ther. Patents 18(10):1141-1159, 2008.

Colyer et al., "Revesal of Diastereofacial Selectivity in Hydride Reductions of N-tert-Butanesulfinyl Imines," J. Org. Chem. 71:6859-6862, 2006.

Corey et al., "Highly Enantioselective Borane Reduction of Ketones Catalyzed by Chiral Oxazaborolidines. Mechanism and Synthetic Implications," J. Am. Chem. Soc. 109:5551-5553, 1987.

Davies et al., "Protection of Hydroxy Groups by Silylation: Use in Peptide Synthesis and as Lipophilicity Modifiers for Peptides," J. Chem Soc. Perkin Trans 1:3043-3048, 1992.

Deguchi et al., "The S1P receptor modulator FTY720 prevents the development of experimental colitis in mice," Oncology Reports 16:699-703, 2006.

Fujishiro et al., "Change From Cyclosporine to Combination Therapy of Mycophenolic Acid With the New Sphinosine-1-phosphate Receptor Agonist, KRP-203, Prevents Host Nephrotoxicity and Transplant Vasculopathy in Rats," J. Heath Lung Transplant 25:825-833, 2006.

Fujishiro et al., "Use of Sphingosine-1-Phosphate 1 Receptor Agonist, KRP-203, in Combination with a Subtherapeutic Dose of Cyclosporine A for Rat Renal Transplantation," Transplantation 82:804-812, 2006.

Fujiwara et al., "Identification of the Hydrophobic Ligand Binding Pocket of the S1P$_1$ Receptor," The Journal of Biological Chemistry 282(4):2374-2385, 2007.

Gonzalez-Cabrera et al., "Full Pharmacological Efficacy of a Novel S1P$_1$ Agonist That Does Not Require S1P-Like Headgroup Interactions," Molecular Pharmacology 74:1308-1318, 2008.

Greene et al, "t-Butyl (BOC) Carbamate: $(CH_3)_3COC(O)NR_2$ (Chart 8)," in Protective Groups in Organic Synthesis, Third Edition, pp. 518-525, 1999. (6 pages).

International Search Report, mailed Jan. 12, 2011, for International Application No. PCT/US10/56759, 3 pages.

International Search Report, mailed Jan. 14, 2011, for International Application No. PCT/US10/56757, 3 pages.

International Search Report, mailed Jan. 19, 2011, for International Application No. PCT/US10/56760, 3 pages.

International Search Report and Written Opinion, mailed Jan. 17, 2013, for International Application No. PCT/US12/37609, 11 pages.

International Search Report and Written Opinion, mailed Mar. 4, 2015, for International Application No. PCT/US2014/063504, 14 pages.

Krieger, "Multiple Sclerosis Therapeutic Pipeline: Opportunities and Challenges," Mount Sinai Journal of Medicine 78:192-206, 2011.

Leinweber et al., "Synthesis of Enantiopure Tricarbonyl(indan-1,2-dione)chromium,"Eur. J. Org. Chem.:5224-5235, 2005.

Oldstone et al., "Dissecting influenza virus pathogenesis uncovers a novel chemical approach to combat the infection," Virology 435:92-101, 2013.

Ros et al., "Enantioselective Synthesis of Vicinal Halohydrins via Dynamic Kinetic Resolution," Organic Letters 8(1):127-130, 2006.

Watzke et al., "Asymmetric Intramolecular Alkylation of Chiral Aromatic Imines via Catalytic C—H Bond Activation," Synlett 15:2383-2389, 2007.

Wu et al., "Regulatory perspectives of Type II prodrug development and time-dependent toxicity management: Nonclinical Pharm/Tox analysis and the role of comparative toxicology," Toxicology 236:1-6, 2007.

Xavier et al., "(S)-Tetrahydro-1-Methyl-3,3-Diphenyl-1H,3H-Pyrrolo-[1,2-c][1,3,2]Oxazaborole-Borane Complex—[Boron, trihydro(tetrahydro-1-methyl-3,3-diphenyl-1H,3H-pyrrolo-[1,2-c][1,3,2]oxazaborole-N$^7$)-,[I-4-(3aS-cis)-]," Organic Syntheses, Coll. vol. 9, p. 676 (1998); vol. 74, p. 50 (1997), 12 pages.

Zanotti-Gerosa et al., "Ruthenium-Catalysed Asymmetric Reduction of Ketones," Platinum Metals Rev. 49(4):158-165, 2005.

Alewijnse et al., "Sphingolipid signalling in the cardiovascular system: Good, bad or both?," European Journal of Pharmacology 585:292-302, 2008.

Cahalan et al., "Actions of a picomolar short-acting S1P$_1$ agonist in S1P$_1$-eGFP knock-in mice," Nature Chemical Biology 7:254-256, 2011.

Vachal et al., "Highly selective and potent agonists of sphingosine-1-phosphate 1 (SIP$_1$) receptor," Bioorganic & Medicinal Chemistry Letters 16:3684-3687, 2006.

Wang et al., "Regulation of vascular permeability by sphingosine 1-phosphate," Microvascular Research 77:39-45, 2009.

WebMD, "Multiple Sclerosis (MS)—Prevention," retrieved from http://www.webmd.com/multiple-sclerosis/tc/multiple-sclerosis-ms-prevention, retrieved on Jun. 15, 2010, 1 page.

Written Opinion of the Intellectual Property Office of Singapore, dated May 5, 2016, for SG Application No. 1021407357P, 10 pages.

\* cited by examiner

SEQUENCE LISTING

<160> NUMBER OF SEQ ID NOS: 4

<210> SEQ ID NO 1
<211> LENGTH: 37
<212> TYPE: DNA
<213> ORGANISM: Artificial Sequence
<220> FEATURE:
<223> OTHER INFORMATION: Forward primer sequence

<400> SEQUENCE: 1
ccagtggttt ctggcggcag ggagtatgtt tgtggcc         37

<210> SEQ ID NO 2
<211> LENGTH: 37
<212> TYPE: DNA
<213> ORGANISM: Artificial Sequence
<220> FEATURE:
<223> OTHER INFORMATION: Reverse primer sequence

<400> SEQUENCE: 2
ggccacaaac atactccctg ccgccagaaa ccactgg         37

<210> SEQ ID NO 3
<211> LENGTH: 30
<212> TYPE: DNA
<213> ORGANISM: Artificial Sequence
<220> FEATURE:
<223> OTHER INFORMATION: Forward primer sequence

<400> SEQUENCE: 3
ctacacagct gccctgctct tgtctggggc         30

<210> SEQ ID NO 4
<211> LENGTH: 30
<212> TYPE: DNA
<213> ORGANISM: Artificial Sequence
<220> FEATURE:
<223> OTHER INFORMATION: Reverse primer sequence

<400> SEQUENCE: 4
gccccagaca agagcagggc agctgtgtag         30

SELECTIVE SPHINGOSINE 1 PHOSPHATE RECEPTOR MODULATORS AND METHODS OF CHIRAL SYNTHESIS

CROSS-REFERENCE TO RELATED APPLICATIONS

This application is a divisional of application of U.S. application Ser. No. 13/740,661 filed Jan. 14, 2013, which is a divisional of U.S. application Ser. No. 12/946,819 filed Nov. 15, 2010 (granted—U.S. Pat. No. 8,362,048 issued Jan. 29, 2013), which claims priority to U.S. Provisional Application No. 61/261,301, filed Nov. 13, 2009 and U.S. Provisional Application No. 61/262,474, filed Nov. 18, 2009, the disclosures of which are incorporated herein in their entireties.

STATEMENT REGARDING SEQUENCE LISTING

The Sequence Listing associated with this application is provided in text format in lieu of a paper copy, and is hereby incorporated by reference into the specification. The name of the text file containing the Sequence Listing is 800059_401D2_SEQUENCE_LISTING.txt. The text file is 1.5 KB, was created on Jul. 2, 2015, and is being submitted electronically via EFS-Web.

FIELD OF THE INVENTION

The invention relates to compounds which are agonists of the sphingosine 1-phosphate receptor subtype 1, methods of their synthesis and methods of their therapeutic and/or prophylactic use.

BACKGROUND

The $S1P_1/EDG_1$ receptor is a G-protein coupled receptor (GPCR) and is a member of the endothelial cell differentiation gene (EDG) receptor family. Endogenous ligands for EDG receptors include lysophospholipids, such as sphingosine-1-phosphate (S1P). Like all GPCRs, ligation of the receptor propagates second messenger signals via activation of G-proteins (alpha, beta and gamma).

Development of small molecule $S1P_1$ agonists and antagonists has provided insight into some physiological roles of the $S1P_1/S1P$-receptor signaling system. Agonism of the $S1P_1$ receptor perturbs lymphocyte trafficking, sequestering them in lymph nodes and other secondary lymphoid tissue. This leads to rapid and reversible lymphopenia, and is probably due to receptor ligation on both lymphatic endothelial cells and lymphocytes themselves (Rosen et al, *Immunol. Rev.*, 195:160-177, 2003). A clinically valuable consequence of lymphocyte sequestration is exclusion of them from sights of inflammation and/or auto-immune reactivity in peripheral tissues.

Agonism of $S1P_1$ has also been reported to promote survival of oligodendrocyte progenitors (Miron et al, *Ann. Neurol.*, 63:61-71, 2008). This activity, in conjunction with lymphocyte sequestration would be useful in treating inflammatory and autoimmune conditions of the central nervous system.

SUMMARY OF THE INVENTION

The present invention is directed to heterocyclic compounds adapted to act as agonists of S1P receptor subtype 1, $S1P_1$; methods of preparation and methods of use, such as in treatment of a malcondition mediated by $S1P_1$ activation, or when activation of $S1P_1$ is medically indicated.

Certain embodiments of the present invention comprise a compound having the structure of Formula I-R or I-S or a pharmaceutically acceptable salt, ester, prodrug, homolog, hydrate or solvate thereof:

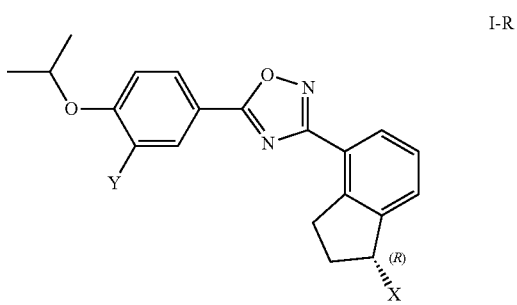

I-R

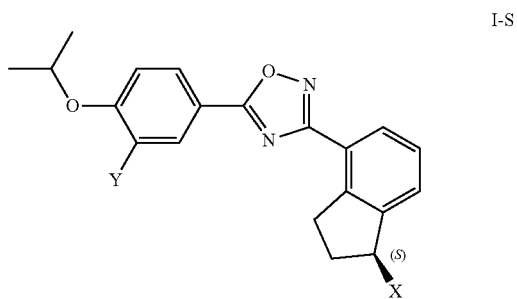

I-S

X can be —NR'R" or —OR''' and Y can be —CN, —Cl, or —$CF_3$.

R' can be H, $C_{1-4}$ alkyl, n-hydroxy $C_{1-4}$ alkyl, —$SO_2$—$R^1$, or —CO—$^1$. R" can be H, —$SO_2$—$R^3$, $C_{1-4}$ alkyl optionally substituted with 1 or more $R^2$, or a ring moiety optionally substituted with $R^4$ wherein such ring moiety is piperidinyl, cyclohexyl, morpholinyl, pyrrolidinyl, imidazolyl, or phenyl. R''' can be H, $C_{1-4}$ alkyl, or —CO—$R^1$. Alternatively, R' and R" taken together with the nitrogen atom to which they are bound form a 4, 5, or 6 membered saturated heterocyclic ring containing 0 or 1 additional heteroatoms where such additional heteroatom is O or N wherein such heterocycle is optionally singly or multiply substituted with substituents independently selected from —OH, oxo, —$NH_2$, n-hydroxy-$C_{1-4}$ alkyl, —COOH, —$(CH_2)_m$—COOH, —$(CH_2)_m$—$COOR^1$, —$N(R^1R^1)$, and —$(CH_2)_m$—CO—$N(R^5R^5)$.

Each $R^1$ can be independently $C_{1-4}$ alkyl or H and each $R^2$ can be independently H, halo, OH, oxo, =NH, $NH_2$, —COOH, F, —$NHR^1$, —$N(R^5R^5)$, —$SO_2$—$R^1$, —$SO_2$—$N(R^5R^{51})$, —$N(R^1)$—$SO_2$—$R^1$, —$COOR^1$, —OCO—$R^1$, —CO—$N(R^5R^5)$, —$N(R^1)$—$COR^1$, $C_{1-3}$ alkyl, $C_{1-3}$ alkoxy, and a ring moiety optionally substituted with $R^4$ wherein such ring moiety is piperazinyl, piperidinyl, morpholinyl, pyrrolidinyl, pyrazolyl, imidazolyl, benzimidazolyl, azetidinyl, cyclobutinyl, or phenyl.

Each $R^3$ can be independently $R^2$, $C_{1-4}$ alkyl, $C_{3-6}$ cycloalkyl, or $C_{1-4}$ alkyl optionally substituted with 1 or more $R^2$; and each $R^4$ can be independently halo, OH, —$NH_2$, —$NHR^1$, —$N(R^1R^1)$, —COOH, —$COOR^1$, —NHCO—$R^1$. Each $R^5$ can be independently $C_{1-4}$ alkyl or H, or alternatively two $R^5$ taken together with the nitrogen atom to which they are bound can form a 4, 5, or 6 membered saturated heterocyclic ring containing 0 or 1 additional heteroatoms where such additional heteroatom is O or N wherein such heterocycle is optionally substituted with —OH, —NH$_2$, —N(R$^1$R$^1$), n-hydroxy C$_{1-4}$ alkyl, —(CH$_2$)$_m$—COOH, —(CH$_2$)$_m$—COOR$^1$;
Each m is independently 0, 1, 2, or 3.

In certain embodiments, a pharmaceutical composition comprising a compound of the invention and a suitable excipient is provided.

In certain embodiments a method of use of an inventive compound comprising preparation of a medicament is provided.

In certain combinations a pharmaceutical combination comprising a compound of the invention and a second medicament is provided. In various embodiments the second medicament is medically indicated for the treatment of multiple sclerosis, transplant rejection, acute respiratory distress syndrome or adult respiratory distress syndrome.

In certain embodiments, a method of activation or agonism of a sphingosine-1-phosphate receptor subtype 1 comprising contacting the receptor subtype 1 with a compound of claim 1 is provided. In various embodiments, the compound of claim 1 activates or agonizes the sphingosine-1-phosphate receptor subtype 1 to a greater degree than the compound activates or agonizes a sphingosine-1-phosphate receptor subtype 3.

In certain embodiments a method of treatment of a malcondition in a patient for which activation or agonism of an S1P$_1$ receptor is medically indicated, is provided. In various embodiment, selective activation or agonism of an S1P$_1$ receptor, such as with respect to an S1P$_3$ receptor, is medically indicated. In various embodiments, the malcondition comprises multiple sclerosis, transplant rejection, or acute respiratory distress syndrome.

In certain embodiments, a method is provided for chiral synthesis of certain compounds including compounds of the invention. In certain other embodiments the invention provides certain intermediate compounds associated with such methods of chiral synthesis.

DETAILED DESCRIPTION OF THE INVENTION

Certain embodiments of the present invention comprise a compound having the structure of Formula I-R or I-S or a pharmaceutically acceptable salt, ester, prodrug, homolog, hydrate or solvate thereof:

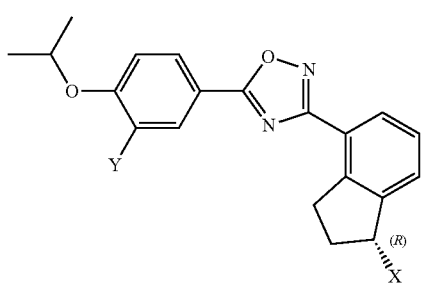

I-R

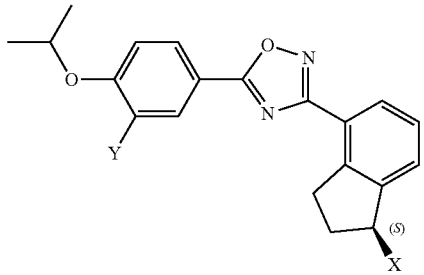

I-S

X can be —NR'R" or —OR'" and Y can be —CN, —Cl, or —CF$_3$.

R' can be H, C$_{1-4}$ alkyl, n-hydroxy C$_{1-4}$ alkyl, —SO$_2$—R$^1$, or —CO—R$^1$. R" can be H, —SO$_2$—R$^3$, C$_{1-4}$ alkyl optionally substituted with 1 or more R$^2$, or a ring moiety optionally substituted with R$^4$ wherein such ring moiety is piperidinyl, cyclohexyl, morpholinyl, pyrrolidinyl, imidazolyl, or phenyl. R'" can be H, C$_{1-4}$ alkyl, or —CO—R$^1$. Alternatively, R' and R" taken together with the nitrogen atom to which they are bound form a 4, 5, or 6 membered saturated heterocyclic ring containing 0 or 1 additional heteroatoms where such additional heteroatom is O or N wherein such heterocycle is optionally singly or multiply substituted with substituents independently selected from —OH, oxo, —NH$_2$, n-hydroxy-C$_{1-4}$ alkyl, —COOH, —(CH$_2$)$_m$—COOH, —(CH$_2$)$_m$—COOR$^1$, —N(R$^1$R$^1$), and —(CH$_2$)$_m$—CO—N(R$^5$R$^5$).

Each R$^1$ can be independently C$_{1-4}$ alkyl or H and each R$^2$ can be independently H, halo, OH, oxo, =NH, NH$_2$, —COOH, F, —NHR$^1$, —N(R$^5$R$^5$), —SO$_2$—R$^1$, —SO$_2$—N(R$^5$R$^5$), —N(R$^1$)—SO$_2$—R$^1$, —COOR$^1$, —OCO—R$^1$, —CO—N(R$^5$R$^5$), —N(R$^1$)—COR$^1$, C$_{1-3}$ alkyl, C$_{1-3}$ alkoxy, and a ring moiety optionally substituted with R$^4$ wherein such ring moiety is piperazinyl, piperidinyl, morpholinyl, pyrrolidinyl, pyrazolyl, thiazolyl, imidazolyl, benzimidazolyl, azetidinyl, cyclobutinyl, or phenyl.

Each R$^3$ can be independently R$^2$, C$_{1-4}$ alkyl, C$_{3-6}$ cycloalkyl, or C$_{1-4}$ alkyl optionally substituted with 1 or more R$^2$; and each R$^4$ can be independently halo, OH, —NH$_2$, —NHR$^1$, —N(R$^1$R$^1$), —COOH, —COOR$^1$, —NHCO—R$^1$. Each R$^5$ can be independently C$_{1-4}$ alkyl or H, or alternatively two R$^5$ taken together with the nitrogen atom to which they are bound can form a 4, 5, or 6 membered saturated heterocyclic ring containing 0 or 1 additional heteroatoms where such additional heteroatom is O or N wherein such heterocycle is optionally substituted with —OH, —NH$_2$, —N(R$^1$R$^1$), n-hydroxy C$_{1-4}$ alkyl, —(CH$_2$)$_m$—COOH, —(CH$_2$)$_m$—COOR$^1$
Each m is independently 0, 1, 2, or 3.

In certain embodiments, the compounds of the invention have the structure of Formula I-R or a pharmaceutically acceptable salt, ester, prodrug, homolog, hydrate or solvate thereof. In other embodiments, the compounds of the invention have the structure of Formula I-S or a pharmaceutically acceptable salt, ester, prodrug, homolog, hydrate or solvate thereof.

In certain embodiments the invention provides compounds which are substantially enantiomerically pure.

In certain embodiments the invention provides compounds which have an EC$_{50}$ as an agonist of the wild type S1P receptor subtype 1 which is at least ten times smaller than the EC$_{50}$ of such compound as an agonist of a mutant S1P receptor subtype 1 having a single mutation with respect to wild type S1P receptor subtype 1 such that the 101$^{st}$ amino acid residue is changed from asparagine to alanine.

In certain embodiments the invention provides compounds which have an $EC_{50}$ as an agonist of the wild type S1P receptor subtype 1 which is at least twenty times smaller than the $EC_{50}$ of such compound as an agonist of a mutant S1P receptor subtype 1 having a single mutation with respect to wild type S1P receptor subtype 1 such that the $101^{st}$ amino acid residue is changed from asparagine to alanine.

In certain embodiments the invention provides compounds which have a therapeutic index of at least 5 as measured in rats following 5 or 14 days of dosing of rats with the compound where the therapeutic index is calculated as a ratio of (i) the highest dose of such compound which achieves less than or equal to a ten percent increase in the ratio of lung to terminal body weight at the conclusion of such 5 or 14 days of dosing, to (ii) the dose of such compound achieving 50% lymphopenia in rats. In certain embodiments, such therapeutic index is at least 10 and in certain embodiments the therapeutic index is at least 20. In certain embodiments, the therapeutic index for a compound is at least five times greater than the therapeutic index for the enantiomer of such compound.

In certain embodiments the invention provides compounds which have a therapeutic index of at least 5 as measured in rats following 5 or 14 days of dosing of rats with the compound where the therapeutic index is calculated as a ratio of (i) the highest dose of such compound which achieves less than or equal to a ten percent increase in the ratio of lung to terminal body weight at the conclusion of such 5 or 14 days of dosing, to (ii) the dose of such compound achieving 50% lymphopenia in rats. In certain embodiments, such therapeutic index is at least 10 and in certain embodiments the therapeutic index is at least 20. In certain embodiments, the therapeutic index for a compound is greater than the therapeutic index for the enantiomer of such compound. In certain embodiments, the therapeutic index for a compound is at least 150% of the therapeutic index for the enantiomer of such compound.

In certain embodiments the invention provides compounds where Y is Cl, in other embodiments the invention provides compounds where Y is $CF_3$ and in other embodiments the invention provides compounds where Y is CN.

In certain embodiments the invention provides compounds where X is —NR'R", in other embodiments the invention provides compounds where X is —OR'". In certain embodiments the invention provides compounds where X is —OR'". In certain embodiments the invention provides compounds where X is —OH and in other embodiments the invention provides compounds where X is —OCO—$R^1$.

In certain embodiments the invention provides compounds where $R_1$ is $C_{1-3}$ alkyl; in other embodiments the invention provides compounds where R' is H.

In certain embodiments the invention provides compounds where R' is —$COR^1$; in other embodiments the invention provides compounds where R' is $SO_2$—$R^1$. In certain embodiments the invention provides compounds where R" is H.

In certain embodiments the invention provides compounds where R" is —$SO_2$—$R^3$; in other embodiments the invention provides compounds where R" is $C_{1-4}$ alkyl where the $C_{1-4}$ alkyl is optionally substituted with 1 or more substituents defined by $R^2$. In certain embodiments the invention provides compounds where R" is —$(CR^aR^b)_n$—$R^2$ and each $R^a$ and each $R^b$ can be independently any of H, hydroxyl and methyl or where $R^a$ and $R^b$ are bound to the same carbon they can be taken together to form oxo (i.e. with the carbon to which they are bound forming a carbonyl moiety). In certain such embodiments n can be 0, 1, 2, or 3 and in certain embodiments n is 2. In certain such embodiments $R_2$ can be —OH, —$NH_2$, —$NHR^1$, —$N(R^5R^5)$, or —COOH.

In certain embodiments the invention provides compounds where $R^3$ is $C_{1-4}$ alkyl optionally substituted with 1 or more $R^2$. In certain embodiments the invention provides compounds where $R^2$ is OH; in other embodiments the invention provides compounds where $R^2$ is $C_{1-3}$ alkoxy. In certain embodiments the invention provides compounds where $R^3$ is $(CH_2)_2$—$OR^1$.

In certain embodiments the invention provides compounds where Y is CN and X is —NH—$SO_2$—$R^3$. In certain embodiments the invention provides compounds where $R^3$ is —$C_2H_5$—$N((R^5R^5)$ or —$CH_2$—CO—$N(R^5R^5)$. In certain embodiments the invention provides compounds where Y is CN and X is —NH—CO—$N(R^5R^5)$.

In certain embodiments X is —$NH_2$ and in certain of such embodiments Y is CN.

In certain embodiments the invention provides compounds which have the structure of Formula II-R or II-S or a pharmaceutically acceptable salt, ester, prodrug, homolog, hydrate or solvate thereof:

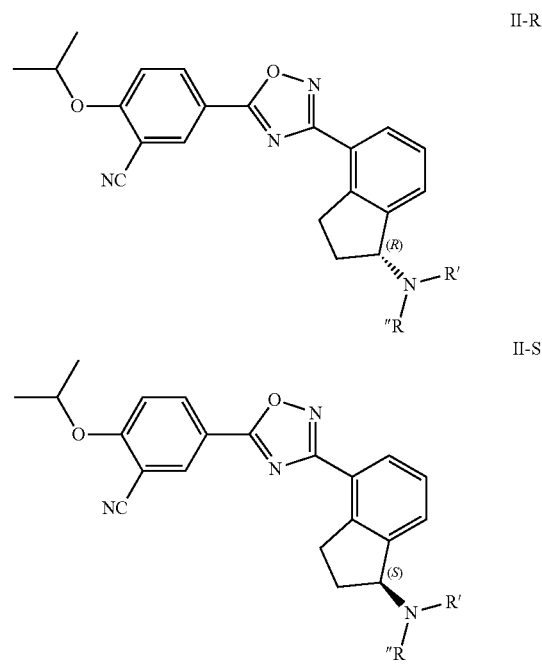

R' can be H, $C_{1-4}$ alkyl, n-hydroxy $C_{1-4}$ alkyl, —$SO_2$—$R^1$, or —CO—$R^1$; and R" can be H, —$(CR^aR^b)_n$—$R^2$, or —$SO_2$—$R^3$. Alternatively, R' and R" taken together with the nitrogen atom to which they are bound form a 4, 5, or 6 membered saturated heterocyclic ring containing 0 or 1 additional heteroatom where such additional heteroatom is O or N wherein such heterocycle is optionally substituted with —OH, —$NH_2$, n-hydroxy-$C_{1-4}$ alkyl, —COOH, —$(CH_2)_m$—COOH, —$(CH_2)_m$—$COOR^1$, —$N(R^1R^1)$, —CO—N$((R^1R^1)$.

Each $R^a$ and each $R^b$ can independently be H, hydroxyl or methyl or $R^a$ and $R^b$ bound to the same carbon can together be oxo.

$R^1$ can be $C_{1-3}$ alkyl or H; each $R^2$ can be independently H, OH, oxo, $NH_2$, —COOH, F, —$NHR^1$, —$N(R^1R^1)$, —$SO_2$—$R^1$, —$SO_2$—$N(R^1R^1)$, —$COOR^1$, —$OCO$—$R^1$, —CO—N$(R^1R^1)$, $C_{1-3}$ alkyl, $C_{1-3}$ alkoxy, piperazinyl, piperidinyl, morpholinyl, pyrrolidinyl, imidazolyl, or phenyl optionally substituted with $R^4$ Each $R^3$ can be independently —$(CR^aR^b)_p$—$R^2$ or $C_{1-4}$ alkyl; and each $R^4$ can be halo, OH, —$NH_2$, —$NHR^1$, —$N(R^1R^1)$, —COOH, —$COOR^1$, or —NHCO—$R^1$.
Each n can be independently 1, 2, or 3, each m can be independently 0, 1, 2, or 3, each p can be independently 0, 1, 2, or 3.
In certain embodiments the invention provides one or more of compounds 1-252:
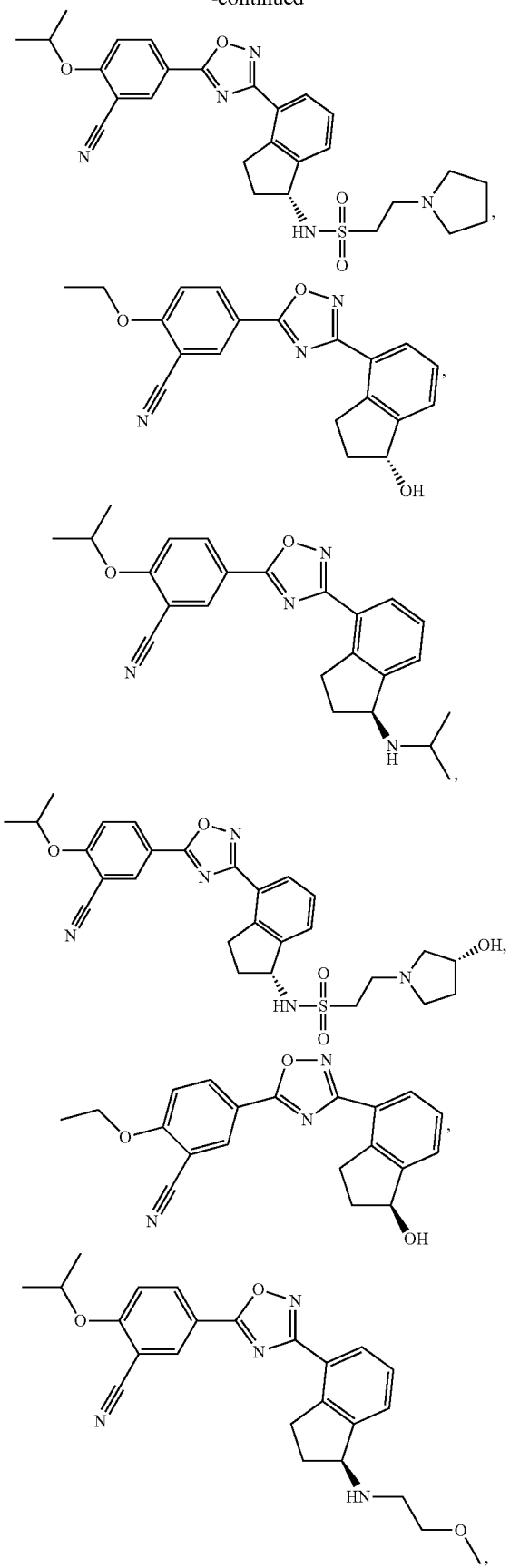

-continued
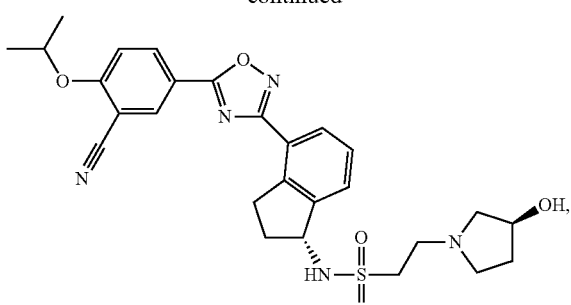
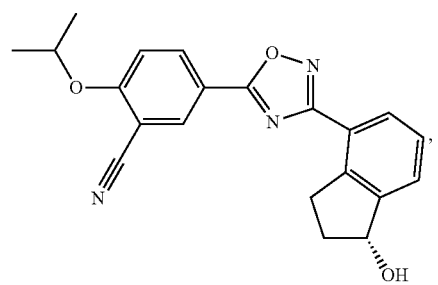
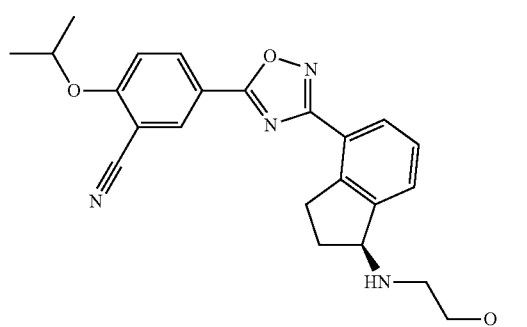
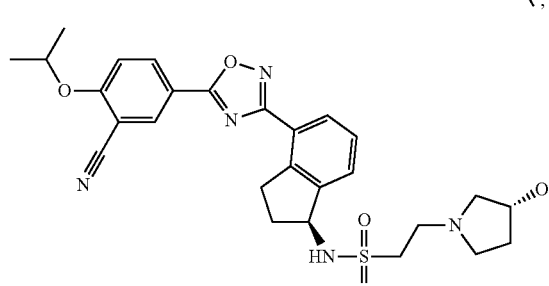
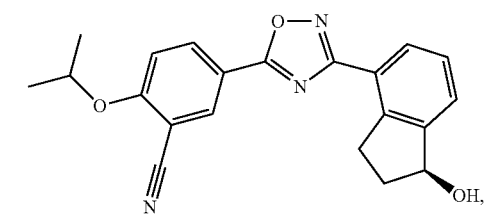
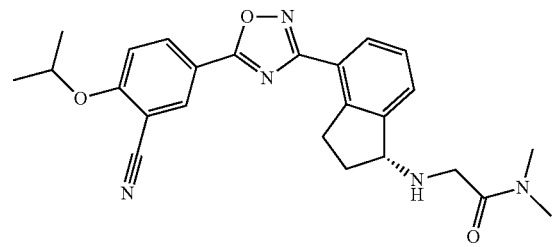
-continued
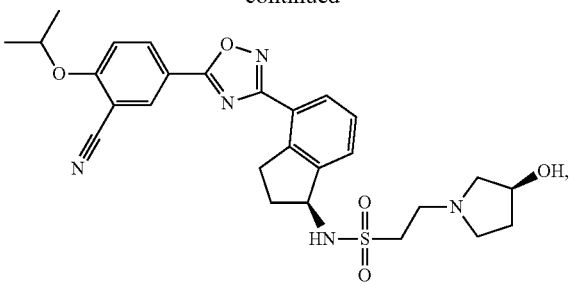
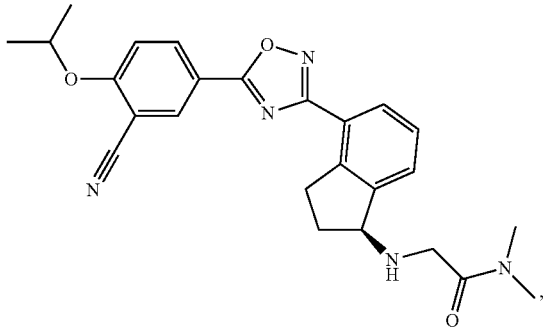
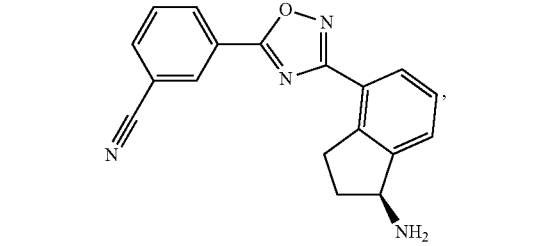

11
-continued
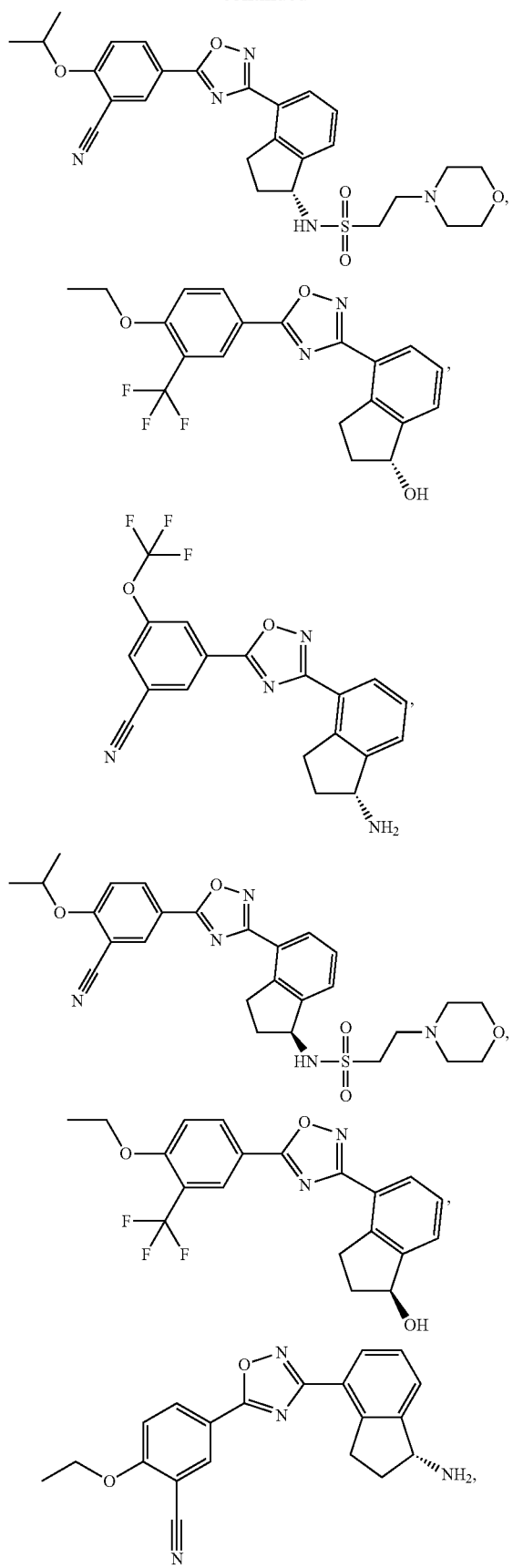
12
-continued
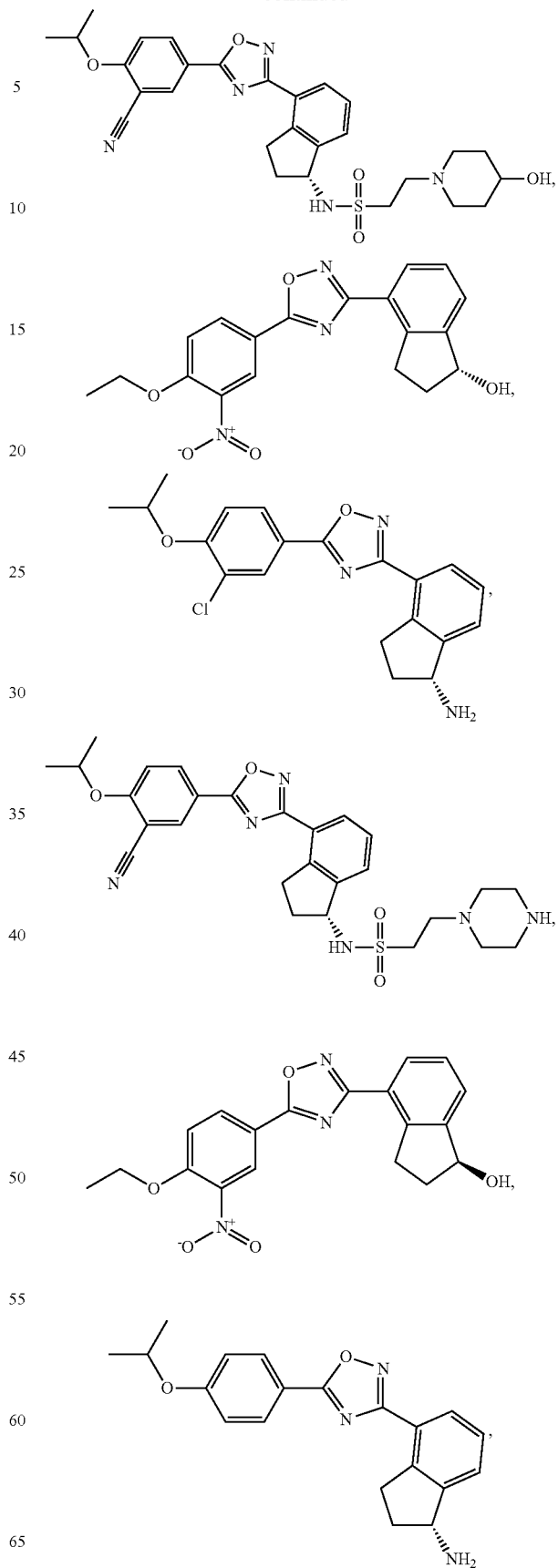

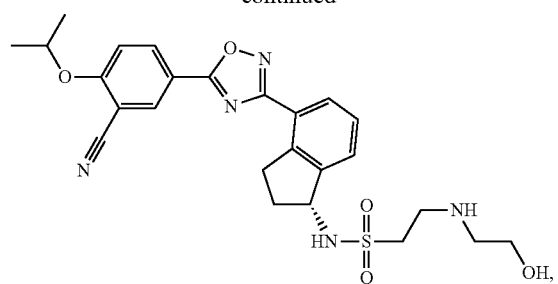
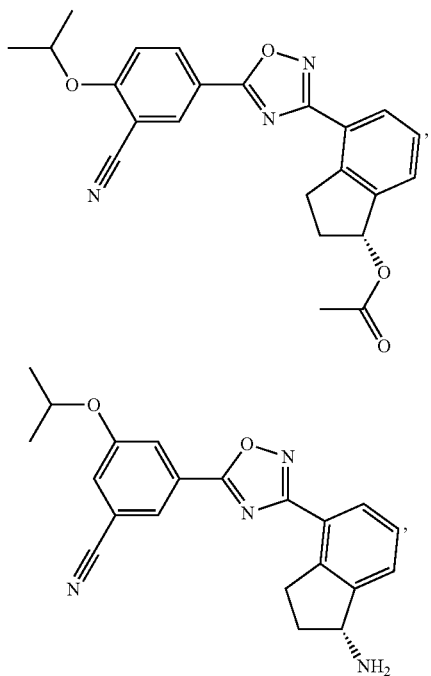
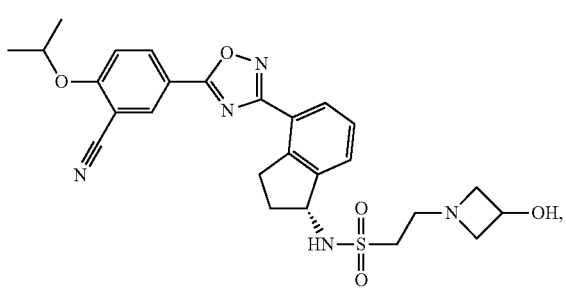
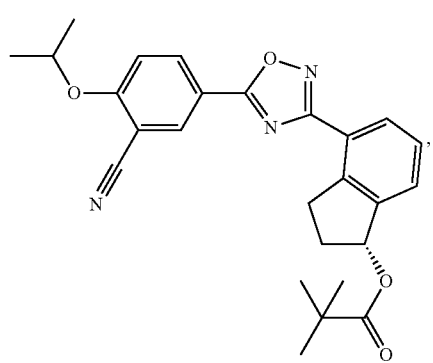
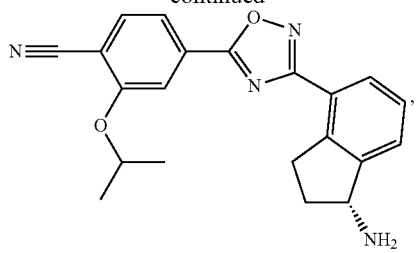
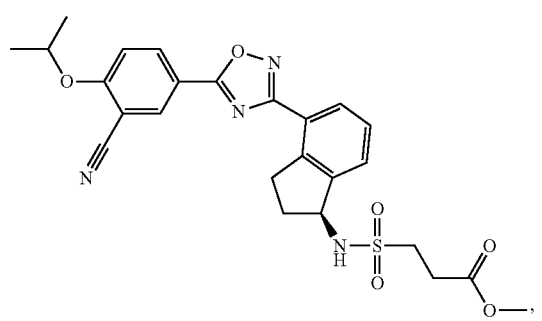
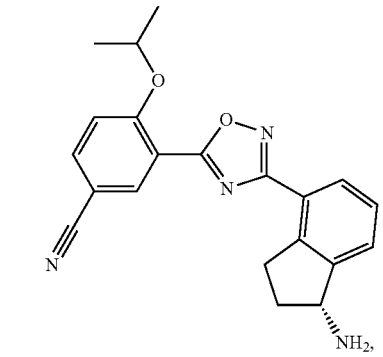
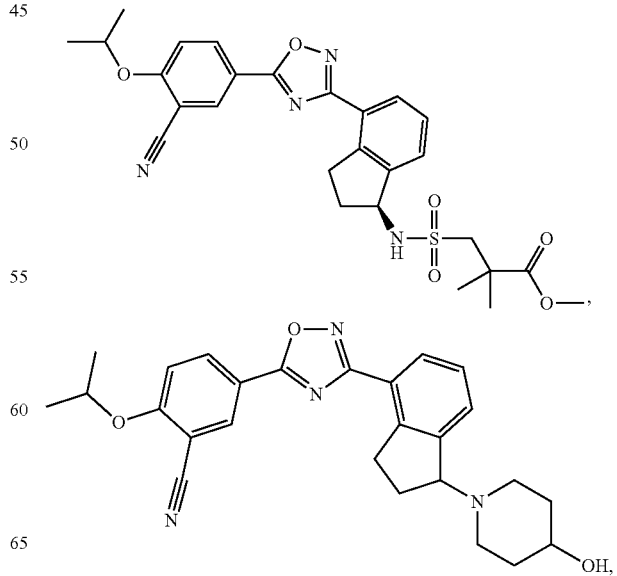

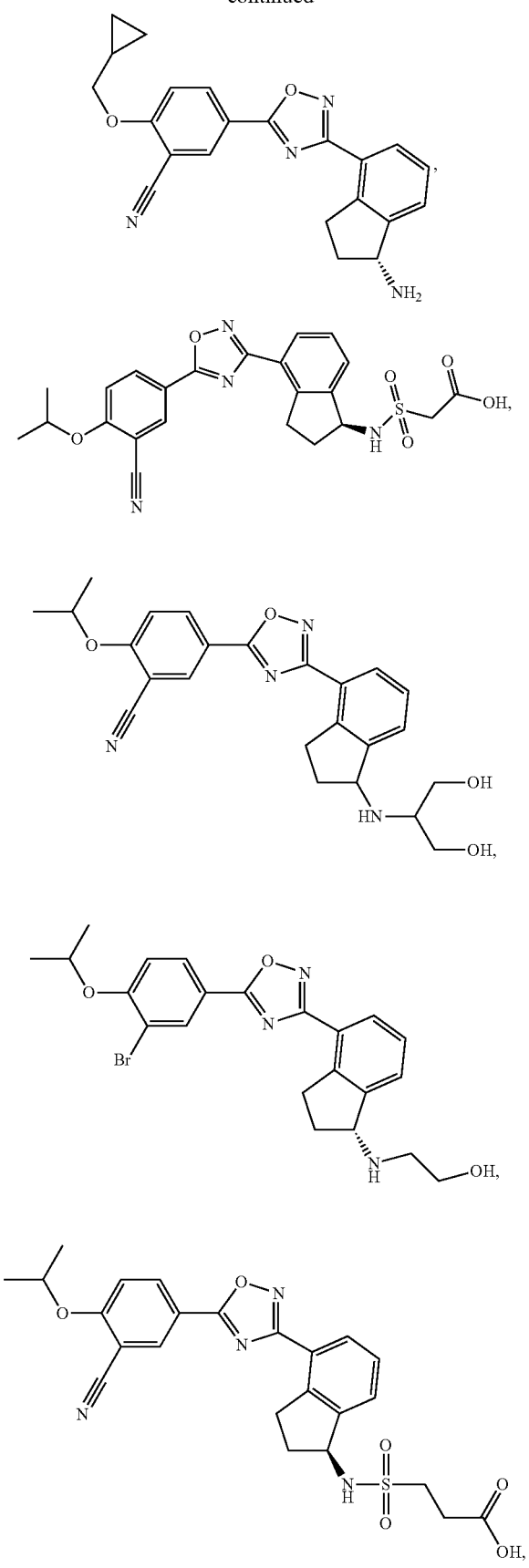
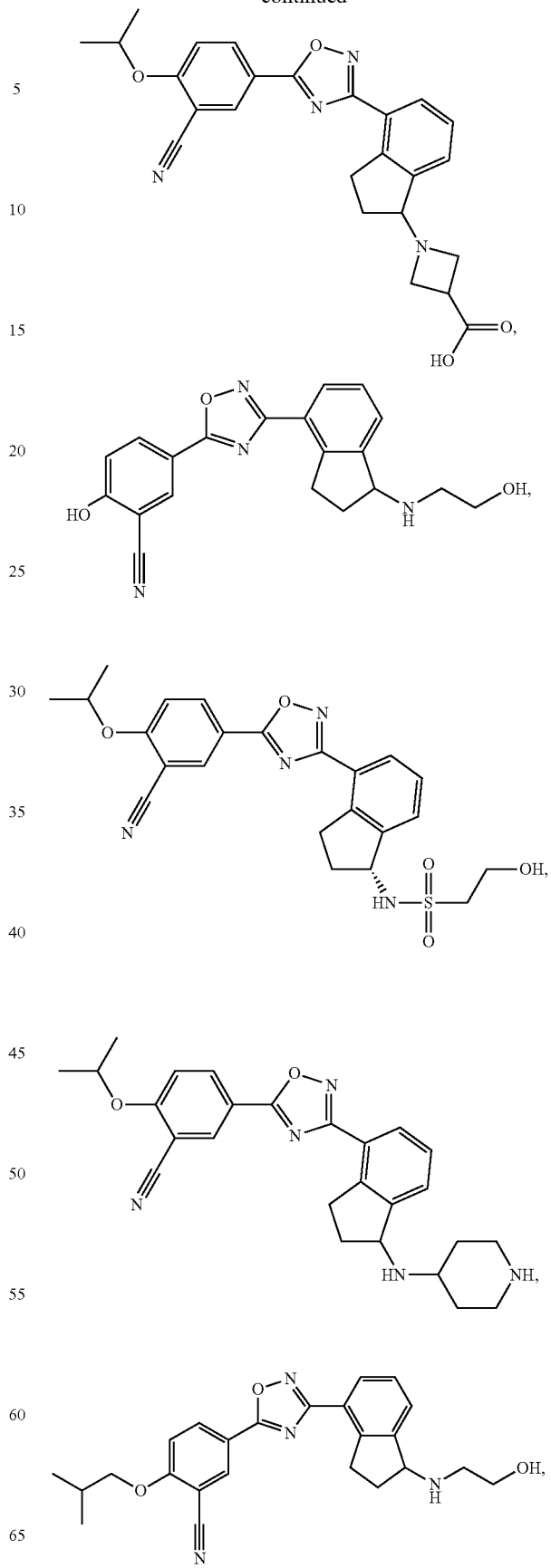

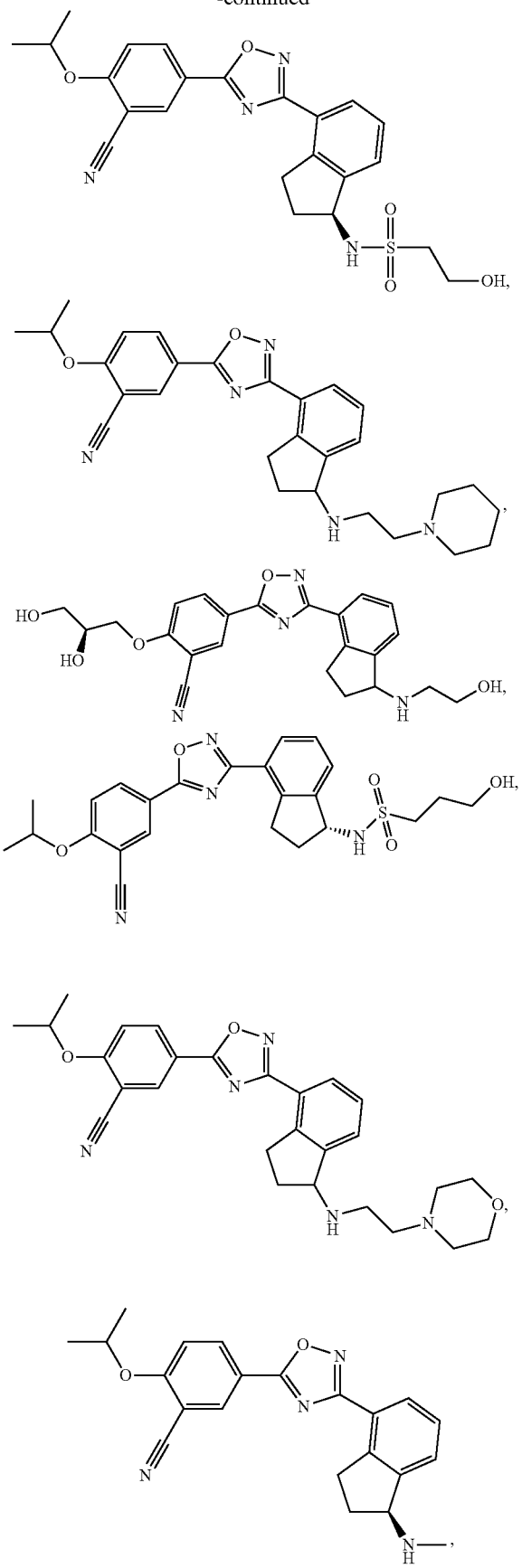

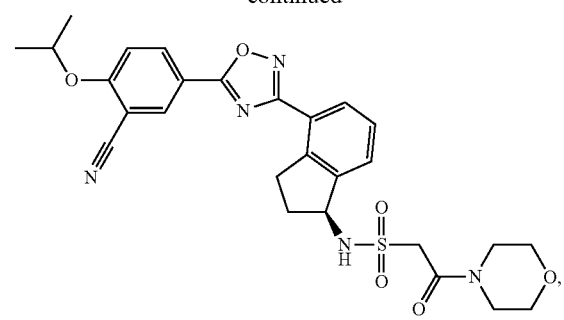
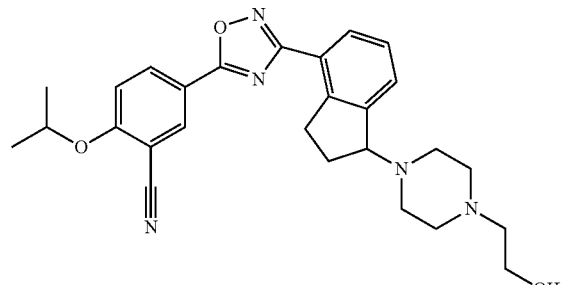
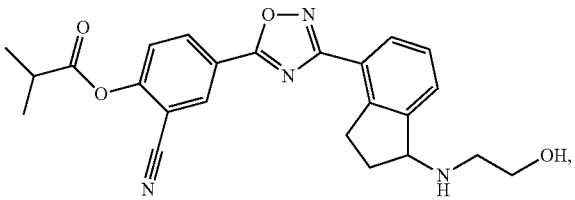
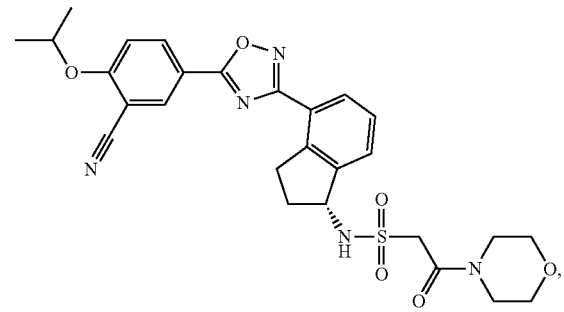
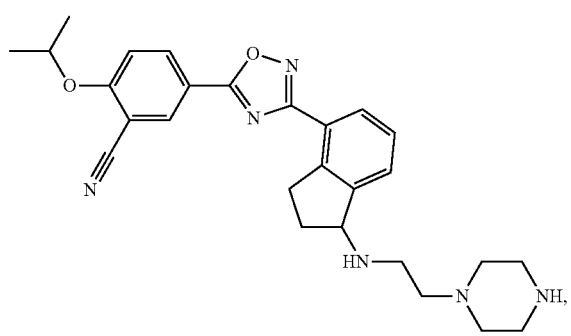
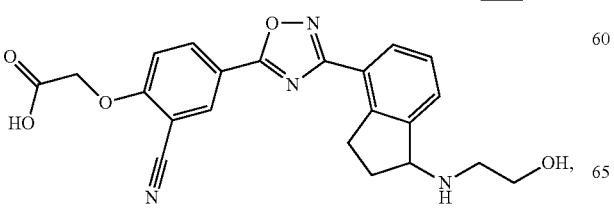
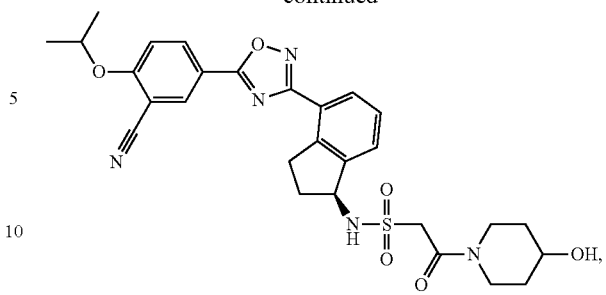
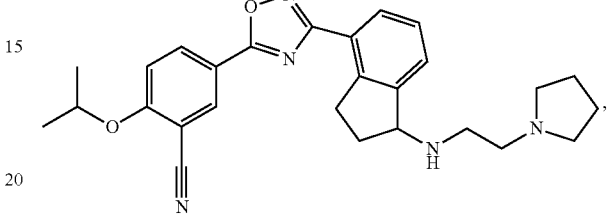
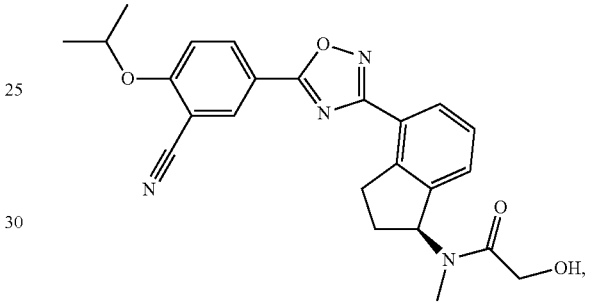
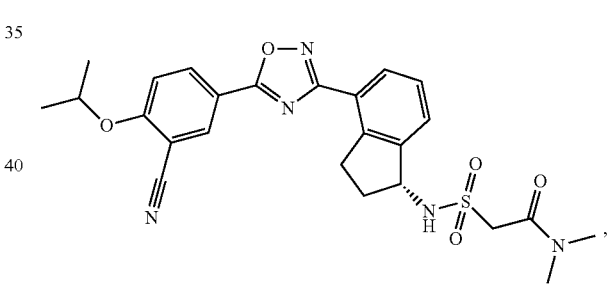
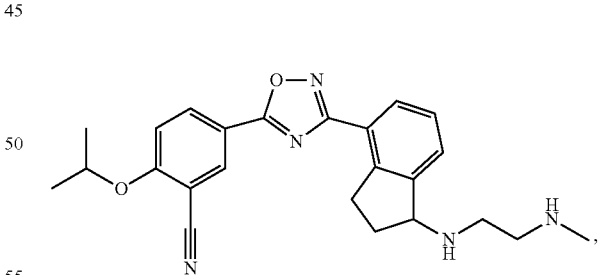
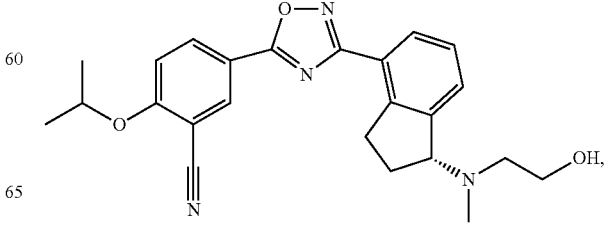

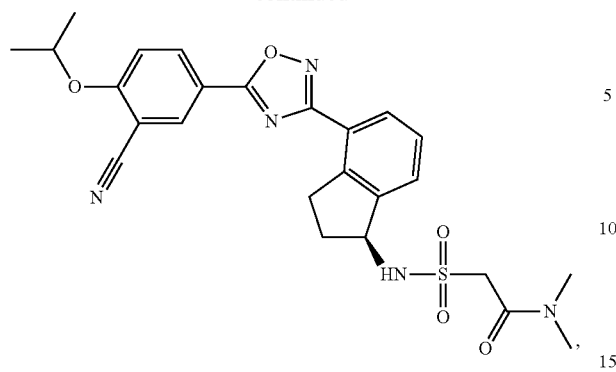
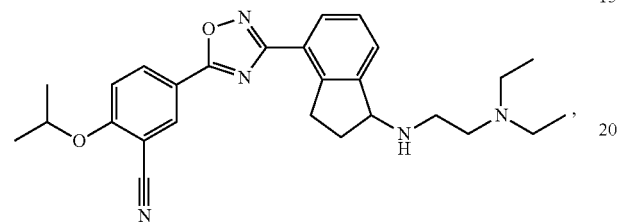
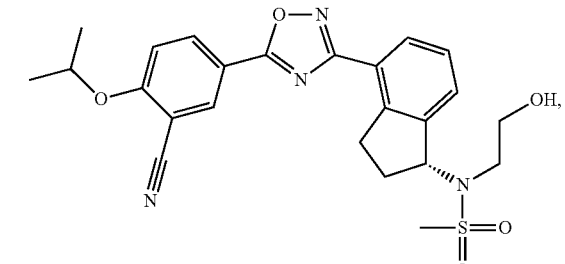
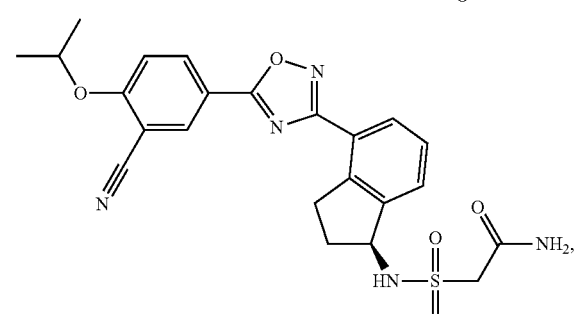
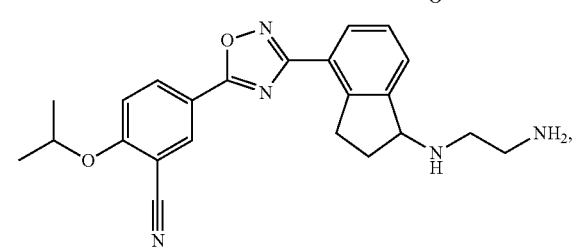
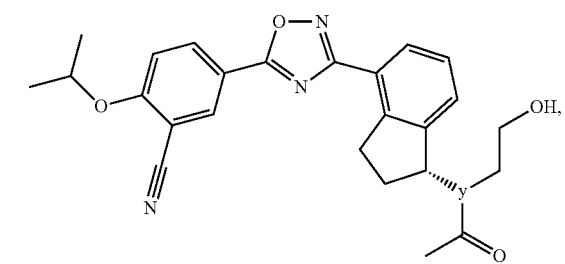
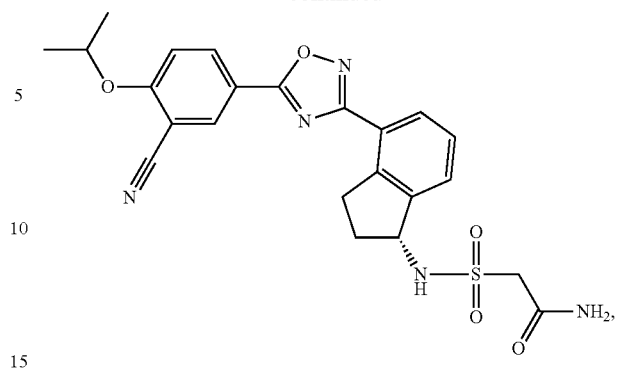
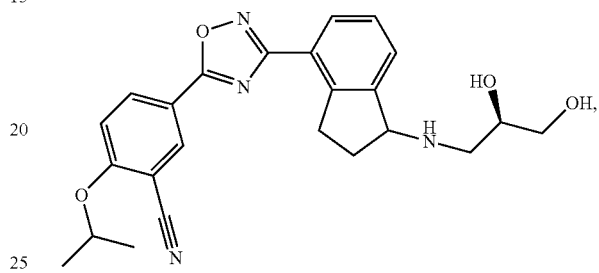
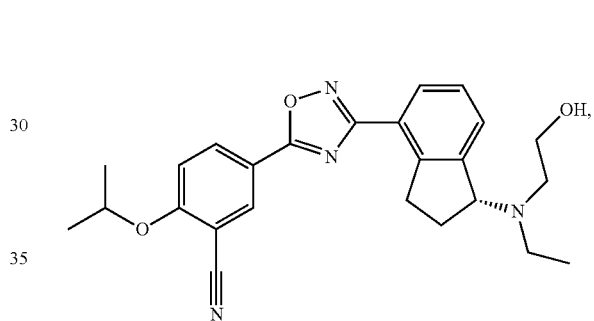
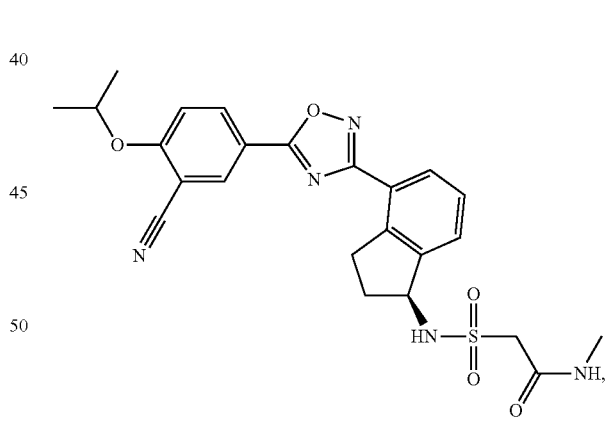
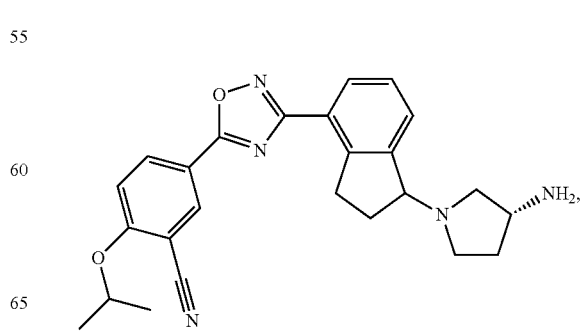

23
-continued
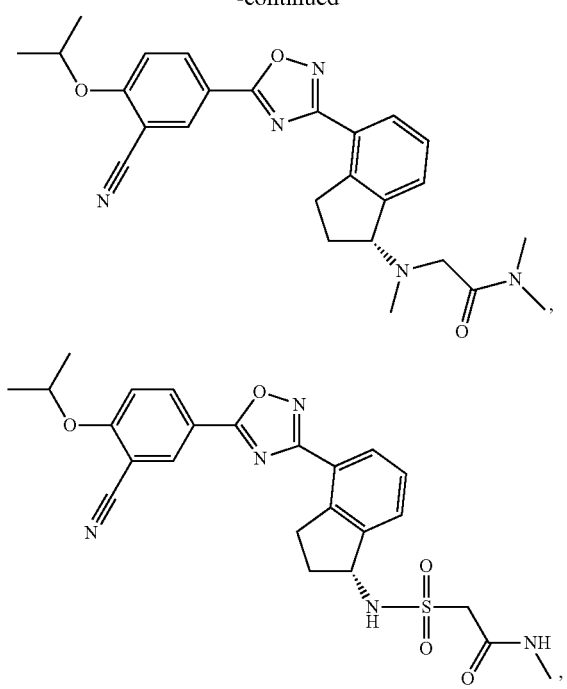
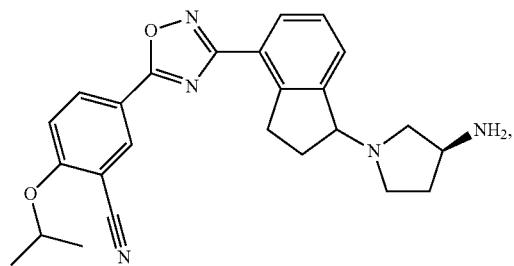
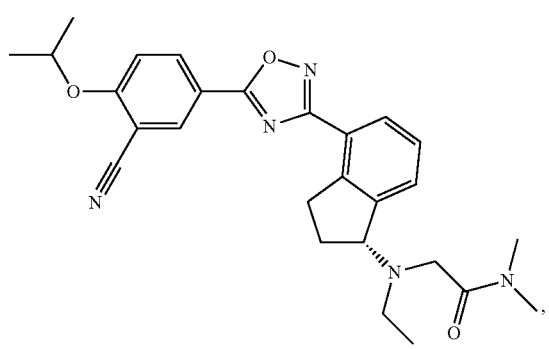
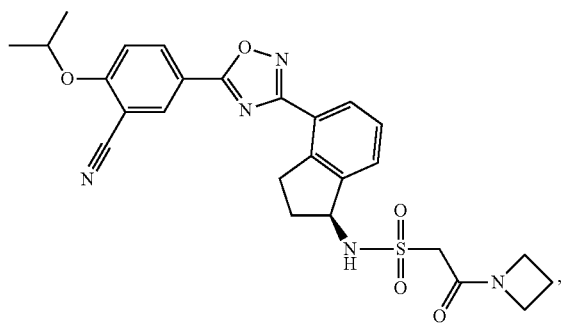
24
-continued
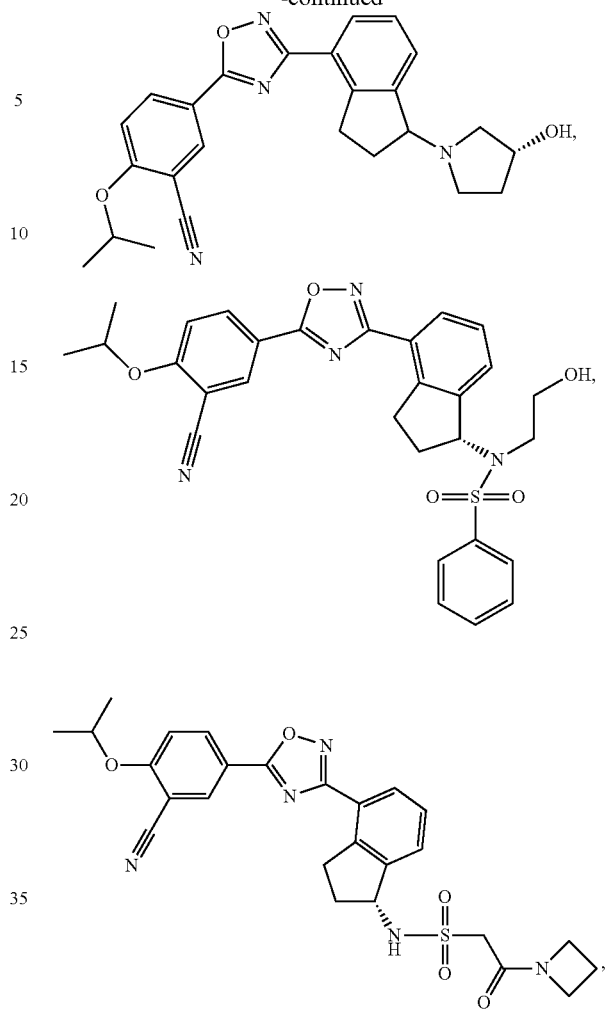
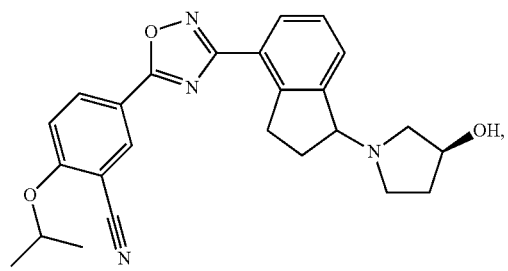
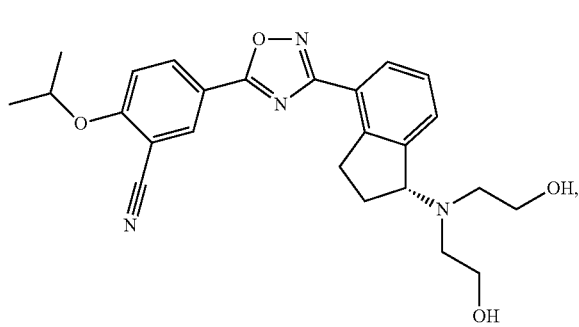

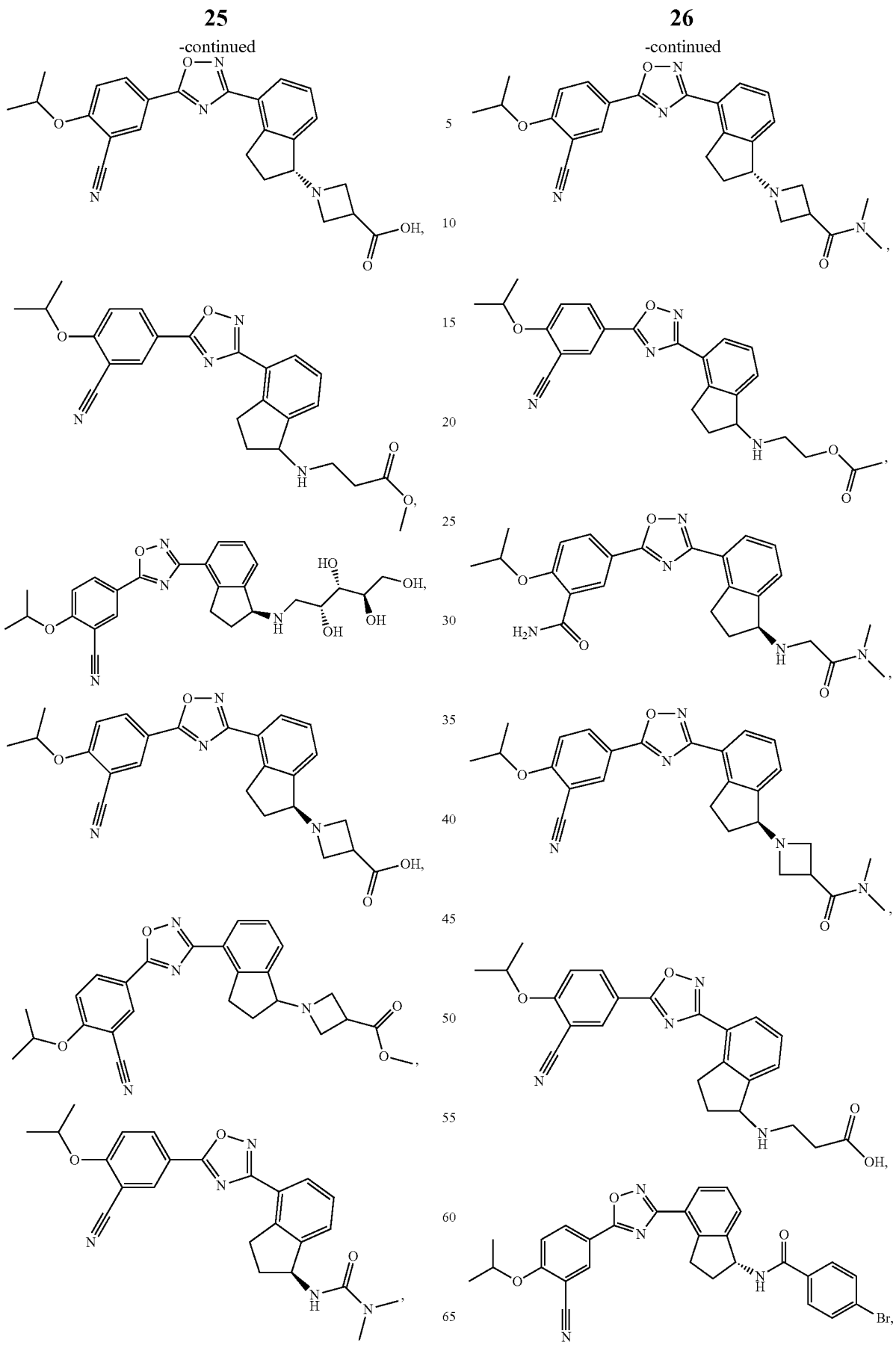

-continued
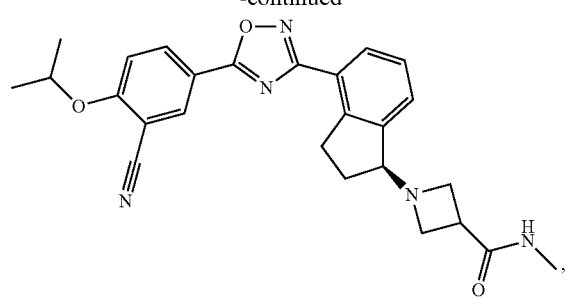
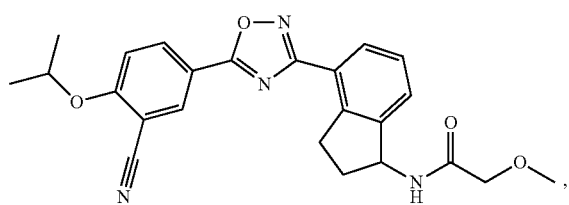
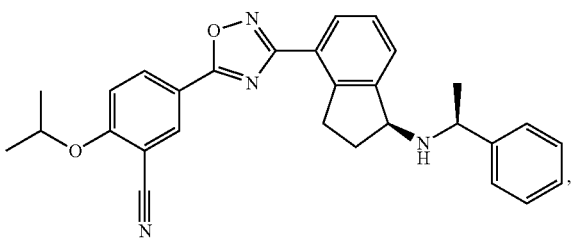
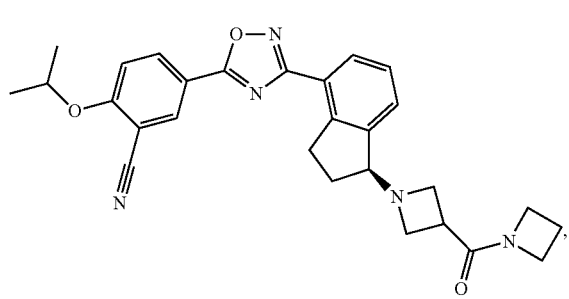
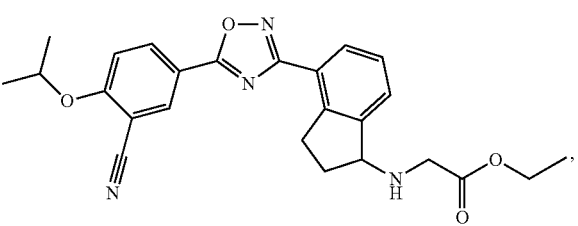
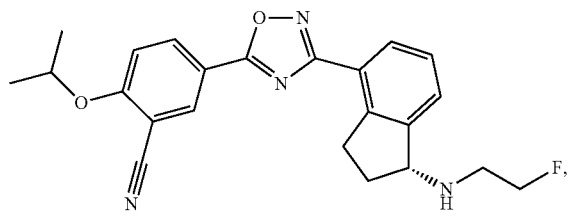
-continued
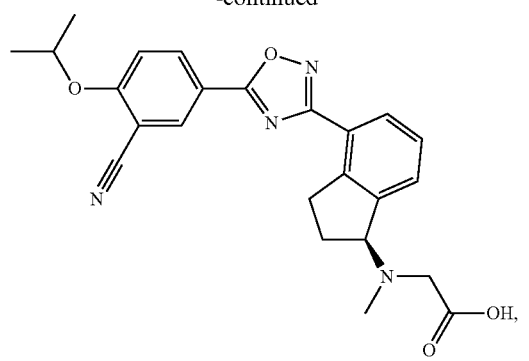
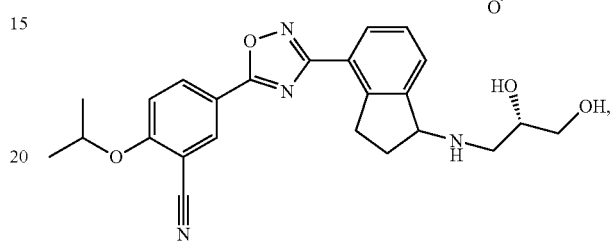
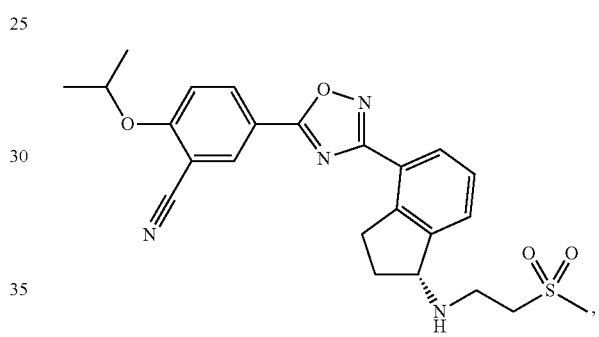
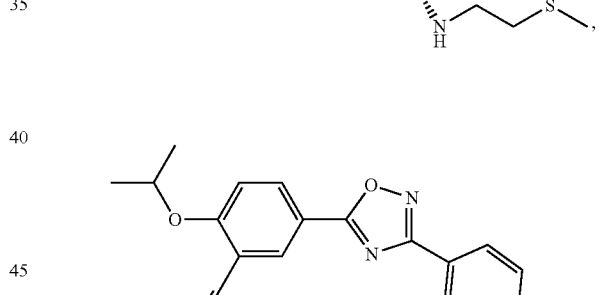
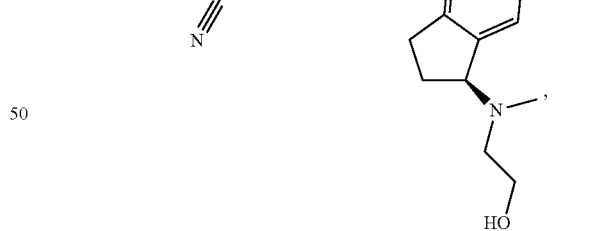
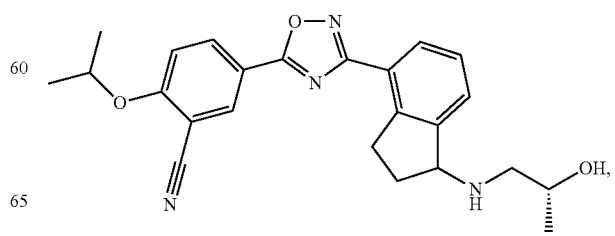

29
-continued
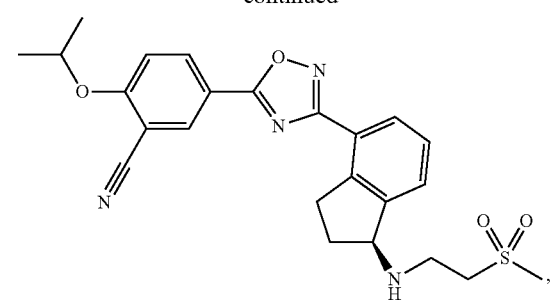
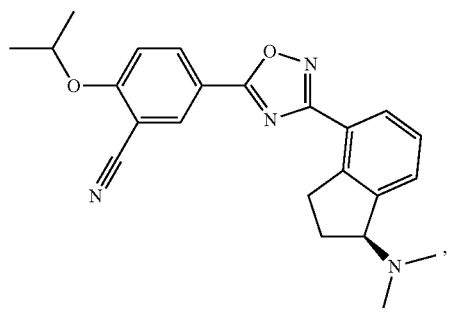
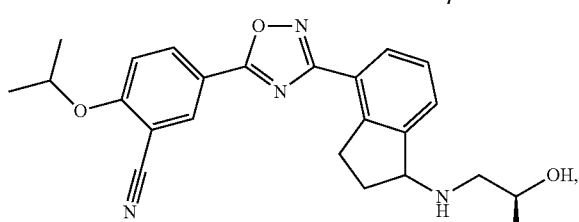
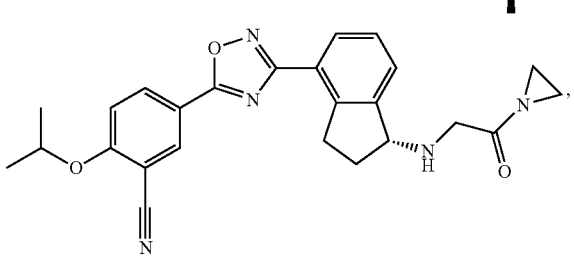
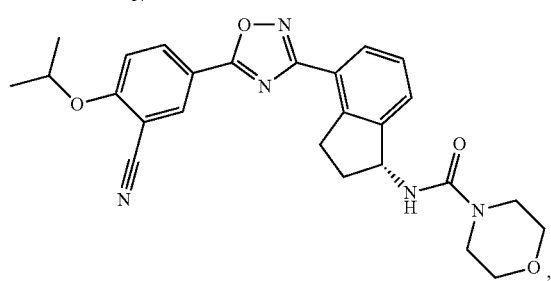
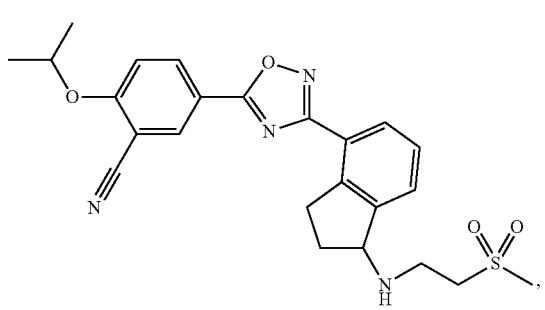
30
-continued
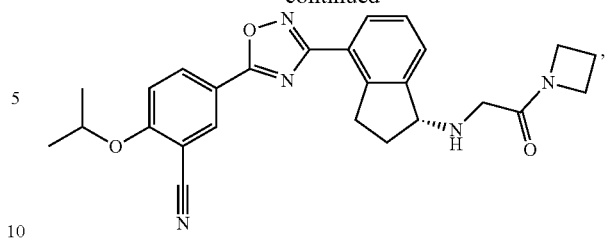
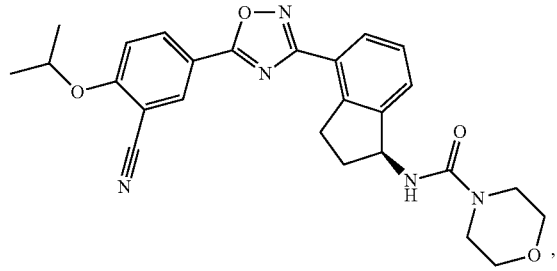
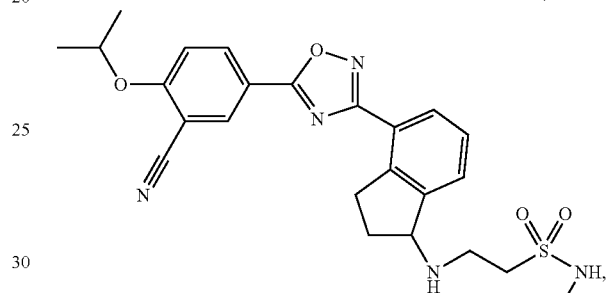
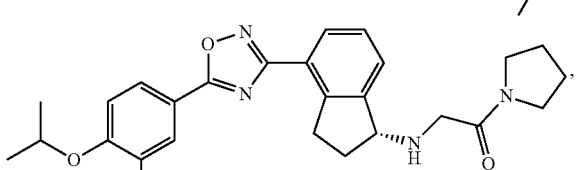
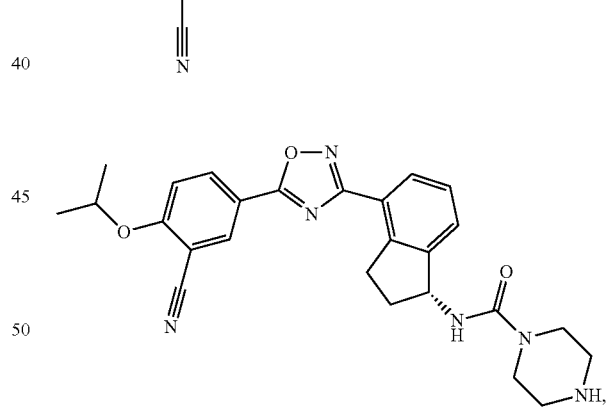
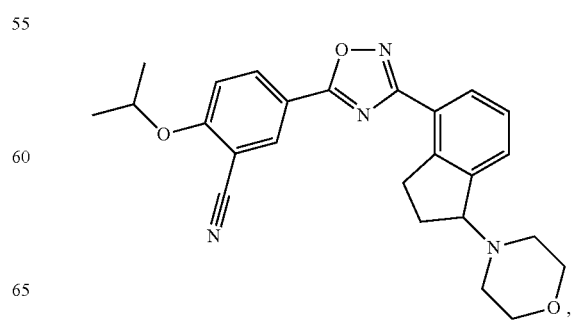

31
-continued
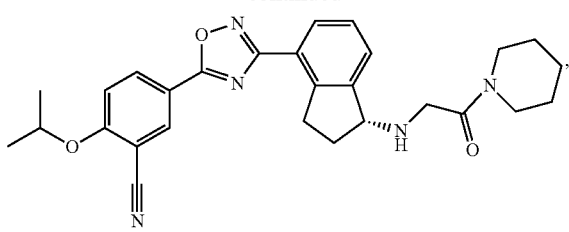
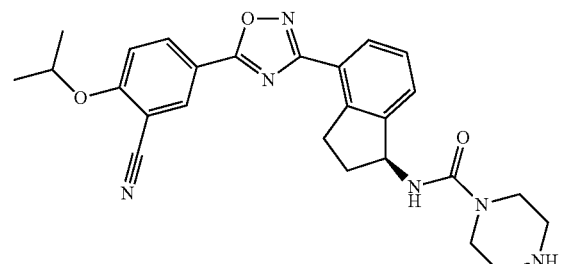
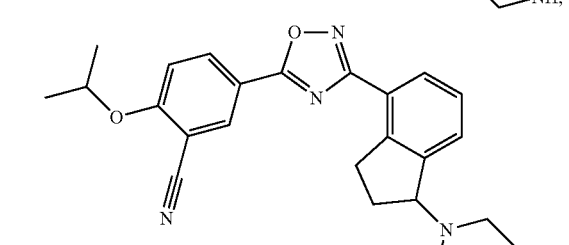
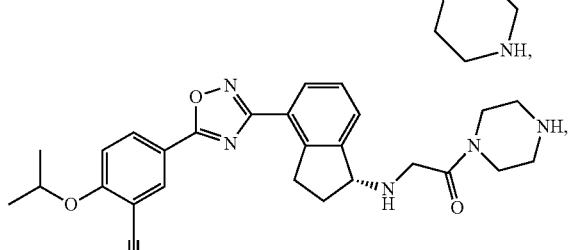
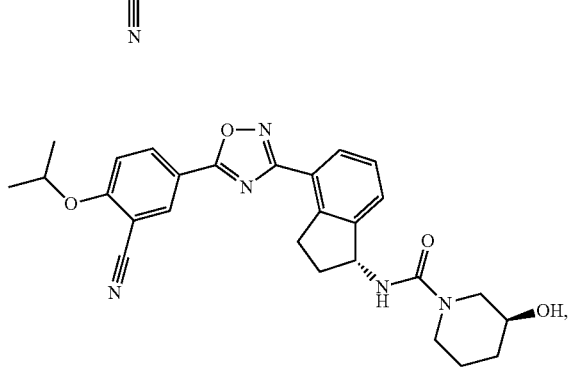
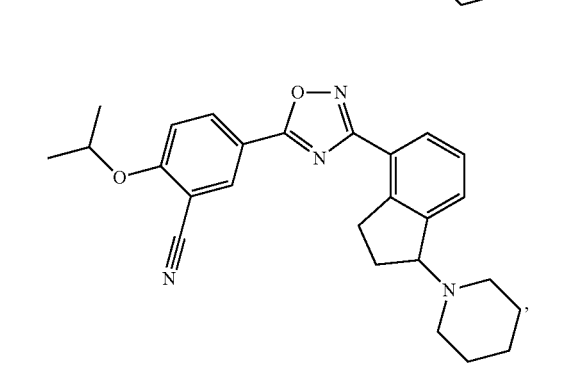
32
-continued
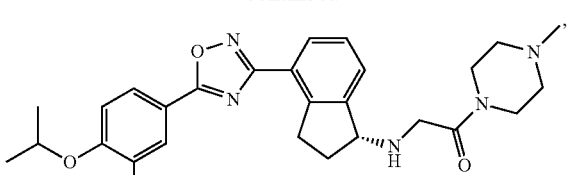
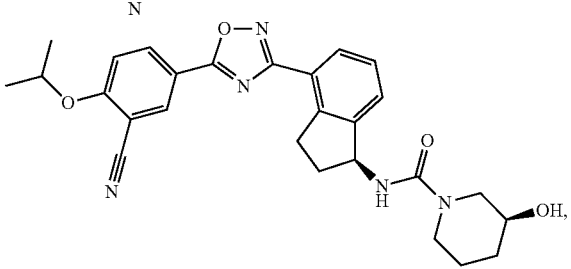
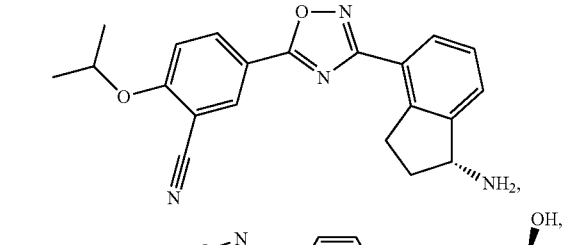
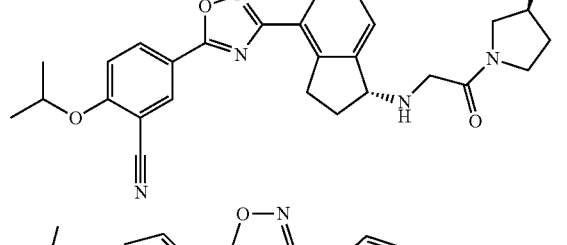
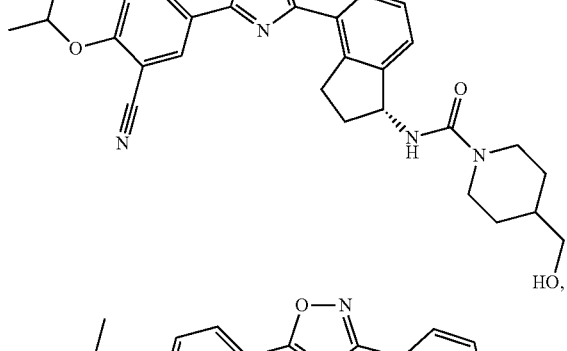
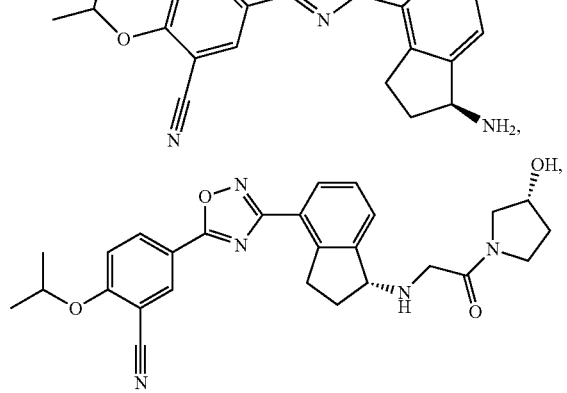

33
-continued
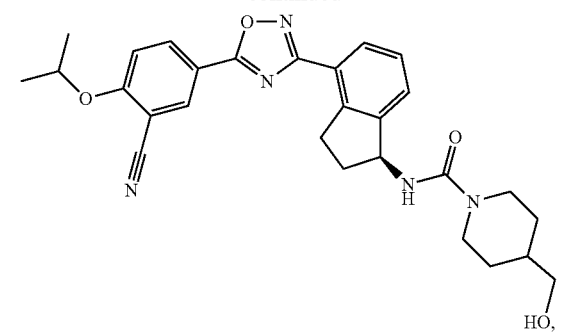
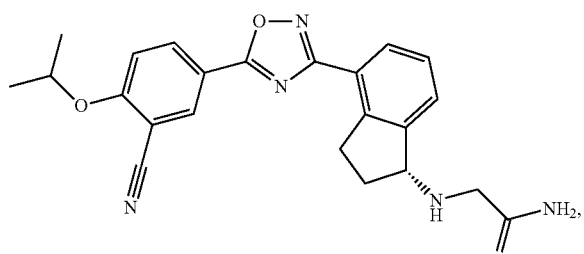
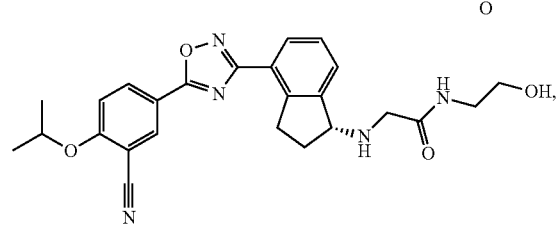
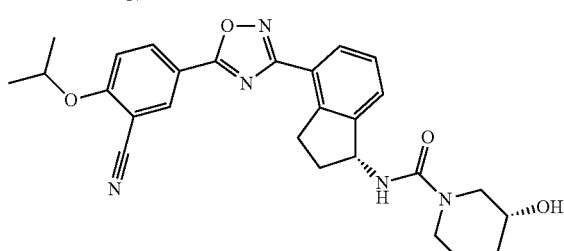
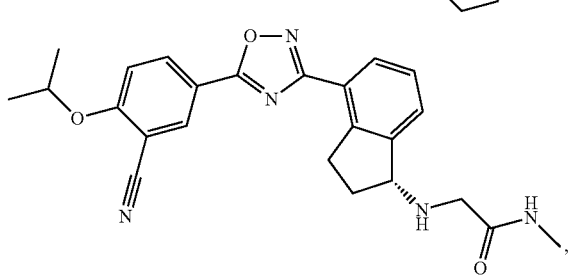
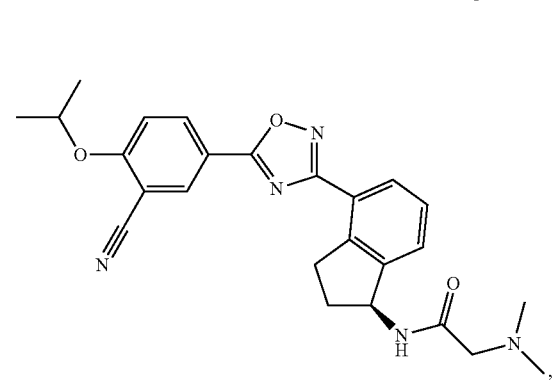
34
-continued
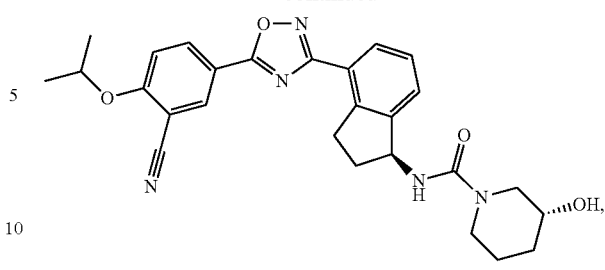
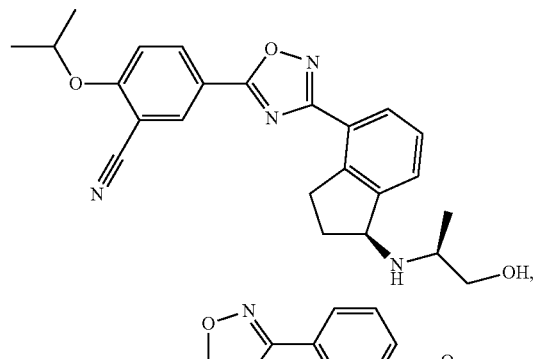
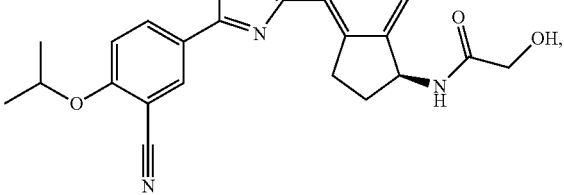
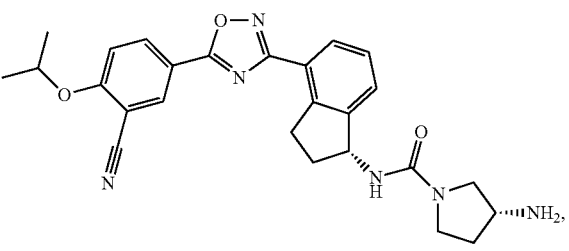
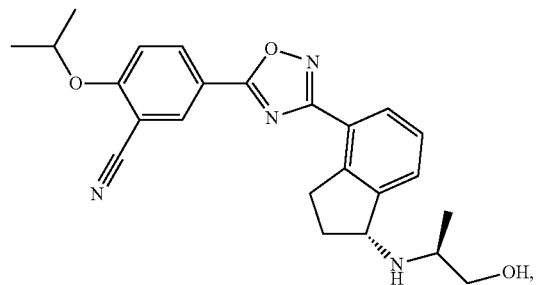
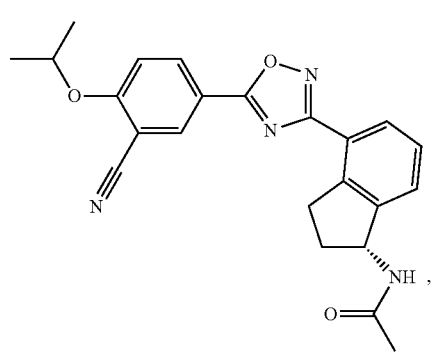

US 9,388,147 B2

35 -continued

36 -continued

| 37 -continued | 38 -continued |
|---|---|
| 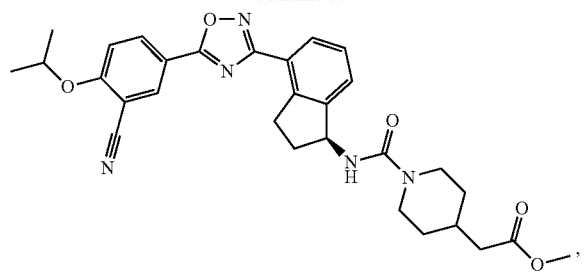 | 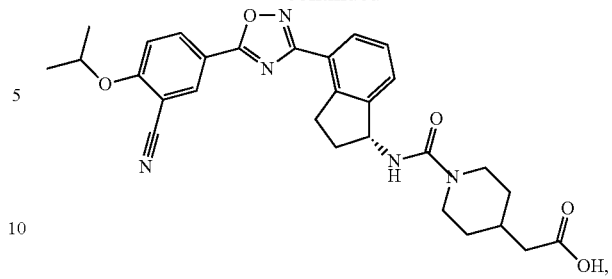 |
| 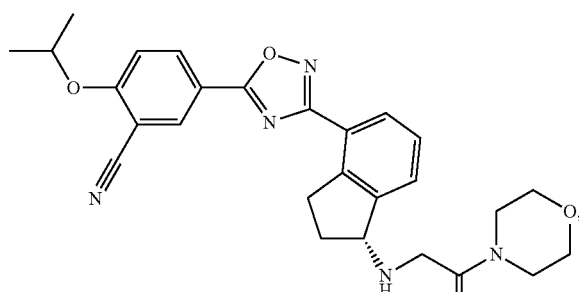 | 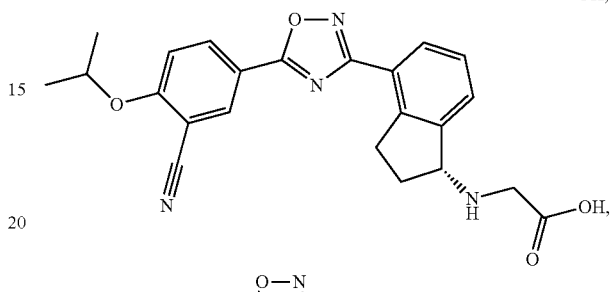 |
| 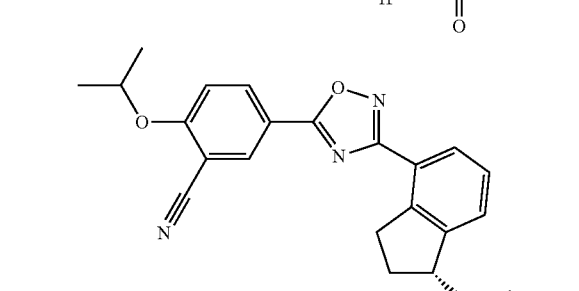 | 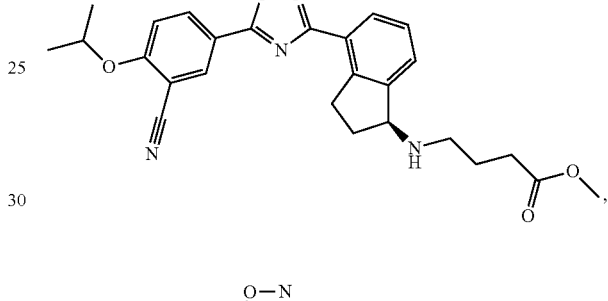 |
| 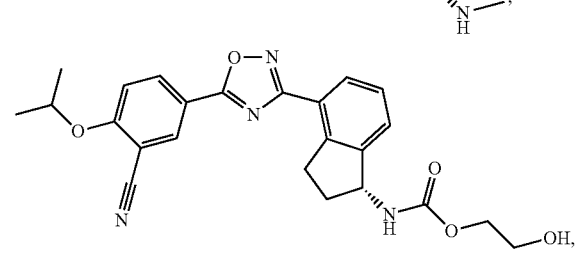 | 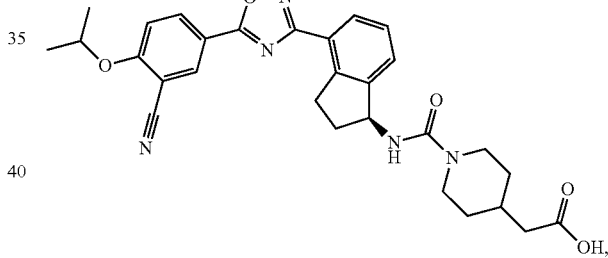 |
| 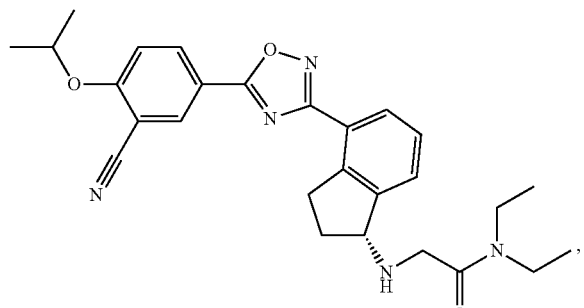 | 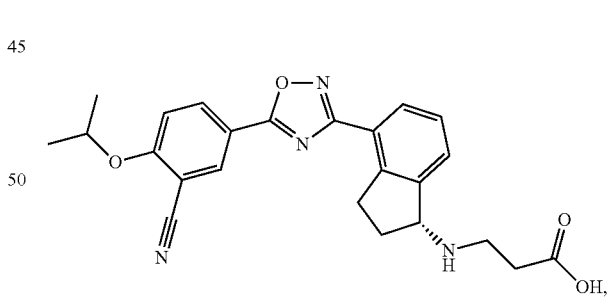 |
| 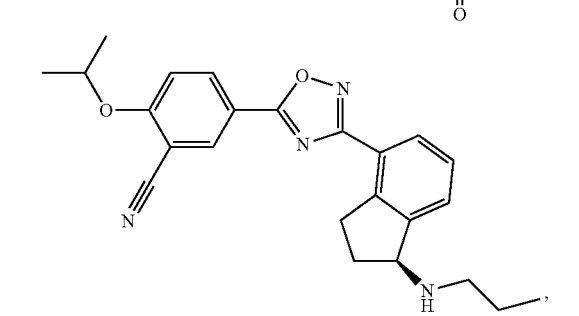 | 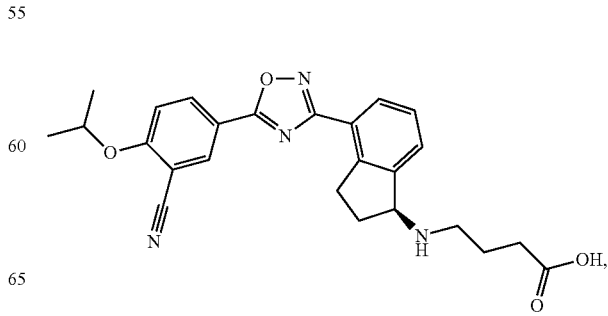 |

-continued
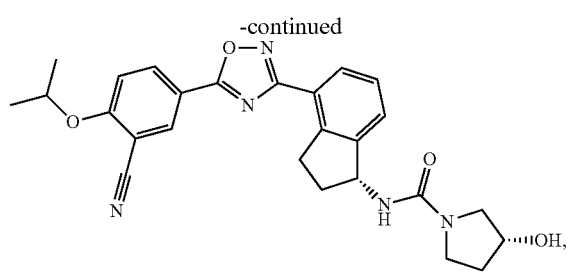
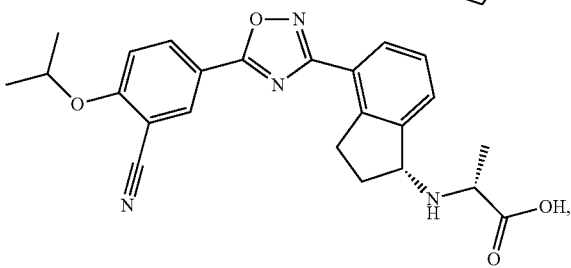
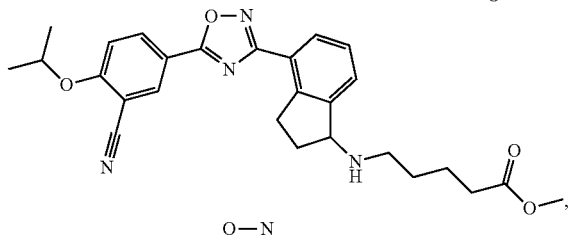
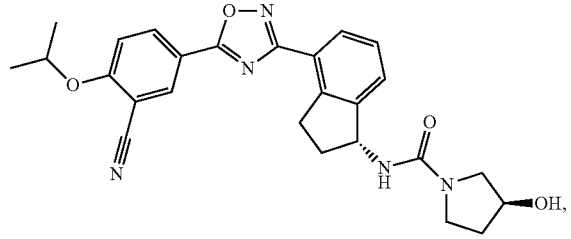
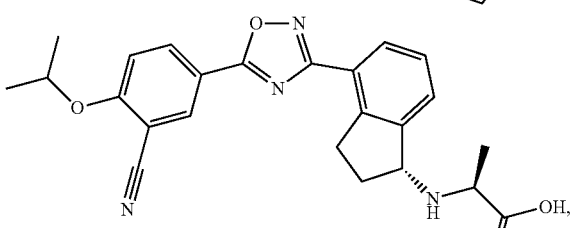
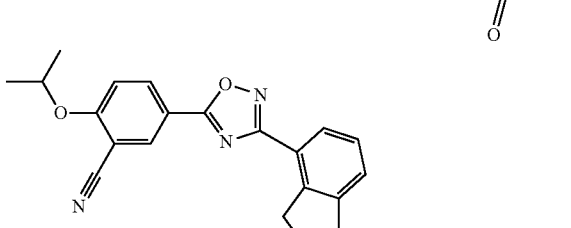
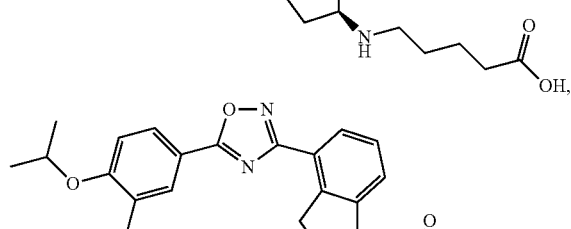
-continued
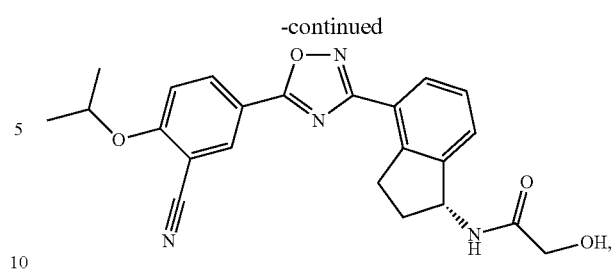
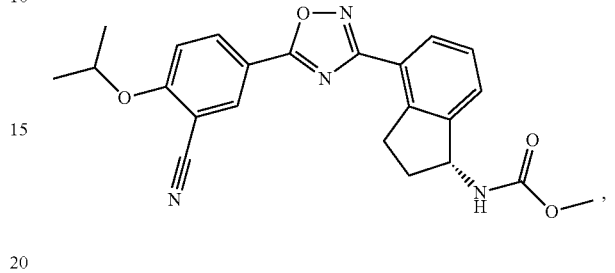
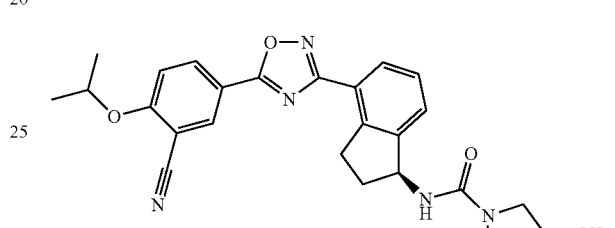
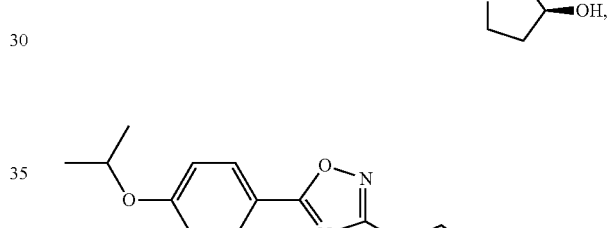
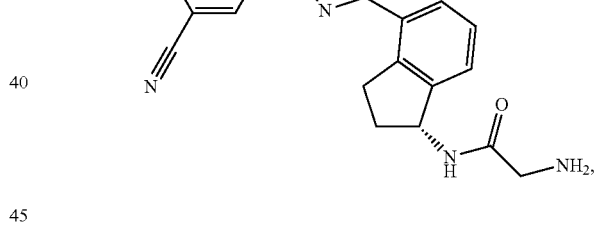
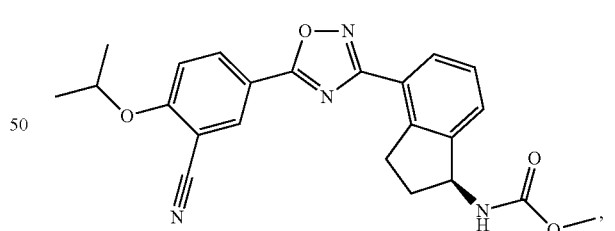
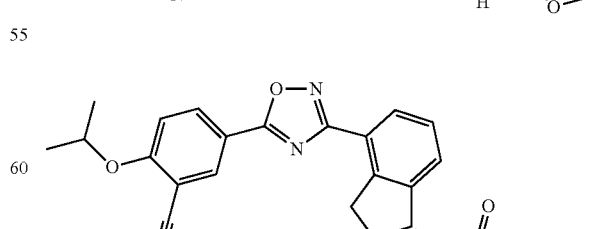

-continued
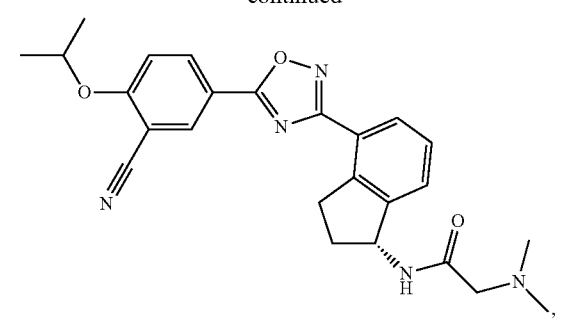
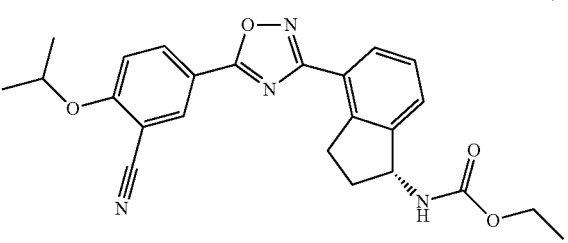
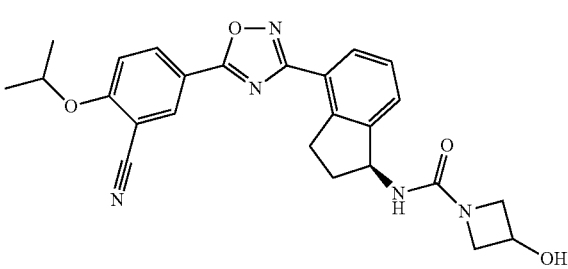
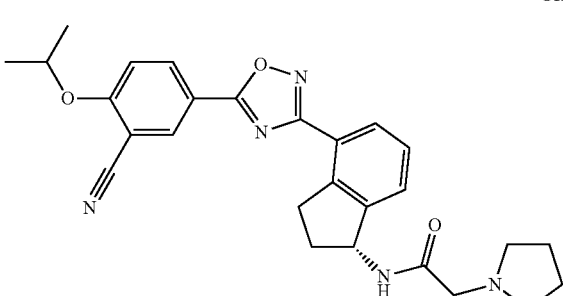
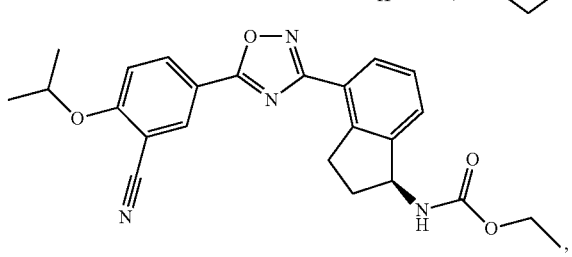
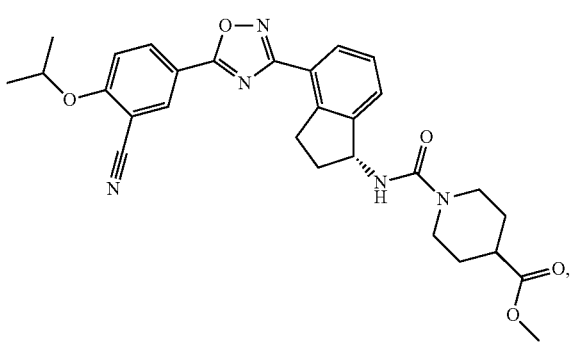
-continued
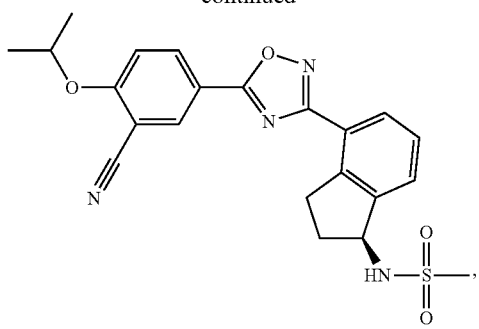
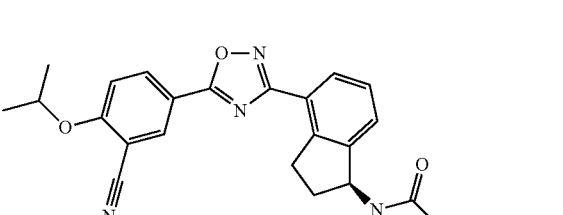
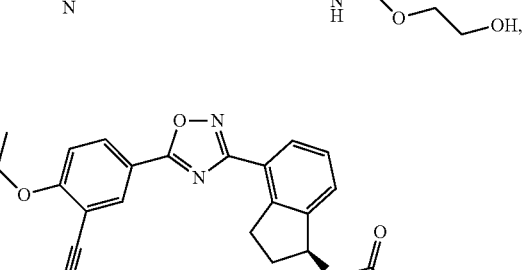
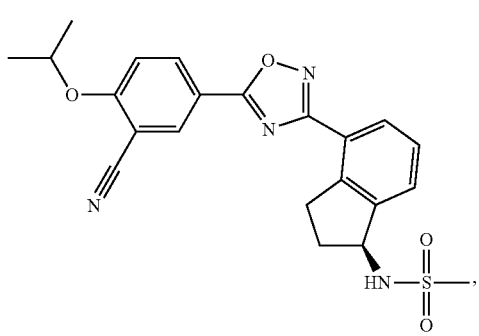
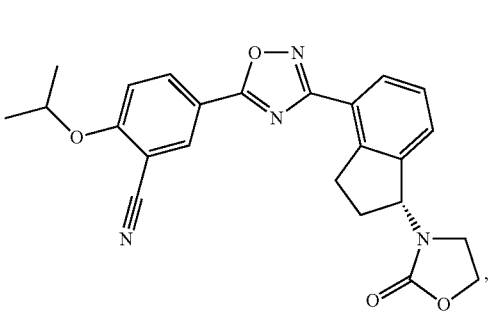

43
-continued
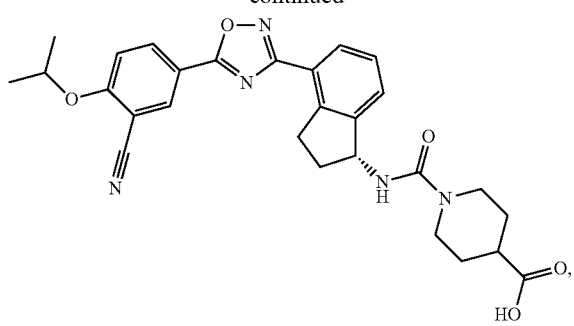
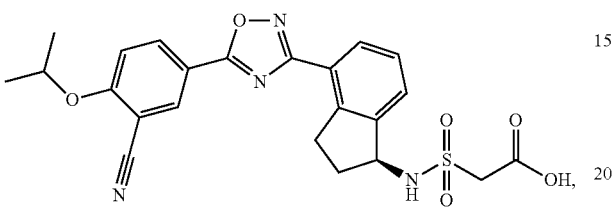
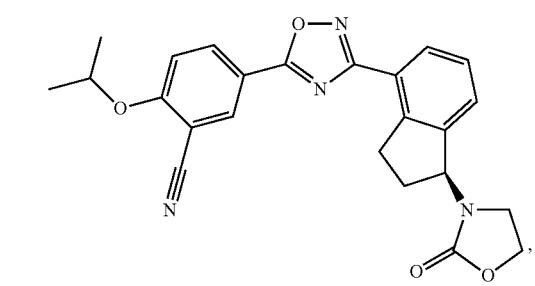
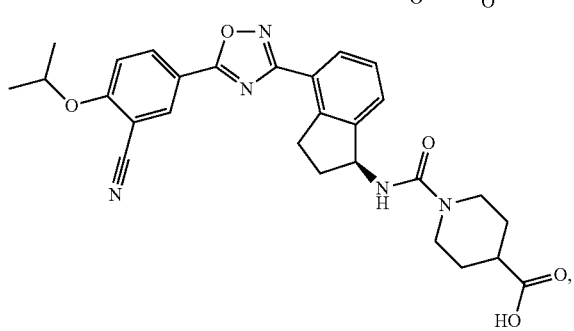
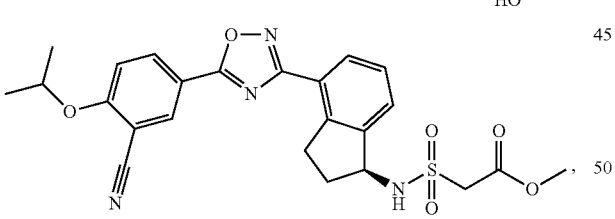
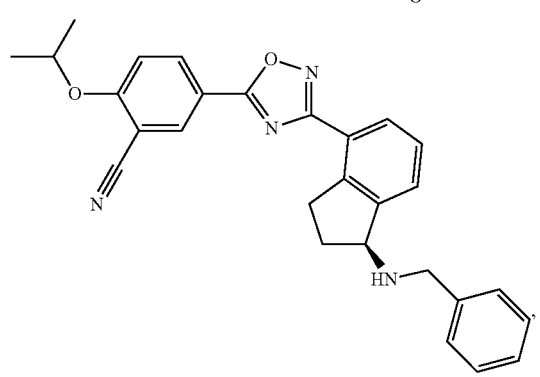
44
-continued
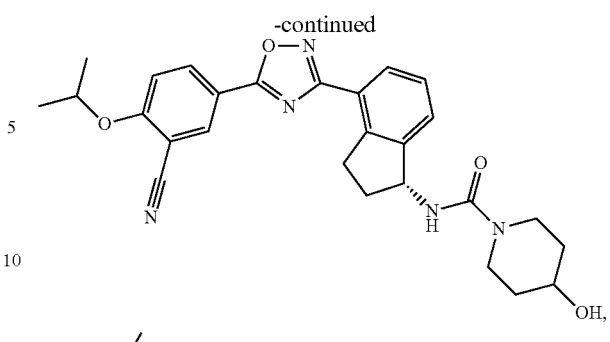
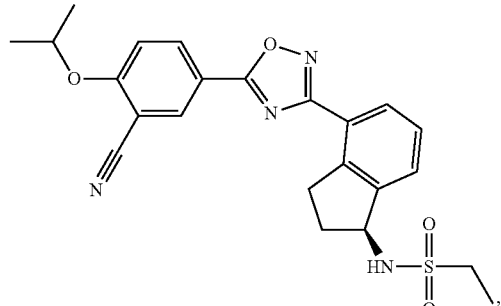
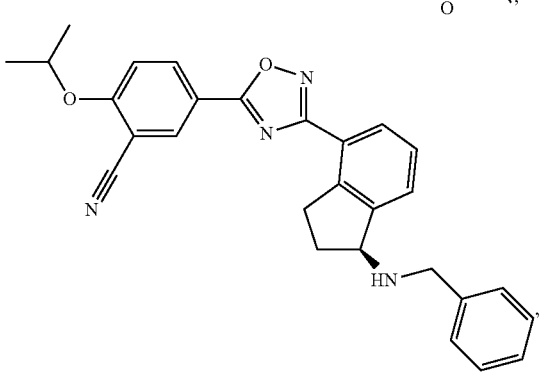
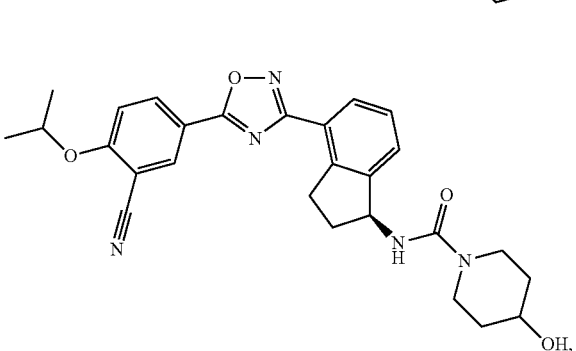
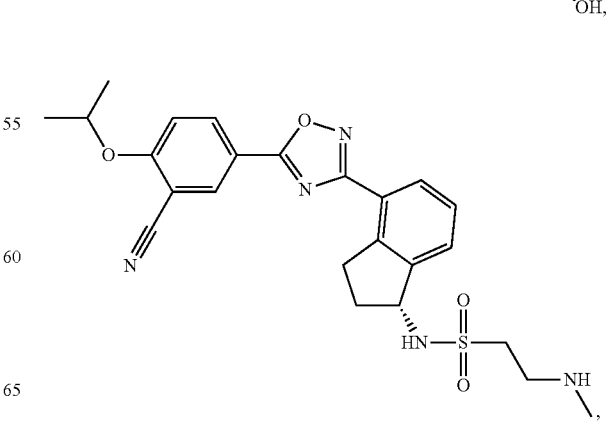

-continued
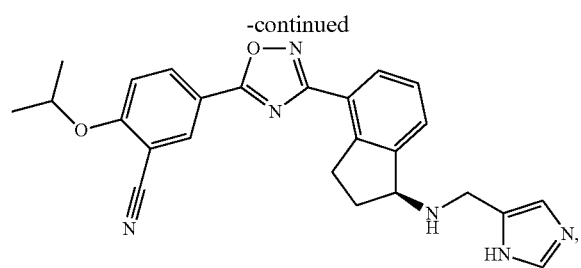
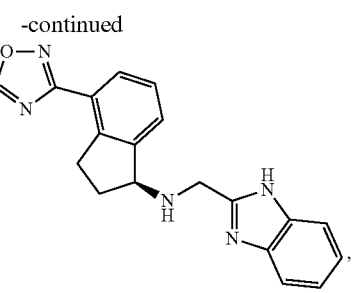
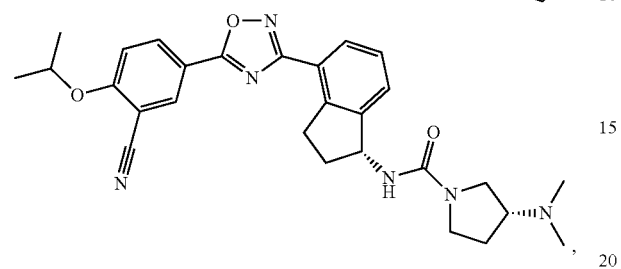
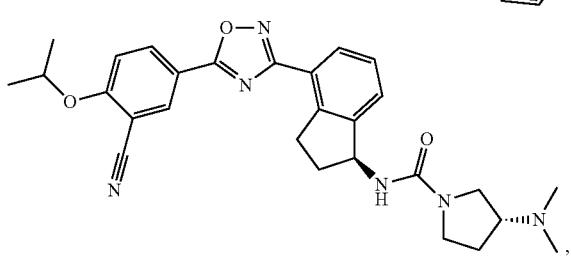
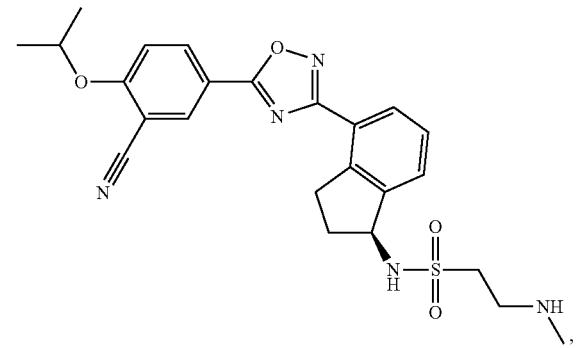
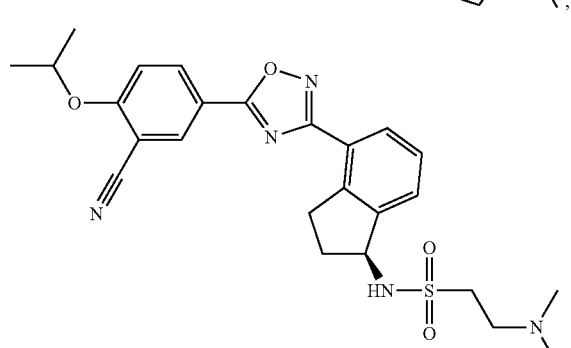
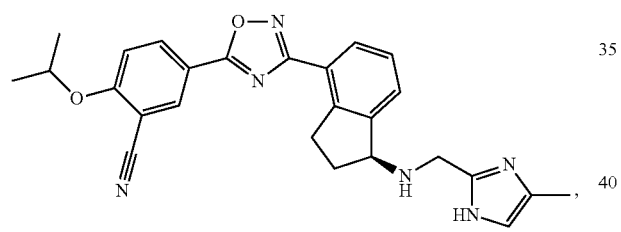
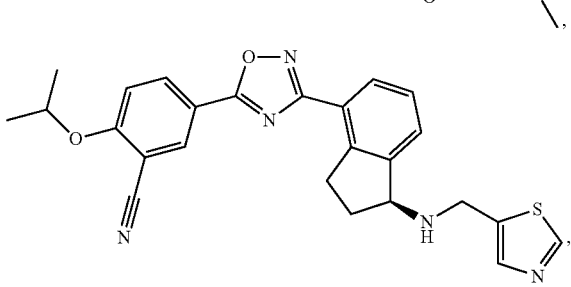
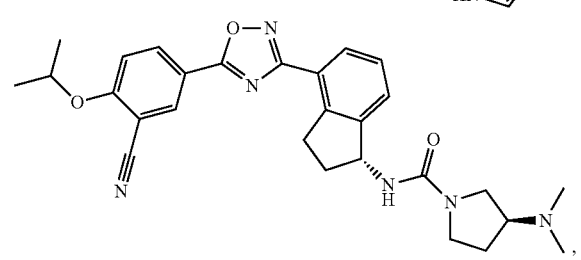
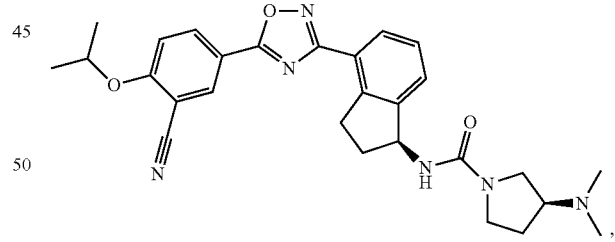
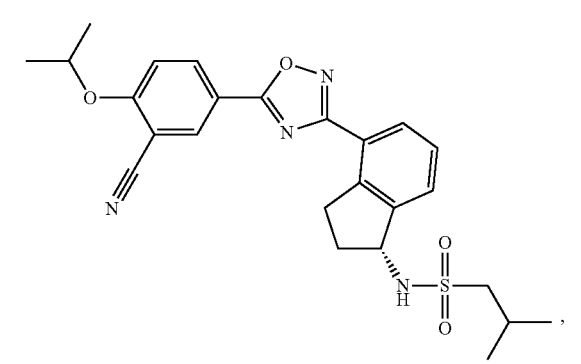
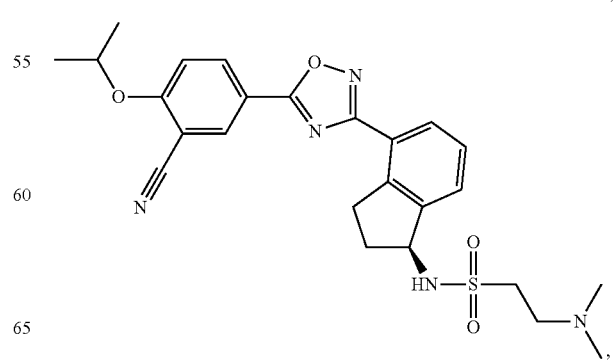

47
-continued
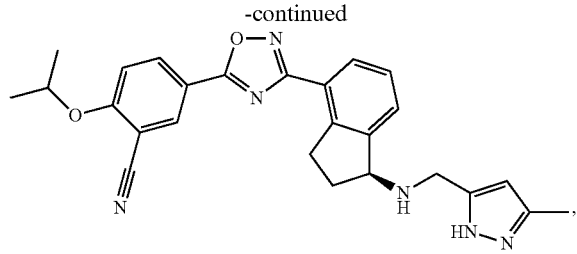
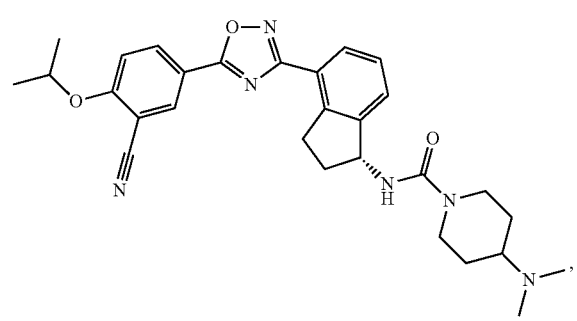
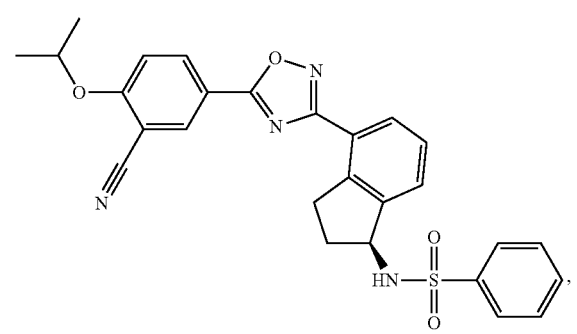
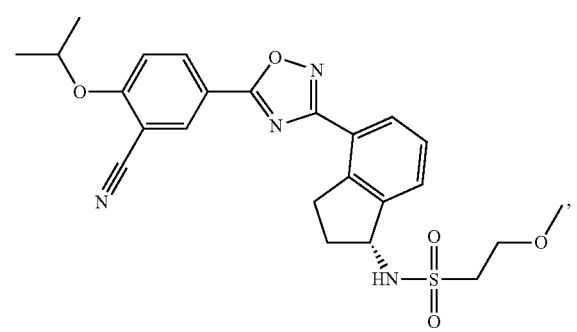
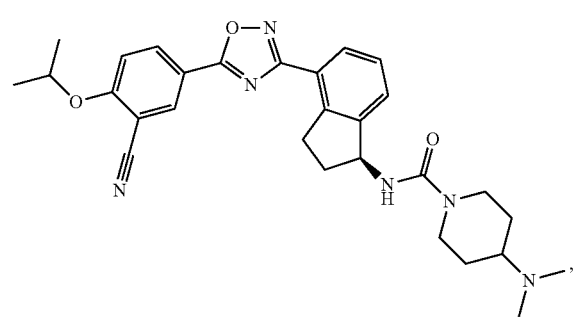
48
-continued
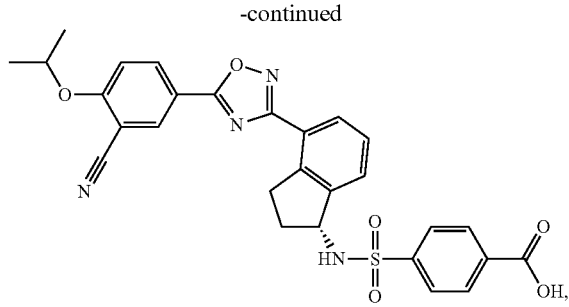
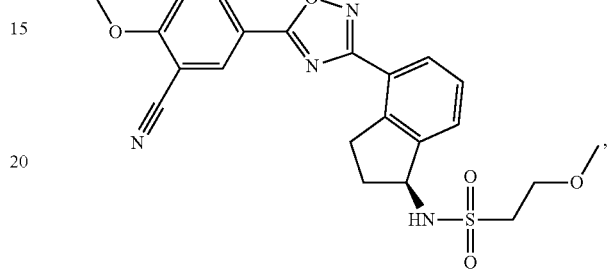
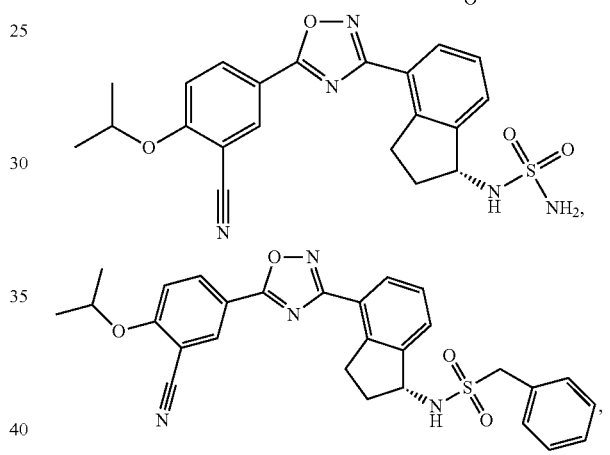
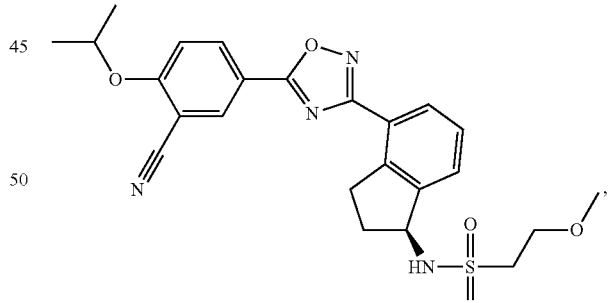
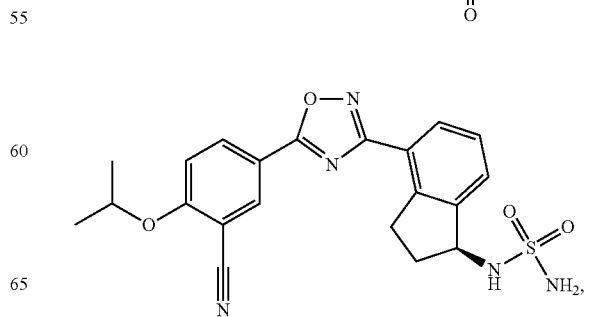

49

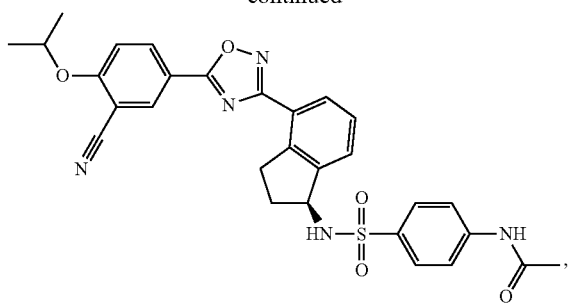

50

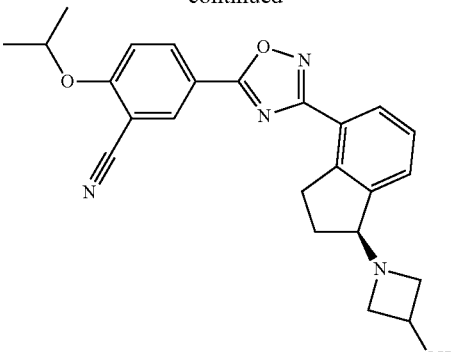

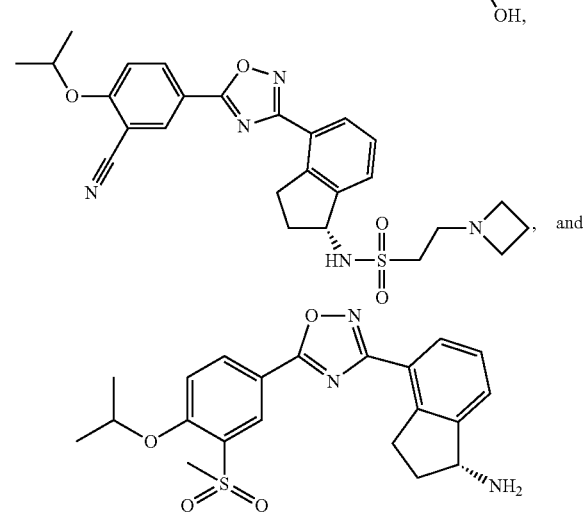

or any pharmaceutically acceptable salt, tautomer, stereoisomer, solvate, hydrate, or prodrug thereof. In certain of such embodiments, the invention provides a compound selected from compounds 49, 50, 85, 86, 90, 91, 138, 139, 163, 164, 186, 187, 211, 234, 235, ands 241 or any pharmaceutically acceptable salt, ester, tautomer, stereoisomer, solvate, hydrate, homolog, or prodrug thereof. In certain of such embodiments, the invention provides compound 50, 86, or 139 or any pharmaceutically acceptable salt, ester, tautomer, solvate, hydrate, homolog, or prodrug thereof. In certain of such embodiments, the invention provides compound 163 or 186 or any pharmaceutically acceptable salt, ester, tautomer, solvate, hydrate, homolog, or prodrug thereof. In certain of such embodiments, the invention provides compound 211, 234, or 241 or any pharmaceutically acceptable salt, ester, tautomer, solvate, hydrate, homolog, or prodrug thereof.

In certain embodiments, an invention compound of Formula I is provided wherein the compound has at least one chiral center and is substantially enantiomerically pure.

In other embodiments, a pharmaceutical composition comprising an invention compound of Formula I and a suitable excipient is provided.

In other embodiments, a pharmaceutical combination comprising an invention compound and a second medicament is provided. In still other embodiments, a pharmaceutical combination comprising an invention compound and a second medicament is provided wherein the second medicament is medically indicated for the treatment of multiple sclerosis, transplant rejection, or adult respiratory distress syndrome.

In certain embodiments, a method of use of an invention compound for preparation of a medicament is provided.

In certain embodiments, a method of activation or agonism of a sphingosine-1-phosphate receptor subtype 1 by contacting the receptor subtype 1 with an effective amount of an invention compound. In further embodiments, a method of activation or agonism of a sphingosine-1-phosphate receptor subtype 1 by contacting the receptor subtype 1 with an effective amount of an invention compound is provided, wherein the compound activates or agonizes the sphingosine-1-phosphate receptor subtype 1 to a greater extent than the compound activates or agonizes a sphingosine-1-phosphate receptor subtype 3. In further embodiments, a method of activation or agonism of a sphingosine-1-phosphate receptor subtype 1 by contacting the receptor subtype 1 with an effective amount of an invention compound is provided, wherein the sphingosine-1-phosphate receptor subtype 1 is disposed within a living mammal.

In certain embodiments, a method is provided for treatment of a malcondition in a patient for which activation or agonism of an sphingosine-1-phosphate receptor subtype 1 is medically indicated, by administering an effective amount of an invention compound to the patient at a frequency and for a duration of time sufficient to provide a beneficial effect to the patient. In further embodiments, a method is provided for treatment of a malcondition in a patient for which activation or agonism of an sphingosine-1-phosphate receptor subtype 1 is medically indicated, by administering an effective amount of an invention compound to the patient at a frequency and for a duration of time sufficient to provide a beneficial effect to the patient, wherein selective activation or agonism of an S1P subtype 1 receptor with respect to other subtypes of S1P receptor is medically indicated. In yet further embodiments, a method is provided for treatment of a malcondition in a patient for which activation or agonism of an sphingosine-1-phosphate receptor subtype 1 is medically indicated, by administering an effective amount of an invention compound to the patient at a frequency and for a duration of time sufficient to provide a beneficial effect to the patient, wherein the malcondition comprises rejection of transplanted organs or tissue; graft-versus-host diseases brought about by transplantation; autoimmune syndromes including rheumatoid arthritis; acute respiratory distress syndrome; adult respiratory distress syndrome; influenza; cancer; systemic erythematosus; Hashimoto's thyroiditis; lymphocytic thyroiditis; multiple sclerosis; myasthenia gravis; type I and II diabetes; uveitis; posterior uveitis; uveitis associated with Behcet's disease; uveomeningitis syndrome; allergic encephalomyelitis; chronic allograft vasculopathy; post-infectious autoimmune diseases including rheumatic fever and post-infectious glomerulonephritis; inflammatory and hyperproliferative skin diseases; cutaneous manifestations of immunologically-mediated disorders; psoriasis; atopic dermatitis; osteomyelitis; contact dermatitis; eczematous dermatitis; seborrhoeic dermatitis; lichen planus; pemphigus; bullous pemphigoid; epidermolysis bullosa; urticaria; angioedema; vasculitis; erythema; cutaneous eosinophilia; acne; alopecia areata; keratoconjunctivitis; vernal conjunctivitis; keratitis; herpetic keratitis; dystrophia epithelialis corneae; corneal leukoma; ocular pemphigus; Mooren's ulcer; ulcerative keratitis; scleritis; Graves' ophthalmopathy; Vogt-Koyanagi-Harada syndrome; sarcoidosis; pollen allergies; reversible obstructive airway disease; bronchial asthma; allergic asthma; intrinsic asthma; extrinsic asthma; dust asthma; chronic or inveterate asthma; late asthma and airway hyper-responsiveness; bronchitis; gastric ulcers; ischemic bowel diseases; inflammatory bowel diseases; necrotizing enterocolitis; intestinal lesions associated with thermal burns; celiac diseases; proctitis; eosinophilic gastroenteritis; mastocytosis; Crohn's disease; ulcerative colitis; vascular damage caused by ischemic diseases and thrombosis; atherosclerosis; fatty heart; myocarditis; cardiac infarction; arteriosclerosis; aortitis syndrome; cachexia due to viral disease; vascular thrombosis; migraine; rhinitis; eczema; interstitial nephritis; IgA-induced nephropathy; Goodpasture's syndrome; hemolytic-uremic syndrome; diabetic nephropathy; glomerulosclerosis; glomerulonephritis; multiple myositis; Guillain-Barre syndrome; Meniere's disease; polyneuritis; multiple neuritis; mononeuritis; radiculopathy; hyperthyroidism; Basedow's disease; thyrotoxicosis; pure red cell aplasia; aplastic anemia; hypoplastic anemia; idiopathic thrombocytopenic purpura; autoimmune hemolytic anemia; agranulocytosis; pernicious anemia; megaloblastic anemia; anerythroplasia; osteoporosis; sarcoidosis; fibroid lung; idiopathic interstitial pneumonia; dermatomyositis; leukoderma vulgaris; ichthyosis vulgaris; photoallergic sensitivity; cutaneous T cell lymphoma; polyarteritis nodosa; Huntington's chorea; Sydenham's chorea; myocardosis; scleroderma; Wegener's granuloma; Sjogren's syndrome; adiposis; eosinophilic fascitis; lesions of gingiva, periodontium, alveolar bone, substantia ossea dentis; male pattern alopecia or alopecia senilis; muscular dystrophy; pyoderma; Sezary's syndrome; chronic adrenal insufficiency; Addison's disease; ischemia-reperfusion injury of organs which occurs upon preservation; endotoxin shock; pseudomembranous colitis; colitis caused by drug or radiation; ischemic acute renal insufficiency; chronic renal insufficiency; lung cancer; malignancy of lymphoid origin; acute or chronic lymphocytic; leukemias; lymphoma; psoriasis; inflammatory lung injury, pulmonary emphysema; cataracta; siderosis; retinitis pigmentosa; senile macular degeneration; vitreal scarring; inflammatory eye disease; corneal alkali burn; dermatitis erythema; ballous dermatitis; cement dermatitis; gingivitis; periodontitis; sepsis; pancreatitis; carcinogenesis; metastasis of carcinoma; hypobaropathy; autoimmune hepatitis; primary biliary cirrhosis; sclerosing cholangitis; partial liver resection; acute liver necrosis; cirrhosis; alcoholic cirrhosis; hepatic failure; fulminant hepatic failure; late-onset hepatic failure; "acute-on-chronic" liver failure. In yet further embodiments, the malcondition is one or more of rejection of transplanted organs or tissue; graft-versus-host diseases brought about by transplantation; autoimmune syndromes including rheumatoid arthritis, multiple sclerosis, myasthenia gravis; pollen allergies; type I diabetes; prevention of psoriasis; Crohn's disease; ulcerative colitis, acute respiratory distress syndrome; adult respiratory distress syndrome; influenza; post-infectious autoimmune diseases including rheumatic fever and post-infectious glomerulonephritis; and metastasis of carcinoma. In yet further embodiments the malcondition is one of influenza, ulcerative colitis, multiple sclerosis, transplant rejection, acute respiratory distress syndrome or adult respiratory distress syndrome.

In certain embodiments, methods are provided for use of an invention compound for preparation of a medicament adapted for treatment of a disorder or a malcondition wherein activation or inhibition of a sphingosine-1-phosphate receptor subtype 1 is medically indicated.

In certain embodiments the invention provides a method for the chiral synthesis of a compound comprising an indane moiety having a chiral carbon in the five-membered ring of the indane moiety where the compound is enantiomerically enriched with respect to the chiral carbon. In such embodiments, the method of the invention provides the steps of (i) providing a compound comprising an indane moiety where the ring carbon of the five-membered ring of the indane moiety where chiral substitution is desired is oxo substituted at such carbon; and (ii) reacting such compound with a chiral reagent selected from the group consisting of a Corey Bakshita Shibata-oxazaborolidine and a chiral sulfinamide of the form RS(=O)NH$_2$ where R is a bulky group [e.g. t-butyl]. In certain embodiments R is t-butyl, sec-butyl, isopropyl, cyclopropyl, adamantyl, C$_{3-6}$ branched alkyl, or optionally bridged C$_{3-8}$ cycloalkyl. In certain of such embodiments, the chiral reagent is a Corey Bakshita Shibata-oxazaborolidine and the compound comprising an indane moiety is enantiomerically enriched with respect to a carbon-oxygen bond on a ring carbon of the five-membered ring of the indane moiety. In further embodiments, the chiral reagent is (R)-(–)-(2)-methyl-CBS-oxazaborolidine or (S)-(–)-(2)-methyl-CBS-oxazaborolidine.

In certain of such embodiments, the compound comprising an indane moiety having a chiral carbon in the five-membered ring of the indane moiety is a compound comprising an oxadiazole-indane moiety having a chiral carbon in the five-membered ring of the indane moiety of Formula III-R or III-S:

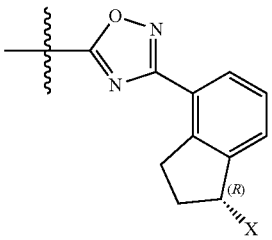

III-R

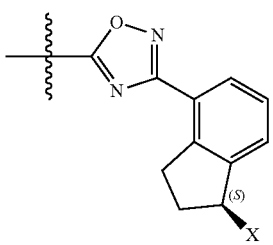

III-S

In certain embodiments, the invention provides a method for the chiral synthesis of the structure of Formula I-R or I-S or a pharmaceutically acceptable salt, ester, prodrug, homolog, hydrate or solvate thereof:

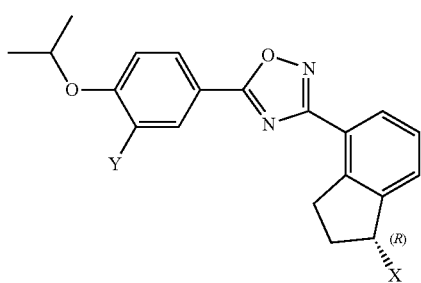

I-R

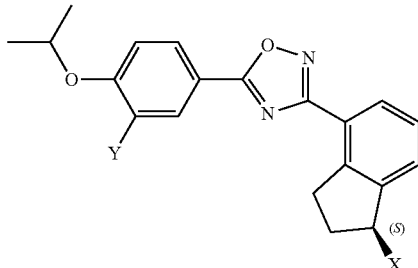

I-S

Where X and Y are as defined above and where the compound is enantiomerically enriched with respect to the chiral carbon. In such embodiments, the method of the invention provides the steps of (i) providing the compound

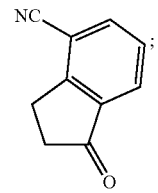 [SMILES: N#Cc1cccc2c1CCC2=O]

and (ii) reacting such compound with a chiral reagent selected from the group consisting of a Corey Bakshita Shibata-oxazaborolidine and a chiral sulfinamide of the form RS(=O)NH$_2$ where R is a bulky group [e.g. t-butyl, branched alkyl or cycloalkyl]; and (iii) forming a chiral center at the indane moiety carbon previously bound to the oxo group by either reacting such compound with a suitable reducing agent along with the chiral reagent in step (ii) or reacting the result of the reaction of such compound with a suitable reducing agent.

In certain of such embodiments, the chiral reagent is a Corey Bakshita Shibata-oxazaborolidine and X is —OR'''. In further embodiments, the chiral reagent is (R)-(–)-(2)-methyl-CBS-oxazaborolidine or (S)-(–)-(2)-methyl-CBS-oxazaborolidine.

In certain of such embodiments the chiral reagent is RS(=O)NH$_2$ where R is branched alkyl or cycloalkyl and X is —NR'R''. In further such embodiments, the chiral reagent is t-Bu-S(=O)NH$_2$.

In certain of such embodiments a suitable reducing reagent includes a borohydride such as BH$_3$-DMS or NaBH$_4$.

Additional steps for the preparation of such compounds can be adapted from the synthetic methods disclosed herein including recrystallization and other processes for purification.

In certain of such embodiments the invention provides a method of synthesizing a chiral compound of the invention by (i) providing a compound comprising an indane moiety where the ring carbon of the five-membered ring of the indane moiety where chiral substitution is desired is oxo substituted at such carbon; (ii) reacting such compound with a chiral reagent selected from the group consisting of a Corey Bakshita Shibata-oxazaborolidine and a chiral sulfinamide of the form RS(=O)NH$_2$ where R is a bulky group [e.g. t-butyl or other branched alkyl or cycloalkyl]; and (iii) forming a chiral center at the indane moiety carbon previously bound to the oxo group by either reacting such compound with a suitable reducing agent along with the chiral reagent in step (ii) or reacting the result of the reaction of such compound with a suitable reducing agent.

In certain embodiments, the compound comprising an indane moiety provided in step (i) is contacted with the chiral reagent to form in step (ii) Formula VI:

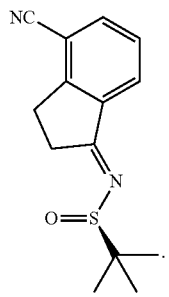

VI

In certain embodiments, the compound of Formula VII-R or VII-S is formed in step (iii):

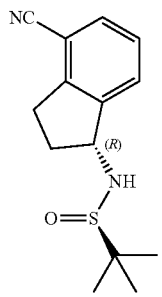

VII-R

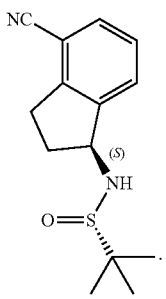

VII-S

In certain embodiments, the compound comprising an indane moiety in step (i) has a cyano substituent on the 4-position of the indane ring.

In certain embodiments, the method further comprises the step of (iv) treating the compound with a chiral center at the indane moiety carbon resulting from step (iii) with a hydroxylamine or a hydroxylamine hydrochloride to convert the cyano substituent to a hydroxyamidine at the 4 position of the indane moiety having the Formula IV-R or IV-S:

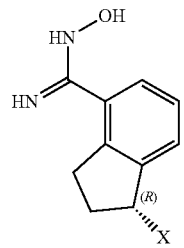

IV-R

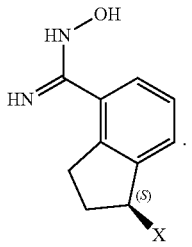

IV-S

In further embodiments, step (iv) is carried out in the presence of a base.

In certain embodiments, the method further comprises the step of (v) contacting Formula IV-R or IV-S with substituted benzoic acid and a coupling reagent to form a compound of Formula V-R or V-S:

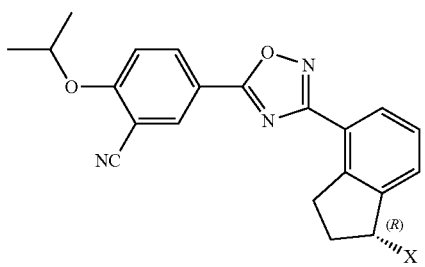

V-R

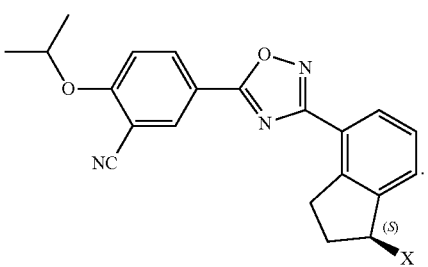

V-S

In further embodiments, the coupling reagent used in step (v) is a mixture comprising hydroxybenzotriazole (HOBt) and 1-ethyl-3-(3-dimethylaminopropyl)-carbodiimide (EDC). Other suitable coupling reagents, for example, HOAt, HATU, HBTU, HOOBt, can be used in the reaction of the invention.

In certain embodiments, the compound comprising an indane moiety having a chiral carbon in the five-membered ring of the indane moiety is a compound of the Formula III-R or III-S:

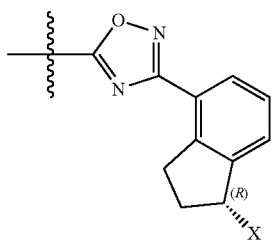

III-R

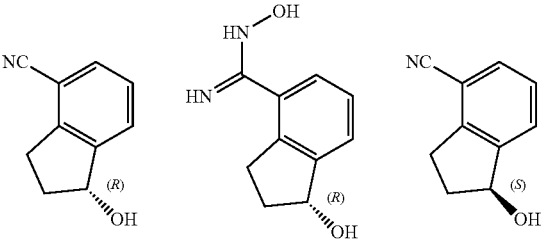

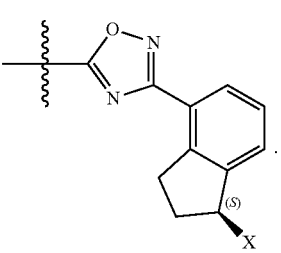

III-S

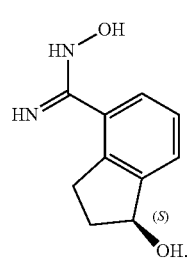

In certain embodiments, the invention provides a compound comprising an indane moiety having a chiral carbon in the five-membered ring of the indane moiety of the disclosure.

In certain embodiments, the compound comprising an indane moiety where the ring carbon of the five-membered ring of the indane moiety where chiral substitution is desired is oxo substituted at such carbon is

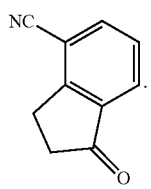 [SMILES: N#Cc1cccc2c1CCC2=O]

In certain of such embodiments, the invention provides a method for chiral synthesis of a chiral compound comprising an indane moiety having a chiral carbon in the five-membered ring of the indane moiety or a chiral compound comprising an oxadiazole-indane moiety having a chiral carbon in the five-membered ring of the indane moiety where the chiral compound has an enantiomeric enrichment of at least 75%, 85%, 90%, 95%, 98%, or 99%.

In certain of such embodiments, the invention provides a method for synthesis of a chiral compound of the invention having an enantiomeric enrichment of at least 75%, 85%, 90%, 95%, 98%, or 99%.

In certain embodiments, the invention provides compounds which can be intermediates in the herein described methods for chiral syntheses. In certain such embodiments, the invention provides one or more of the following compounds:

In certain other such embodiments, the invention provides one or more of the following compounds:

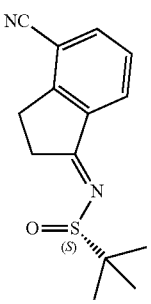
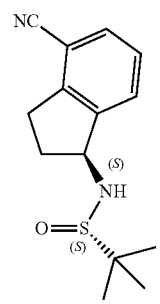

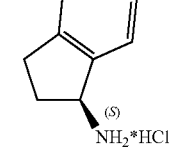
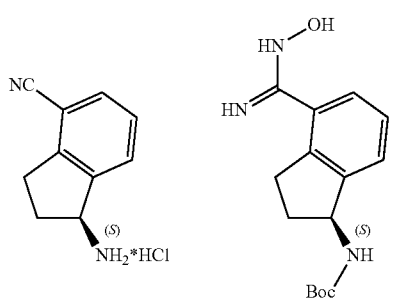

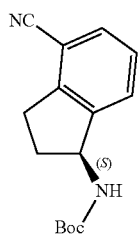

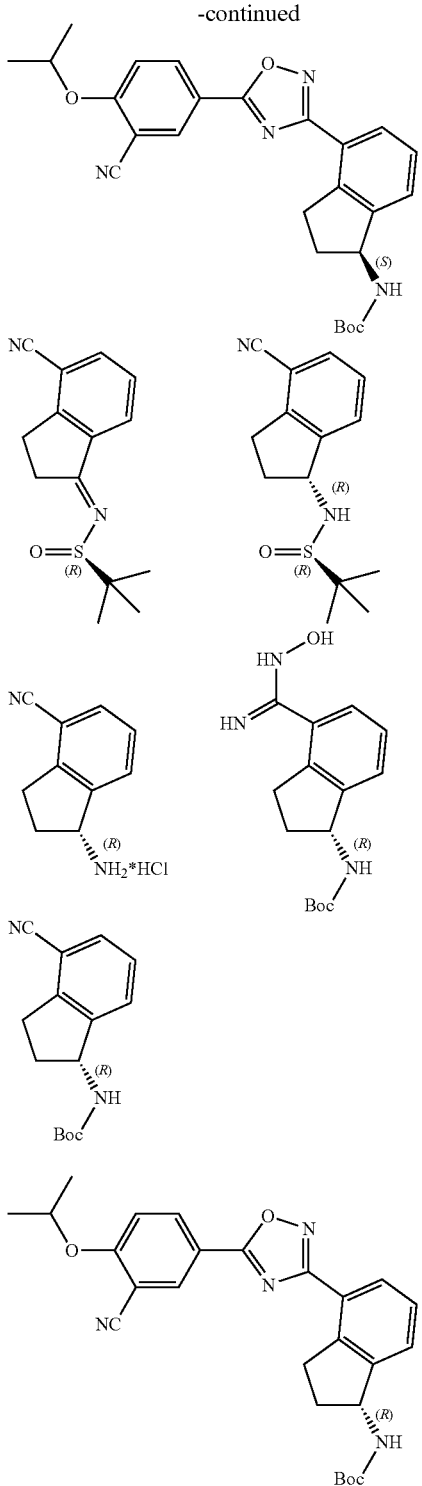

In certain embodiments, a method for the synthesis of a compound comprising an indane moiety having a chiral carbon in the five-membered ring of the indane moiety where the compound is enantiomerically enriched with respect to the chiral carbon is provided. In certain embodiments, a method comprising a step of providing a compound of the structures described herein is provided.

Protecting groups can render chemical functionality inert to specific reaction conditions and can be appended to and removed from such functionality in a molecule without substantially damaging the remainder of the molecule. Practitioners in the art would be familiar with suitable protecting groups for use in the synthetic methods of the invention. See, e.g., Greene and Wuts, *Protective Groups in Organic Synthesis*, $2^{nd}$ ed., John Wiley & Sons, New York, 1991.

As used in the specification and the appended claims, the singular forms "a," "an" and "the" include plural referents unless the context clearly dictates otherwise.

As used herein, "individual" (as in the subject of the treatment) means both mammals and non-mammals. Mammals include, for example, humans; non-human primates, e.g. apes and monkeys; cattle; horses; sheep; and goats. Non-mammals include, for example, fish and birds.

The term "$S1P_1$" as used herein refers to subtype 1 of a sphingosine-1-phosphate receptor, while other sphingosine-1-phosphate receptor subtypes are referred to in a corresponding manner, for example, sphingosine-1-phosphate receptor subtype 3 is referred to as "$S1P_3$".

A "receptor", as is well known in the art, is a biomolecular entity usually comprising a protein that specifically binds a structural class of ligands or a single native ligand in a living organism, the binding of which causes the receptor to transduce the binding signal into another kind of biological action, such as signaling a cell that a binding event has occurred, which causes the cell to alter its function in some manner. An example of transduction is receptor binding of a ligand causing alteration of the activity of a "G-protein" in the cytoplasm of a living cell. Any molecule, naturally occurring or not, that binds to a receptor and activates it for signal transduction, is referred to as an "agonist" or "activator." Any molecule, naturally occurring or not, that binds to a receptor, but does not cause signal transduction to occur, and which can block the binding of an agonist and its consequent signal transduction, is referred to as an "antagonist."

An "$S1P_1$ compound" or "$S1P_1$ agonist" or "$S1P_1$ activator" or "$S1P_1$ inhibitor" or "$S1P_1$ antagonist" as the terms are used herein refer to compounds that interact in some way with the S1P receptor subtype 1. They can be agonist or activators, or they can be antagonists or inhibitors. An "$S1P_1$ compound" of the invention can be selective for action on subtype 1 of the S1P receptor family; for example a compound of the invention can act at a lower concentration on subtype 1 of the S1P receptor family than on other subtypes of the S1P receptor family; more specifically, an "$S1P_1$ compound" of the invention can selectively act on subtype 1 receptors compared to its action on subtype 3, or "$S1P_3$," receptors.

In certain embodiments, compounds of the invention are orthostatic agonists. In certain other embodiments, compounds of the invention are allosteric agonists. Receptor agonists may be classified as either orthosteric or allosteric. An orthosteric agonist binds to a site in the receptor that significantly overlaps with the binding of the natural ligand and replicates the key interactions of the natural ligand with the receptor. An orthosteric agonist will activate the receptor by a molecular mechanism similar to that of the natural ligand, will be competitive for the natural ligand, and will be competitively antagonized by pharmacological agents that are competitive antagonists for the natural ligand. An allosteric agonist binds to a site in the receptor that makes some significant interactions that are partly or wholly non-overlapping with the natural ligand. Allosteric agonists are true agonists and not allosteric potentiators. Consequently, they activate receptor signaling alone and without a requirement for a sub-maximal concentration of the natural ligand. Allosteric agonists may be identified when an antagonist known to be competitive for the orthosteric ligand shows non-competitive antagonism. The allosteric agonist site can also be mapped by receptor mutagenesis. The introduction of single point mutations in receptors that retain receptor activation by allosteric agonist, while diminishing or abolishing signaling induced by orthosteric agonist or vice versa provide formal evidence for differences in binding interactions. Orthosteric agonists may destabilize GPCR structure and conformation, while allosteric agonists may either stabilize or destabilize GPCR structure and conformation. Allosteric agonists, by virtue of their different interactions with receptor, may be pharmaceutically useful because the allosteric site may confer additional opportunities for agonist potency and selectivity within a related family of receptor subtypes that share a similar orthosteric ligand. In addition, the allosteric site may require very different physical and chemical properties of an agonist compared to the orthosteric ligand. These chemico-physical properties, which include hydrophobicity, aromaticity, charge distribution and solubility may also provide advantages in generating agonists of varying pharmacokinetic, oral bioavailability, distributional and metabolism profiles that facilitate the development of effective pharmaceutical substances.

"Substantially" as the term is used herein means completely or almost completely; for example, a composition that is "substantially free" of a component either has none of the component or contains such a trace amount that any relevant functional property of the composition is unaffected by the presence of the trace amount, or a compound is "substantially pure" is there are only negligible traces of impurities present.

Substantially enantiomerically pure means a level of enantiomeric enrichment of one enantiomer with respect to the other enantiomer of at least 90%, 95%, 98%, 99%, 99.5% or 99.9%.

"Treating" or "treatment" within the meaning herein refers to an alleviation of symptoms associated with a disorder or disease, or inhibition of further progression or worsening of those symptoms, or prevention or prophylaxis of the disease or disorder.

The expression "effective amount", when used to describe use of a compound of the invention in providing therapy to a patient suffering from a disorder or malcondition mediated by a sphingosine-1-phospate receptor of subtype 1 refers to the amount of a compound of the invention that is effective to bind to as an agonist or as an antagonist a $S1P_1$ receptor in the individual's tissues, wherein the $S1P_1$ is implicated in the disorder, wherein such binding occurs to an extent sufficient to produce a beneficial therapeutic effect on the patient. Similarly, as used herein, an "effective amount" or a "therapeutically effective amount" of a compound of the invention refers to an amount of the compound that alleviates, in whole or in part, symptoms associated with the disorder or condition, or halts or slows further progression or worsening of those symptoms, or prevents or provides prophylaxis for the disorder or condition. In particular, a "therapeutically effective amount" refers to an amount effective, at dosages and for periods of time necessary, to achieve the desired therapeutic result by acting as an agonist of sphingosine-1-phosphate receptor subtype 1 ($S1P_1$) activity. A therapeutically effective amount is also one in which any toxic or detrimental effects of compounds of the invention are outweighed by the therapeutically beneficial effects. For example, in the context of treating a malcondition mediated by activation of $S1P_1$, a therapeutically effective amount of an $S1P_1$ agonist of the invention is an amount sufficient to control the malcondition, to mitigate the progress of the malcondition, or to relieve the symptoms of the malcondition. Examples of malconditions that can be so treated include multiple sclerosis, transplant rejection, adult respiratory distress syndrome.

Diseases, disorders and conditions which may be treated by compounds of the invention include rejection of transplanted organs or tissue; graft-versus-host diseases brought about by transplantation; autoimmune syndromes including rheumatoid arthritis; acute respiratory distress syndrome; adult respiratory distress syndrome; influenza; cancer; systemic erythematosus; Hashimoto's thyroiditis; lymphocytic thyroiditis; multiple sclerosis; myasthenia gravis; type I and II diabetes; uveitis; posterior uveitis; uveitis associated with Behcet's disease; uveomeningitis syndrome; allergic encephalomyelitis; chronic allograft vasculopathy; post-infectious autoimmune diseases including rheumatic fever and post-infectious glomerulonephritis; inflammatory and hyperproliferative skin diseases; cutaneous manifestations of immunologically-mediated disorders; psoriasis; atopic dermatitis; osteomyelitis; contact dermatitis; eczematous dermatitis; seborrhoeic dermatitis; lichen planus; pemphigus; bullous pemphigoid; epidermolysis bullosa; urticaria; angioedema; vasculitis; erythema; cutaneous eosinophilia; acne; alopecia areata; keratoconjunctivitis; vernal conjunctivitis; keratitis; herpetic keratitis; dystrophia epithelialis corneae; corneal leukoma; ocular pemphigus; Mooren's ulcer; ulcerative keratitis; scleritis; Graves' ophthalmopathy; Vogt-Koyanagi-Harada syndrome; sarcoidosis; pollen allergies; reversible obstructive airway disease; bronchial asthma; allergic asthma; intrinsic asthma; extrinsic asthma; dust asthma; chronic or inveterate asthma; late asthma and airway hyper-responsiveness; bronchitis; gastric ulcers; ischemic bowel diseases; inflammatory bowel diseases; necrotizing enterocolitis; intestinal lesions associated with thermal burns; celiac diseases; proctitis; eosinophilic gastroenteritis; mastocytosis; Crohn's disease; ulcerative colitis; vascular damage caused by ischemic diseases and thrombosis; atherosclerosis; fatty heart; myocarditis; cardiac infarction; arteriosclerosis; aortitis syndrome; cachexia due to viral disease; vascular thrombosis; migraine; rhinitis; eczema; interstitial nephritis; IgA-induced nephropathy; Goodpasture's syndrome; hemolytic-uremic syndrome; diabetic nephropathy; glomerulosclerosis; glomerulonephritis; multiple myositis; Guillain-Barre syndrome; Meniere's disease; polyneuritis; multiple neuritis; mononeuritis; radiculopathy; hyperthyroidism; Basedow's disease; thyrotoxicosis; pure red cell aplasia; aplastic anemia; hypoplastic anemia; idiopathic thrombocytopenic purpura; autoimmune hemolytic anemia; agranulocytosis; pernicious anemia; megaloblastic anemia; anerythroplasia; osteoporosis; sarcoidosis; fibroid lung; idiopathic interstitial pneumonia; dermatomyositis; leukoderma vulgaris; ichthyosis vulgaris; photoallergic sensitivity; cutaneous T cell lymphoma; polyarteritis nodosa; Huntington's chorea; Sydenham's chorea; myocardosis; scleroderma; Wegener's granuloma; Sjogren's syndrome; adiposis; eosinophilic fasciitis; lesions of gingiva, periodontium, alveolar bone, substantia ossea dentis; male pattern alopecia or alopecia senilis; muscular dystrophy; pyoderma; Sezary's syndrome; chronic adrenal insufficiency; Addison's disease; ischemia-reperfusion injury of organs which occurs upon preservation; endotoxin shock; pseudomembranous colitis; colitis caused by drug or radiation; ischemic acute renal insufficiency; chronic renal insufficiency; lung cancer; malignancy of lymphoid origin; acute or chronic lymphocytic; leukemias; lymphoma; psoriasis; inflammatory lung injury, pulmonary emphysema; cataracta; siderosis; retinitis pigmentosa; senile macular degeneration; vitreal scarring; inflammatory eye disease; corneal alkali burn; dermatitis erythema; ballous dermatitis; cement dermatitis; gingivitis; periodontitis; sepsis; pancreatitis; carcinogenesis; metastasis of carcinoma; hypobaropathy; autoimmune hepatitis; primary biliary cirrhosis; sclerosing cholangitis; partial liver resection; acute liver necrosis; cirrhosis; alcoholic cirrhosis; hepatic failure; fulminant hepatic failure; late-onset hepatic failure; "acute-on-chronic" liver failure. Particularly preferred diseases and conditions which may be treated with compounds of the invention comprise the group consisting of rejection of transplanted organs or tissue; graft-versus-host diseases brought about by transplantation; autoimmune syndromes including rheumatoid arthritis, multiple sclerosis, myasthenia gravis; pollen allergies; type I diabetes; prevention of psoriasis; Crohn's disease; ulcerative colitis, acute respiratory distress syndrome; adult respiratory distress syndrome; influenza; post-infectious autoimmune diseases including rheumatic fever and post-infectious glomerulonephritis; and metastasis of carcinoma.

Furthermore, compounds of Formula I-R or I-S are also useful, in combination with one or several immunosuppressant agents, for the treatment of diseases, disorders and conditions associated with an activated immune system and selected from the list as above-mentioned. According to a preferred embodiment of the invention, said immunosuppressant agent is selected from the group comprising or consisting of cyclosporin, daclizumab, basiliximab, everolimus, tacrolimus (FK506), azathiopirene, leflunomide, 15-deoxyspergualin, or other immunosuppressant drugs All chiral, diastereomeric, racemic forms of a structure are intended, unless a particular stereochemistry or isomeric form is specifically indicated. Compounds used in the present invention can include enriched or resolved optical isomers at any or all asymmetric atoms as are apparent from the depictions, at any degree of enrichment. Both racemic and diastereomeric mixtures, as well as the individual optical isomers can be synthesized so as to be substantially free of their enantiomeric or diastereomeric partners, and these are all within the scope of certain embodiments of the invention.

The isomers resulting from the presence of a chiral center comprise a pair of non-superimposable isomers that are called "enantiomers." Single enantiomers of a pure compound are optically active, i.e., they are capable of rotating the plane of plane polarized light. Single enantiomers are designated according to the Cahn-Ingold-Prelog system. Once the priority ranking of the four groups is determined, the molecule is oriented so that the lowest ranking group is pointed away from the viewer. Then, if the descending rank order of the other groups proceeds clockwise, the molecule is designated (R) and if the descending rank of the other groups proceeds counterclockwise, the molecule is designated (S). In the examples, the Cahn-Ingold-Prelog ranking is A>B>C>D. The lowest ranking atom, D is oriented away from the viewer.

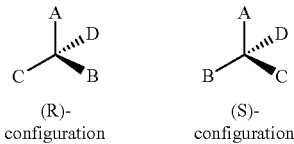

(R)-configuration    (S)-configuration

"Isolated optical isomer" means a compound which has been substantially purified from the corresponding optical isomer(s) of the same formula. Preferably, the isolated isomer is at least about 80%, more preferably at least 90% pure, even more preferably at least 98% pure, most preferably at least about 99% pure, by weight.

Rotational Isomerism

It is understood that due to chemical properties (i.e., resonance lending some double bond character to the C—N bond) of restricted rotation about the amide bond linkage (as illustrated below) it is possible to observe separate rotamer species and even, under some circumstances, to isolate such species, example shown below. It is further understood that certain structural elements, including steric bulk or substituents on the amide nitrogen, may enhance the stability of a rotamer to the extent that a compound may be isolated as, and exist indefinitely, as a single stable rotamer. The present invention therefore includes any possible stable rotamers of compounds of the invention which are biologically active in the treatment of a disease, disorder or condition for which a compound of the invention may be effective as described herein.

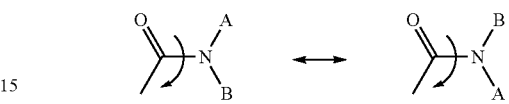

Regioisomerism

The preferred compounds of the present invention have a particular spatial arrangement of substituents on the aromatic rings, which is related to the structure activity relationship demonstrated by the compound class. Often such substitution arrangement is denoted by a numbering system; however, numbering systems are often not consistent between different ring systems. In six-membered aromatic systems, the spatial arrangements are specified by the common nomenclature "para" for 1,4-substitution, "meta" for 1,3-substitution and "ortho" for 1,2-substitution as shown below.

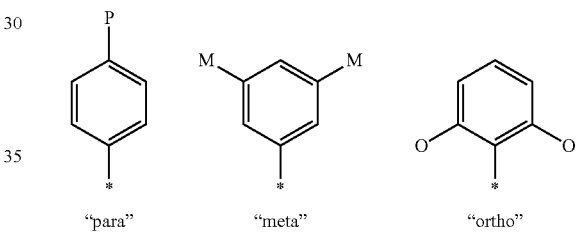

"para"    "meta"    "ortho"

All structures encompassed within a claim are "chemically feasible", by which is meant that the structure depicted by any combination or subcombination of optional substituents meant to be recited by the claim is physically capable of existence with at least some stability as can be determined by the laws of structural chemistry and by experimentation. Structures that are not chemically feasible are not within a claimed set of compounds.

In general, "substituted" refers to an organic group as defined herein in which one or more bonds to a hydrogen atom contained therein are replaced by one or more bonds to a non-hydrogen atom such as, but not limited to, a halogen (i.e., F, Cl, Br, and I); an oxygen atom in groups such as hydroxyl groups, alkoxy groups, aryloxy groups, aralkyloxy groups, oxo(carbonyl) groups, carboxyl groups including carboxylic acids, carboxylates, and carboxylate esters; a sulfur atom in groups such as thiol groups, alkyl and aryl sulfide groups, sulfoxide groups, sulfone groups, sulfonyl groups, and sulfonamide groups; a nitrogen atom in groups such as amines, hydroxylamines, nitriles, nitro groups, N-oxides, hydrazides, azides, and enamines; and other heteroatoms in various other groups. Non-limiting examples of substituents that can be bonded to a substituted carbon (or other) atom include F, Cl, Br, I, OR', OC(O)N(R')$_2$, CN, CF$_3$, OCF$_3$, R', O, S, C(O), S(O), methylenedioxy, ethylenedioxy, N(R')$_2$, SR', SOR', SO$_2$R', SO$_2$N(R')$_2$, SO$_3$R', C(O)R', C(O)C(O)R', C(O)CH$_2$C(O)R', C(S)R', C(O)OR', OC(O)R', C(O)N(R')$_2$, OC(O)N(R')$_2$, C(S)N(R')$_2$, (CH$_2$)$_{0-2}$NHC(O)R', (CH$_2$)$_{0-2}$N(R)N(R)$_2$, N(R')N(R')C(O)R', N(R')N(R')C(O)OR', N(R')N(R')CON(R')$_2$, N(R')SO$_2$R', N(R')SO$_2$N(R')$_2$, N(R)C(O)OR', N(R')C(O)R', N(R')C(S)R', N(R')C(O)N(R')$_2$, N(R')C(S)N(R')$_2$, N(COR')COR', N(OR')R', C(=NH)N(R')$_2$, C(O)N(OR')R', or C(=NOR')R' wherein R' can be hydrogen or a carbon-based moiety, and wherein the carbon-based moiety can itself be further substituted.

Substituted alkyl, alkenyl, alkynyl, cycloalkyl, and cycloalkenyl groups as well as other substituted groups also include groups in which one or more bonds to a hydrogen atom are replaced by one or more bonds, including double or triple bonds, to a carbon atom, or to a heteroatom such as, but not limited to, oxygen in carbonyl (oxo), carboxyl, ester, amide, imide, urethane, and urea groups; and nitrogen in imines, hydroxyimines, oximes, hydrazones, amidines, guanidines, and nitriles. The substituents of the substituted groups can further be substituted with alkyl, alkenyl, cycloalkyl, aryl, heteroaryl, and alkynyl groups as defined herein, which can themselves be further substituted. For example, an $C_{1-4}$ alkyl group can be substituted with an amide, and the amide can further be substituted with another $C_{1-4}$ alkyl, which can further be substituted.

Substituted ring groups such as substituted aryl, heterocyclyl and heteroaryl groups also include rings and fused ring systems in which a bond to a hydrogen atom is replaced with a bond to a carbon atom. Therefore, substituted aryl, heterocyclyl and heteroaryl groups can also be substituted with alkyl, alkenyl, cycloalkyl, aryl, heteroaryl, and alkynyl groups as defined herein, which can themselves be further substituted.

The term "heteroatoms" as used herein refers to non-carbon and non-hydrogen atoms, capable of forming covalent bonds with carbon, and is not otherwise limited. Typical heteroatoms are N, O, and S. When sulfur (S) is referred to, it is understood that the sulfur can be in any of the oxidation states in which it is found, thus including sulfoxides (R—S(O)—R') and sulfones (R—S(O)$_2$—R'), unless the oxidation state is specified; thus, the term "sulfone" encompasses only the sulfone form of sulfur; the term "sulfide" encompasses only the sulfide (R—S—R') form of sulfur. When the phrases such as "heteroatoms selected from the group consisting of O, NH, NR' and S, "or" [variable] is O, S . . . " are used, they are understood to encompass all of the sulfide, sulfoxide and sulfone oxidation states of sulfur.

Alkyl groups include straight chain and branched alkyl groups and cycloalkyl groups having from 1 to about 20 carbon atoms ($C_{1-20}$ alkyl), and typically from 1 to 12 carbons ($C_{1-12}$ alkyl) or, in some embodiments, from 1 to 8 carbon atoms ($C_{1-8}$ alkyl) or, in some embodiments, from 1 to 4 carbon atoms ($C_{1-4}$ alkyl) or, in some embodiments, from 1 to 3 carbon atoms ($C_{1-3}$ alkyl). Examples of straight chain alkyl groups include, but are not limited to methyl, ethyl, n-propyl, n-butyl, n-pentyl, n-hexyl, n-heptyl, and n-octyl groups. Examples of branched alkyl groups include, but are not limited to, isopropyl, iso-butyl, sec-butyl, t-butyl, neopentyl, isopentyl, and 2,2-dimethylpropyl groups. Representative substituted alkyl groups can be substituted one or more times with any of the groups listed above, for example, amino, hydroxy, cyano, carboxy, nitro, thio, alkoxy, and halogen groups. The group "n-hydroxy $C_{1-4}$ alkyl" represents an $C_{1-4}$ alkyl substituted with a terminal hydroxy group.

Cycloalkyl groups are alkyl groups forming a ring structure, which can be substituted or unsubstituted. Examples of cycloalkyl include, but are not limited to, cyclopropyl, cyclobutyl, cyclopentyl, cyclohexyl, cycloheptyl, and cyclooctyl groups. In some embodiments, the cycloalkyl group has 3 to 8 ring members, whereas in other embodiments the number of ring carbon atoms range from 3 to 5, 3 to 6, or 3 to 7. Cycloalkyl groups further include polycyclic cycloalkyl groups such as, but not limited to, norbornyl, adamantyl, bornyl, camphenyl, isocamphenyl, and carenyl groups, and fused rings such as, but not limited to, decalinyl, and the like. Cycloalkyl groups also include rings that are substituted with straight or branched chain alkyl groups as defined above. Representative substituted cycloalkyl groups can be mono-substituted or substituted more than once, such as, but not limited to, 2,2-, 2,3-, 2,4- 2,5- or 2,6-disubstituted cyclohexyl groups or mono-, di- or tri-substituted norbornyl or cycloheptyl groups, which can be substituted with, for example, amino, hydroxy, cyano, carboxy, nitro, thio, alkoxy, and halogen groups.

The terms "carbocyclic" and "carbocycle" denote a ring structure wherein the atoms of the ring are carbon. In some embodiments, the carbocycle has 3 to 8 ring members, whereas in other embodiments the number of ring carbon atoms is 4, 5, 6, or 7. Unless specifically indicated to the contrary, the carbocyclic ring can be substituted with as many as N substituents wherein N is the size of the carbocyclic ring with for example, amino, hydroxy, cyano, carboxy, nitro, thio, alkoxy, and halogen groups.

(Cycloalkyl)alkyl groups, also denoted cycloalkylalkyl, are alkyl groups as defined above in which a hydrogen or carbon bond of the alkyl group is replaced with a bond to a cycloalkyl group as defined above.

Alkenyl groups include straight and branched chain and cyclic alkyl groups as defined above, except that at least one double bond exists between two carbon atoms. Thus, alkenyl groups have from 2 to about 20 carbon atoms, and typically from 2 to 12 carbons or, in some embodiments, from 2 to 8 carbon atoms. Examples include, but are not limited to —CH=CH(CH$_3$), —CH=C(CH$_3$)$_2$, —C(CH$_3$)=CH$_2$, —C(CH$_3$)=CH(CH$_3$), —C(CH$_2$CH$_3$)=CH$_2$, vinyl, cyclohexenyl, cyclopentenyl, cyclohexadienyl, butadienyl, pentadienyl, and hexadienyl among others.

The term "cycloalkenyl" alone or in combination denotes a cyclic alkenyl group wherein at least one double bond is present in the ring structure. Cycloalkenyl groups include cycloalkyl groups having at least one double bond between two adjacent carbon atoms. Thus for example, cycloalkenyl groups include but are not limited to cyclohexenyl, cyclopentenyl, and cyclohexadienyl groups.

(Cycloalkenyl)alkyl groups are alkyl groups as defined above in which a hydrogen or carbon bond of the alkyl group is replaced with a bond to a cycloalkenyl group as defined above.

Alkynyl groups include straight and branched chain alkyl groups, except that at least one triple bond exists between two carbon atoms. Thus, alkynyl groups have from 2 to about 20 carbon atoms, and typically from 2 to 12 carbons or, in some embodiments, from 2 to 8 carbon atoms. Examples include, but are not limited to —CCH, —CC(CH$_3$), —CC(CH$_2$CH$_3$), —CH$_2$CCH, —CH$_2$CC(CH$_3$), and —CH$_2$CC(CH$_2$CH$_3$), among others.

Aryl groups are cyclic aromatic hydrocarbons that do not contain heteroatoms. Thus aryl groups include, but are not limited to, phenyl, azulenyl, heptalenyl, biphenyl, indacenyl, fluorenyl, phenanthrenyl, triphenylenyl, pyrenyl, naphthacenyl, chrysenyl, biphenylenyl, anthracenyl, and naphthyl groups. In some embodiments, aryl groups contain 6-14 carbons in the ring portions of the groups. The phrase "aryl groups" includes groups containing fused rings, such as fused aromatic-aliphatic ring systems (e.g., indanyl, tetrahydronaphthyl, and the like), and also includes substituted aryl groups that have other groups, including but not limited to alkyl, halo, amino, hydroxy, cyano, carboxy, nitro, thio, or alkoxy groups, bonded to one of the ring atoms. Representative substituted aryl groups can be mono-substituted or substituted more than once, such as, but not limited to, 2-, 3-, 4-, 5-, or 6-substituted phenyl or naphthyl groups, which can be substituted with groups including but not limited to those listed above.

Aralkyl groups are alkyl groups as defined above in which a hydrogen or carbon bond of an alkyl group is replaced with a bond to an aryl group as defined above. Representative aralkyl groups include benzyl and phenylethyl groups and fused (cycloalkylaryl)alkyl groups such as 4-ethyl-indanyl.

The aryl moiety or the alkyl moiety or both are optionally substituted with other groups, including but not limited to alkyl, halo, amino, hydroxy, cyano, carboxy, nitro, thio, or alkoxy groups. Aralkenyl group are alkenyl groups as defined above in which a hydrogen or carbon bond of an alkyl group is replaced with a bond to an aryl group as defined above.

Heterocyclyl groups include aromatic and non-aromatic ring compounds (heterocyclic rings) containing 3 or more ring members, of which one or more is a heteroatom such as, but not limited to, N, O, S, or P. In some embodiments, heterocyclyl groups include 3 to 20 ring members, whereas other such groups have 3 to 15 ring members. At least one ring contains a heteroatom, but every ring in a polycyclic system need not contain a heteroatom. For example, a dioxolanyl ring and a benzdioxolanyl ring system (methylenedioxyphenyl ring system) are both heterocyclyl groups within the meaning herein. A heterocyclyl group designated as a $C_2$-heterocyclyl can be a 5-membered ring with two carbon atoms and three heteroatoms, a 6-membered ring with two carbon atoms and four heteroatoms and so forth. Likewise a $C_4$-heterocyclyl can be a 5-membered ring with one heteroatom, a 6-membered ring with two heteroatoms, and so forth. The number of carbon atoms plus the number of heteroatoms sums up to equal the total number of ring atoms. A saturated heterocyclic ring refers to a heterocyclic ring containing no unsaturated carbon atoms.

The phrase "heterocyclyl group" includes fused ring species including those having fused aromatic and non-aromatic groups. The phrase also includes polycyclic ring systems containing a heteroatom such as, but not limited to, quinuclidyl and also includes heterocyclyl groups that have substituents, including but not limited to alkyl, halo, amino, hydroxy, cyano, carboxy, nitro, thio, or alkoxy groups, bonded to one of the ring members. A heterocyclyl group as defined herein can be a heteroaryl group or a partially or completely saturated cyclic group including at least one ring heteroatom. Heterocyclyl groups include, but are not limited to, pyrrolidinyl, furanyl, tetrahydrofuranyl, dioxolanyl, piperidinyl, piperazinyl, morpholinyl, pyrrolyl, pyrazolyl, triazolyl, tetrazolyl, oxazolyl, isoxazolyl, thiazolyl, pyridinyl, thiophenyl, benzothiophenyl, benzofuranyl, dihydrobenzofuranyl, indolyl, dihydroindolyl, azaindolyl, indazolyl, benzimidazolyl, azabenzimidazolyl, benzoxazolyl, benzothiazolyl, benzothiadiazolyl, imidazopyridinyl, isoxazolopyridinyl, thianaphthalenyl, purinyl, xanthinyl, adeninyl, guaninyl, quinolinyl, isoquinolinyl, tetrahydroquinolinyl, quinoxalinyl, and quinazolinyl groups. Heterocyclyl groups can be substituted. Representative substituted heterocyclyl groups can be mono-substituted or substituted more than once, including but not limited to, rings containing at least one heteroatom which are mono, di, tri, tetra, penta, hexa, or higher-substituted with substituents such as those listed above, including but not limited to alkyl, halo, amino, hydroxy, cyano, carboxy, nitro, thio, and alkoxy groups.

Heteroaryl groups are aromatic ring compounds containing 5 or more ring members, of which, one or more is a heteroatom such as, but not limited to, N, O, and S. A heteroaryl group designated as a $C_2$-heteroaryl can be a 5-membered ring with two carbon atoms and three heteroatoms, a 6-membered ring with two carbon atoms and four heteroatoms and so forth. Likewise a $C_4$-heteroaryl can be a 5-membered ring with one heteroatom, a 6-membered ring with two heteroatoms, and so forth. The number of carbon atoms plus the number of heteroatoms sums up to equal the total number of ring atoms. Heteroaryl groups include, but are not limited to, groups such as pyrrolyl, pyrazolyl, triazolyl, tetrazolyl, oxazolyl, isoxazolyl, thiazolyl, pyridinyl, thiophenyl, benzothiophenyl, benzofuranyl, indolyl, azaindolyl, indazolyl, benzimidazolyl, azabenzimidazolyl, benzoxazolyl, benzothiazolyl, benzothiadiazolyl, imidazopyridinyl, isoxazolopyridinyl, thianaphthalenyl, purinyl, xanthinyl, adeninyl, guaninyl, quinolinyl, isoquinolinyl, tetrahydroquinolinyl, tetrahydroisoquinolinyl, quinoxalinyl, and quinazolinyl groups. The terms "heteroaryl" and "heteroaryl groups" include fused ring compounds such as wherein at least one ring, but not necessarily all rings, are aromatic, including tetrahydroquinolinyl, tetrahydroisoquinolinyl, indolyl and 2,3-dihydro indolyl. The term also includes heteroaryl groups that have other groups bonded to one of the ring members, including but not limited to alkyl, halo, amino, hydroxy, cyano, carboxy, nitro, thio, or alkoxy groups. Representative substituted heteroaryl groups can be substituted one or more times with groups such as those listed above.

Additional examples of aryl and heteroaryl groups include but are not limited to phenyl, biphenyl, indenyl, naphthyl (1-naphthyl, 2-naphthyl), N-hydroxytetrazolyl, N-hydroxytriazolyl, N-hydroxyimidazolyl, anthracenyl (1-anthracenyl, 2-anthracenyl, 3-anthracenyl), thiophenyl (2-thienyl, 3-thienyl), furyl (2-furyl, 3-furyl), indolyl, oxadiazolyl, isoxazolyl, quinazolinyl, fluorenyl, xanthenyl, isoindanyl, benzhydryl, acridinyl, thiazolyl, pyrrolyl (2-pyrrolyl), pyrazolyl (3-pyrazolyl), imidazolyl (1-imidazolyl, 2-imidazolyl, 4-imidazolyl, 5-imidazolyl), triazolyl (1,2,3-triazol-1-yl, 1,2,3-triazol-2-yl 1,2,3-triazol-4-yl, 1,2,4-triazol-3-yl), oxazolyl (2-oxazolyl, 4-oxazolyl, 5-oxazolyl), thiazolyl (2-thiazolyl, 4-thiazolyl, 5-thiazolyl), pyridyl (2-pyridyl, 3-pyridyl, 4-pyridyl), pyrimidinyl (2-pyrimidinyl, 4-pyrimidinyl, 5-pyrimidinyl, 6-pyrimidinyl), pyrazinyl, pyridazinyl (3-pyridazinyl, 4-pyridazinyl, 5-pyridazinyl), quinolyl (2-quinolyl, 3-quinolyl, 4-quinolyl, 5-quinolyl, 6-quinolyl, 7-quinolyl, 8-quinolyl), isoquinolyl (1-isoquinolyl, 3-isoquinolyl, 4-isoquinolyl, 5-isoquinolyl, 6-isoquinolyl, 7-isoquinolyl, 8-isoquinolyl), benzo[b]furanyl (2-benzo[b]furanyl, 3-benzo[b]furanyl, 4-benzo[b]furanyl, 5-benzo[b]furanyl, 6-benzo[b]furanyl, 7-benzo[b]furanyl), 2,3-dihydro-benzo[b]furanyl (2-(2,3-dihydro-benzo[b]furanyl), 3-(2,3-dihydro-benzo[b]furanyl), 4-(2,3-dihydro-benzo[b]furanyl), 5-(2,3-dihydro-benzo[b] furanyl), 6-(2,3-dihydro-benzo[b]furanyl), 7-(2,3-dihydro-benzo[b]furanyl), benzo[b]thiophenyl (2-benzo[b]thiophenyl, 3-benzo[b]thiophenyl, 4-benzo[b]thiophenyl, 5-benzo[b]thiophenyl, 6-benzo[b]thiophenyl, 7-benzo[b]thiophenyl), 2,3-dihydro-benzo[b]thiophenyl, (2-(2,3-dihydro-benzo[b]thiophenyl), 3-(2,3-dihydro-benzo[b] thiophenyl), 4-(2,3-dihydro-benzo[b]thiophenyl), 5-(2,3-dihydro-benzo[b]thiophenyl), 6-(2,3-dihydro-benzo[b] thiophenyl), 7-(2,3-dihydro-benzo[b]thiophenyl), indolyl (1-indolyl, 2-indolyl, 3-indolyl, 4-indolyl, 5-indolyl, 6-indolyl, 7-indolyl), indazole (1-indazolyl, 3-indazolyl, 4-indazolyl, 5-indazolyl, 6-indazolyl, 7-indazolyl), benzimidazolyl (1-benzimidazolyl, 2-benzimidazolyl, 4-benzimidazolyl, 5-benzimidazolyl, 6-benzimidazolyl, 7-benzimidazolyl, 8-benzimidazolyl), benzoxazolyl (1-benzoxazolyl, 2-benzoxazolyl), benzothiazolyl (1-benzothiazolyl, 2-benzothiazolyl, 4-benzothiazolyl, 5-benzothiazolyl, 6-benzothiazolyl, 7-benzothiazolyl), carbazolyl (1-carbazolyl, 2-carbazolyl, 3-carbazolyl, 4-carbazolyl), 5H-dibenz[b,f]azepine (5H-dibenz[b,f]azepin-1-yl, 5H-dibenz[b,f]azepine-2-yl, 5H-dibenz[b,f]azepine-3-yl, 5H-dibenz[b,f]azepine-4-yl, 5H-dibenz[b,f]azepine-5-yl), 10,11-dihydro-5H-dibenz[b,f] azepine (10,11-dihydro-5H-dibenz[b,f]azepine-1-yl, 10,11-dihydro-5H-dibenz[b,f]azepine-2-yl, 10,11-dihydro-5H-dibenz[b,f]azepine-3-yl, 10,11-dihydro-5H-dibenz[b,f] azepine-4-yl, 10,11-dihydro-5H-dibenz[b,f]azepine-5-yl), and the like.

Heterocyclylalkyl groups are alkyl groups as defined above in which a hydrogen or carbon bond of an alkyl group is replaced with a bond to a heterocyclyl group as defined above. Representative heterocyclyl alkyl groups include, but are not limited to, furan-2-yl methyl, furan-3-yl methyl, pyridine-2-yl methyl (α-picolyl), pyridine-3-yl methyl (β-picolyl), pyridine-4-yl methyl (γ-picolyl), tetrahydrofuran-2-yl ethyl, and indol-2-yl propyl. Heterocyclylalkyl groups can be substituted on the heterocyclyl moiety, the alkyl moiety, or both.

Heteroarylalkyl groups are alkyl groups as defined above in which a hydrogen or carbon bond of an alkyl group is replaced with a bond to a heteroaryl group as defined above. Heteroarylalkyl groups can be substituted on the heteroaryl moiety, the alkyl moiety, or both.

By a "ring system" as the term is used herein is meant a moiety comprising one, two, three or more rings, which can be substituted with non-ring groups or with other ring systems, or both, which can be fully saturated, partially unsaturated, fully unsaturated, or aromatic, and when the ring system includes more than a single ring, the rings can be fused, bridging, or spirocyclic. By "spirocyclic" is meant the class of structures wherein two rings are fused at a single tetrahedral carbon atom, as is well known in the art.

A "monocyclic, bicyclic or polycyclic, aromatic or partially aromatic ring" as the term is used herein refers to a ring system including an unsaturated ring possessing 4n+2 pi electrons, or a partially reduced (hydrogenated) form thereof. The aromatic or partially aromatic ring can include additional fused, bridged, or spiro rings that are not themselves aromatic or partially aromatic. For example, naphthalene and tetrahydronaphthalene are both a "monocyclic, bicyclic or polycyclic, aromatic or partially aromatic ring" within the meaning herein. Also, for example, a benzo-[2.2.2]-bicyclooctane is also a "monocyclic, bicyclic or polycyclic, aromatic or partially aromatic ring" within the meaning herein, containing a phenyl ring fused to a bridged bicyclic system. A fully saturated ring has no double bonds therein, and is carbocyclic or heterocyclic depending on the presence of heteroatoms within the meaning herein.

The term "alkoxy" refers to an oxygen atom connected to an alkyl group, including a cycloalkyl group, as are defined above. Examples of linear alkoxy groups include but are not limited to methoxy, ethoxy, n-propoxy, n-butoxy, n-pentyloxy, n-hexyloxy, and the like. Examples of branched alkoxy include but are not limited to isopropoxy, sec-butoxy, tert-butoxy, isopentyloxy, isohexyloxy, and the like. Examples of cyclic alkoxy include but are not limited to cyclopropyloxy, cyclobutyloxy, cyclopentyloxy, cyclohexyloxy, and the like.

The terms "aryloxy" and "arylalkoxy" refer to, respectively, an aryl group bonded to an oxygen atom and an aralkyl group bonded to the oxygen atom at the alkyl moiety. Examples include but are not limited to phenoxy, naphthyloxy, and benzyloxy.

An "acyl" group as the term is used herein refers to a group containing a carbonyl moiety wherein the group is bonded via the carbonyl carbon atom. The carbonyl carbon atom is also bonded to another carbon atom, which can be part of an alkyl, aryl, aralkyl cycloalkyl, cycloalkylalkyl, heterocyclyl, heterocyclylalkyl, heteroaryl, heteroarylalkyl group or the like. In the special case wherein the carbonyl carbon atom is bonded to a hydrogen, the group is a "formyl" group, an acyl group as the term is defined herein. An acyl group can include 0 to about 12-20 additional carbon atoms bonded to the carbonyl group. An acyl group can include double or triple bonds within the meaning herein. An acryloyl group is an example of an acyl group. An acyl group can also include heteroatoms within the meaning here. A nicotinoyl group (pyridyl-3-carbonyl) group is an example of an acyl group within the meaning herein. Other examples include acetyl, benzoyl, phenylacetyl, pyridylacetyl, cinnamoyl, and acryloyl groups and the like. When the group containing the carbon atom that is bonded to the carbonyl carbon atom contains a halogen, the group is termed a "haloacyl" group. An example is a trifluoroacetyl group.

The term "amine" includes primary, secondary, and tertiary amines having, e.g., the formula N(group)$_3$ wherein each group can independently be H or non-H, such as alkyl, aryl, and the like. Amines include but are not limited to RNH$_2$, for example, alkylamines, arylamines, alkylarylamines; R$_2$NH wherein each R is independently selected, such as dialkylamines, diarylamines, aralkylamines, heterocyclylamines and the like; and R$_3$N wherein each R is independently selected, such as trialkylamines, dialkylarylamines, alkyldiarylamines, triarylamines, and the like. The term "amine" also includes ammonium ions as used herein.

An "amino" group is a substituent of the form —NH$_2$, —NHR, —NR$_2$, —NR$_3^+$, wherein each R is independently selected, and protonated forms of each. Accordingly, any compound substituted with an amino group can be viewed as an amine.

An "ammonium" ion includes the unsubstituted ammonium ion NH$_4^+$, but unless otherwise specified, it also includes any protonated or quaternarized forms of amines. Thus, trimethylammonium hydrochloride and tetramethylammonium chloride are both ammonium ions, and amines, within the meaning herein.

The term "amide" (or "amido") includes C- and N-amide groups, i.e., —C(O)NR'R", and —NR'C(O)R" groups, respectively. The R' and R" of the C-amide may join together to form a heterocyclic ring with the nitrogen atom. Amide groups therefore include but are not limited to carbamoyl groups (—C(O)NH$_2$) and formamide groups (—NHC(O)H). A "carboxamido" group is a group of the formula C(O)NR$_2$, wherein R can be H, alkyl, aryl, etc.

The term "urethane" (or "carbamyl") includes N- and O-urethane groups, i.e., —NRC(O)OR and —OC(O)NR$_2$ groups, respectively.

The term "sulfonamide" (or "sulfonamido") includes S- and N-sulfonamide groups, i.e., —SO$_2$NR$_2$ and —NRSO$_2$R groups, respectively. Sulfonamide groups therefore include but are not limited to sulfamoyl groups (—SO$_2$NH$_2$).

The term "amidine" or "amidino" includes groups of the formula —C(NR)NR$_2$. Typically, an amidino group is —C(NH)NH$_2$.

The term "guanidine" or "guanidino" includes groups of the formula —NRC(NR)NR$_2$. Typically, a guanidino group is —NHC(NH)NH$_2$.

"Halo," "halogen," and "halide" include fluorine, chlorine, bromine and iodine.

The terms "comprising," "including," "having," "composed of," are open-ended terms as used herein, and do not preclude the existence of additional elements or components. In a claim element, use of the forms "comprising," "including," "having," or "composed of" means that whatever element is comprised, had, included, or composes is not necessarily the only element encompassed by the subject of the clause that contains that word.

A "salt" as is well known in the art includes an organic compound such as a carboxylic acid, a sulfonic acid, or an amine, in ionic form, in combination with a counterion. For example, acids in their anionic form can form salts with cations such as metal cations, for example sodium, potassium, and the like; with ammonium salts such as NH$_4^+$ or the cations of various amines, including tetraalkyl ammonium salts such as tetramethylammonium and alkyl ammonium salts such as tromethamine salts, or other cations such as trimethylsulfonium, and the like. A "pharmaceutically acceptable" or "pharmacologically acceptable" salt is a salt formed from an ion that has been approved for human consumption and is generally non-toxic, such as a chloride salt or a sodium salt. A "zwitterion" is an internal salt such as can be formed in a molecule that has at least two ionizable groups, one forming an anion and the other a cation, which serve to balance each other. For example, amino acids such as glycine can exist in a zwitterionic form. A "zwitterion" is a salt within the meaning herein. The compounds of the present invention may take the form of salts. The term "salts" embraces addition salts of free acids or free bases which are compounds of the invention. Salts can be "pharmaceutically-acceptable salts." The term "pharmaceutically-acceptable salt" refers to salts which possess toxicity profiles within a range that affords utility in pharmaceutical applications. Pharmaceutically unacceptable salts may nonetheless possess properties such as high crystallinity, which have utility in the practice of the present invention, such as for example utility in process of synthesis, purification or formulation of compounds of the invention.

Suitable pharmaceutically-acceptable acid addition salts may be prepared from an inorganic acid or from an organic acid. Examples of inorganic acids include hydrochloric, hydrobromic, hydriodic, nitric, carbonic, sulfuric, and phosphoric acids. Appropriate organic acids may be selected from aliphatic, cycloaliphatic, aromatic, aralyphatic, heterocyclic, carboxylic and sulfonic classes of organic acids, examples of which include formic, acetic, propionic, succinic, glycolic, gluconic, lactic, malic, tartaric, citric, ascorbic, glucuronic, maleic, fumaric, pyruvic, aspartic, glutamic, benzoic, anthranilic, 4-hydroxybenzoic, phenylacetic, mandelic, embonic (pamoic), methanesulfonic, ethanesulfonic, benzenesulfonic, pantothenic, trifluoromethanesulfonic, 2-hydroxyethanesulfonic, p-toluenesulfonic, sulfanilic, cyclohexylaminosulfonic, stearic, alginic, β-hydroxybutyric, salicylic, galactaric and galacturonic acid. Examples of pharmaceutically unacceptable acid addition salts include, for example, perchlorates and tetrafluoroborates.

Suitable pharmaceutically acceptable base addition salts of compounds of the invention include, for example, metallic salts including alkali metal, alkaline earth metal and transition metal salts such as, for example, calcium, magnesium, potassium, sodium and zinc salts. Pharmaceutically acceptable base addition salts also include organic salts made from basic amines such as, for example, N,N'-dibenzylethylenediamine, chloroprocaine, choline, diethanolamine, ethylenediamine, meglumine (N-methylglucamine) and procaine. Examples of pharmaceutically unacceptable base addition salts include lithium salts and cyanate salts. Although pharmaceutically unacceptable salts are not generally useful as medicaments, such salts may be useful, for example as intermediates in the synthesis of compounds, for example in their purification by recrystallization. All of these salts may be prepared by conventional means from the corresponding compound by reacting, for example, the appropriate acid or base with the compound. The term "pharmaceutically acceptable salts" refers to nontoxic inorganic or organic acid and/or base addition salts, see, for example, Lit et al., Salt Selection for Basic Drugs (1986), *Int J. Pharm.*, 33, 201-217, incorporated by reference herein Nonlimiting examples of potential salts of this invention include but are not limited to hydrochloride, citrate, glycolate, fumarate, malate, tartrate, mesylate, esylate, cinnamate, isethionate, sulfate, phosphate, diphosphate, nitrate, hydrobromide, hydroiodide, succinate, formate, acetate, dichloroacetate, lactate, p-toluenesulfonate, pamitate, pidolate, pamoate, salicylate, 4-aminosalicylate, benzoate, 4-acetamido benzoate, glutamate, aspartate, glycolate, adipate, alginate, ascorbate, besylate, camphorate, camphorsulfonate, camsylate, caprate, caproate, cyclamate, laurylsulfate, edisylate, gentisate, galactarate, gluceptate, gluconate, glucuronate, oxoglutarate, hippurate, lactobionate, malonate, maleate, mandalate, napsylate, napadisylate, oxalate, oleate, sebacate, stearate, succinate, thiocyanate, undecylenate, and xinafoate.

A "hydrate" is a compound that exists in a composition with water molecules. The composition can include water in stoichiometic quantities, such as a monohydrate or a dihydrate, or can include water in random amounts. As the term is used herein a "hydrate" refers to a solid form, i.e., a compound in water solution, while it may be hydrated, is not a hydrate as the term is used herein.

A "homolog" of a compound of the invention is a compound having one or more atoms of the compound replaced by an isotope of such atom. For example, homologs include compounds with deuterium in place of some hydrogen atoms of the compound such as compounds of the invention in which the methyl groups of the isopropoxy moiety of Formulas I-R and I-S are fully or partially deuterated (e.g., $(D_3C)_2C$—O—). Isotopic substitutions which may be made in the formation of homologs of the invention include non-radioactive (stable) atoms such as deuterium and carbon 13, as well as radioactive (unstable) atoms such as tritium, carbon 14, iodine 123, iodine 125, etc.

A "solvate" is a similar composition except that a solvent other that water replaces the water. For example, methanol or ethanol can form an "alcoholate", which can again be stoichiometic or non-stoichiometric. As the term is used herein a "solvate" refers to a solid form, i.e., a compound in solution in a solvent, while it may be solvated, is not a solvate as the term is used herein.

A "prodrug" as is well known in the art is a substance that can be administered to a patient where the substance is converted in vivo by the action of biochemicals within the patients body, such as enzymes, to the active pharmaceutical ingredient. Examples of prodrugs include esters of carboxylic acid groups, which can be hydrolyzed by endogenous esterases as are found in the bloodstream of humans and other mammals.

Any compound which can be converted in vivo to the active drug by chemical or biochemical transformations functions as a prodrug. Prodrugs of claimed compounds are covered under this invention.

Some examples of prodrugs within the scope of this invention include:

i. If the compound contains a hydroxyl group, the hydroxyl group may be modified to form an ester, carbonate, or carbamate. Examples include acetate, pivalate, methyl and ethyl carbonates, and dimethylcarbamate. The ester may also be derived from amino acids such as glycine, serine, or lysine.

ii. If the compound contains an amine group, the amine group may be modified to form an amide. Examples include acetamide or derivatization with amino acids such as glycine, serine, or lysine.

Certain compounds of the invention and their salts may exist in more than one crystal form and the present invention includes each crystal form and mixtures thereof. In addition, the compounds of the present invention can exist in unsolvated as well as solvated forms with pharmaceutically acceptable solvents such as water to form hydrates or adducts with alcohols such as $C_{1-4}$-alkanols, and the like. Furthermore, compounds of this invention can be isolated in association with solvent molecules by crystallization from evaporation of an appropriate solvent. Such solvents include but are not limited to toluene, tetrahydrofuran, dioxane, dimethylformamide, acetonitrile, acetates such as methyl acetate, ethyl acetate, butyl acetate, isobutyl acetate, propyl- and isopropyl acetate, ethers such as diethyl ether and ethyl ether, alcohols such as methanol, ethanol, 1- or 2-butanol, 1- or 2-propanol, pentanol, and dimethylsulfoxide. In general, a depiction for the compound by structure or name is considered to embrace the compound in any form (e.g., by itself, as a hydrate, solvate, or otherwise in a mixture).

In addition, where features or aspects of the invention are described in terms of Markush groups, those skilled in the art will recognize that the invention is also thereby described in terms of any individual member or subgroup of members of the Markush group. For example, if X is described as selected from the group consisting of bromine, chlorine, and iodine, claims for X being bromine and claims for X being bromine and chlorine are fully described. Moreover, where features or aspects of the invention are described in terms of Markush groups, those skilled in the art will recognize that the invention is also thereby described in terms of any combination of individual members or subgroups of members of Markush groups. Thus, for example, if X is described as selected from the group consisting of bromine, chlorine, and iodine, and Y is described as selected from the group consisting of methyl, ethyl, and propyl, claims for X being bromine and Y being methyl are fully described.

Compositions and Combination Treatments

The $S1P_1$ compounds, their pharmaceutically acceptable salts or hydrolyzable esters of the present invention may be combined with a pharmaceutically acceptable carrier to provide pharmaceutical compositions useful for treating the biological conditions or disorders noted herein in mammalian species, and more preferably, in humans. The particular carrier employed in these pharmaceutical compositions may vary depending upon the type of administration desired (e.g. intravenous, oral, topical, suppository, or parenteral).

In preparing the compositions in oral liquid dosage forms (e.g. suspensions, elixirs and solutions), typical pharmaceutical media, such as water, glycols, oils, alcohols, flavoring agents, preservatives, coloring agents and the like can be employed. Similarly, when preparing oral solid dosage forms (e.g. powders, tablets and capsules), carriers such as starches, sugars, diluents, granulating agents, lubricants, binders, disintegrating agents and the like can be employed.

Another aspect of an embodiment of the invention provides compositions of the compounds of the invention, alone or in combination with another $S1P_1$ inhibitor or another type of therapeutic agent, or both. As set forth herein, compounds of the invention include stereoisomers, tautomers, solvates, hydrates, salts including pharmaceutically acceptable salts, and mixtures thereof. Compositions containing a compound of the invention can be prepared by conventional techniques, e.g. as described in Remington: *The Science and Practice of Pharmacy*, 19th Ed., 1995, incorporated by reference herein. The compositions can appear in conventional forms, for example capsules, tablets, aerosols, solutions, suspensions or topical applications.

Typical compositions include a compound of the invention and a pharmaceutically acceptable excipient which can be a carrier or a diluent. For example, the active compound will usually be mixed with a carrier, or diluted by a carrier, or enclosed within a carrier which can be in the form of an ampoule, capsule, sachet, paper, or other container. When the active compound is mixed with a carrier, or when the carrier serves as a diluent, it can be solid, semi-solid, or liquid material that acts as a vehicle, excipient, or medium for the active compound. The active compound can be adsorbed on a granular solid carrier, for example contained in a sachet. Some examples of suitable carriers are water, salt solutions, alcohols, polyethylene glycols, polyhydroxyethoxylated castor oil, peanut oil, olive oil, gelatin, lactose, terra alba, sucrose, dextrin, magnesium carbonate, sugar, cyclodextrin, amylose, magnesium stearate, talc, gelatin, agar, pectin, acacia, stearic acid or lower alkyl ethers of cellulose, silicic acid, fatty acids, fatty acid amines, fatty acid monoglycerides and diglycerides, pentaerythritol fatty acid esters, polyoxyethylene, hydroxymethylcellulose and polyvinylpyrrolidone. Similarly, the carrier or diluent can include any sustained release material known in the art, such as glyceryl monostearate or glyceryl distearate, alone or mixed with a wax.

The formulations can be mixed with auxiliary agents which do not deleteriously react with the active compounds. Such additives can include wetting agents, emulsifying and suspending agents, salt for influencing osmotic pressure, buffers and/or coloring substances preserving agents, sweetening agents or flavoring agents. The compositions can also be sterilized if desired.

The route of administration can be any route which effectively transports the active compound of the invention which inhibits the enzymatic activity of the focal adhesion kinase to the appropriate or desired site of action, such as oral, nasal, pulmonary, buccal, subdermal, intradermal, transdermal or parenteral, e.g., rectal, depot, subcutaneous, intravenous, intraurethral, intramuscular, intranasal, ophthalmic solution or an ointment, the oral route being preferred.

For parenteral administration, the carrier will typically comprise sterile water, although other ingredients that aid solubility or serve as preservatives can also be included. Furthermore, injectable suspensions can also be prepared, in which case appropriate liquid carriers, suspending agents and the like can be employed.

For topical administration, the compounds of the present invention can be formulated using bland, moisturizing bases such as ointments or creams.

If a solid carrier is used for oral administration, the preparation can be tabletted, placed in a hard gelatin capsule in powder or pellet form or it can be in the form of a troche or lozenge. If a liquid carrier is used, the preparation can be in the form of a syrup, emulsion, soft gelatin capsule or sterile injectable liquid such as an aqueous or non-aqueous liquid suspension or solution.

Injectable dosage forms generally include aqueous suspensions or oil suspensions which can be prepared using a suitable dispersant or wetting agent and a suspending agent Injectable forms can be in solution phase or in the form of a suspension, which is prepared with a solvent or diluent. Acceptable solvents or vehicles include sterilized water, Ringer's solution, or an isotonic aqueous saline solution. Alternatively, sterile oils can be employed as solvents or suspending agents. Preferably, the oil or fatty acid is non-volatile, including natural or synthetic oils, fatty acids, mono-, di- or tri-glycerides.

For injection, the formulation can also be a powder suitable for reconstitution with an appropriate solution as described above. Examples of these include, but are not limited to, freeze dried, rotary dried or spray dried powders, amorphous powders, granules, precipitates, or particulates. For injection, the formulations can optionally contain stabilizers, pH modifiers, surfactants, bioavailability modifiers and combinations of these. The compounds can be formulated for parenteral administration by injection such as by bolus injection or continuous infusion. A unit dosage form for injection can be in ampoules or in multi-dose containers.

The formulations of the invention can be designed to provide quick, sustained, or delayed release of the active ingredient after administration to the patient by employing procedures well known in the art. Thus, the formulations can also be formulated for controlled release or for slow release.

Compositions contemplated by the present invention can include, for example, micelles or liposomes, or some other encapsulated form, or can be administered in an extended release form to provide a prolonged storage and/or delivery effect. Therefore, the formulations can be compressed into pellets or cylinders and implanted intramuscularly or subcutaneously as depot injections. Such implants can employ known inert materials such as silicones and biodegradable polymers, e.g., polylactide-polyglycolide. Examples of other biodegradable polymers include poly(orthoesters) and poly (anhydrides).

For nasal administration, the preparation can contain a compound of the invention which inhibits the enzymatic activity of the focal adhesion kinase, dissolved or suspended in a liquid carrier, preferably an aqueous carrier, for aerosol application. The carrier can contain additives such as solubilizing agents, e.g., propylene glycol, surfactants, absorption enhancers such as lecithin (phosphatidylcholine) or cyclodextrin, or preservatives such as parabens.

For parenteral application, particularly suitable are injectable solutions or suspensions, preferably aqueous solutions with the active compound dissolved in polyhydroxylated castor oil.

Dosage forms can be administered daily, or more than once a day, such as twice or thrice daily. Alternatively dosage forms can be administered less frequently than daily, such as every other day, or weekly, if found to be advisable by a prescribing physician.

An embodiment of the invention also encompasses prodrugs of a compound of the invention which on administration undergo chemical conversion by metabolic or other physiological processes before becoming active pharmacological substances. Conversion by metabolic or other physiological processes includes without limitation enzymatic (e.g, specific enzymatically catalyzed) and non-enzymatic (e.g., general or specific acid or base induced) chemical transformation of the prodrug into the active pharmacological substance. In general, such prodrugs will be functional derivatives of a compound of the invention which are readily convertible in vivo into a compound of the invention. Conventional procedures for the selection and preparation of suitable prodrug derivatives are described, for example, in Design of Prodrugs, ed. H. Bundgaard, Elsevier, 1985.

In another embodiment, there are provided methods of making a composition of a compound described herein including formulating a compound of the invention with a pharmaceutically acceptable carrier or diluent. In some embodiments, the pharmaceutically acceptable carrier or diluent is suitable for oral administration. In some such embodiments, the methods can further include the step of formulating the composition into a tablet or capsule. In other embodiments, the pharmaceutically acceptable carrier or diluent is suitable for parenteral administration. In some such embodiments, the methods further include the step of lyophilizing the composition to form a lyophilized preparation.

The compounds of the invention can be used therapeutically in combination with i) one or more other $S1P_1$ inhibitors and/or ii) one or more other types of protein kinase inhibitors and/or one or more other types of therapeutic agents which can be administered orally in the same dosage form, in a separate oral dosage form (e.g., sequentially or non-sequentially) or by injection together or separately (e.g., sequentially or non-sequentially).

Accordingly, in another embodiment the invention provides combinations, comprising:
a) a compound of the invention as described herein; and
b) one or more compounds comprising:
   i) other compounds of the present invention,
   ii) other medicaments adapted for treatment of a malcondition for which activation of $S1P_1$ is medically indicated, for example multiple sclerosis, transplant rejection, or adult respiratory distress syndrome.

Combinations of the invention include mixtures of compounds from (a) and (b) in a single formulation and compounds from (a) and (b) as separate formulations. Some combinations of the invention can be packaged as separate formulations in a kit. In some embodiments, two or more compounds from (b) are formulated together while a compound of the invention is formulated separately.

The dosages and formulations for the other agents to be employed, where applicable, will be as set out in the latest edition of the Physicians' Desk Reference, incorporated herein by reference.

Methods of Treatment

In certain embodiments, the present invention encompasses orally bioavailable compounds that specifically agonize $S1P_1$ without binding ($S1P_2$, $S1P_3$ and $S1P_4$), or having significant specificity over ($S1P_5$), other EDG receptors. A selective $S1P_1$ agonist can be used to treat diseases with an autoimmune, hyperactive immune-response, angiogenesis or inflammatory components, but would not be limited to such conditions. Selective $S1P_1$ agonists have advantages over current therapies by increasing the therapeutic window because of reduced toxicity due to engagement of other EDG receptors.

In certain embodiments, the present invention encompasses compounds that bind with high affinity and specificity to the $S1P_1$ receptor in an agonist manner. Upon ligation of the $S1P_1$ receptor with agonist, signaling proceeds through $G_{\alpha i}$, inhibiting the generation of cAMP by adenylate cyclase.

In certain embodiments, the present invention provides a method for activating or agonizing (i.e., to have an agonic effect, to act as an agonist) a sphingosine-1-phosphate receptor subtype, such as $S1P_1$, with a compound of the invention. The method involves contacting the receptor with a suitable concentration of an inventive compound to bring about activation of the receptor. The contacting can take place in vitro, for example in carrying out an assay to determine the S1P receptor activation activity of an inventive compound undergoing experimentation related to a submission for regulatory approval.

In certain embodiments, the method for activating an S1P receptor, such as $S1P_1$, can also be carried out in vivo, that is, within the living body of a mammal, such as a human patient or a test animal. The inventive compound can be supplied to the living organism via one of the routes as described above, e.g., orally, or can be provided locally within the body tissues, for example by injection of a tumor within the organism. In the presence of the inventive compound, activation of the receptor takes place, and the effect thereof can be studied.

An embodiment of the present invention provides a method of treatment of a malcondition in a patient for which activation of an S1P receptor, such as $S1P_1$, is medically indicated, wherein the patient is administered the inventive compound in a dosage, at a frequency, and for a duration to produce a beneficial effect on the patient. The inventive compound can be administered by any suitable means, examples of which are described above.

Preparation of Certain Embodiments

Scheme 1:

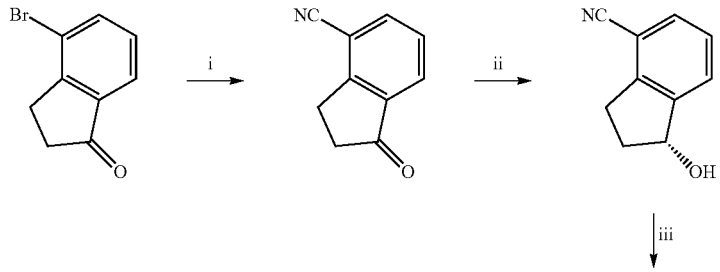

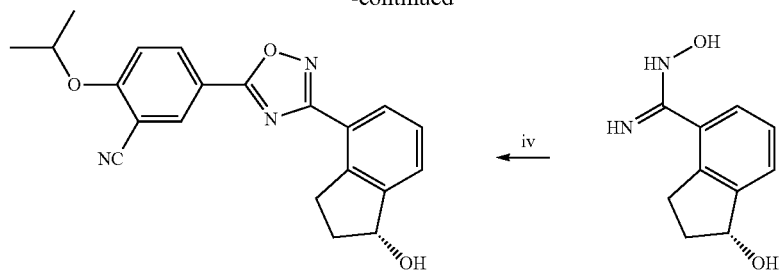

Reagents: (i) $Zn(CN)_2$, $Pd(PPh_3)_4$, NMP; (ii) (S)-(−)-2-methyl-CBS-oxazaborolidine, $BH_3$-DMS, toluene; (iii) $NH_2OH*HCl$, $Na_2CO_3$ or TEA, EtOH; (iv) HOBt, EDC, substituted benzoic acid, DMF.

The (S)-enantiomer was prepared in the same manner outlined in Scheme 1 using (R)-(+)-2-methyl-CBS-oxazaborolidine in step (ii). Racemic material can be prepared in the same manner outlined in Scheme 1 using $NaBH_4$ in (ii).

Scheme 2:

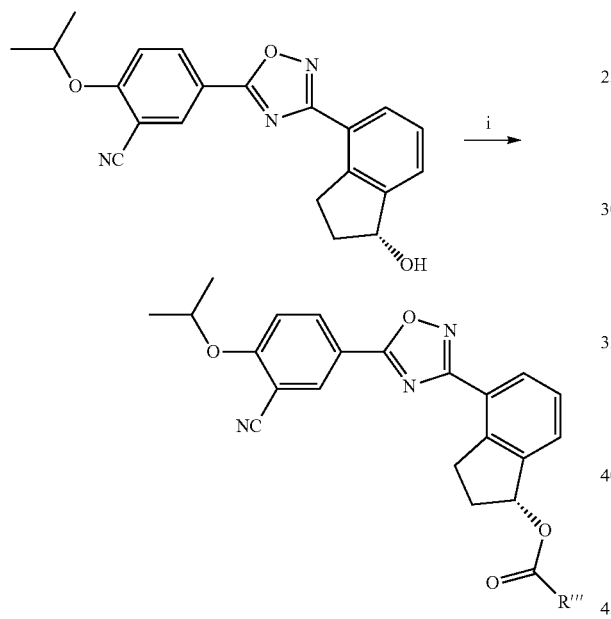

Reagents: (i) Pyridine, R′″—COCl, DCM.

The (S)-enantiomer and racemic material can be prepared in the same manner outlined in Scheme 2 using the appropriate starting materials.

Scheme 3:

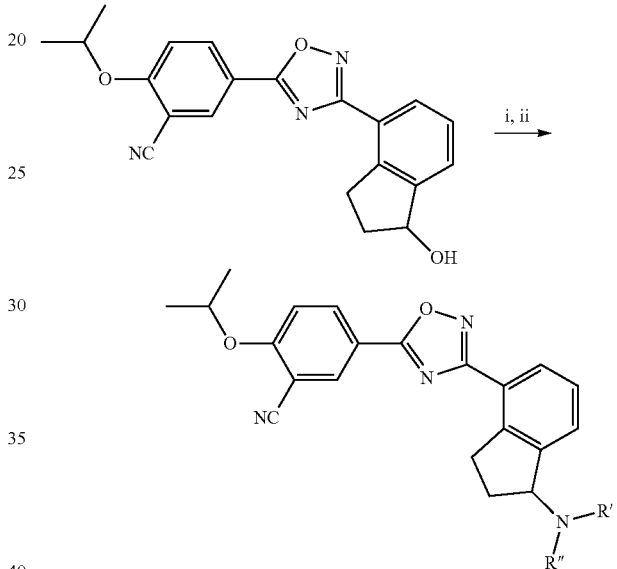

Reagents: (i) (a) MsCl, pyridine; (b) TsCl, pyridine; (c) NsCl, pyridine; (d) $SOCl_2$, DCM; (e) $SOCl_2$, pyridine, DCM; (f) $NaN_3$, $PPh_3$, $CBr_4$; (ii) (a) DIEA, DMA, HNR′R″; (b) DIEA, NaBr or NaI, DMA, HNR′R″.

Enantiomerically enriched material can be prepared in the same manner outlined in Scheme 3 using the (R)- or (S)-indanols.

Scheme 4:

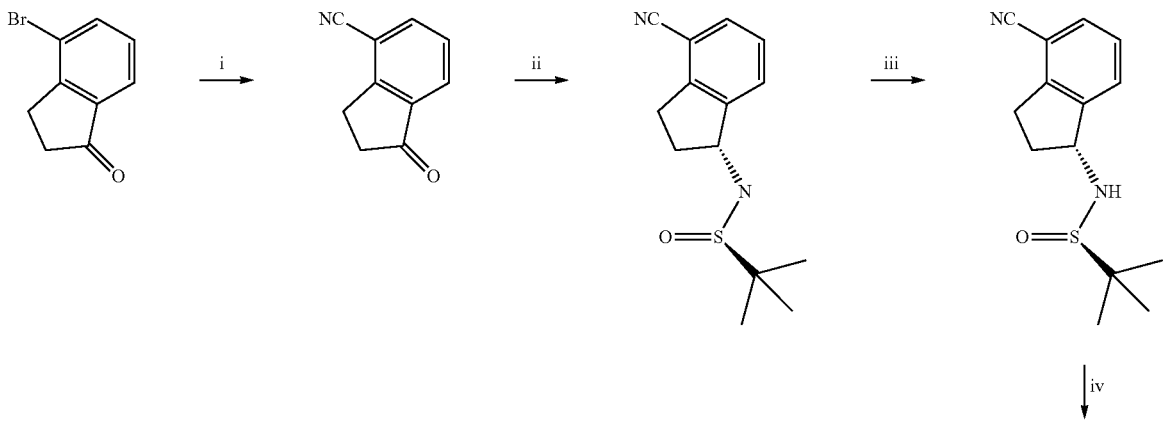

79 80

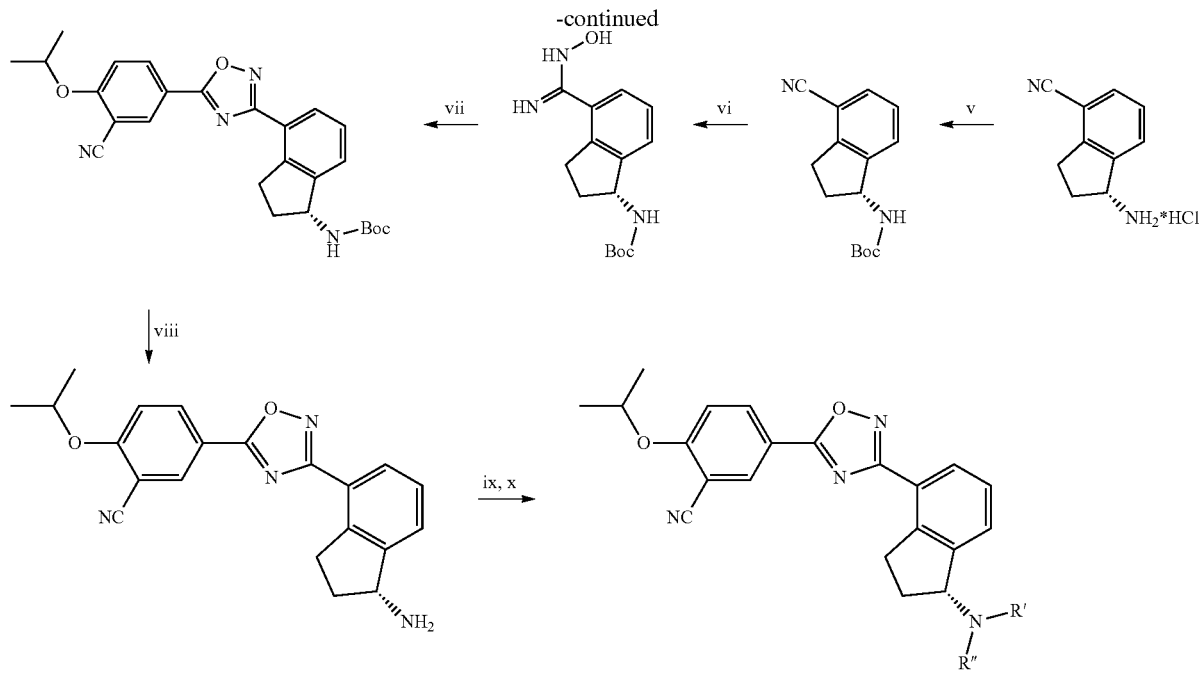

-continued

Reagents: (i) Zn(CN)$_2$, Pd(PPh$_3$)$_4$, NMP; (ii) (R)-2-methyl-propane-2-sulfinamide, Ti(OEt)$_4$, toluene; (iii) NaBH$_4$, THF; (iv) 4M HCl in dioxane, MeOH; (v) Boc$_2$O, TEA, DCM; (vi) NH$_2$OH HCl, TEA, EtOH; (vii) HOBt, EDC, substituted benzoic acid, DMF (viii) 4M HCl in dioxane; (ix) (a) R'-LG or R"-LG, where LG represents a leaving group, K$_2$CO$_3$, CH$_3$CN; (b) R$^1$—CO$_2$H or R$^2$—CO$_2$H, HOBt, EDC, DMF or R$^1$—COCl or R$^2$—COCl, TEA, DCM; (c) R$^1$—SO$_2$Cl or R$^3$—SO$_2$Cl, TEA, DCM (d) R$^2$—CHO, HOAc, NaBH$_4$ or NaCNBH$_3$ or Na(OAc)$_3$BH, MeOH; (e) R$^1$—OCOCl or R$^2$—OCOCl, DIEA, DMF; (f) HN(R$^5$R$^5$), CDI, TEA, DCM;

(g) H$_2$NSO$_2$NH$_2$, A, dioxane; (h) dimethyloxirane, A, EtOH; (x) (a) If R' or R"=H, then reactions (ix)(a-d) can be performed; (b) If R' or R" contains an ester then (i) hydrolysis NaOH, EtOH or (ii) reduction NaBH$_4$, MeOH can be performed; (c) If R' or R" contains an acid then couplings HN(R$^5$R$^5$), HOBt, EDC, DMF can be performed; (d) If R' or R" contains an appropriate activated alkene then Michael additions HN(R$^5$R$^5$), DMF can be performed.

The (S)-enantiomer was prepared in the same manner outlined in Scheme 4 using (S)-2-methylpropane-2-sulfinamide in step (ii).

Scheme 5:

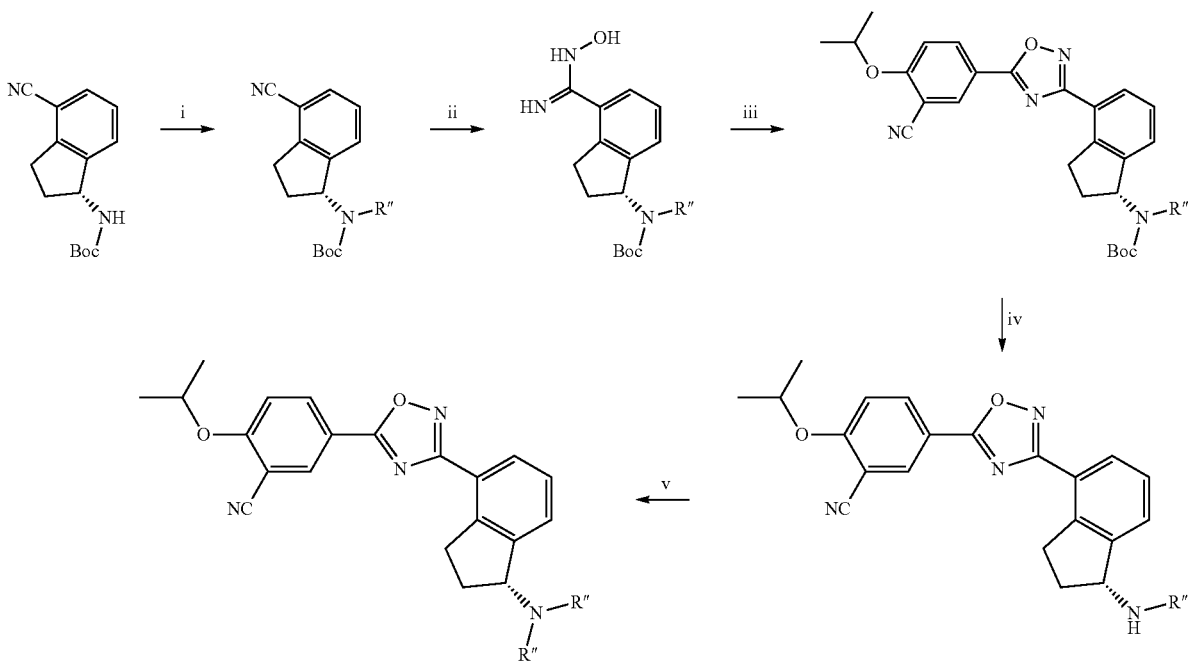

Reagents: (i) NaH, DMF, and R"-halide; (ii) NH$_2$OH*HCl or Na$_2$CO$_3$, TEA, EtOH; (iii) HOBt, EDC, substituted benzoic acid, DMF; (iv) 4M HCl in dioxane; (v) (a) R'-LG, TEA, DCM; (b) R$^1$—SO$_2$Cl or R$^3$—SO$_2$Cl, TEA, DCM; (c) R$^1$—COCl or R$^2$—COCl, TEA, DCM or R$^1$—CO$_2$H or R$^2$—CO$_2$H, HOBt, EDC, DMF or R$^1$—COCl or R$^2$—COCl, TEA, DCM; (d) R$^2$—CHO, HOAc, NaBH$_4$ or NaCNBH$_3$ or Na(OAc)$_3$BH, MeOH;

(a) If R' or R" contains an ester then (i) hydrolysis NaOH, EtOH or (ii) reduction NaBH$_4$, MeOH can be performed; (b) If R' or R" contains an acid then couplings H(R$^5$R$^5$), HOBt, EDC, DMF can be performed; (c) If R' or R" contains an appropriately activated alkene, then Michael additions HN(R$^5$R$^5$)DMF can be performed.

The (S)-enantiomer was prepared in the same manner outlined in Scheme 5 from (S)-tert-butyl 4-cyano-2,3-dihydro-1H-inden-1-ylcarbamate.

EXAMPLES

General Methods $^1$H NMR (400 MHz) and $^{13}$C NMR (100 MHz) were obtained in solution of deuteriochloroform (CDCl$_3$), deuteriomethanol (CD$_3$OD) or dimethyl sulfoxide-D$_6$ (DMSO). NMR spectra were processed using Mestrec 5.3.0 and 6.0.1. $^{13}$C NMR peaks that are bracketed are two rotomers of the same carbon. Mass spectra (LCMS) were obtained using an Agilent 1100/6110 HPLC system equipped with a Thompson ODS-A, 100A, 5μ (50λ4.6 mm) column using water with 0.1% formic acid as the mobile phase A, and acetonitrile with 0.1% formic acid as the mobile phase B. The gradient was 20-100% with mobile phase B over 2.5 min then held at 100% for 2.5 mins. The flow rate was 1 mL/min. Unless otherwise indicated, the LCMS data provided uses this method. For more hydrophobic compounds, the following gradient was used, denoted as Method 1: 40-95% over 0.5 min, hold at 95% for 8.5 min, then return to 40% over 2 min, with a flow rate of 1 mL/min. Final compounds were checked for purity using Method 2:5% for 1 min, 5-95% over 9 min, then hold at 95% for 5 min, with a flow rate of 1 mL/min. Enantiomeric excess was determined by integration of peaks that were separated on a Chiralpak AD-H, 250×4.6 mm column, 5 μm particle size. Flow rate of 1 mL/min and an isocratic mobile phase. Unless otherwise indicated, the chiral data provided uses this method. Alternatively, chiral separations were performed under the following conditions, denoted as Chiral Method 1: Chiralpak AY-H, 250×4.6 mm column, 5 μm particle size. Flow rate of 1 mL/min and an isocratic mobile phase. Chiral Method 2: Chiralcel OZ-3, 250×4.6, 3 μm particle size at a flow rate of 0.75 ml/min. The pyridine, dichloromethane (DCM), tetrahydrofuran (THF), and toluene used in the procedures were from Aldrich Sure-Seal bottles kept under nitrogen (N$_2$). All reactions were stirred magnetically and temperatures are external reaction temperatures. Chromatographies were carried out using a Combiflash Rf flash purification system (Teledyne Isco) equipped with Redisep (Teledyne Isco) silica gel (SiO$_2$) columns. Preparative HPLC purifications were done on Varian ProStar/PrepStar system using water containing 0.05% trifluoroacetic acid as mobile phase A, and acetonitrile with 0.05% trifluoroacetic acid as mobile phase B. The gradient was 10-80% with mobile phase B over 12 min, hold at 80% for 2 min, and then return to 10% over 2 min with flow rate of 22 mL/min. Other methods similar to this may have been employed. Fractions were collected using a Varian Prostar fraction collector and were evaporated using a Savant SpeedVac Plus vacuum pump. Compounds with salt-able centers were presumed to be the trifluoroacetic acid (TFA) salt. Microwave heating was performed using a Biotage Initiator microwave reactor equipped with Biotage microwave vessels. The following abbreviations are used: ethyl acetate (EA), triethylamine (TEA), diethyl amine (DEA), hydroxybenzotriazole (HOBt), 1-ethyl-3-(3-dimethylaminopropyl) carbodiimide hydrochloride (EDC), isopropanol (IPA), dimethylformamide (DMF), dimethyl acetamide (DMA). Norit is activated charcoal.

Experimental Procedures 1-oxo-2,3-dihydro-1H-indene-4-carbonitrile (INT-1)

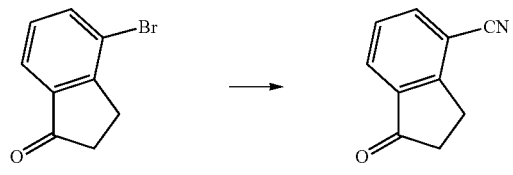 [SMILES: O=C1CCc2c(Br)cccc21 ; N#Cc1cccc2c1CCC2=O]

To a stirred solution of 4-bromo-2,3-dihydro-1H-inden-1-one (100.0 g, 0.48 mol) in 150 mL of 1-methy-2-pyrrolidine (NMP) was added zinc cyanide (111.8 g, 0.95 mol) and tetrakis(triphenylphosphine)palladium [Pd(PPh$_3$)$_4$] (2.75 g, 0.024 mol). The solution was degassed with N$_2$ and the reaction mixture heated at 95° C. for 7 h. Upon cooling, the reaction mixture was poured onto ice water (3.5 L). The compound and inorganic Zn salts precipitated. The solid was collected and partitioned between DCM (3λ100 mL) and water. The organic layers were filtered to remove the Zn salts, and the filtrate was concentrated and crystallized from a 4:1 mixture of EtOH and MeOH (400 mL) to give 45.5 g (60%) of 1-oxo-2,3-dihydro-1H-indene-4-carbonitrile INT-1 as a light yellow solid. LCMS-ESI (m/z) calculated for C$_{10}$H$_7$NO: 157.2. found 158.1 [M+H]$^+$, t$_R$=2.67 min. $^1$H NMR (400 MHz, CDCl$_3$) δ 8.00-7.90 (m, 1H), 7.86 (dd, J=7.5, 1.1, 1H), 7.50 (t, J=7.6, 1H), 3.40-3.19 (m, 2H), 2.90-2.61 (m, 2H). $^{13}$C NMR (101 MHz, CDCl$_3$) δ 204.70, 157.90, 138.38, 137.88, 128.44, 128.28, 116.31, 111.70, 36.01, 25.49.

(S)-1-hydroxy-2,3-dihydro-1H-indene-4-carbonitrile (INT-2)

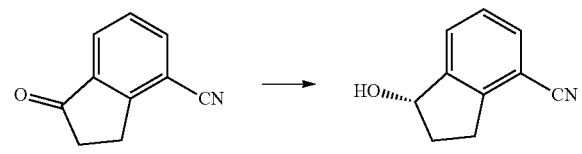 [SMILES: N#Cc1cccc2c1CCC2=O ; N#Cc1cccc2c1CC[C@@H]2O]

To a 3-neck flask with an internal thermometer and an addition funnel was added (R)-(+)-2-methyl-CBS-oxazaborolidine solution in toluene (3.0 mL) and borane-dimethylsulfide (300 μL). The reaction was stirred at room temperature for 10 min then diluted with DCM (25 mL). Borane-dimethylsulfide (6.0 mL) was added and, after stirring for 5 min, the reaction was cooled to −20° C. 1-Oxo-2,3-dihydro-1H-indene-4-carbonitrile INT-1 (4.7 g, 30 mmol) in DCM (25 mL) was added dropwise by addition funnel over 20 min while maintaining the reaction at −20±5° C. The reaction was stirred for 1 h then quenched by the dropwise addition of MeOH (20 mL). After hydrogen evolution ceased, MeOH (30 mL) was added and removed by heating at atmospheric pressure. MeOH (50 mL) was added in two and removed by heating twice. All the solvent was evaporated to give a solid which was recrystallized from EA (9 mL) and hexane (22 mL). The compound was filtered and washed with 5:1 hexane/EA (30 mL) to provide 3.73 g (78%) of (S)-1-hydroxy-2,3-dihydro-1H-indene-4-carbonitrile INT-2 as a white powder. LCMS-ESI (m/z) calculated for $C_{10}H_9NO$: 159.1. found 160.1 [M+H]$^+$, $t_R$=2.39 min. $^1$H NMR (400 MHz, CDCl$_3$) δ 7.62 (d, J=7.6 Hz, 1H), 7.53 (d, J=7.6 Hz, 1H), 7.32 (t, J=7.6 Hz, 1H), 5.28 (d, J=4.1 Hz, 1H), 3.23 (ddd, J=17.0, 8.7, 4.4 Hz, 1H), 3.04-2.90 (m, 1H), 2.64-2.51 (m, 1H), 2.00 (dddd, J=13.4, 8.7, 7.1, 5.7 Hz, 1H), 1.91 (d, J=5.4 Hz, 1H). Chiral HPLC: (S)-1-hydroxy-2,3-dihydro-1H-indene-4-carbonitrile was eluted in 20% IPA in hexane: >99.9% ee, $t_R$=7.42 min. The (R)-enantiomer was obtained in an analogous fashion using (S)-(−)-2-methyl-CBS-oxazaborolidine. $t_R$ for (R)-enantiomer=6.79 min.

(+/−)
1-hydroxy-2,3-dihydro-1H-indene-4-carbonitrile

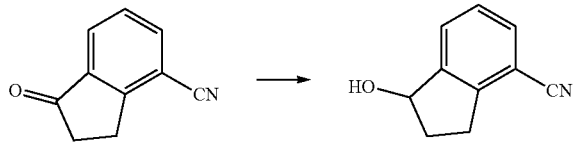 [SMILES: N#Cc1cccc2c1CCC2=O ; N#Cc1cccc2c1CCC2O]

To a stirred suspension of 1-oxo-2,3-dihydro-1H-indene-4-carbonitrile (1.2 g, 7.64 mmol) and silica gel (catalytic) in EtOH at 0° C. was added NaBH$_4$ (237.2 mg, 7.64 mmol). The reaction was allowed to warm to room temperature and stirred for 2 h. The solvent was removed under reduced pressure, and the product was purified by chromatography (50% EA/hexane) to afford 1.02 g (82.3%) of 1-hydroxy-2,3-dihydro-1H-indene-4-carbonitrile as white solid. LCMS-ESI (m/z) calculated for $C_{10}H_9NO$; 159.18. found 160.1 [M+H]$^+$, $t_R$=2.39 min.

(S)-N,1-dihydroxy-2,3-dihydro-1H-indene-4-carboximidamide (INT-3)

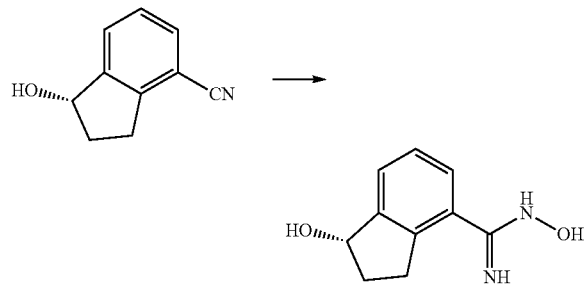

To hydroxylamine hydrochloride (0.87 g, 12.5 mmol) and sodium carbonate (1.32 g, 12.5 mmol) in EtOH (20 mL) was added (S)-1-hydroxy-2,3-dihydro-1H-indene-4-carbonitrile INT-2 (1.59 g, 10 mmol) in one portion and the solution was heated to reflux. After 16 h, the reaction was cooled and filtered to remove the solids. The EtOH was removed and the compound purified by chromatography (MeOH/DCM) to give 1.74 g (90%) of (S)-N,1-dihydroxy-2,3-dihydro-1H-indene-4-carboximidamide INT-3 as a white foam. LCMS-ESI (m/z) calculated for $C_{10}H_{12}N_2O_2$: 192.1. found: 193.1 [M+H]$^+$, $t_R$=0.56 min. $^1$H NMR (400 MHz, MeOD) δ 10.30 (s, 1H), 9.97 (s, 1H), 7.72-7.58 (m, 1H), 7.46-7.37 (m, 2H), 5.22 (t, J=6.5, 1H), 3.17-3.03 (m, 1H), 2.99-2.83 (m, 1H), 2.49 (dddd, J=11.4, 8.0, 7.0, 4.4, 1H), 2.02-1.88 (m, 1H). (R)-N,1-dihydroxy-2,3-dihydro-1H-indene-4-carboximidamide is made in an analogous fashion from (R)-1-hydroxy-2,3-dihydro-1H-indene-4-carbonitrile.

General Procedure 1. Preparation of Indanols

To the benzoic acid (1 eq) in DMF (0.15 M) was added HOBt (1.5 eq) and EDC (1.5 eq). The reaction was stirred at room temperature for 2-16 h until the acid was fully activated. (R)- or (S)-N,1-dihydroxy-2,3-dihydro-1H-indene-4-carboximidamide was added in one portion and the reaction was stirred at room temperature for 2 h until complete formation of the pre-cyclized intermediate. The reaction mixture was then heated to 85° C. for 18 h. The reaction mixture was cooled to room temperature and water was added and the mixture was allowed to stand. The resulting precipitate was filtered. The material was purified by chromatography (EA/hexane) or recrystallized to give the 5-(3-(1-hydroxy-2,3-dihydro-1H-inden-4-yl)-1,2,4-oxadiazol-5-yl)-benzenes as white solids.

Compounds 1-12 were prepared using General Procedure 1.

(S)-5-(3-(1-hydroxy-2,3-dihydro-1H-inden-4-yl)-1,2,4-oxadiazol-5-yl)-2-isopropoxy-benzonitrile (Compound 6)

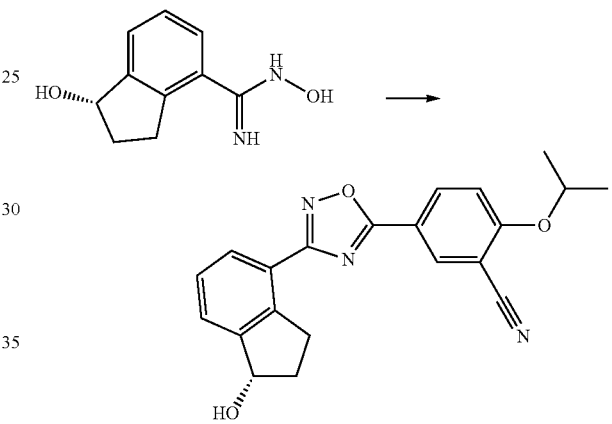

Prepared using General Procedure 1. To 3-cyano-4-isopropoxybenzoic acid (93.2 mg, 0.45 mmol) in DMF (3 mL) was added HOBt (104.3 mg, 0.68 mmol) and EDC (130.6 mg, 0.68 mmol). The reaction was stirred at room temperature for 16 h until the acid was fully activated. (S)-N,1-dihydroxy-2,3-dihydro-1H-indene-4-carboximidamide INT-2 (97 mg, 0.5 mmol) was added in one portion and the reaction was stirred at room temperature for 2 h. The crude material was heated to 85° C. for 18 h. The reaction mixture was cooled to room temperature. Water (15 mL) was added and the mixture was allowed to stand and the dark brown precipitate was filtered. The precipitate was purified by silica gel chromatography (EA/hexane) to give 73 mg (40%) of (S)-5-(3-(1-hydroxy-2,3-dihydro-1H-inden-4-yl)-1,2,4-oxadiazol-5-yl)-2-isopropoxybenzonitrile 6 as a white solid. LCMS-ESI (m/z) calculated for $C_{21}H_{19}N_3O_3$: 361.1. found 362.1 [M+H]$^+$, $t_R$=3.63 min. $^1$H NMR (400 MHz, CDCl$_3$) δ 8.46 (d, J=2.1, 1H), 8.36 (dd, J=8.9, 2.2, 1H), 8.16 (dd, J=7.7, 0.5, 1H), 7.63 (d, J=7.5, 1H), 7.46 (t, J=7.6, 1H), 7.15 (d, J=9.0, 1H), 5.36 (dd, J=12.6, 6.8, 1H), 4.82 (hept, J=6.1, 1H), 3.54 (ddd, J=17.5, 8.7, 4.6, 1H), 3.31-3.18 (m, 1H), 2.63 (dddd, J=13.2, 8.4, 7.1, 4.7, 1H), 2.07 (dddd, J=14.1, 8.7, 6.6, 5.5, 1H), 1.84 (d, J=7.1, 1H), 1.50 (d, J=6.1, 6H). $^{13}$C NMR (101 MHz, DMSO) δ 173.07, 168.30, 162.46, 148.27, 142.29, 134.57, 133.77, 127.53, 127.28, 127.05, 122.26, 116.00, 115.25, 114.87, 102.43, 74.05, 72.49, 35.03, 30.80, 21.46. Chiral HPLC: (S)-5-(3-(1-hydroxy-2,3-dihydro-1H-inden-4-yl)-1,2,4-oxadiazol-5-yl)-2-isopropoxybenzonitrile was eluted with 20% IPA in hexane: >99.9% ee, $t_R$=25.07 min. (R)-5-(3-(1-hydroxy-2,3-dihydro-1H-inden-4-yl)-1,2,4-oxadiazol-5-yl)-2-isopropoxybenzonitrile 5 and racemic material were obtained in an analogous fashion from (R)-1-hydroxy-2,3-dihydro-1H-indene-4-carbonitrile and racemic 1-hydroxy-2,3-dihydro-1H-indene-4-carbonitrile respectively using General Procedure 1. $t_R$ for (R)-enantiomer=17.60 min.

(R)-4-(5-(3-cyano-4-isopropoxyphenyl)-1,2,4-oxadiazol-3-yl)-2,3-dihydro-1H-inden-1-yl acetate (Compound 13)

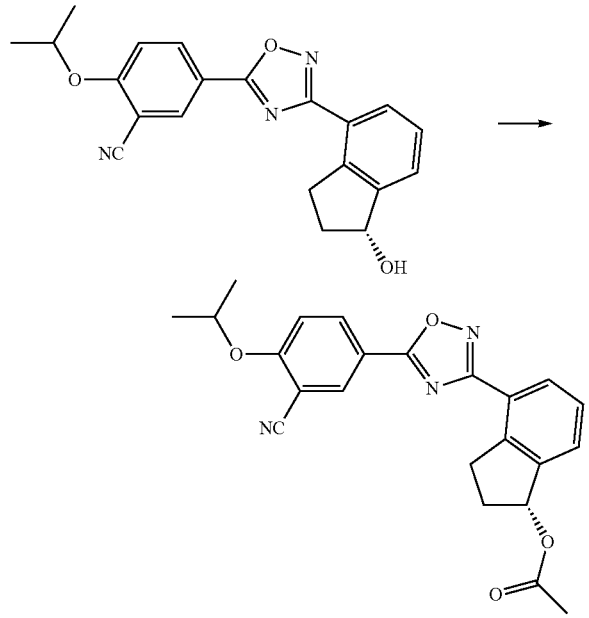

To a flask containing (R)-5-(3-(1-hydroxy-2,3-dihydro-1H-inden-4-yl)-1,2,4-oxadiazol-5-yl)-2-isopropoxybenzonitrile 5 (36 mg, 0.10 mmol) in DCM (1 mL) was added pyridine (24 µL, 0.3 mmol) and acetyl chloride (21 µL, 0.3 mmol). The reaction was stirred at room temperature for 4 days. The crude reaction mixture was washed with saturated sodium bicarbonate, dried over magnesium sulfate, and purified by chromatography (EA/hexane) to give 37 mg (92%) of (R)-4-(5-(3-cyano-4-isopropoxyphenyl)-1,2,4-oxadiazol-3-yl)-2,3-dihydro-1H-inden-1-yl acetate 13 as a white solid. LCMS-ESI (m/z) calculated for $C_{23}H_{21}N_3O_4$: 403.2. found 426.1 [M+Na]$^+$, $t_R$=4.19 min. $^1$H NMR (400 MHz, CDCl$_3$) δ 8.37 (d, J=2.1, 1H), 8.27 (dd, J=8.9, 2.2, 1H), 8.10 (dd, J=7.7, 0.9, 1H), 7.53 (d, J=7.4, 1H), 7.35 (t, J=7.7, 1H), 7.06 (d, J=9.0, 1H), 6.21 (dd, J=7.2, 3.7, 1H), 4.73 (hept, J=6.1, 1H), 3.44 (ddd, J=17.5, 8.3, 6.3, 1H), 3.26 (ddd, J=17.6, 8.7, 4.8, 1H), 2.52 (tdd, J=14.9, 7.9, 6.3, 1H), 2.21-2.06 (m, 1H), 2.02 (s, 3H), 1.41 (d, J=6.1, 6H).

(R)-4-(5-(3-cyano-4-isopropoxyphenyl)-1,2,4-oxadiazol-3-yl)-2,3-dihydro-1H-inden-1-yl pivalate (Compound 14)

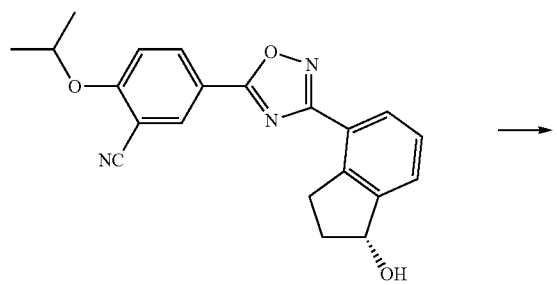

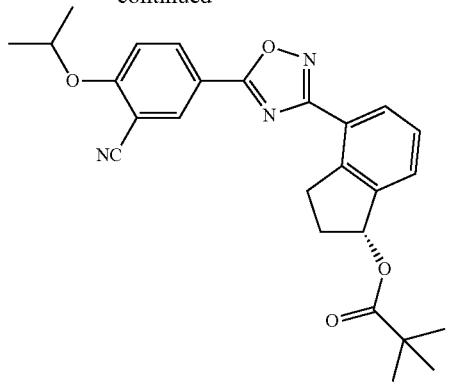

To a flask containing (R)-5-(3-(1-hydroxy-2,3-dihydro-1H-inden-4-yl)-1,2,4-oxadiazol-5-yl)-2-isopropoxybenzonitrile 5 (36 mg, 0.10 mmol) in DCM (1 mL) was added pyridine (24 µL, 0.3 mmol) and pivaloyl chloride (37 µL, 0.3 mmol). The reaction was stirred at room temperature for 4 days. The crude reaction mixture was washed with saturated sodium bicarbonate, dried over magnesium sulfate, and purified by chromatography (EA/hexane) to give 23 mg (52%) of (R)-4-(5-(3-cyano-4-isopropoxyphenyl)-1,2,4-oxadiazol-3-yl)-2,3-dihydro-1H-inden-1-yl pivalate 14 as a white solid. LCMS-ESI (m/z) calculated for $C_{26}H_{27}N_3O_4$: 445.2, $t_R$=4.7 min. $^1$H NMR (400 MHz, CDCl$_3$) δ 8.37 (d, J=2.2, 1H), 8.28 (dd, J=8.9, 2.2, 1H), 8.12-8.05 (m, 1H), 7.46 (d, J=7.4, 1H), 7.34 (t, J=7.6, 1H), 7.06 (d, J=9.0, 1H), 6.19 (dd, J=7.3, 4.6, 1H), 4.73 (hept, J=6.1, 1H), 3.44 (ddd, J=17.5, 8.7, 5.4, 1H), 3.24 (ddd, J=17.5, 8.6, 5.7, 1H), 2.56 (tdd, J=8.6, 7.4, 5.4, 1H), 2.12-1.99 (m, 1H), 1.41 (d, J=6.1, 6H), 1.14 (s, 9H).

General Procedure 2. Preparation of Indane Amines from Indanols

To a flask containing racemic 5-(3-(1-hydroxy-2,3-dihydro-1H-inden-4-yl)-1,2,4-oxadiazol-5-yl)-2-isopropoxybenzonitrile (1 eq) in DCM (0.14M) at 0° C. was added SOCl$_2$ (2 eq). After stirring for 30 min, the reaction mixture was concentrated in vacuo and placed under high vacuum for 2 h. The resulting crude chloride was dissolved in DMA (0.02M). The amine (3 eq), DIEA (3 eq), and in some cases NaBr (3 eq) were added and the resulting reactions were stirred at 55-60° C. overnight and purified either by preparative HPLC or column chromatography. If the amine contained a ether, the material could be further hydrolysed with NaOH to the acid. Diamines protected with Boc groups can be deprotected using TFA.

Compounds 15-48 were prepared using General Procedure 2.

5-(3-(1-((1-hydroxy-2-methylpropan-2-yl)amino)-2,3-dihydro-1H-inden-4-yl)-1,2,4-oxadiazol-5-yl)-2-isopropoxybenzonitrile (Compound 15)

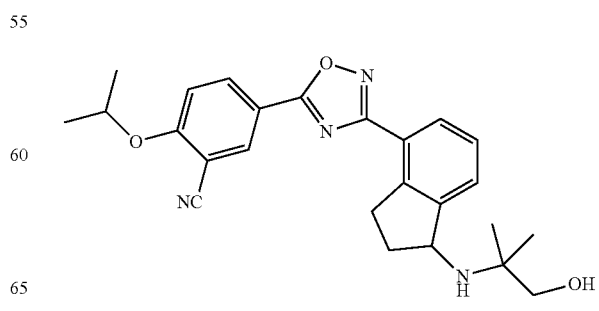

Prepared using General Procedure 2 from 2-amino-2-methylpropan-1-ol. LCMS-ESI (m/z) calculated for $C_{25}H_{28}N_4O_3$: 432.5. found 433.2 [M+H]$^+$, $t_R$=6.58 min (Method 2).

5-(3-(1-(4-hydroxypiperidin-1-yl)-2,3-dihydro-1H-inden-4-yl)-1,2,4-oxadiazol-5-yl)-2-isopropoxybenzonitrile (Compound 16)

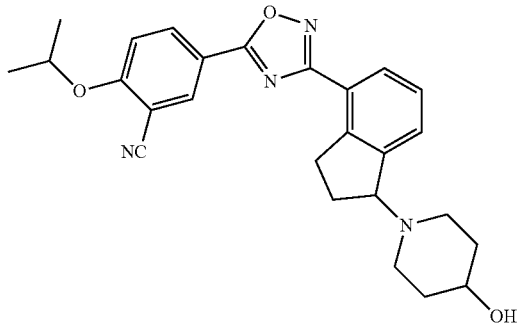 [SMILES: CC(C)Oc1ccc(-c2nc(-c3cccc4c3CCC4N3CCC(O)CC3)no2)cc1C#N]

Prepared using General Procedure 2 from piperidin-4-ol. LCMS-ESI (m/z) calculated for $C_{26}H_{28}N_4O_3$: 444.5. found 445.2 [M+H]$^+$, $t_R$=6.42 min (Method 2).

5-(3-(1-((1,3-dihydroxypropan-2-yl)amino)-2,3-dihydro-1H-inden-4-yl)-1,2,4-oxadiazol-5-yl)-2-isopropoxybenzonitrile (Compound 17)

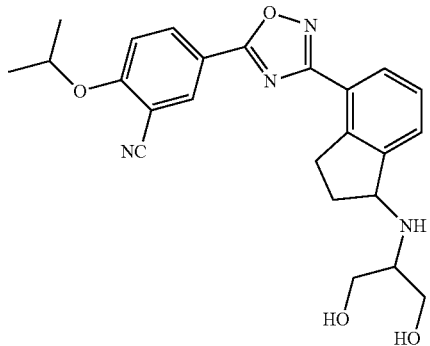 [SMILES: CC(C)Oc1ccc(-c2nc(-c3cccc4c3CCC4NC(CO)CO)no2)cc1C#N]

Prepared using General Procedure 2 from 2-aminopropane-1,3-diol. LCMS-ESI (m/z) calculated for $C_{24}H_{26}N_4O_4$: 434.5. found 435.2 [M+H]$^+$, $t_R$=6.24 min (Method 2).

Methyl 1-(4-(5-(3-cyano-4-isopropoxyphenyl)-1,2,4-oxadiazol-3-yl)-2,3-dihydro-1H-inden-1-yl)azetidine-3-carboxylate

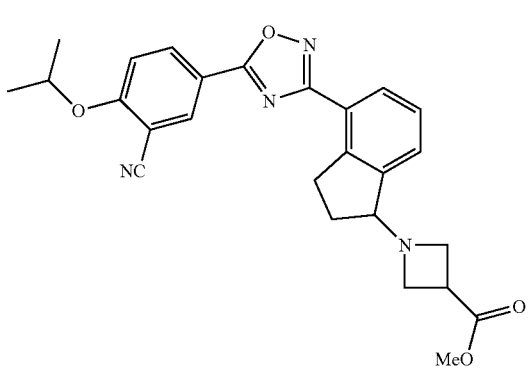 [SMILES: COC(=O)C1CN(C2CCc3c(-c4noc(-c5ccc(OC(C)C)c(C#N)c5)n4)cccc32)C1]

Prepared using General Procedure 2 from methyl azetidine-3-carboxylate. LCMS-ESI (m/z) calculated for $C_{26}H_{26}N_4O_4$: 458.4. found 459.2 [M+H]$^+$, $t_R$=2.64 min.

1-(4-(5-(3-cyano-4-isopropoxyphenyl)-1,2,4-oxadiazol-3-yl)-2,3-dihydro-1H-inden-1-yl)azetidine-3-carboxylic acid (Compound 18)

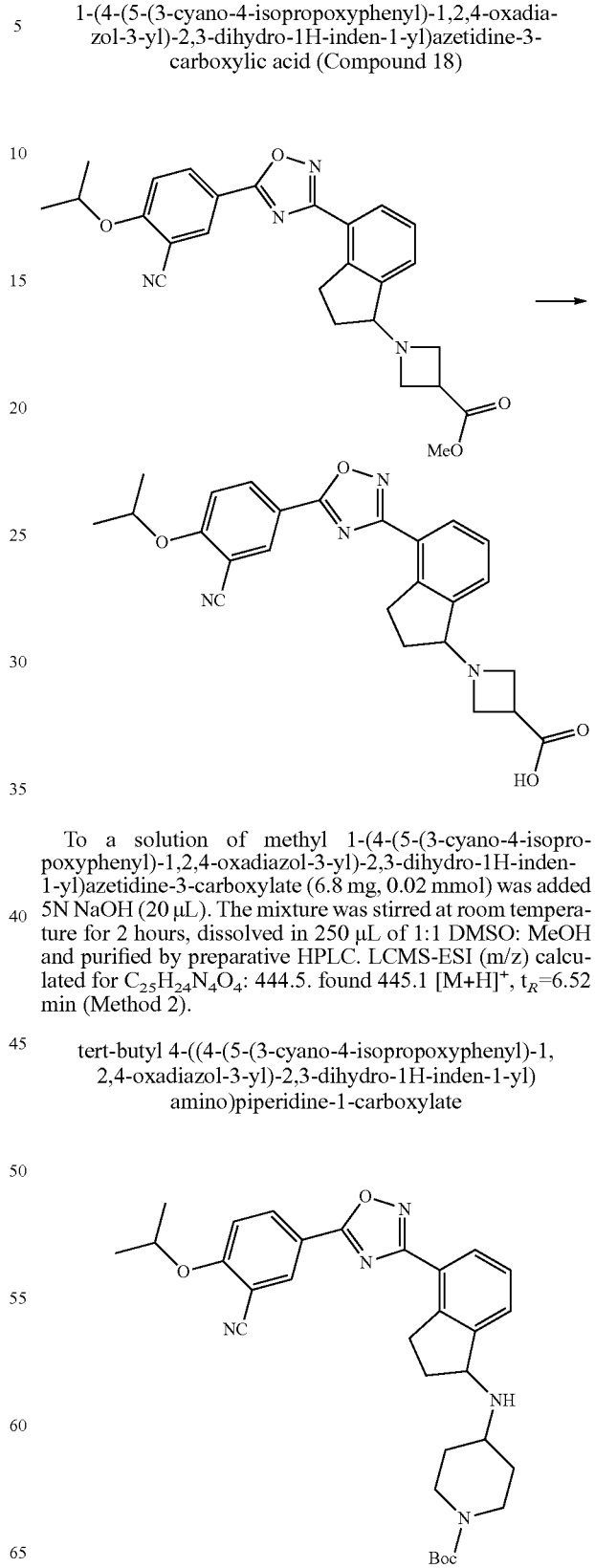

To a solution of methyl 1-(4-(5-(3-cyano-4-isopropoxyphenyl)-1,2,4-oxadiazol-3-yl)-2,3-dihydro-1H-inden-1-yl)azetidine-3-carboxylate (6.8 mg, 0.02 mmol) was added 5N NaOH (20 µL). The mixture was stirred at room temperature for 2 hours, dissolved in 250 µL of 1:1 DMSO: MeOH and purified by preparative HPLC. LCMS-ESI (m/z) calculated for $C_{25}H_{24}N_4O_4$: 444.5. found 445.1 [M+H]$^+$, $t_R$=6.52 min (Method 2).

tert-butyl 4-((4-(5-(3-cyano-4-isopropoxyphenyl)-1,2,4-oxadiazol-3-yl)-2,3-dihydro-1H-inden-1-yl)amino)piperidine-1-carboxylate

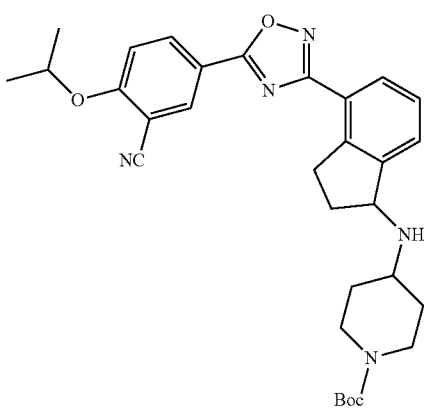 [SMILES: CC(C)Oc1ccc(-c2nc(-c3cccc4c3CCC4NC3CCN(C(=O)OC(C)(C)C)CC3)no2)cc1C#N]

Prepared using General Procedure 2 from tert-butyl 4-aminopiperidine-1-carboxylate. LCMS-ESI (m/z) calculated for $C_{31}H_{37}N_5O_4$: 543.7. found 544.3 $[M+H]^+$, $t_R$=2.82 min.

2-isopropoxy-5-(3-(1-(piperidin-4-ylamino)-2,3-dihydro-1H-inden-4-yl)-1,2,4-oxadiazol-5-yl)benzonitrile (Compound 19)

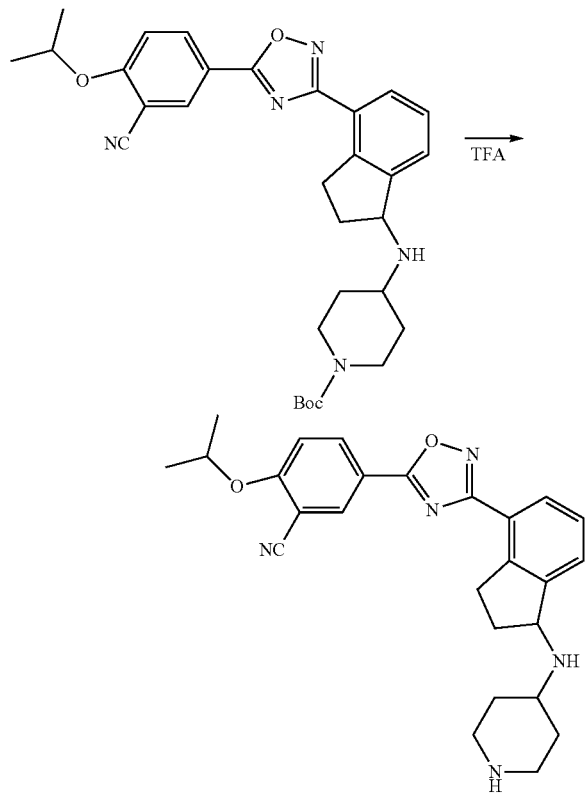

A solution of tert-butyl 4-((4-(5-(3-cyano-4-isopropoxyphenyl)-1,2,4-oxadiazol-3-yl)-2,3-dihydro-1H-inden-1-yl)amino)piperidine-1-carboxylate (15.7 mg, 0.03 mmol) in neat TFA (1 mL) was stirred for 30 min and concentrated to provide 12 mg (99%) of 2-isopropoxy-5-(3-(1-(piperidin-4-ylamino)-2,3-dihydro-1H-inden-4-yl)-1,2,4-oxadiazol-5-yl)benzonitrile. LCMS-ESI (m/z) calculated for $C_{26}H_{29}N_5O_2$: 443.5. found 444.2 $[M+H]^+$, $t_R$=5.31 min (Method 2).

2-((4-(5-(3-cyano-4-isopropoxyphenyl)-1,2,4-oxadiazol-3-yl)-2,3-dihydro-1H-inden-1-yl)amino)-N-methylethanesulfonamide (Compound 45)

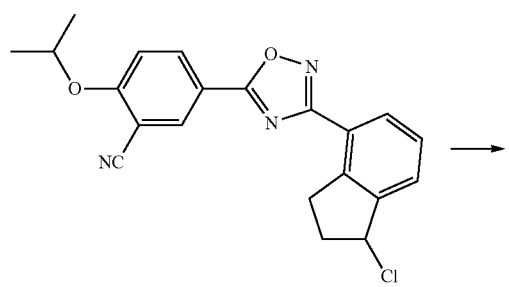

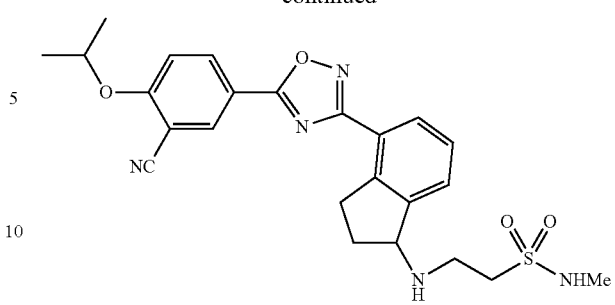

Prepared using General Procedure 2. 5-(3-(1-chloro-2,3-dihydro-1H-inden-4-yl)-1,2,4-oxadiazol-5-yl)-2-isopropoxy-benzonitrile (152 mg, 0.4 mmol) was dissolved in DMA (2 mL) and treated with 2-amino-N-methylethanesulfamide hydrochloride (209 mg, 1.2 mmol), sodium bromide (123 mg, 1.2 mmol), and diisopropylethylamine (210 µL, 1.2 mmol). The reaction mixture was heated to 60° C. for 24 h. The crude reaction mixture was poured into water (30 mL) and the resultant precipitate was collected and purified by chromatography (EA/hexane then MeOH/DCM) to give 30 mg (16%) of 2-((4-(5-(3-cyano-4-isopropoxyphenyl)-1,2,4-oxadiazol-3-yl)-2,3-dihydro-1H-inden-1-yl)amino)-N-methylethane sulfonamide 45 as a brown oil. LCMS-ESI (m/z) calculated for $C_{24}H_{27}N_5O_4S$: 481.2. found 482.1 $[M+H]^+$, $t_R$=2.56 min. $^1H$ NMR (400 MHz, CDCl$_3$) δ 8.40 (d, J=2.2 Hz, 1H), 8.31 (dd, J=8.9, 2.2 Hz, 1H), 8.06 (d, J=7.4 Hz, 1H), 7.46 (d, J=7.5 Hz, 1H), 7.37 (t, J=7.6 Hz, 1H), 7.10 (d, J=9.0 Hz, 1H), 4.77 (hept, J=12.1, 6.1 Hz, 1H), 4.32 (t, J=6.6 Hz, 1H), 3.43 (ddd, J=17.4, 8.6, 4.9 Hz, 1H), 3.32-3.11 (m, 5H), 2.77 (s, 3H), 2.52-2.42 (m, 1H), 1.98-1.83 (m, 1H), 1.45 (d, J=6.1 Hz, 6H). $^{13}C$ NMR (101 MHz, CDCl$_3$) δ 173.22, 169.08, 162.93, 146.06, 143.70, 134.27, 134.09, 128.46, 127.25, 126.91, 123.50, 116.98, 115.49, 113.75, 104.03, 72.93, 63.12, 50.70, 41.86, 33.05, 32.02, 29.43, 21.91.

(R)-N-(4-cyano-2,3-dihydro-1H-indene-1-ylidene)-2-methylpropane-2-sulfinamide (INT-4)

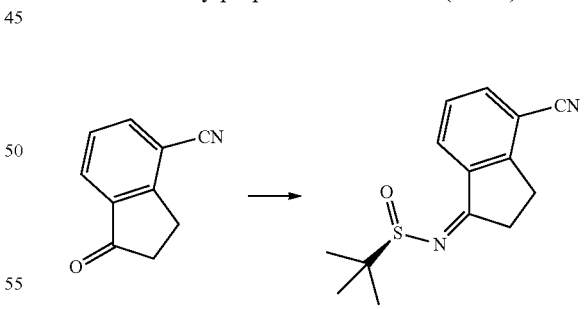

To 1-oxo-2,3-dihydro-1H-indene-4-carbonitrile INT-1 (42.5 g, 0.27 mol) and (R)-2-methylpropane-2-sulfinamide (36.0 g, 0.30 mol) in toluene (530 mL) was added titanium tetraethoxide (84.1 mL, 92.5 g, 0.40 mol) and the reaction mixture was heated at 60° C. for 12 h under N$_2$. The crude (R)-N-(4-cyano-2,3-dihydro-1H-inden-1-ylidene)-2-methylpropane-2-sulfinamide INT-4 was used directly in the next experiment. LCMS-ESI (m/z) calculated for $C_{14}H_{16}N_2OS$: 260.3. found 261.1 $[M+H]^+$, $t_R$=3.19 min.

(R)-N-((R)-4-cyano-2,3-dihydro-1H-inden-1-yl)-2-methylpropane-2-sulfinamide (INT-5)

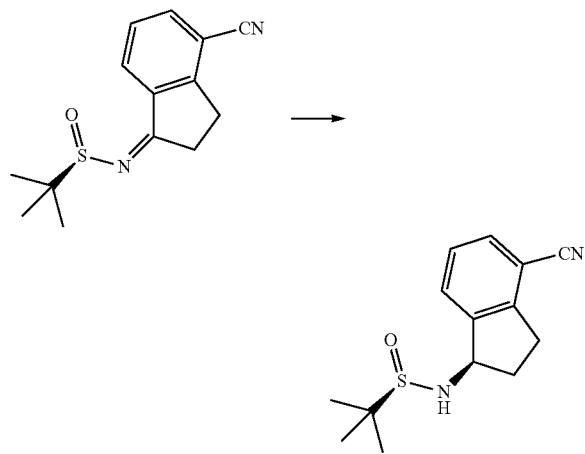

To a flask containing the crude suspension of (R)-N-(4-cyano-2,3-dihydro-1H-inden-1-ylidene)-2-methylpropane-2-sulfinamide INT-4 under $N_2$ was added THF (1.0 L) and the reaction mixture cooled to −78° C. Sodium borohydride (40.9 g, 1.08 mol) was added portion-wise over 30 mins. (The internal temperature did not rise during the addition). The reaction mixture was stirred at −78° C. for 30 mins, half out of the bath for 30 mins, then warmed to 0° C. over 1 h. The 0° C. reaction mixture was placed in an ice bath and quenched with brine (100 mL) followed by saturated sodium potassium tartrate (420 mL) and the Ti salts precipitated. The reaction mixture was diluted with EA (1.5 L) and stirred at room temperature overnight. The organic layers were decanted and washed successively with saturated $NH_4Cl$, water, and brine. The organic layers were dried over $MgSO_4$ and filtered through a pad of $MgSO_4$. The filtrate was concentrated to produce 52.9 g of crude (R)—N—((R)-4-cyano-2,3-dihydro-1H-inden-1-yl)-2-methylpropane-2-sulfinamide INT-5 as a brown oil, which was used directly in the next step. LCMS-ESI (m/z) calculated for $C_{14}H_{18}N_2OS$: 262.3. found 263.1 $[M+H]^+$, $t_R$=2.99 min. $^1H$ NMR (400 MHz, $CDCl_3$) δ 7.89 (d, J=7.7, 1H), 7.56 (t, J=6.8, 1H), 7.36 (t, J=7.7, 1H), 4.97 (q, J=7.5, 1H), 3.50 (d, J=7.6, 1H), 3.22 (ddd, J=16.9, 8.8, 3.9, 1H), 3.01 (dt, J=22.4, 6.9, 1H), 2.70-2.53 (m, 1H), 2.15-1.95 (m, 1H), 1.33-1.20 (m, 9H).

(R)-1-amino-2,3-dihydro-1H-inden-1-yl)-4-carbonitrile (INT-6)

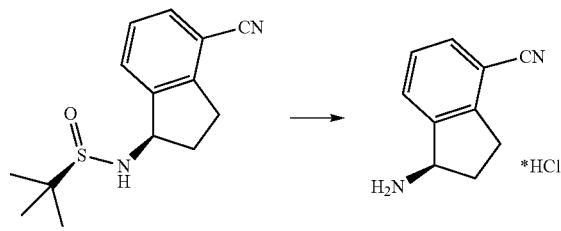 [SMILES: CC(C)(C)[S@@](=O)N[C@@H]1CCc2c(C#N)cccc21 ; N#Cc1cccc2c1CC[C@H]2N]

To crude (R)—N—((R)-4-cyano-2,3-dihydro-1H-inden-1-yl)-2-methylpropane-2-sulfinamide INT-5 (52.9 g, 0.20 mol) in MeOH (200 mL) was added 4N HCl in dioxane (152.0 mL, 0.60 mol) and the resulting yellow suspension was stirred at room temperature for 1.5 h. The crude reaction mixture was diluted with MeOH (500 mL) and filtered to remove some Ti by-products. The filtrate was concentrated and the resulting solid refluxed in acetonitrile (500 mL). The resulting white solid was collected to produce 13.0 g (31% over 3 steps) of the HCl salt of (R)-1-amino-2,3-dihydro-1H-indene-1-yl)-4-carbonitrile INT-6. LCMS-ESI (m/z) calculated for $C_{10}H_{10}N_2$: 158.2. found 142.0 $[M-NH_2]^+$, $t_R$=0.84 min. $^1H$ NMR (400 MHz, DMSO) δ 8.61 (s, 3H), 7.96 (d, J=7.7, 1H), 7.83 (d, J=7.5, 1H), 7.52 (t, J=7.7, 1H), 4.80 (s, 1H), 3.23 (ddd, J=16.6, 8.7, 5.2, 1H), 3.05 (ddd, J=16.6, 8.6, 6.3, 1H), 2.62-2.51 (m, 1H), 2.15-2.01 (m, 1H). $^{13}C$ NMR (101 MHz, DMSO) δ 148.09, 141.15, 132.48, 130.32, 127.89, 117.27, 108.05, 54.36, 39.08, 29.64. The free base can be prepared by extraction with 1N $NaHCO_3$ and DCM. LCMS-ESI (m/z) calculated for $C_{10}H_{10}N_2$: 158.2. found 142.0 $[M-NH_2]^+$, $t_R$=0.83 min. $^1H$ NMR (400 MHz, $CDCl_3$) δ 7.52-7.38 (m, 2H), 7.23 (dd, J=17.4, 9.8, 1H), 4.35 (t, J=7.6, 1H), 3.11 (ddd, J=16.8, 8.7, 3.2, 1H), 2.89 (dt, J=16.9, 8.5, 1H), 2.53 (dddd, J=12.8, 8.1, 7.3, 3.2, 1H), 1.70 (dtd, J=12.8, 8.8, 8.0, 1H). $^{13}C$ NMR (101 MHz, DMSO) δ 150.16, 146.67, 130.19, 128.74, 127.38, 117.77, 107.42, 56.86, 38.86, 29.14. Chiral HPLC: (R)-1-amino-2,3-dihydro-1H-inden-1-yl)-4-carbonitrile was eluted using 5% EtOH in hexanes, plus 0.05% TEA: 95% ee, $t_R$=23.02 min. The (S)-enantiomer INT-7 was prepared in an analogous fashion using (S)-2-methylpropane-2-sulfinamide. $t_R$ for (S)-enantiomer=20.17 min.

(R)-tert-butyl 4-cyano-2,3-dihydro-1H-inden-1-ylcarbamate (INT-8)

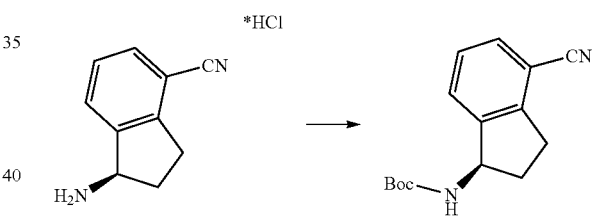

To (R)-1-amino-2,3-dihydro-1H-inden-1-yl)-4-carbonitrile HCl INT-6 (11.6 g, 59.6 mmol) in DCM (100 mL) at 0° C. was added TEA (12.0 mL, 131.0 mmol). To the resulting solution was added a solution of Boc anhydride (14.3 g, 65.6 mmol) in DCM (30 mL) and the reaction mixture stirred at room temperature for 1.5 h. The reaction mixture was washed with brine, and the organic layers were dried over $MgSO_4$ and filtered. Additional DCM was added to a total volume of 250 mL and Norit (4.5 g) was added. The product was refluxed for 15 mins and the hot mixture filtered through a pad of celite/silica. The filtrate was concentrated and recrystallized from EA (50 mL) and hexane (150 mL) to produce 12.93 g (84%) of (R)-tert-butyl 4-cyano-2,3-dihydro-1H-inden-1-ylcarbamate INT-8 as an off-white solid. LCMS-ESI (m/z) calculated for $C_{15}H_{18}N_2O_2$: 258.3. found 281.1 $[M+Na]^+$, $t_R$=3.45 min. Elemental Analysis determined for $C_{15}H_{18}N_2O_2$; C calculated=69.74%. found=69.98%. H calculated=7.02%. found=7.14%. N calculated=10.84%. found=10.89%. $^1H$ NMR (400 MHz, $CDCl_3$) δ 7.64-7.49 (m, 2H), 7.34 (dt, J=7.7, 3.8, 1H), 5.36-5.20 (m, 1H), 4.78 (d, J=6.8, 1H), 3.20 (ddd, J=16.9, 8.9, 3.3, 1H), 3.02 (dt, J=25.4, 8.4, 1H), 2.82-2.53 (m, 1H), 1.88 (dq, J=13.2, 8.6, 1H), 1.55-1.44 (m, 9H). $^{13}C$ NMR (101 MHz, DMSO) δ 155.52, 146.68, 146.32, 130.89, 128.70, 127.63, 117.51, 107.76, 77.98, 55.09, 31.88, 29.11, 28.19. Chiral HPLC: (R)-tert-butyl 4-cyano-2,3-dihydro-1H-inden-1-ylcarbamate was eluted using 2.5% EtOH in hexanes: >99.9% ee, $t_R$=19.36 min. The (S)-enantiomer INT-9 was prepared in an analogous fashion using (S)-1-amino-2,3-dihydro-1H-indene-1-yl)-4-carbonitrile HCl. $t_R$ for (S)-enantiomer=28.98 min.

General Procedure 3. Preparation of Indane Amide Oximes

To (R)- or (S)-tert-butyl 4-cyano-2,3-dihydro-1H-inden-1-ylcarbamate (1 eq) in EtOH (0.56 M) was added hydroxylamine hydrochloride (3 eq) and TEA (3 eq) and the reaction mixture heated at 85° C. for 1-2 h. The organic soluble amide oximes were isolated by removal of the solvent and partitioning between water and DCM. The water soluble amide oximes were chromatographed or used directly in the cyclization. Pure amide oximes can be obtained by recrystallization from alcoholic solvents.

(R)-tert-butyl 4-(N-hydroxycarbamimidoyl)-2,3-dihydro-1H-inden-1-ylcarbamate (INT-10)

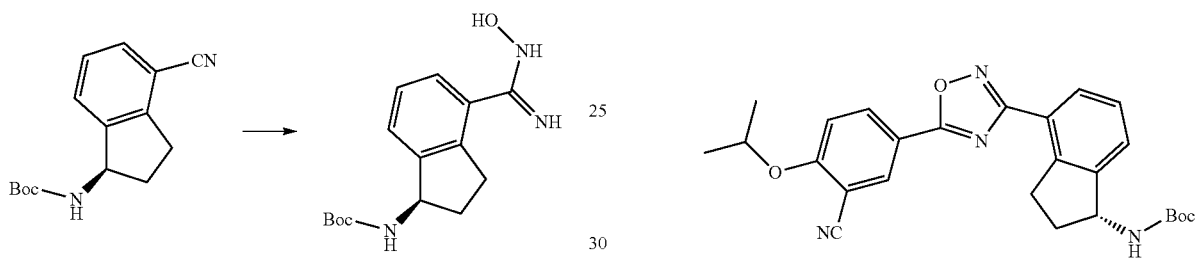

Prepared using General Procedure 3. To (R)-tert-butyl 4-cyano-2,3-dihydro-1H-inden-1-ylcarbamate INT-8 (15.0 g, 58.2 mmol) in EtOH (100 mL) was added hydroxylamine hydrochloride (12.1 g, 174.2 mmol) and TEA (17.6 mL, 174.2 mmol) and the reaction mixture heated at 85° C. for 2 h. The solvents were removed and the resulting white solid was partitioned between water and DCM. The organic layers were dried over $Na_2SO_4$, concentrated, and recrystallized from isopropanol (50 mL) to afford 14.4 g (85%) of (R)-tert-butyl 4-(N-hydroxycarbamimidoyl)-2,3-dihydro-1H-inden-1-ylcarbamate INT-10 as white crystalline solid. LCMS-ESI (m/z) calculated for $C_{15}H_{21}N_3O_3$: 291.4. found 292.1 [M+H]$^+$, $t_R$=2.04 min. $^1$H NMR (400 MHz, DMSO) δ 9.53 (s, 1H), 7.38-7.32 (m, 1H), 7.32-7.12 (m, 3H), 5.68 (s, 2H), 4.97 (q, J=8.5, 1H), 3.07 (ddd, J=16.6, 8.7, 2.6, 1H), 2.86 (dt, J=16.8, 8.4, 1H), 2.30 (ddd, J=12.6, 7.6, 3.6, 1H), 1.75 (dq, J=12.3, 9.0, 1H), 1.44 (s, 9H).

General Procedure 4. Cyclization to Indane Oxadiazole Amines

A solution of the appropriate acid (1 eq), HOBt (1.3 eq), and EDC (1.3 eq) in DMF (0.08 M in acid) was stirred at room temperature under an atmosphere of $N_2$. After the complete formation of the HOBt-acid complex (1-3 h), the (R)- or (S)-amide oxime (1.1 eq) was added to the mixture. After complete formation of the coupled intermediate (ca. 0.5-2 h), the mixture was heated to 75-95° C. until the cyclization was complete (8-12 h). The reaction mixture was diluted with saturated $NaHCO_3$ and extracted with EA. The combined organic extracts were dried, concentrated, and either purified by chromatography (EA/hexanes) or taken on directly. The oxadiazole was treated with HCl (5N in dioxane, 5 eq) at 50-60° C. for 0.5-6 h. The reaction mixture could be extracted (DCM/$NaHCO_3$), or the resulting HCl salt concentrated, suspended in $Et_2O$, and collected. Pure indane amines can be obtained by recrystallization from alcoholic solvents or by chromatography.

(R)-tert-butyl 4-(5-(3-cyano-4-isopropoxyphenyl)-1, 2,4-oxadiazol-3-yl)-2,3-dihydro-1H-inden-1-ylcarbamate (INT-12)

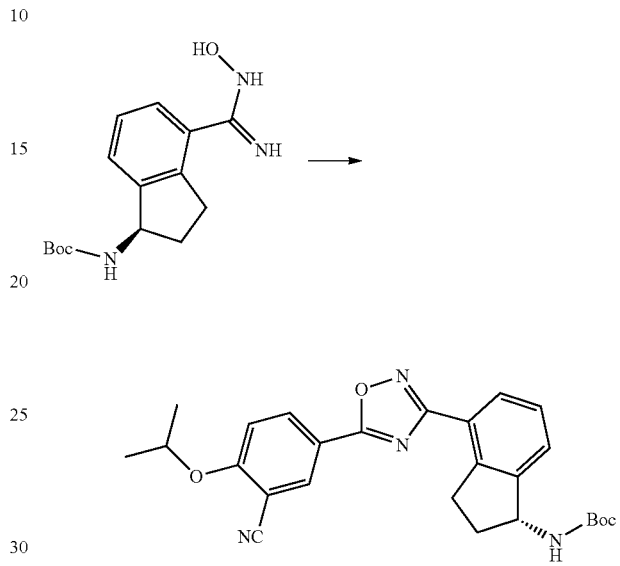

Prepared using General Procedure 4. To a solution of 3-cyano-4-isopropoxybenzoic acid (7.74 g, 37.7 mmol) in DMF (50 mL) was added HOBt (6.02 g, 44.6 mmol) and EDC (8.53 g, 44.6 mmol) at room temperature. The reaction was stirred for 2 h until complete formation of the HOBt-acid complex. (R)-tert-butyl 4-(N-hydroxycarbamimidoyl)-2,3-dihydro-1H-inden-1-ylcarbamate INT-10 (10.0 g, 34.3 mmol) was added and the reaction mixture stirred at room temperature for 2 h until the formation of INT-11, (R)-tert-butyl 4-(N-(3-cyano-4-isopropoxybenzolyloxy)carbamimidoyl)-2,3-dihydro-1H-inden-1-ylcarbamate. The mixture was partitioned between EA and $NaHCO_3$ and the organic layer was collected and dried over $MgSO_4$. INT-11 (16.3 g, 34.0 mmol) was re-dissolved in DMF (50 mL) and the mixture was heated to 95° C. for 12 hrs. The reaction was diluted with $NaHCO_3$ (200 mL) and extracted with EA (3×50 mL). The organic layer was dried over $Na_2SO_4$ and concentrated under reduced pressure to produce 12.8 g (81%) of (R)-tert-butyl 4-(5-(3-cyano-4-isopropoxyphenyl)-1,2,4-oxadiazol-3-yl)-2,3-dihydro-1H-inden-1-ylcarbamate INT-12 as a light brown solid and used without further purification in the next step. LCMS-ESI (m/z) calculated for $C_{26}H_{28}N_4O_4$: 460.5. found 483.2 [M+Na]$^+$, $t_R$=4.25 min. $^1$H NMR (400 MHz, CDCl$_3$) δ 8.43 (d, J=2.1, 1H), 8.34 (dd, J=8.9, 2.2, 1H), 8.09 (d, J=7.6, 1H), 7.51 (d, J=7.5, 1H), 7.39 (t, J=7.6, 1H), 7.12 (d, J=9.0, 1H), 5.28 (d, J=8.2, 1H), 4.80 (hept, J=6.0, 1H), 3.47 (ddd, J=17.4, 8.9, 3.5, 1H), 3.27-3.03 (m, 1H), 2.68 (d, J=8.7, 1H), 1.87 (td, J=16.7, 8.5, 1H), 1.53-1.43 (m, 15H). $^{13}$C NMR (101 MHz, CDCl3) δ 173.00, 168.82, 162.70, 155.68, 145.31, 142.96, 134.05, 133.83, 128.25, 127.21, 126.79, 123.09, 116.78, 115.24, 113.52, 103.87, 79.52, 72.70, 55.72, 33.86, 31.47, 28.39, 21.70. Chiral HPLC: (R)-tert-butyl 4-(5-(3-cyano-4-isopropoxyphenyl)-1,2,4-oxadiazol-3-yl)-2,3-dihydro-1H-inden-1-ylcarbamate was eluted using 20% i-PrOH in hexanes: >99.9% ee, $t_R$=13.33 min. The (S)-enantiomer INT-13 was prepared in an analogous fashion using (S)-tert-butyl 4-cyano-2,3-dihydro-1H-inden-1-ylcarbamate using General Procedures 3 and 4 ($t_R$ for (S)-enantiomer=16.31 min).

(R)-5-(3-(1-amino-2,3-dihydro-1H-inden-4-yl)-1,2,4-oxadiazol-5-yl)-2-isopropoxy-benzonitrile hydrochloride (Compound 49)

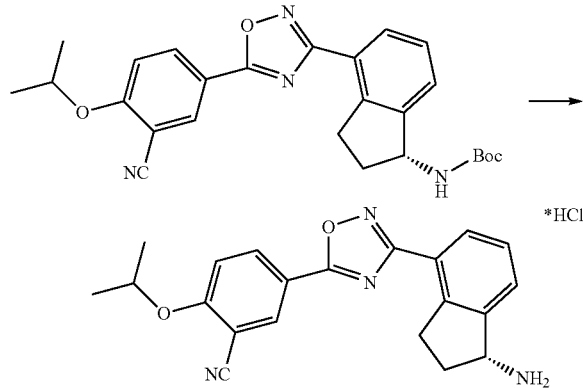

To (R)-tert-butyl 4-(5-(3-cyano-4-isopropoxyphenyl)-1,2,4-oxadiazol-3-yl)-2,3-dihydro-1H-inden-1-ylcarbamate (12.8 g, 27.8 mmol) in dioxane (200 mL) was added 4N HCl in dioxane (69 mL). The solution was heated to 55° C. for 1 h, and product precipitated. Dioxane was removed and the resulting solid suspended in ether and collected. The material was recrystallized from MeOH (200 mL) to produce 8.11 g (81%) of (R)-5-(3-(1-amino-2,3-dihydro-1H-inden-4-yl)-1,2,4-oxadiazol-5-yl)-2-isopropoxybenzonitrile 49 as the HCl salt. LCMS-ESI (m/z): calcd for: $C_{21}H_{20}N_4O_2$: 360.4. found 383.2 [M+Na]$^+$, $t_R$=2.49 min. Elemental Analysis and NMR spectra determined for $C_{21}H_{21}N_4O_2Cl*0.5$ $H_2O$; C calculated=62.14%. found=62.25%. H calculated=5.46%. found=5.30%. N calculated=13.80%. found=13.84%. Cl calculated=8.73%. found=8.34%. $^1$H NMR (400 MHz, DMSO) δ 8.71 (s, 3H), 8.49 (d, J=2.3, 1H), 8.39 (dd, J=9.0, 2.3, 1H), 8.11 (d, J=7.6, 1H), 7.91 (d, J=7.6, 1H), 7.55 (t, J=8.5, 2H), 4.97 (hept, J=6.1, 1H), 4.80 (s, 1H), 3.47 (ddd, J=17.4, 8.7, 5.3, 1H), 3.23 (ddd, J=17.4, 8.6, 6.4, 1H), 2.55 (ddd, J=13.7, 8.3, 3.2, 1H), 2.22-1.97 (m, 1H), 1.38 (d, J=6.0, 6H). $^{13}$C NMR (101 MHz, CDCl$_3$) δ 173.28, 167.98, 162.53, 143.69, 141.29, 134.59, 133.80, 128.93, 128.11, 127.55, 122.72, 115.87, 115.24, 114.91, 102.46, 72.54, 54.38, 31.51, 29.91, 21.47. Chiral HPLC of the free base: (R)-5-(3-(1-amino-2,3-dihydro-1H-inden-4-yl)-1,2,4-oxadiazol-5-yl)-2-isopropoxy benzonitrile was eluted using 15% i-PrOH in hexanes plus 0.3% DEA: >99.9% ee, $t_R$=30.80 min. (S)-5-(3-(1-amino-2,3-dihydro-1H-inden-4-yl)-1,2,4-oxadiazol-5-yl)-2-isopropoxy-benzonitrile 50 was prepared in an analogous fashion from (S)-tert-butyl 4-cyano-2,3-dihydro-1H-inden-1-ylcarbamate: >99.9% ee, $t_R$ for (S)-enantiomer=28.58 min.

General Procedure 5. Alkylation of Indane Amines

To a 0.2M solution of the (R)- or (S)-indane amine in CH$_3$CN (0.15 M) was added K$_2$CO$_3$ (2 eq) and the appropriate alkyl halide or mesylate (1.1 eq). In some cases, TEA (1.1 eq) was also added. The mixture was heated under convention heating or microwave irradiation at 80-160° C. for 30 minute intervals until starting material is consumed or di-alkylation of the amine becomes prevalent. If necessary, additional alkyl halide or mesylate is added to drive the reaction. The reaction mixture is concentrated, re-suspended in EA and washed with water. The organic layer is dried and concentrated, then purified by chromatography (MeOH/DCM) to provide the desired product.

Compounds 51-56, 58, 118, 124, 140-142, and 144 were prepared using General Procedure 5.

(R)-methyl 2-((methylsulfonyl)oxy)propanoate

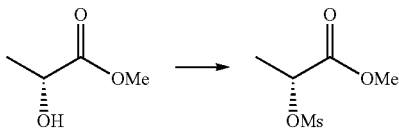

A stirred solution of (R)-methyl 2-hydroxypropanoate (1.0 g, 9.61 mmol) in toluene (15 mL) was cooled to 0° C. Methanesulfonyl chloride (0.82 mL, 10.6 mmol) was added drop wise. After 2 h, the solution was warmed to room temperature and further stirred for 45 min. The resulting heavy white precipitate was removed by vacuum filtration and the clear solution was concentrated to provide 1.75 g (99%) of (R)-methyl 2-((methylsulfonyl)oxy)propanoate as a colorless oil. $^1$H NMR (400 MHz, CDCl$_3$) δ 5.14 (q, J=7.0 Hz, 1H), 3.81 (d, J=4.5 Hz, 3H), 3.16 (d, J=4.5 Hz, 3H), 1.62 (d, J=7.0 Hz, 3H). (S)-methyl 2-((methylsulfonyl)oxy)propanoate was prepared in an analogous fashion using (S)-methyl 2-hydroxypropanoate.

(S)-methyl 2-(((S)-4-(5-(3-cyano-4-isopropoxyphenyl)-1,2,4-oxadiazol-3-yl)-2,3-dihydro-1H-inden-1-yl)amino)propanoate

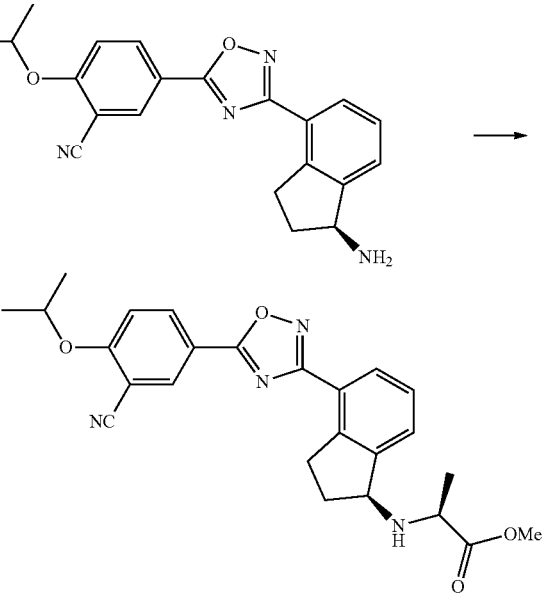

Prepared using General Procedure 5. To a solution of (S)-5-(3-(1-amino-2,3-dihydro-1H-inden-4-yl)-1,2,4-oxadiazol-5-yl)-2-isopropoxybenzonitrile 50 (75.0 mg, 0.21 mol) in CH$_3$CN (290 mL) was added (R)-methyl 2-((methylsulfonyl)oxy)propanoate (75.8 mg, 0.42 mmol) and K$_2$CO$_3$ (57 mg, 0.42 mmol). The reaction mixture was heated to 150° C. using microwave irradiation for 1.5 h. Additional (R)-methyl 2-((methylsulfonyl)oxy)propanoate (36 mg, 0.21 mmol) was added and the mixture was heated for an additional 0.5 h at 150° C. The reaction mixture was concentrated, redissolved in DCM, and chromatographed (EA/hexanes) to provide 33 mg (35%) of (S)-methyl 2-(((((S)-4-(5-(3-cyano-4-isopropoxyphenyl)-1,2,4-oxadiazol-3-yl)-2,3-dihydro-1H-inden-1-yl)amino)propanoate as a white powder. LCMS-ESI (m/z) calculated for $C_{25}H_{26}N_4O_4$: 446.5. found 447.2 [M+H]$^+$, $t_R$=2.61 min. $^1$H NMR (400 MHz, CDCl$_3$) δ 8.46-8.40 (m, 1H), 8.37-8.30 (m, 1H), 8.11-8.03 (m, 1H), 7.52 (s, 1H), 7.42-7.34 (m, 1H), 7.16-7.07 (m, 1H), 4.88-4.71 (m, 1H), 4.34-4.20 (m, 1H), 3.65-3.54 (s, 3H), 3.55-3.35 (m, 1H), 3.27-3.03 (m, 2H), 2.52-2.35 (m, 1H), 1.95-1.76 (m, 1H), 1.48 (d, J=6.1 Hz, 6H), 1.36 (d, J=6.9 Hz, 3H).

(R)-methyl 2-(((S)-4-(5-(3-cyano-4-isopropoxyphenyl)-1,2,4-oxadiazol-3-yl)-2,3-dihydro-1H-inden-1-yl)amino)propanoate

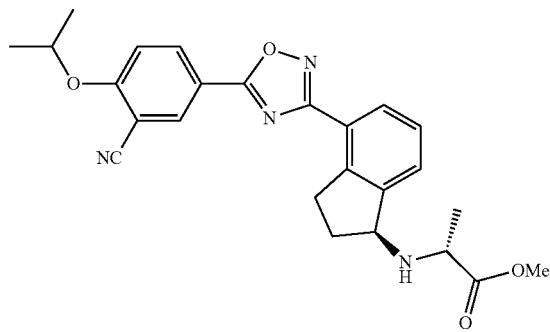 [SMILES: COC(=O)[C@@H](C)N[C@H]1CCc2c(-c3noc(-c4ccc(OC(C)C)c(C#N)c4)n3)cccc21]

Prepared using General Procedure 5. LCMS-ESI (m/z) calculated for $C_{25}H_{26}N_4O_4$: 446.5. found 447.2 [M+H]$^+$, $t_R$=2.61 min.

(R)-methyl 2-(((R)-4-(5-(3-cyano-4-isopropoxyphenyl)-1,2,4-oxadiazol-3-yl)-2,3-dihydro-1H-inden-1-yl)amino)propanoate

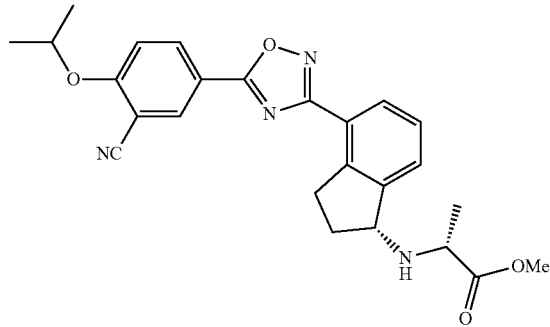 [SMILES: COC(=O)[C@@H](C)N[C@@H]1CCc2c(-c3noc(-c4ccc(OC(C)C)c(C#N)c4)n3)cccc21]

Prepared using General Procedure 5. LCMS-ESI (m/z) calculated for $C_{25}H_{26}N_4O_4$: 446.5. found 447.1 [M+H]$^+$, $t_R$=2.61 min. $^1$H NMR (400 MHz, CDCl$_3$) δ 8.42 (d, J=2.1 Hz, 1H), 8.33 (dd, J=8.9, 2.2 Hz, 1H), 8.06 (d, J=7.6 Hz, 1H), 7.53 (d, J=7.5 Hz, 1H), 7.38 (d, J=7.5 Hz, 1H), 7.12 (d, J=9.0 Hz, 1H), 4.87-4.72 (m, 1H), 4.26 (s, 1H), 3.76 (s, 3H), 3.63-3.52 (m, 1H), 3.53-3.36 (m, 1H), 3.11 (s, 1H), 2.52-2.26 (m, 1H), 2.11-1.78 (m, 1H), 1.47 (d, J=5.5 Hz, 6H), 1.35 (t, J=6.3 Hz, 3H).

(S)-methyl 2-(((R)-4-(5-(3-cyano-4-isopropoxyphenyl)-1,2,4-oxadiazol-3-yl)-2,3-dihydro-1H-inden-1-yl)amino)propanoate

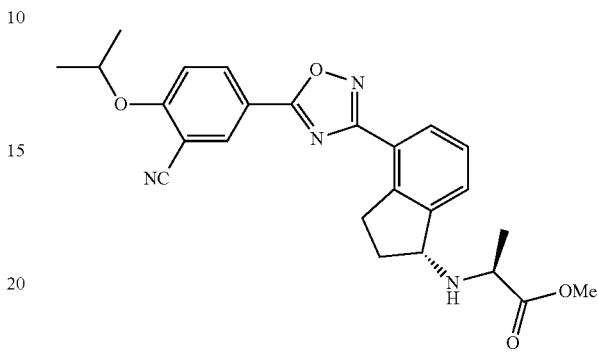

Prepared using General Procedure 5. LCMS-ESI (m/z) calculated for $C_{25}H_{26}N_4O_4$: 446.5. found 447.1 [M+H]$^+$, $t_R$=2.65 min. $^1$H NMR (400 MHz, CDCl$_3$) δ 8.42 (d, J=2.0 Hz, 1H), 8.33 (dd, J=8.9, 2.0 Hz, 1H), 8.07 (d, J=7.6 Hz, 1H), 7.54 (d, J=7.4 Hz, 1H), 7.38 (t, J=7.6 Hz, 1H), 7.12 (d, J=9.0 Hz, 1H), 4.88-4.69 (m, 1H), 4.26 (t, J=6.1 Hz, 1H), 3.76 (s, 3H), 3.66-3.39 (m, 1H), 3.31-3.12 (m, 1H), 2.46-2.28 (m, 1H), 2.11-1.81 (m, 2H), 1.47 (d, J=6.0 Hz, 6H), 1.37 (d, J=7.0 Hz, 3H).

5-(3-((S)-1-(((S)-1-hydroxypropan-2-yl)amino)-2,3-dihydro-1H-inden-4-yl)-1,2,4-oxadiazol-5-yl)-2-isopropoxybenzonitrile (Compound 53)

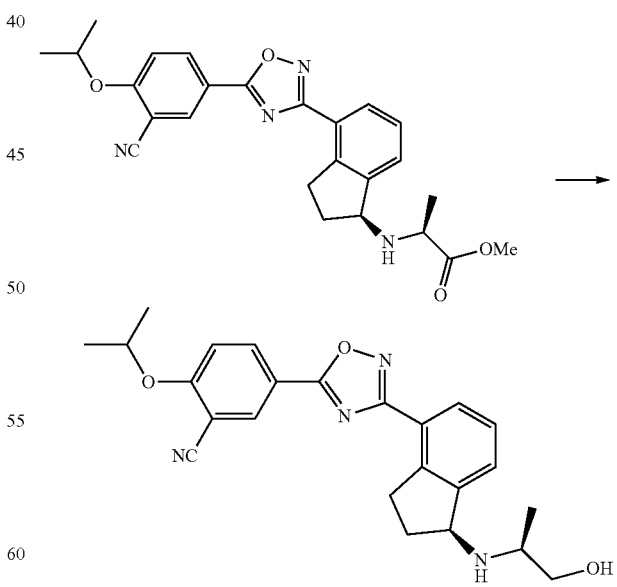

To a solution of (S)-methyl 2-(((S)-4-(5-(3-cyano-4-isopropoxyphenyl)-1,2,4-oxadiazol-3-yl)-2,3-dihydro-1H-inden-1-yl)amino)propanoate (33 mg, 0.07 mmol) in MeOH (2 mL) at 0° C. was added NaBH$_4$ (14 mg, 0.4 mmol). The reaction was allowed to warm to room temperature after 1 h.

Incremental amounts of NaBH₄ (~10-15 mg each) were added at 1 h intervals until LC/MS indicated >80% conversion to product. The reaction mixture was diluted with 1N HCl and extracted with DCM (2×). The combined organic layers were dried over Na₂SO₄ and concentrated. The resulting crude solid was dissolved in DCM and chromatographed (MeOH/DCM) to provide 12.1 mg (40%) of 5-(3-((S)-1-(((S)-1-hydroxypropan-2-yl)amino)-2,3-dihydro-1H-inden-4-yl)-1,2,4-oxadia-zol-5-yl)-2-isopropoxybenzonitrile 53. LCMS-ESI (m/z) calculated for C₂₅H₂₆N₄O₄: 418.5. found 419.1 [M+H]⁺, t$_R$=2.56 min. ¹H NMR (400 MHz, CDCl₃) δ 8.24 (d, J=2.2 Hz, 1H), 8.14 (dd, J=8.9, 2.2 Hz, 1H), 7.88 (d, J=7.6 Hz, 1H), 7.28 (d, J=7.5 Hz, 1H), 7.19 (t, J=7.6 Hz, 1H), 6.92 (d, J=9.1 Hz, 1H), 4.69-4.51 (m, 1H), 4.21 (m, 1H), 3.43 (m, 1H), 3.37-3.19 (m, 1H), 3.10 (m, 2H), 2.95-2.78 (m, 1H), 2.46 (dd, J=6.5, 4.6 Hz, 1H), 2.34-2.17 (m, 1H), 1.81-1.65 (m, 1H), 1.28 (d, J=6.1 Hz, 6H), 0.98 (d, J=6.4 Hz, 3H). Chiral HPLC eluting with 10% IPA/hexanes, plus 0.3% TEA, t$_R$=13.72 min.

5-(3-((R)-1-(((S)-1-hydroxypropan-2-yl)amino)-2,3-dihydro-1H-inden-4-yl)-1,2,4-oxadiazol-5-yl)-2-isopropoxybenzonitrile (Compound 54)

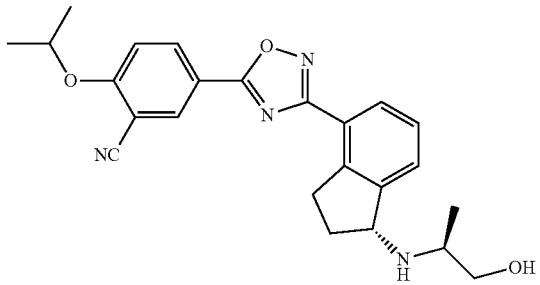 [SMILES: CC(C)Oc1ccc(-c2nc(-c3cccc4c3CC[C@H]4N[C@@H](C)CO)no2)cc1C#N]

Prepared in the same manner as compound 53 to give 5-(3-((R)-1-(((S)-1-hydroxypropan-2-yl)amino)-2,3-dihydro-1H-inden-4-yl)-1,2,4-oxadiazol-5-yl)-2-isopropoxy-benzo-nitrile 54. LCMS-ESI (m/z) calculated for C₂₅H₂₆N₄O₄: 418.5. found 419.2 [M+H]⁺, t$_R$=2.52 min. ¹H NMR (400 MHz, CDCl₃) δ 8.41 (d, J=2.1 Hz, 1H), 8.33 (dd, J=8.9, 2.2 Hz, 1H), 8.06 (d, J=7.6 Hz, 1H), 7.55 (d, J=7.5 Hz, 1H), 7.37 (t, J=7.6 Hz, 1H), 7.12 (d, J=9.0 Hz, 1H), 4.79 (dt, J=12.2, 6.1 Hz, 1H), 4.33 (dd, J=16.1, 7.4 Hz, 1H), 3.68 (ddd, J=10.0, 5.5, 4.2 Hz, 1H), 3.47 (ddd, J=17.3, 8.8, 3.7 Hz, 1H), 3.36-3.24 (m, 2H), 2.99 (t, J=5.5 Hz, 1H), 2.51-2.36 (m, 1H), 1.82 (ddd, J=15.9, 12.7, 8.4 Hz, 1H), 1.46 (t, J=11.3 Hz, 6H), 1.16 (dd, J=12.3, 7.3 Hz, 3H). Chiral HPLC eluting with 10% IPA/hexanes, plus 0.3% TEA, t$_R$=33.15 min.

5-(3-((S)-1-(((R)-1-hydroxypropan-2-yl)amino)-2,3-dihydro-1H-inden-4-yl)-1,2,4-oxadiazol-5-yl)-2-isopropoxybenzonitrile (Compound 55)

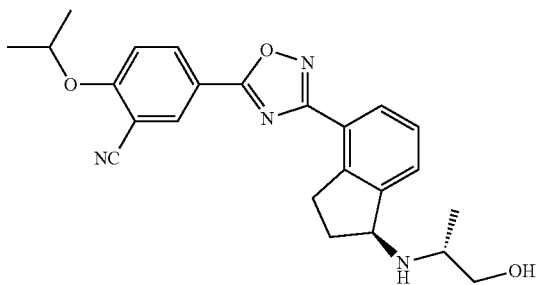 [SMILES: CC(C)Oc1ccc(-c2nc(-c3cccc4c3CC[C@@H]4N[C@H](C)CO)no2)cc1C#N]

Prepared in the same manner as compound 53 to give 5-(3-((S)-1-(((R)-1-hydroxypropan-2-yl)amino)-2,3-dihydro-1H-inden-4-yl)-1,2,4-oxadiazol-5-yl)-2-isopropoxy-benzo-nitrile 55. LCMS-ESI (m/z) calculated for C₂₅H₂₆N₄O₄: 418.5. found 419.2 [M+H]⁺, t$_R$=2.52 min. ¹H NMR (400 MHz, CDCl₃) δ 8.43 (d, J=2.1 Hz, 1H), 8.34 (dd, J=8.9, 2.2 Hz, 1H), 8.07 (d, J=7.6 Hz, 1H), 7.55 (s, 1H), 7.39 (s, 1H), 7.12 (d, J=9.0 Hz, 1H), 4.87-4.71 (m, 1H), 4.39-4.29 (m, 1H), 3.73-3.66 (m, 1H), 3.49 (s, 2H), 3.34-3.24 (m, 1H), 3.24-3.01 (m, 2H), 2.73-2.57 (m, 1H), 1.90-1.75 (m, 1H), 1.48 (d, J=6.1 Hz, 6H), 1.18 (d, J=6.5 Hz, 3H). Chiral HPLC: 10% IPA/hexanes, plus 0.3% TEA, t$_R$=29.36 min.

5-(3-((R)-1-(((R)-1-hydroxypropan-2-yl)amino)-2,3-dihydro-1H-inden-4-yl)-1,2,4-oxadiazol-5-yl)-2-isopropoxybenzonitrile (Compound 56)

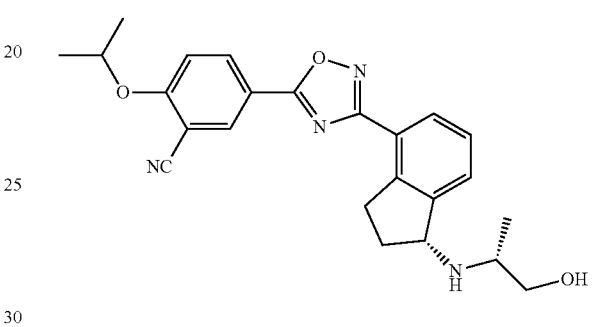

Prepared in the same manner as compound 53 to give 5-(3-((R)-1-(((R)-1-hydroxypropan-2-yl)amino)-2,3-dihydro-1H-inden-4-yl)-1,2,4-oxadiazol-5-yl)-2-isopropoxy-benzo-nitrile 56. LCMS-ESI (m/z) calculated for C₂₅H₂₆N₄O₄: 418.5. found 419.2 [M+H]⁺, t$_R$=2.52 min. ¹H NMR (400 MHz, CDCl₃) δ 8.43 (d, J=2.2 Hz, 1H), 8.34 (dd, J=8.9, 2.2 Hz, 1H), 8.08 (d, J=7.6 Hz, 1H), 7.48 (d, J=7.4 Hz, 1H), 7.39 (t, J=7.6 Hz, 1H), 7.12 (d, J=9.0 Hz, 1H), 4.87-4.73 (m, 1H), 4.41 (t, J=6.4 Hz, 1H), 3.64 (dd, J=10.5, 4.1 Hz, 1H), 3.49 (s, 2H), 3.30 (dd, J=10.5, 7.3 Hz, 1H), 3.26-3.12 (m, 1H), 3.07 (s, 1H), 2.52-2.38 (m, 1H), 2.00-1.87 (m, 1H), 1.48 (d, J=6.1 Hz, 6H), 1.18 (d, J=6.4 Hz, 3H). Chiral HPLC eluting with 10% IPA/hexanes, plus 0.3% TEA, t$_R$=37.38 min.

(R)-5-(3-(1-((2-fluoroethyl)amino)-2,3-dihydro-1H-inden-4-yl)-1,2,4-oxadiazol-5-yl)-2-isopropoxybenzonitrile (Compound 124)

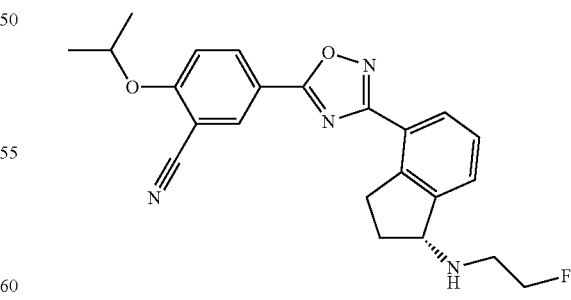

Prepared using General Procedure 5 from (R)-5-(3-(1-amino-2,3-dihydro-1H-inden-4-yl)-1,2,4-oxadiazol-5-yl)-2 isopropoxybenzonitrile 49, 2-fluoroethyl methanesulfonate, K₂CO₃ and TEA under microwave irradiation at 140° C. for 2 h. LCMS-ESI (m/z) calculated for C₂₃H₂₃FN₄O₂: 406.4. found 407.1 [M+H]⁺, t$_R$=6.89 min (Method 2). ¹H NMR (400

MHz, MeOD) δ 8.41-8.38 (m, 2H), 8.28-8.23 (m, 1H), 7.79 (d, J=7.6 Hz, 1H), 7.56 (t, J=7.7, 1H), 7.46-7.37 (m, 1H), 5.00-4.90 (m, 2H), 4.83 (t, J=4.0 Hz, 1H), 4.71 (t, J=4.0 Hz, 1H), 3.56-3.33 (m, 4H), 2.71-2.66 (m, 1H), 2.41-2.34 (m, 1H), 1.44 (d, J=6.1 Hz, 6H).

General Procedure 6. Preparation of Indane Acids

To the solution of (R)- or (S)-indane amine (1 eq) in CH₃CN (0.1 M) was added K₂CO₃ (3 eq) and the bromo methyl esters (1 eq) or mesylate methyl esters (1 eq). The reaction was heated to 80° C. for 30 min or until the reaction was complete. The solvent was evaporated, and the residues partitioned between EA and water. The organic layer was collected, dried over MgSO₄, and purified by chromatography (MeOH/DCM with 0.025% TEA) to give the indane methyl ester as white solid. The indane methyl ester was dissolved in EtOH (0.03 M) and NaOH aqueous (11.8 M) was added. The reaction mixture was stirred for 4 h at 40° C. The crude material was purified by preparative HPLC.

Compounds 61-64 and 145-148 were prepared using General Procedure 6.

(R)-3-((4-(5-(3-cyano-4-isopropoxyphenyl)-1,2,4-oxadiazol-3-yl)-2,3-dihydro-1H-inden-1-yl)amino)propanoic acid (Compound 62)

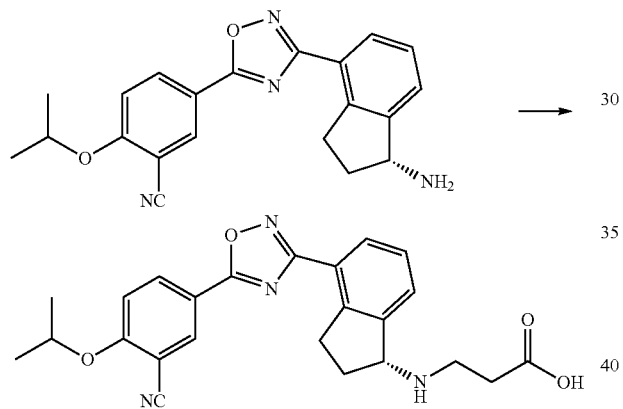

Prepared using General Procedure 6. To the solution of (R)-5-(3-(1-amino-2,3-dihydro-1H-inden-4-yl)-1,2,4-oxadiazol-5-yl)-2-isopropoxybenzonitrile 49 (90.0 mg, 0.25 mmol) and K₂CO₃ (103.5 mg, 0.75 mmol) was added methyl 3-bromopropanoate (41.8 mg, 0.25 mmol). The reaction was heated to 80° C. for 30 min and repeated four time at 80° C. for 30 min with additional methyl 3-bromopropanoate (41.8 mg, 0.25 mmol) added each time. The solvent was evaporated, and the residues partitioned between EA and water. The organic layer was collected, dried over MgSO₄, and purified by chromatography (MeOH/DCM with 0.025% TEA) to give 71 mg (63%) of (R)-methyl 3-((4-(5-(3-cyano-4-isopropoxyphenyl)-1,2,4-oxadiazol-3-yl)-2,3-dihydro-1H-inden-1-yl)amino)propanoate as a solid. LCMS-ESI (m/z) calculated for C₂₅H₂₆N₄O₄: 446.5. found 447.2 [M+H]⁺, $t_R$=2.61 min. ¹H NMR (400 MHz, CDCl3) □δ 8.40 (d, J=2.1, 1H), 8.31 (dd, J=8.9, 2.2, 1H), 8.04 (d, J=7.6, 1H), 7.49 (d, J=7.5, 1H), 7.35 (t, J=7.6, 1H), 7.09 (d, J=9.0, 1H), 4.77 (dt, J=12.2, 6.1, 1H), 4.31 (t, J=6.8, 1H), 3.73-3.58 (m, 3H), 3.43 (ddd, J=17.4, 8.7, 4.6, 1H), 3.24-3.08 (m, 1H), 3.04-2.85 (m, 2H), 2.56 (t, J=6.5, 2H), 2.47 (dtd, J=12.8, 8.4, 4.7, 1H), 1.99-1.82 (m, 1H), 1.54-1.32 (m, 6H).

To (R)-methyl 3-(4-(5-(3-cyano-4-isopropoxyphenyl)-1,2,4-oxadiazol-3-yl)-2,3-dihydro-1H-inden-1-ylamino)propanoate (71.0 mg, 0.16 mmol) in EtOH (5 ml) was added aqueous NaOH (1.9 mL, 1M). The solution was stirred at 40° C. for 4 h. The reaction mixture was poured onto ice (10 mL) and neutralized to pH 7 with 1M HCl. The solution was partitioned between DCM and H₂O. The organic layer was collected, dried under vacuum, and purified by preparative HPLC to give 29.7 mg (31%) of (R)-3-((4-(5-(3-cyano-4-isopropoxyphenyl)-1,2,4-oxadiazol-3-yl)-2,3-dihydro-1H-inden-1-yl)amino)propanoic acid 62. LCMS-ESI (m/z): calcd for: C₂₄H₂₄N₄O₄, 432.5; [M+H]⁺ found 433.20, $t_R$=2.51 min. ¹H NMR (400 MHz, MeOD) δ 8.46 (d, J=2.1, 1H), 8.45-8.40 (m, 1H), 8.29-8.23 (m, 1H), 7.82-7.73 (m, 1H), 7.60-7.52 (m, 1H), 7.45 (d, J=9.0, 1H), 5.06-4.92 (m, 2H), 3.69-3.52 (m, 1H), 3.51-3.37 (m, 1H), 3.26 (s, 2H), 2.75-2.58 (m, 1H), 2.56-2.46 (m, 2H), 2.44-2.29 (m, 1H), 1.46 (d, J=6.0, 6H).

General Procedure 7. Preparation of Indane Amides via Acid Coupling

To the appropriate acid (1.1 eq) in DMF (0.04 M) was added HOBt (1.3 eq), and EDC (1.3 eq). The reaction was stirred at room temperature for 0.5 h or until the acid was fully activated. The (R)- or (S)-indane amine (1 eq) was added in one portion and the reaction mixture stirred at room temperature for 12 h. The reaction mixture was diluted with EA and washed with NaHCO₃. The resulting combined organic layers were dried over Na₂SO₄, concentrated and purified by preparative HPLC or chromatography (MeOH/DCM) to afford the indane amides.

Compounds 65-68, 136, and 137 were prepared using General Procedure 7.

(R)-N-(4-(5-(3 cyano-4-isopropoxyphenyl)-1,2,4-oxadiazol-3-yl)-2,3-dihydro-1H-inden-1-yl)-2-hydroxyacetamide (Compound 65)

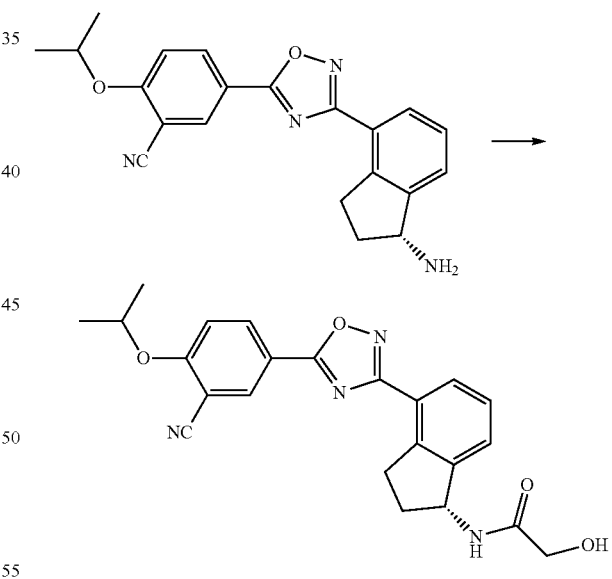

Prepared using General Procedure 7. To 2-hydroxyacetic acid (7 mg, 0.08 mmol) in DMF (2 mL) was added HOBt (12 mg, 0.09 mmol) and EDC (17 mg, 0.09 mmol). The reaction mixture was stirred at room temperature for 0.5 h until the acid was fully activated. (R)-5-(3-(1-amino-2,3-dihydro-1H-inden-4-yl)-1,2,4-oxadiazol-5-yl)-2-isopropoxybenzonitrile 49 (25.0 mg, 0.07 mmol) was added in one portion and the reaction was stirred at room temperature for 12 h. The reaction mixture was diluted with EA and washed with NaHCO₃. The combined aqueous layers were back-extracted with EA. The resulting combined organic layers were dried over Na₂SO₄ and concentrated to a brown oil which was purified by chromatography (MeOH/DCM) to provide 14 mg (48%) of (R)-N-(4-(5-(3-cyano-4-isopropoxyphenyl)-1,2,4-oxadiazol-3-yl)-2,3-dihydro-1H-inden-1-yl)-2-hydroxy acetamide 65 as a white solid. LCMS-ESI (m/z) calculated for $C_{22}H_{22}N_4O_4$: 418.5. found 419.0 [M+H]$^+$, $t_R$=2.47 min. $^1$H NMR (400 MHz, CDCl$_3$) δ 8.39 (d, J=2.2 Hz, 1H), 8.32 (dd, J=8.9, 2.2 Hz, 1H), 8.08 (d, J=7.6 Hz, 1H), 7.45 (d, J=7.5 Hz, 1H), 7.38 (t, J=7.6 Hz, 1H), 7.12 (d, J=9.0 Hz, 1H), 6.76 (d, J=8.6 Hz, 1H), 5.61 (d, J=8.1 Hz, 1H), 4.80 (dt, J=12.2, 6.1 Hz, 1H), 4.20 (s, 2H), 3.49 (m, 1H), 3.23 (dd, J=17.1, 8.5 Hz, 1H), 2.80-2.60 (m, 1H), 1.93 (dd, J=13.0, 8.4 Hz, 1H), 1.47 (t, J=5.6 Hz, 6H). $^{13}$C NMR (101 MHz, CDCl$_3$) δ 173.11, 171.21, 168.78, 162.78, 144.48, 143.21, 134.11, 133.88, 128.56, 127.42, 126.83, 123.29, 116.76, 115.26, 113.55, 103.90, 72.77, 62.25, 54.00, 33.52, 31.71, 21.72.

General Procedure 8A. Preparation of Indane Sulfonamides via Sulfonyl Chlorides

To a stirred solution of (R)- or (S)-indane amine (1 eq) in DCM (0.05M) was added TEA (2 eq) and the appropriate sulfonyl chloride (2 eq.) at room temperature. The reaction mixture was stirred at room temperature for 18 h. The solvent was evaporated and the pure product isolated after preparative HPLC purification.

Compounds 69, 70, 73, 76, 79-82 and 163-167 were prepared using General Procedure 8A.

(S,)-N-(4-(5-(3 cyano-4-isopropoxyphenyl)-1,2,4-oxadiazol-3-yl)-2,3-dihydro-1H-inden-1-yl)methanesulfonamide (Compound 69)

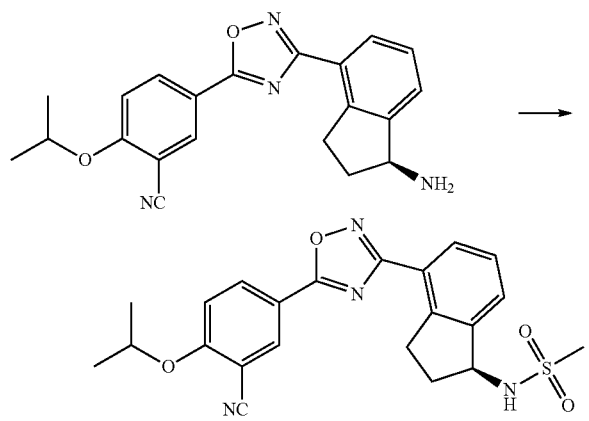

Prepared using General Procedure 8A: To a stirred solution of (S)-5-(3-(1-amino-2,3-dihydro-1H-inden-4-yl)-1,2,4-oxadiazol-5-yl)-2-isopropoxybenzonitrile 50 (18 mg, 0.05 mmol) in DCM (1 mL) was added TEA (13.9 µL, 0.1 mmol) and methanesulfonyl chloride (19 mg, 0.1 mmol). After 1 h, additional TEA (13.9 µL, 0.1 mmol) and methanesulfonyl chloride (19 mg, 0.1 mmol) were added. After an additional 1 h of stirring the solvent was evaporated and purified by preparative HPLC to afford 9.8 mg (45%) of (S)-N-(4-(5-(3-cyano-4-isopropoxyphenyl)-1,2,4-oxadiazol-3-yl)-2,3-dihydro-1H-inden-1-yl) methane sulfonamide 69. LCMS-ESI (m/z) calculated for $C_{22}H_{22}N_4O_4S$: 438.1. found 439.1 [M+H]$^+$, $t_R$=3.70 min. $^1$H NMR (400 MHz, CDCl$_3$) δ 8.41 (d, J=2.2 Hz, 1H), 8.32 (dd, J=8.9, 2.2 Hz, 1H), 8.12 (d, J=7.7 Hz, 1H), 7.60 (d, J=7.6 Hz, 1H), 7.43 (t, J=7.6 Hz, 1H), 7.11 (d, J=9.0 Hz, 1H), 5.07 (dd, J=16.5, 7.8 Hz, 1H), 4.78 (hept, J=6.1 Hz, 1H), 4.48 (d, J=9.3 Hz, 1H), 3.51 (ddd, J=17.5, 8.8, 3.4 Hz, 1H), 3.29-3.12 (m, 1H), 3.09 (s, 3H), 2.74 (dtd, J=12.9, 8.0, 3.5 Hz, 1H), 2.07-1.92 (m, 1H), 1.46 (d, J=6.1 Hz, 6H).

(S)-N-(4-(5-(3 cyano-4-isopropoxyphenyl)-1,2,4-oxadiazol-3-yl)-2,3-dihydro-1H-inden-1-yl)ethenesulfonamide (INT-14)

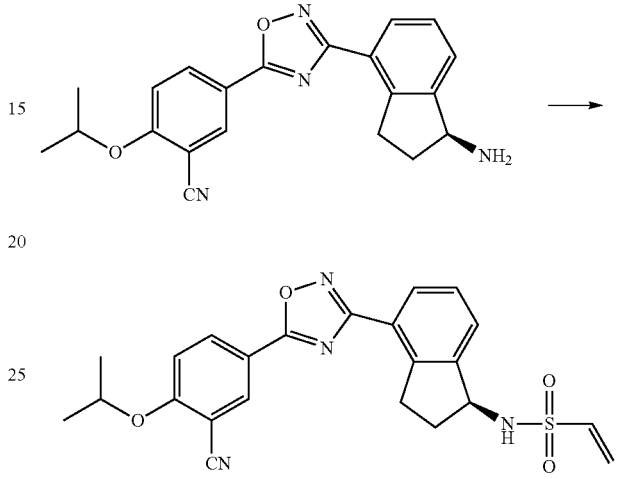

To a stirred solution of (S)-5-(3-(1-amino-2,3-dihydro-1H-inden-4-yl)-1,2,4-oxadiazol-5-yl)-2-isopropoxybenzonitrile 50 (180 mg, 0.5 mmol) in DCM (2 mL) at 0° C. was added TEA (348 µL, 2.5 mmol) and 2-chloroethanesulfonyl chloride (245 mg, 1.5 mmol). The reaction mixture was warmed to room temperature and stirred for 30 min. Additional TEA (348 µL, 2.5 mmol) and 2-chloroethanesulfonyl chloride (245 mg, 1.5 mmol) were added and the reaction was stirred for 1 h. The solvent was removed and the product was purified by chromatography (EA/hexane) to give 144 mg (64%) of (S)-N-(4-(5-(3-cyano-4-isopropoxyphenyl)-1,2,4-oxadiazol-3-yl)-2,3-dihydro-1H-inden-1-yl)ethenesulfonamide INT-14 as a white solid. LCMS-ESI (m/z) calculated for $C_{23}H_{22}N_4O_4S$: 450.1. found 473.1 [M+Na]$^+$, $t_R$=3.84 min. $^1$H NMR (400 MHz, CDCl$_3$) δ 8.32 (d, J=2.1 Hz, 1H), 8.27 (dd, J=8.9, 2.2 Hz, 1H), 8.04 (d, J=7.6 Hz, 1H), 7.55 (d, J=7.5 Hz, 1H), 7.37 (t, J=7.6 Hz, 1H), 7.09 (d, J=9.0 Hz, 1H), 6.64 (dd, J=16.5, 9.9 Hz, 1H), 6.32 (d, J=16.5 Hz, 1H), 5.97 (d, J=9.9 Hz, 1H), 4.94-4.85 (m, 1H), 4.83 (d, J=9.1 Hz, 1H), 4.75 (hept, J=6.1 Hz, 1H), 3.42 (ddd, J=17.4, 8.8, 3.3 Hz, 1H), 3.17-3.01 (m, 1H), 2.63 (dtd, J=13.0, 8.0, 3.4 Hz, 1H), 1.99-1.86 (m, 1H), 1.44 (d, J=6.1 Hz, 6H). $^{13}$C NMR (101 MHz, CDCl$_3$) δ 173.20, 168.72, 162.89, 143.74, 142.71, 137.15, 134.16, 134.00, 128.91, 127.62, 127.15, 126.54, 123.38, 116.77, 115.38, 113.70, 103.96, 72.89, 58.59, 34.71, 31.56, 21.83. (R)-N-(4-(5-(3-cyano-4-isopropoxyphenyl)-1,2,4-oxadiazol-3-yl)-2,3-dihydro-1H-inden-1-yl) ethane sulfonamide was made in an analogous fashion from (R)-5-(3-(1-amino-2,3-dihydro-1H-inden-4-yl)-1,2,4-oxadiazol-5-yl)-2-isopropoxybenzonitrile 49.

General Procedure 8B. Preparation of Indane Sulfonamides via Michael Addition

To a stirred solution of the (R)- or (S)-indane vinyl sulfonamide (1 eq) in DMF (0.1M) was added the appropriate amine (10 eq). The reaction mixture was stirred at 80° C. for 18 h. The products were purified by preparative HPLC.

Compounds 74, 75, 77, 78, and 168-181 were prepared using General Procedure 8B.

(S)-N-(4-(5-(3 cyano-4-isopropoxyphenyl)-1,2,4-oxadiazol-3-yl)-2,3-dihydro-1H-inden-1-yl)-2-(dimethylamino)ethanesulfonamide (Compound 78)

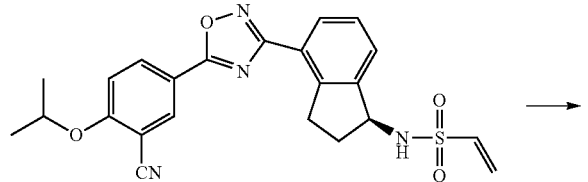

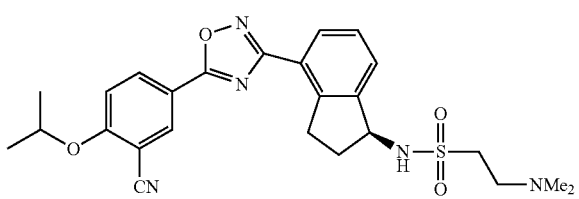

Prepared using General Procedure 8B. To a solution of (S)-N-(4-(5-(3-cyano-4-isopropoxyphenyl)-1,2,4-oxadiazol-3-yl)-2,3-dihydro-1H-inden-1-yl)ethenesulfonamide INT-14 (22.50 mg, 0.05 mmol) in DMF (0.5 mL) was added 2N methylamine in THF (0.25 mL, 0.50 mmol) and the reaction mixture was heated to 80° C. for 18 h. The crude product was purified by preparative HPLC to give 17.6 mg (58%) of the TFA salt of (S)-N-(4-(5-(3-cyano-4-isopropoxyphenyl)-1,2,4-oxadiazol-3-yl)-2,3-dihydro-1H-inden-1-yl)-2-(dimethylamino) ethane sulfonamide 78 as a white solid. LCMS-ESI (m/z) calculated for $C_{25}H_{29}N_5O_4S$: 495.2. found 496.2 [M+H]$^+$, $t_R$=2.65 min. $^1$H NMR (400 MHz, CDCl$_3$) δ 8.27-8.14 (m, 2H), 7.93 (d, J=7.6 Hz, 1H), 7.48 (d, J=7.3 Hz, 1H), 7.29 (t, J=7.5 Hz, 1H), 7.05 (d, J=9.9 Hz, 1H), 6.27 (s, 1H), 4.93-4.81 (m, 1H), 4.74 (hept, J=6.1 Hz, 1H), 3.70-3.57 (m, 2H), 3.57-3.43 (m, 2H), 3.43-3.23 (m, J=8.0 Hz, 1H), 3.12-2.93 (m, J=16.9, 8.3 Hz, 1H), 2.86 (s, 6H), 2.65-2.44 (m, 1H), 2.06-1.83 (m, J=11.6 Hz, 1H), 1.43 (d, J=6.0 Hz, 6H). $^{13}$C NMR (101 MHz, CDCl$_3$) δ 172.96, 168.45, 162.75, 143.40, 142.55, 133.90, 128.76, 127.46, 126.98, 123.19, 116.53, 115.28, 113.59, 103.68, 72.82, 58.75, 52.07, 48.41, 43.38, 33.89, 31.39, 21.72.

5-(3-((1R)-1-(3-chloro-2-hydroxypropylamino)-2,3-dihydro-1H-inden-4-yl)-1,2,4-oxadiazol-5-yl)-2-isopropoxybenzonitrile (INT-15)

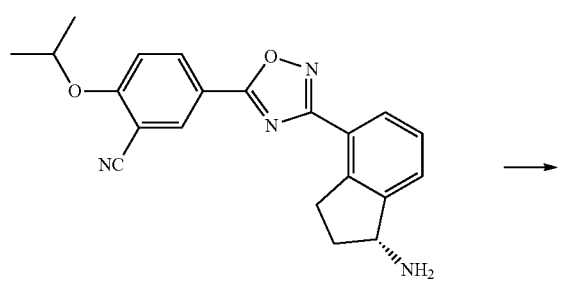

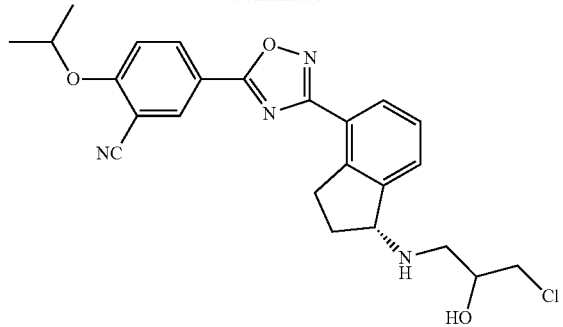

To a flask containing (R)-5-(3-(1-amino-2,3-dihydro-1H-inden-4-yl)-1,2,4-oxadiazol-5-yl)-2-isopropoxybenzonitrile 49 (84 mg, 0.23 mmol) was added 2 mL of IPA. The cloudy, white mixture was cooled to 0° C. and epichlorohydrin (20.7 µL, 0.26 mmol) was added and the reaction mixture stirred at room temperature overnight. The IPA was removed by concentration in vacuo and water (500 µl) and aliquots of epichlorohydrin (20.7 µL, 0.26 mmol) were added every hour (4 total) at room temperature until conversion was complete. The reaction mixture was concentrated, dissolved in DCM and purified by chromatography (MeOH/DCM) to provide 19.3 mg (18%) of 5-(3-((1R)-1-(3-chloro-2-hydroxypropylamino)-2,3-dihydro-1H-inden-4-yl)-1,2,4-oxadiazol-5-yl)-2-isopropoxybenzonitrile INT-15 as a white solid. LCMS-ESI (m/z) calculated for $C_{24}H_{25}ClN_4O_3$: 452.9. found 453.1 [M+H]$^+$, $t_R$=2.62 min.

Preparation of (R)-5-(3-(1-(3-hydroxyazetidin-1-yl)-2,3-dihydro-1H-inden-4-yl)-1,2,4-oxadiazol-5-yl)-2-isopropoxybenzonitrile (Compound 83)

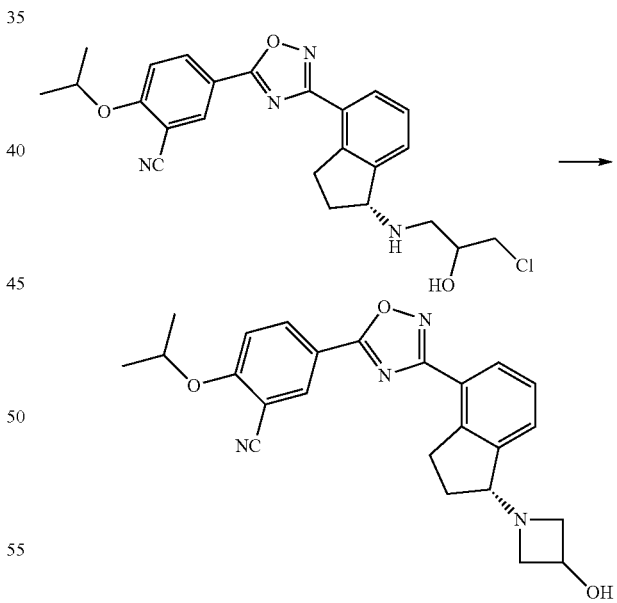

To a flask containing 5-(3-((1R)-1-(3-chloro-2-hydroxypropylamino)-2,3-dihydro-1H-inden-4-yl)-1,2,4-oxadiazol-5-yl)-2-isopropoxybenzonitrile INT-15 (77.0 mg, 0.17 mmol) in CH$_3$CN (4 mL) was added TEA (44.5 µL, 0.32 mmol). The reaction mixture was heated at 75° C. overnight then concentrated in vacuo, dissolved in DCM and purified by chromatography (MeOH/DCM) to provide 19 mg (27%) of (R)-5-(3-(1-(3-hydroxyazetidin-1-yl)-2,3-dihydro-1H-inden-4-yl)-1,2,4-oxadiazol-5-yl)-2-isopropoxybenzonitrile 83 as a white solid. LCMS-ESI (m/z) calculated for $C_{24}H_{24}N_4O_3$: 416.5. found 417.1 [M+H]$^+$, $t_R$=6.19 min (Method 2). $^1$H NMR (400 MHz, CDCl$_3$) δ 8.42 (d, J=2.2 Hz, 1H), 8.33 (dd, J=8.9, 2.2 Hz, 1H), 8.09 (dd, J=7.7, 0.7 Hz, 1H), 7.44 (d, J=7.4 Hz, 1H), 7.35 (t, J=7.6 Hz, 1H), 7.11 (d, J=9.0 Hz, 1H), 4.79 (dt, J=12.2, 6.1 Hz, 1H), 4.46 (p, J=5.8 Hz, 1H), 3.99 (dd, J=7.0, 3.5 Hz, 1H), 3.70 (dt, J=19.2, 5.6 Hz, 2H), 3.47 (d, J=6.7 Hz, 1H), 3.41 (dd, J=16.6, 8.7 Hz, 1H), 3.28 (ddd, J=17.5, 8.8, 4.2 Hz, 1H), 3.20-3.13 (m, 1H), 3.13-3.05 (m, 1H), 2.13 (dddd, J=16.9, 12.6, 8.4, 5.5 Hz, 2H), 1.47 (d, J=6.1 Hz, 6H). (S)-5-(3-(1-(3-hydroxyazetidin-1-yl)-2,3-dihydro-1H-inden-4-yl)-1,2,4-oxadiazol-5-yl)-2-isopropoxybenzonitrile 84 was prepared in an analogous fashion from (S)-5-(3-(1-amino-2,3-dihydro-1H-inden-4-yl)-1,2,4-oxadiazol-5-yl)-2-isopropoxybenzonitrile 50.

General Procedure 9. Alkylation of Cyano Indane Amines

To a flame-dried flask under N$_2$ was added the (R)- or (S)-cyano indane amine (1 eq) in anhydrous DMF (0.14 M). The reaction mixture was cooled to 0° C. and sodium hydride (5 eq, 60% in oil, 160.6 mmol) was added portionwise. After stirring at 0° C. for 2.75 h, the alkyl halide was added. The ice bath was removed after 5 minutes and the reaction mixture was allowed to warm to room temperature. After 1.5 h, the reaction mixture was quenched by the slow addition of sat. NaHCO$_3$ at 0° C. Once gas evolution was complete the reaction was extracted with EA. The organic layers were washed with water and brine, dried over MgSO$_4$ and concentrated. The product was purified by chromatography (EA/hexanes) or preparative HPLC.

Compounds 85-91, 105, 107, and 143 were prepared using General Procedures 9, 3, and 4 sequentially.

(R)-tert-butyl 2-(tert-butyldimethylsilyloxy)ethyl(4-cyano-2,3-dihydro-1H-inden-1-yl)carbamate (INT-16)

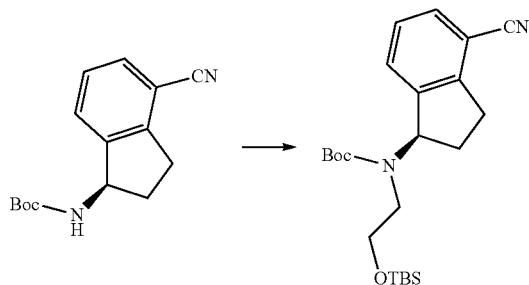 [SMILES: CC(C)(C)OC(=O)N[C@@H]1CCc2c(C#N)cccc21 ; CC(C)(C)OC(=O)N(CCO[Si](C)(C)C(C)(C)C)[C@@H]1CCc2c(C#N)cccc21]

Prepared using General Procedure 9. To a flame-dried flask under N$_2$ was added (R)-tert-butyl 4-cyano-2,3-dihydro-1H-inden-1-ylcarbamate INT-8 (8.3 g, 32.1 mmol) in anhydrous DMF (240 mL). The reaction mixture was cooled to 0° C. and sodium hydride (3.8 g, 60% in oil, 160.6 mmol) was added portionwise. After stirring at 0° C. for 2.75 h, (2-bromoethoxy)(tert-butyl)dimethylsilane (16.9 mL, 70.7 mmol) was added. The ice bath was removed after 5 mins and the reaction mixture was allowed to warm to room temperature. After 1.5 h, the reaction mixture was quenched by the slow addition of sat. NaHCO$_3$ at 0° C. Once gas evolution was complete the reaction was extracted with EA. The organic layers were washed with water and brine, dried over MgSO$_4$ and concentrated. The product was purified by chromatography (EA/hexanes) to provide 10.76 g (80%) of (R)-tert-butyl 2-(tert-butyldimethylsilyloxy)ethyl(4-cyano-2,3-dihydro-1H-inden-1-yl)carbamate INT-16 as a colorless oil. LCMS-ESI (m/z) calculated for $C_{23}H_{36}N_2O_3Si$: 416.6. found 317.2 [M-Boc]$^+$ and 439.0 [M+Na]$^+$, $t_R$=4.04 min (Method 1). $^1$H NMR (400 MHz, CDCl$_3$) δ 7.46 (d, J=7.6, 1H), 7.38-7.32 (m, 1H), 7.33-7.18 (m, 1H), 5.69 (s, 0.5H), 5.19 (s, 0.5H), 3.70 (ddd, J=48.8, 26.6, 22.9, 1.5H), 3.50-3.37 (m, 1H), 3.17 (ddd, J=16.7, 9.4, 2.2, 2H), 2.93 (m, 1.5H), 2.45 (s, 1H), 2.21 (dd, J=24.5, 14.5, 1H), 1.56-1.37 (bs, 4.5H), 1.22 (bs, 4.5H), 0.87-0.74 (m, 9H), −0.04 (dd, J=26.6, 8.2, 6H). $^{13}$C NMR (101 MHz, CDCl$_3$) δ 155.03, 146.55, 145.54, 131.16, 130.76, [128.11, 127.03], 117.58, 109.20, 79.88, [63.93, 61.88], [61.44, 60.34], [49.73, 46.76], 30.30, 29.70, 28.44, 28.12, [25.87, 25.62], −5.43. (S)-tert-butyl 2-(tert-butyldimethylsilyloxy)ethyl(4-cyano-2,3-dihydro-1H-inden-1-yl)carbamate INT-17 is prepared in an analogous fashion using INT-9.

(R)-tert-butyl 2-(tert-butyldimethylsilyloxy)ethyl (4-(N-hydroxycarbamimidoyl)-2,3-dihydro-1H-inden-1-yl)carbamate (INT-18)

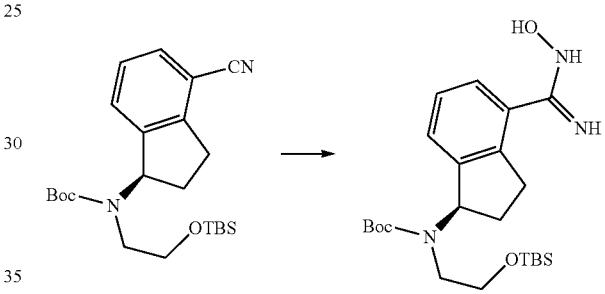

Prepared using General Procedure 3. To a solution of (R)-tert-butyl 2-(tert-butyldimethylsilyloxy)ethyl(4-cyano-2,3-dihydro-1H-inden-1-yl)carbamate INT-16 (12.0 g, 28.9 mmol) in EtOH (120 mL), under an atmosphere of N$_2$ was added hydroxylamine-HCl (6.0 g, 86.5 mmol) and triethylamine (13.4 mL, 9.7 g, 86.5 mmol). The reaction mixture was refluxed at 80° C. for 4 h. The reaction mixture was cooled to room temperature and concentrated to dryness and then diluted with DCM (500 mL). The organic layer was washed with NaHCO$_3$, water, and brine. The combined organic layers were dried over MgSO$_4$ and concentrated to produce 11.8 g of (R)-tert-butyl 2-(tert-butyldimethylsilyloxy)ethyl (4-(N-hydroxycarbamimidoyl)-2,3-dihydro-1H-inden-1-yl)carbamate INT-18 as a white foamy solid, which was used without purification in the next experiment. LCMS-ESI (m/z) calculated for $C_{23}H_{39}N_3O_4Si$: 449.7. found 350.2 [M-Boc]$^+$ and 472.2 [M+Na]$^+$, $t_R$=1.79 min (Method 1). $^1$H NMR (400 MHz, CDCl3) δ 7.32 (t, J=7.3 Hz, 1H), 7.21-7.07 (m, 2H), 5.69 (s, 0.5H), 5.19 (s, 0.5H), 4.89 (s, 2H), 3.85-3.50 (m, 2H), 3.31 (ddd, J=12.2, 9.2, 2.5 Hz, 2H), 3.28-3.03 (m, 2H), 3.03-2.70 (m, 1H), 2.29 (t, J=23.6 Hz, 1H), 1.43 (bs, 4.5H), 1.28 (bs, 4.5H), 1.16-1.04 (m, 1H), 0.90-0.71 (m, 9H), 0.08-0.14 (m, 6H). $^{13}$C NMR (101 MHz, CDCl$_3$) δ 170.99, [156.20, 155.62], 152.38, [144.53, 143.57], [141.82, 141.21], 129.61, 126.78, [126.59, 126.25], [125.02, 124.77], [79.91, 79.68], 64.04, 61.88, [61.57, 61.23], [46.03, 45.76], 30.76, 30.21, [28.53, 28.28], 25.95, [25.66, 25.29], 25.13, [18.28, 17.94], 3.72, −5.34. (S)-tert-butyl 2-(tert-butyldimethylsilyloxy)ethyl (4-(N-hydroxycarbamimidoyl)-2,3-dihydro-1H-inden-1-yl)carbamate INT-19 is prepared in an analogous fashion using INT-17.

(R)-tert-butyl 2-(tert-butyldimethylsilyloxy)ethyl(4-(5-(3-cyano-4-isopropoxyphenyl)-1,2,4-oxadiazol-3-yl)-2,3-dihydro-1H-inden-1-yl)carbamate and (R)-tert-butyl 4-(5-(3-cyano-4-isopropoxyphenyl)-1,2,4-oxadiazol-3-yl)-2,3-dihydro-1H-inden-1-yl)(2-hydroxethyl)carbamate

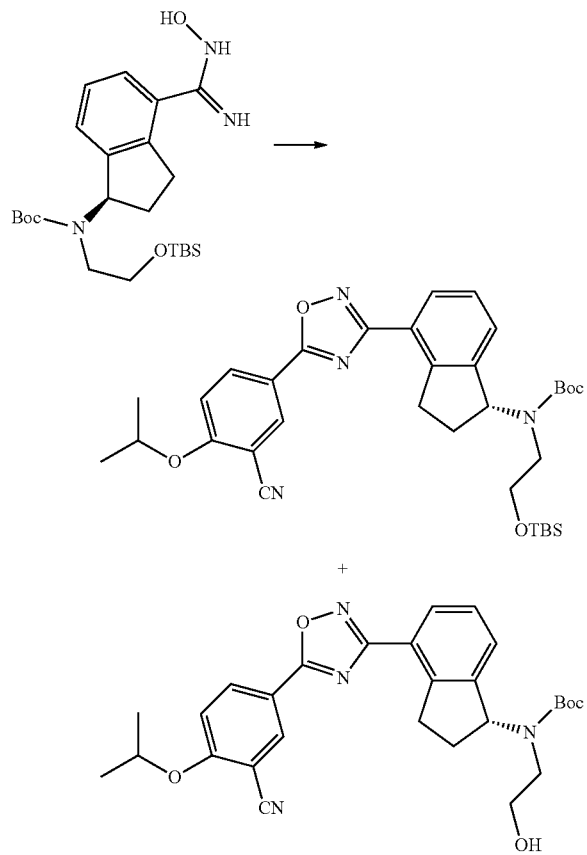

Prepared using General Procedure 4. To a solution of 3-cyano-4-isopropoxybenzoic acid (4.5 g, 21.9 mmol) in anhydrous DMF (100 mL) was added HOBt (5.4 g, 40.0 mmol) and EDC (5.6 g, 29.6 mmol). After 1 h, (R)-tert-butyl 2-(tert-butyldimethylsilyloxy)ethyl (4-(N-hydroxycarbamimidoyl)-2,3-dihydro-1H-inden-1-yl)carbamate INT-18 (11.8 g, 26.3 mmol) was added and the reaction mixture was stirred at room temperature for 2 h. LCMS analysis showed complete conversion to the intermediate, (R)-tert-butyl 2-(tert-butyldimethylsilyloxy)ethyl (4-(N-(3-cyano-4-isopropoxybenzoyloxy)carbamimidoyl)-2,3-dihydro-1H-inden-1-yl)carbamate INT-20. The reaction mixture was then heated to 80° C. for 12 h. The reaction mixture was cooled to room temperature and diluted with EA (250 mL). NaHCO$_3$ (250 mL) and water (350 mL) were added until all the solids dissolved. The mixture was extracted with EA and the organic layers washed successively with water and brine. The organic layers were dried over MgSO$_4$ and concentrated to produce 15.3 g of a mixture of (R)-tert-butyl 2-(tert-butyldimethylsilyloxy)ethyl(4-(5-(3-cyano-4-isopropoxyphenyl)-1,2,4-oxadiazol-3-yl)-2,3-dihydro-1H-inden-1-yl)carbamate INT-21, and the corresponding material without the TBS protecting group, (R)-tert-butyl 4-(5-(3-cyano-4-isopropoxyphenyl)-1,2,4-oxadiazol-3-yl)-2,3-dihydro-1H-inden-1-yl) (2-hydroxyethyl)carbamate INT-22. The mixture was a brown oil, which could used directly without further purification or purified by chromatography (EA/hexane). INT-21: LCMS-ESI (m/z) calculated for C$_{34}$H$_{46}$N$_4$O$_5$Si: 618.8. found 519.2 [M-Boc]$^+$ and 641.3 [M+Na]$^+$, t$_R$=7.30 min (Method 1). $^1$H NMR (400 MHz, CDCl$_3$) δ 8.43 (d, J=2.1, 1H), 8.34 (dd, J=8.9, 2.2, 1H), 8.07 (d, J=8.1, 1H), 7.46-7.26 (m, 2H), 7.12 (d, J=9.0, 1H), 5.85 (s, 0.5H), 5.37 (s, 0.5H), 4.80 (dt, J=12.2, 6.1, 1H), 3.92-3.32 (m, 3.5H), 3.17 (s, 2H), 2.95 (s, 0.5H), 2.62-2.39 (m, 1H), 2.38-2.05 (m, 1H), 1.53 (s, 4.5H), 1.48 (d, J=6.1, 6H), 1.33-1.27 (m, 4.5H), 0.94-0.77 (m, 9H), 0.01 (d, J=20.9, 6H). $^{13}$C NMR (101 MHz, DMSO) δ 173.02, 169.00, 162.75, [156.22, 155.52], [145.18, 144.12], [143.39, 142.76], 134.16, 133.89, 128.20, [128.01, 127.85], [127.04, 126.90], 126.43, 123.31, 116.93, 115.30, 113.55, 103.96, [79.95, 79.68], 72.73, 67.61, 63.42, [61.91, 61.77], 60.99, 46.11, 31.78, [30.47, 29.87], [28.55, 28.26], 25.93, 21.75, 18.30, 0.00, −5.37. INT-22: LCMS-ESI calculated for C$_{28}$H$_{32}$N$_4$O$_5$: 504.6. found 527.2 [M+Na]$^+$, t$_R$=2.65 min (Method 1). $^1$H NMR (400 MHz, CDCl$_3$) δ 8.36 (d, J=2.1, 1H), 8.27 (dd, J=8.9, 2.2, 1H), 8.03 (d, J=7.2, 1H), 7.35-7.26 (m, 2H), 7.06 (d, J=9.0, 1H), 5.44 (s, 1H), 4.73 (dt, J=12.2, 6.1, 1H), 3.64 (s, 2H), 3.44 (ddd, J=17.5, 9.5, 3.2, 2H), 3.11 (dt, J=17.4, 8.6, 3H), 2.54-2.38 (m, 1H), 2.04 (td, J=17.6, 8.8, 1H), 1.50-1.24 (m, 15H). (S)-tert-butyl 2-(tert-butyldimethylsilyloxy)ethyl (4-(5-(3-cyano-4-isopropoxyphenyl)-1,2,4-oxadiazol-3-yl)-2,3-dihydro-1H-inden-1-yl)carbamate INT-23 and (S)-tert-butyl 4-(5-(3-cyano-4-isopropoxyphenyl)-1,2,4-oxadiazol-3-yl)-2,3-dihydro-1H-inden-1-yl) (2-hydroxyethyl)carbamate INT-24 were made in an analogous fashion.

(R)-5-(3-(1-(2-hydroxyethylamino)-2,3-dihydro-1H-inden-4-yl)-1,2,4-oxadiazol-5-yl)-2-isopropoxybenzonitrile (Compound 85)

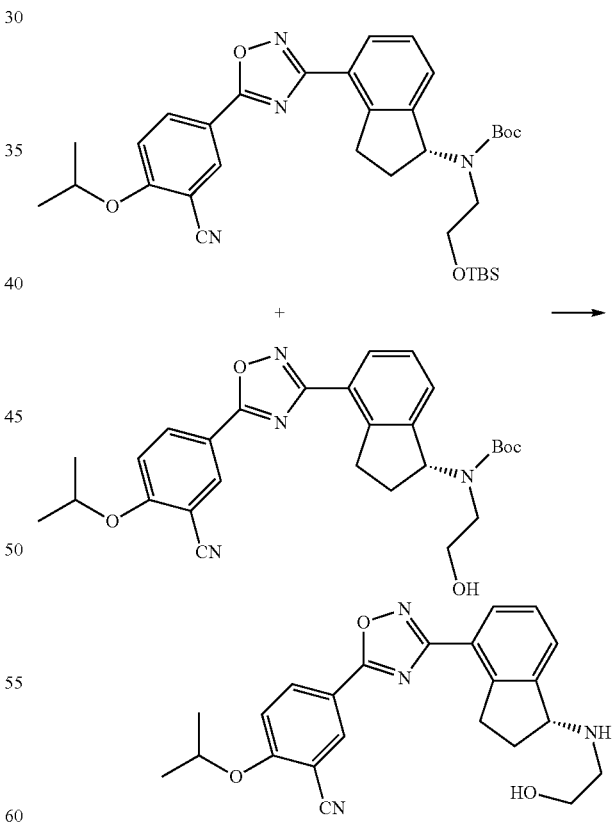

To a solution of (R)-tert-butyl 2-(tert-butyldimethylsilyloxy)ethyl(4-(5-(3-cyano-4-isopropoxyphenyl)-1,2,4-oxadiazol-3-yl)-2,3-dihydro-1H-inden-1-yl)carbamate INT-21 and (R)-tert-butyl 4-(5-(3-cyano-4-isopropoxyphenyl)-1,2,4-oxadiazol-3-yl)-2,3-dihydro-1H-inden-1-yl) (2-hydroxyethyl)carbamate INT-22 (13.9 g, 27.5 mmol) in dioxane (70 mL) at 0° C. was added 4N HCl in dioxane (68.8 g, 275.4 mmol). The reaction mixture was warmed to room temperature and then heated to 50° C. for 1 h. The resulting suspension was cooled to room temperature and Et₂O (75 mL) was added. The precipitate was collected by filtration, washed with Et₂O and dried to produce 10.5 g of an off-white solid. The HCl salt was recrystallized from MeOH (165 mL) to produce 5.98 g (56% overall yield from (R)-tert-butyl 2-(tert-butyldimethylsilyloxy)ethyl(4-cyano-2,3-dihydro-1H-inden-1-yl)carbamate) of (R)-5-(3-(1-(2-hydroxyethylamino)-2,3-dihydro-1H-inden-4-yl)-1,2,4-oxadiazol-5-yl)-2-isopropoxybenzonitrile 85 as a white solid. LCMS-ESI (m/z) calculated for $C_{23}H_{24}N_4O_3$: 404.5. found 405.4 [M+H]⁺, $t_R$=2.44 min. ¹H NMR (400 MHz, DMSO) δ 9.25 (s, 2H), 8.53 (d, J=2.3, 1H), 8.42 (dd, J=9.0, 2.3, 1H), 8.17 (d, J=7.7, 1H), 7.97 (d, J=7.6, 1H), 7.63-7.50 (m, 2H), 5.28 (t, J=5.0, 1H), 4.99 (hept, J=6.1, 1H), 4.92 (s, 1H), 3.72 (q, J=5.2, 2H), 3.57-3.43 (m, 1H), 3.27 (ddd, J=17.6, 9.1, 5.0, 1H), 3.15-2.85 (m, J=24.2, 2H), 2.53 (dtd, J=9.0, 5.5, 5.3, 3.6, 1H), 2.30 (ddd, J=13.4, 8.9, 4.6, 1H), 1.39 (d, J=6.0, 6H). ¹³C NMR (101 MHz, DMSO) δ 173.25, 167.86, 162.47, 144.56, 139.13, 134.53, 133.77, 129.30, 128.93, 127.45, 122.83, 115.79, 115.15, 114.84, 102.40, 72.46, 61.04, 56.51, 46.38, 31.53, 27.74, 21.37. Elemental analysis for $C_{23}H_{25}N_4O_3Cl$: C calc.=62.65%. found=62.73%; H calc.=5.71%. found=5.60%; N calc.=12.71%. found=12.64%; Cl calc.=8.04%. found=8.16%. Chiral HPLC of the free base: (R)-5-(3-(1-(2-hydroxyethylamino)-2,3-dihydro-1H-inden-4-yl)-1,2,4-oxadiazol-5-yl)-2-isopropoxy-benzo-nitrile was eluted using 10% i-PrOH in hexanes plus 0.3% DEA: >99.9% ee, $t_R$=37.72 min. (S)-5-(3-(1-(2-hydroxyethylamino)-2,3-dihydro-1H-inden-4-yl)-1,2,4-oxadiazol-5-yl)-2-isopropoxy benzonitrile 86 was obtained in analogous fashion from (S)-tert-butyl 2-(tert-butyldimethylsilyloxy)ethyl(4-(5-(3-cyano-4-isopropoxyphenyl)-1,2,4-oxadiazol-3-yl)-2,3-dihydro-1H-inden-1-yl)carbamate INT-23 and (S)-tert-butyl 4-(5-(3-cyano-4-isopropoxyphenyl)-1,2,4-oxadiazol-3-yl)-2,3-dihydro-1H-inden-1-yl) (2-hydroxyethyl)carbamate INT-24: >99.9% ee, $t_R$ for (S)-enantiomer=35.86 min.

(R)-2-(tert-butoxycarbonyl(4-(5-(3-cyano-4-isopropoxyphenyl)-1,2,4-oxadiazol-3-yl)-2,3-dihydro-1H-inden-1-yl)amino)acetic acid (INT-25)

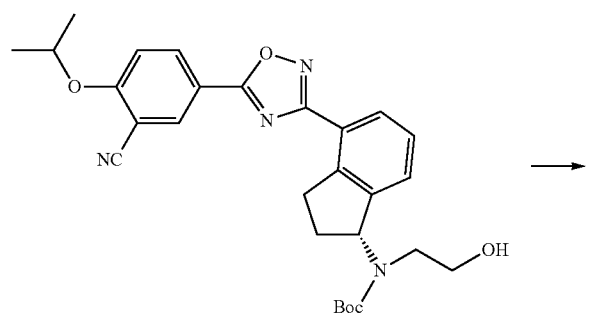

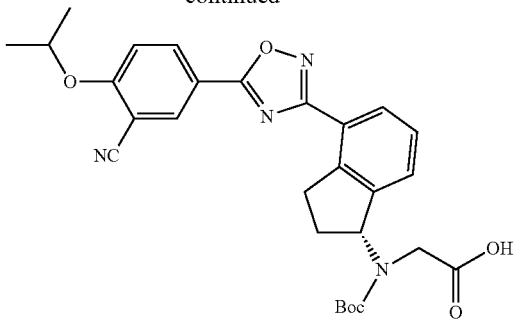

(R)-tert-butyl 4-(5-(3-cyano-4-isopropoxyphenyl)-1,2,4-oxadiazol-3-yl)-2,3-dihydro-1H-inden-1-yl) (2-hydroxyethyl)carbamate INT-22 (4.8 g, 9.5 mmol) was dissolved in $CH_3CN$ (48 mL) and 0.67 M pH 6.7 sodium phosphate buffer (38 mL). To the reaction mixture was added TEMPO (0.10 g, 0.67 mmol) and the reaction was heated to 35° C. Sodium chlorite (1.72 g, 19 mmol) in water (9.5 mL) and sodium hypochlorite (0.28 mL, 0.19 mmol) in water (5.70 mL) were simultaneously added dropwise from separate addition funnels over 1 hour. After addition, the reaction was heated to 35° C. for an additional hour. The reaction was cooled to room temperature, water (80 mL) was added, and the pH of the reaction mixture was adjusted to 8.5 with 2.0 N NaOH (12 mL). The reaction was quenched by pouring into an ice cold solution of sodium sulfite (2.9 g in 50 mL of water) and the temperature was maintained below 20° C. After stirring for 30 min at room temperature, Et₂O (50 mL) was added and the organic layer was separated and discarded. The aqueous layer was acidified with 1.0 N HCl (55 mL) to pH 3.0 and extracted with EA (3×100 mL). The organic layer was dried over MgSO₄ and filtered to give 4.9 g (>99%) of (R)-2-(tert-butoxycarbonyl(4-(5-(3-cyano-4-isopropoxyphenyl)-1,2,4-oxadiazol-3-yl)-2,3-dihydro-1H-inden-1-yl)amino)acetic acid INT-25 as a white foam. LCMS-ESI (m/z) calculated for $C_{28}H_{30}N_4O_6$: 518.2. found 541.2 [M+Na]⁺, $t_R$=3.97 min. ¹H NMR (400 MHz, CDCl₃) δ 8.33 (d, J=2.2 Hz, 1H), 8.24 (dd, J=8.9, 2.2 Hz, 1H), 8.08-7.94 (m, J=6.9 Hz, 1H), 7.41-7.22 (m, 2H), 7.03 (d, J=9.1 Hz, 1H), 5.85 (t, J=7.9 Hz, 0.6H), 5.51 (t, J=7.8 Hz, 0.4H), 4.70 (hept, J=6.2 Hz, 1H), 3.88 (d, J=17.1 Hz, 0.4H), 3.69 (d, J=18.0 Hz, 0.6H), 3.56 (d, J=17.2 Hz, 0.4H), 3.43 (d, J=18.0 Hz, 0.6H), 3.40-3.25 (m, 1H), 3.07 (dt, J=17.3, 8.5 Hz, 1H), 2.53-2.38 (m, 1H), 1.93-1.77 (m, 1H), 1.39 (s, 9H), 1.38 (d, J=6.1 Hz, 6H).

General Procedure 10. Amide Formation

To the boc-protected (R)- or (S)-indane amino acid (1 equivalent) in DMF (2 M) was added HOBt (3 eq) and EDC (3 eq) and the reaction was stirred at room temperature for 30 min. The amine (3 eq) was added and the reaction was stirred at room temperature for 2 h until complete. The Boc protected product was precipitated out of water or extracted (DCM/5% MeOH) and dried over MgSO₄. The solid was dissolved in 4M HCl in dioxane and the mixture was heated to 50° C. After 1 h, the solvent was removed under reduced pressure and the solid residue was purified by recrystallization or preparative HPLC.

Compounds 59, 60, 90, 127-135 were prepared using General Procedure 10.

(R)-2-(4-(5-(3-cyano-4-isopropoxyphenyl)-1,2,4-oxadiazol-3-yl)-2,3-dihydro-1H-inden-1-ylamino)-N,N-dimethylacetamide hydrochloride (Compound 90)

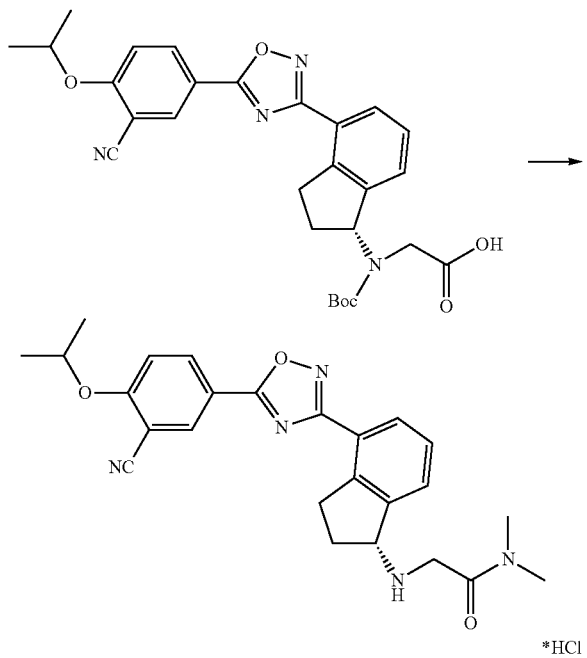

*HCl

Prepared using General Procedure 10. To 4.9 g (9.5 mmol) of (R)-2-(tert-butoxycarbonyl(4-(5-(3-cyano-4-isopropoxyphenyl)-1,2,4-oxadiazol-3-yl)-2,3-dihydro-1H-inden-1-yl)amino)acetic acid INT-25 in DMF (20 mL) was added HOBt (4.4 g, 28.5 mmol) and EDC (5.5 g, 28.5 mmol) and the reaction mixture was stirred at room temperature for 30 min. Dimethylamine (2.0N in THF, 14.25 mL, 28.5 mmol) was added and the reaction was stirred at room temperature for 2 h. The reaction mixture was poured into water (300 mL) and the precipitate was filtered. The solid was thoroughly washed with water (200 mL). The solid was dissolved in DCM with 5% MeOH, dried over $MgSO_4$ and filtered. 4M HCl in dioxane was added and the mixture was heated to 50° C. After 1 h, the solvent was removed under reduced pressure and the solid residue was recrystallized from 120 mL MeOH/120 mL $Et_2O$/70 mL hexane/10 mL of IPA mixture to provide 3.37 g (74%) of (R)-2-(4-(5-(3-cyano-4-isopropoxyphenyl)-1,2,4-oxadiazol-3-yl)-2,3-dihydro-1H-inden-1-ylamino)-N,N-dimethylacetamide hydrochloride 90 as a white powder. LCMS-ESI (m/z) calculated for $C_{25}H_{27}N_5O_3$: 445.5. found 446.2 $[M+H]^+$, $t_R$=2.52 min. Elemental analysis of $C_{25}H_{28}N_5O_3Cl\cdot H_2O$: C calc.=60.05%. found=59.68%; H calc.=6.05%. found=6.45%; N calc.=14.01%. found=13.91%; Cl calc.=7.09. found=6.98%. $^1H$ NMR (400 MHz, DMSO) δ 9.44 (s, 2H), 8.53 (d, J=2.3 Hz, 1H), 8.41 (dd, J=9.0, 2.3 Hz, 1H), 8.16 (d, J=7.6 Hz, 1H), 7.96 (d, J=7.6 Hz, 1H), 7.62-7.52 (m, 2H), 5.05-4.92 (m, 1H), 4.88 (dd, J=7.0, 4.2 Hz, 1H), 4.11 (d, J=16.1 Hz, 1H), 4.02 (d, J=16.0 Hz, 1H), 3.51 (ddd, J=17.2, 8.2, 6.6 Hz, 1H), 3.25 (ddd, J=17.4, 8.8, 5.0 Hz, 1H), 2.97 (s, 3H), 2.91 (s, 3H), 2.60-2.51 (m, 1H), 2.33 (dq, J=9.0, 4.9 Hz, 1H), 1.39 (d, J=6.0 Hz, 6H). $^{13}C$ NMR (101 MHz, DMSO) δ 173.33, 167.95, 164.97, 162.56, 144.68, 139.16, 134.61, 133.85, 129.43, 128.70, 127.63, 122.90, 115.87, 115.24, 114.92, 102.48, 72.54, 61.28, 44.84, 35.77, 34.98, 31.52, 27.68, 21.45. Chiral HPLC of the free base: (R)-2-(4-(5-(3-cyano-4-isopropoxyphenyl)-1,2,4-oxadiazol-3-yl)-2,3-dihydro-1H-inden-1-ylamino)-N,N-dimethylacetamide was eluted using 15% i-PrOH in hexanes plus 0.3% DEA: 98.5% ee, $t_R$=41.19 min. (S)-2-(4-(5-(3-cyano-4-isopropoxyphenyl)-1,2,4-oxadiazol-3-yl)-2,3-dihydro-1H-inden-1-ylamino)-N,N-dimethyl-acetamide 91 can be obtained in an analogous fashion from (S)-2-(tert-butoxycarbonyl(4-(5-(3-cyano-4-isopropoxyphenyl)-1,2,4-oxadiazol-3-yl)-2,3-dihydro-1H-inden-1-yl)amino)acetic acid. $t_R$ for (S)-enantiomer=34.35 min. An alternative route is described below.

Compound 91 was made from INT-9 using General Procedures 9, 3, and 4 sequentially.

(S)-tert-butyl 4-cyano-2,3-dihydro-1H-inden-1-yl(2-(dimethylamino)-2-oxoethyl)-carbamate

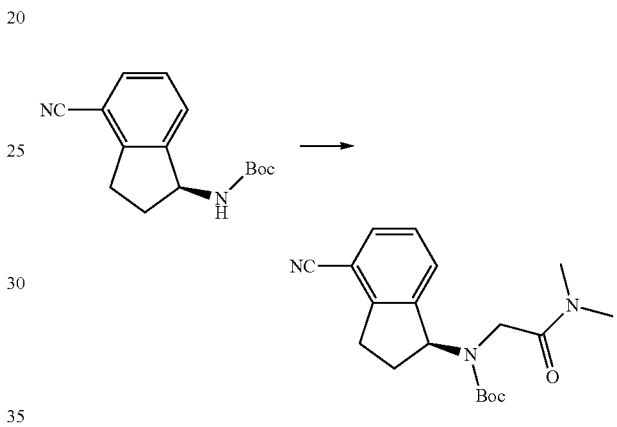

Prepared using General Procedure 9. To a solution of (S)-tert-butyl 4-cyano-2,3-dihydro-1H-inden-1-ylcarbamate INT-9 (3.0 g, 1.16 mmol) in DMF (20 mL) was added NaH (1.39 g of 60% dispersion in mineral oil, 34.8 mmol) at 0° C. with stirring for 3 h before the addition of 2-chloro-N,N-dimethylacetamide (2.82 g, 23.2 mmol). The reaction mixture was stirred at 0° C. for 0.5 h and then warmed to room temperature for 1 h. The reaction mixture was quenched with water (3 mL) slowly at 0° C. The mixture was partitioned between EA (3×20 mL) and water (50 mL). The combined organic layers were concentrated and purified by chromatography (DCM/MeOH) to provide product 3.82 g (96.0%) of (S)-tert-butyl 4-cyano-2,3-dihydro-1H-inden-1-yl(2-(dimethylamino)-2-oxoethyl)carbamate as a light brown solid. LCMS-ESI (m/z) calculated for $C_{19}H_{25}ClN_6O_6$: 343.4. found 366.1 $[M+Na]^+$, $t_R$=3.16 min.

(S)-tert-butyl 2-(dimethylamino)-2-oxoethyl(4-(N-hydroxycarbamimidoyl)-2,3-dihydro-1H-inden-1-yl)carbamate

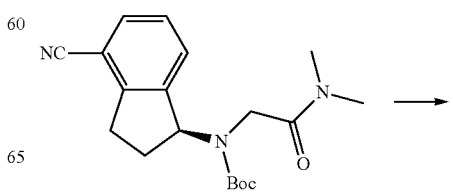

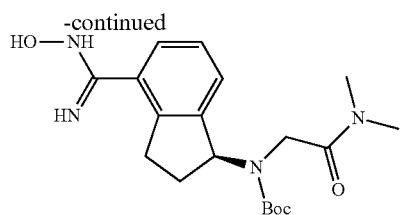

Prepared using General Procedure 3. To a solution of (S)-tert-butyl 4-cyano-2,3-dihydro-1H-inden-1-yl(2-(dimethylamino)-2-oxoethyl)carbamate (3.8 g, 11.07 mmol) in EtOH (20 mL) was added hydroxylamine hydrochloride (1.92 g, 27.67 mmol) and triethylamine (2.8 g, 27.67 mmol). The reaction solution was heated to 85° C. for 2 h. The solvent was removed under vacuum and the residue partitioned between DCM (3×10 mL) and water (10 mL). The combined organic layers were dried over MgSO$_4$ and concentrated under vacuum to produce 4.10 g (87.7%) of (S)-tert-butyl 2-(dimethylamino)-2-oxoethyl(4-(N-hydroxycarbamimidoyl)-2,3-dihydro-1H-inden-1-yl)carbamate, which was 65% pure and used directly in the next experiment. LCMS-ESI (m/z) calculated for $C_{19}H_{28}N_4O_4$; 376.45. found 377.2 [M+H]$^+$, $t_R$=1.85 min.

(S)-tert-butyl 4-(5-(3-cyano-4-isopropoxyphenyl)-1,2,4-oxadiazol-3-yl)-2,3-dihydro-1H-inden-1-yl(2-(dimethylamino)-2-oxoethyl)carbamate

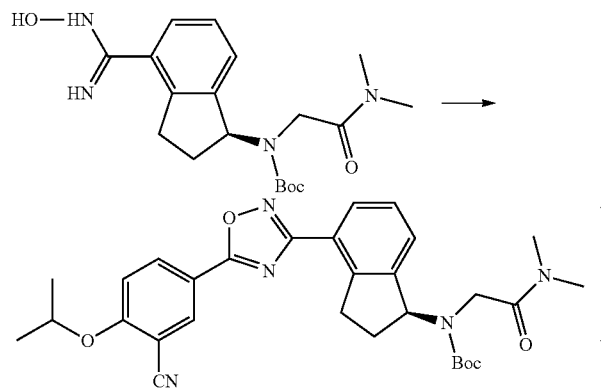

Prepared using General Procedure 4. To a solution of 3-cyano-4-isopropoxybenzoic acid (1.35 g, 6.6 mmol) in DMF (15 mL) was added HOBt (1.34 g, 9.9 mmol) and EDC (1.89 g, 9.9 mmol) at room temperature. The reaction was stirred for 2 h followed by addition of (S)-tert-butyl 2-(dimethylamino)-2-oxoethyl (4-(N-hydroxycarbamimidoyl)-2,3-dihydro-1H-inden-1-yl)carbamate (3.82 g, 6.6 mmol). The reaction mixture was stirred at room temperature for 2 h. The mixture was partitioned between EA (3×10 mL) and NaHCO$_3$ (50 mL). The organic layers were combined, dried with MgSO$_4$, and concentrated to produce the intermediate (S)-tert-butyl 4-(N-(3-cyano-4-isopropoxybenzoyloxy)carbamimidoyl)-2,3-dihydro-1H-inden-1-yl (2-(dimethylamino)-2-oxoethyl)carbamate. This intermediate (3.2 g, 5.68 mmol) was dissolved in DMF (15 mL) and heated to 95° C. for 8 h. The reaction was diluted with NaHCO$_3$ (30 mol) and extracted with EA (3×15 mL). The organic phase was dried over MgSO$_4$ and concentrated under reduced pressure to give 2.36 g (78.4%) of (S)-tert-butyl 4-(5-(3-cyano-4-isopropoxyphenyl)-1,2,4-oxadiazol-3-yl)-2,3-dihydro-1H-inden-1-yl(2-(dimethylamino)-2-oxoethyl)carbamate as light brown solid, and used without further purification in the next experiment.

(S)-2-(4-(5-(3-cyano-4-isopropoxyphenyl)-1,2,4-oxadiazol-3-yl)-2,3-dihydro-1H-inden-1-ylamino)-N,N-dimethylacetamide (Compound 91)

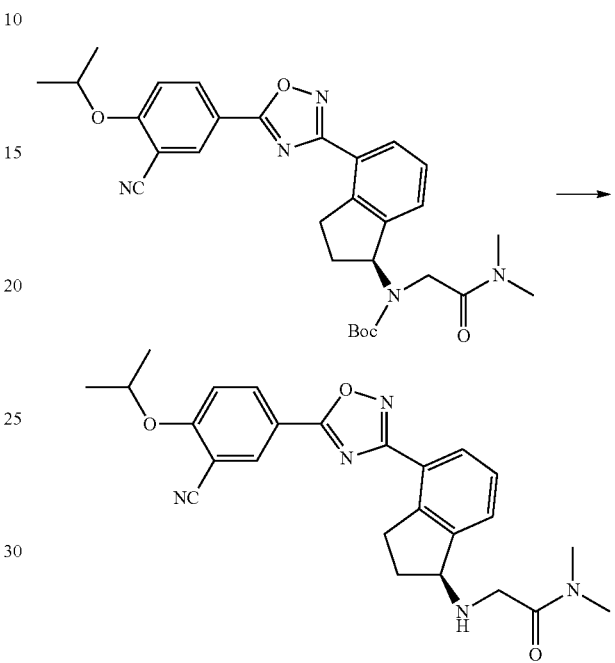

To a solution of the crude (S)-tert-butyl 4-(5-(3-cyano-4-isopropoxyphenyl)-1,2,4-oxadiazol-3-yl)-2,3-dihydro-1H-inden-1-yl(2-(dimethylamino)-2-oxoethyl)carbamate (2.36 g, 4.33 mmol) in dioxane (5 mL) was added 4 N HCl in dioxane (10 mL). The solution was stirred at room temperature for 2 h. The reaction mixture was concentrated and then suspended in Et$_2$O. The resulting solid was filtered and dried to obtain 2.3 g (78.4%) of the HCl salt of (S)-2-(4-(5-(3-cyano-4-isopropoxyphenyl)-1,2,4-oxadiazol-3-yl)-2,3-dihydro-1H-inden-1-ylamino)-N,N-dimethyl acetamide 91 which was 95% pure. The material can be further recrystallized from isopropanol. LCMS-ESI (m/z) calculated for $C_{25}H_{27}N_5O_3$: 445.51. found 446.2 [M+H]$^+$, $t_R$=2.55 min. $^1$H NMR and $^{13}$C for $C_{25}H_{28}N_5O_3Cl$: (400 MHz, DMSO) δ 9.46 (s, 2H), 8.53 (d, J=2.3, 1H), 8.42 (dd, J=9.0, 2.3, 1H), 8.17 (d, J=7.6, 1H), 7.97 (d, J=7.6, 1H), 7.67-7.51 (m, 2H), 4.99 (hept, J=6.1, 1H), 4.90 (s, 1H), 4.12 (d, J=16.0, 1H), 4.04 (d, J=16.0, 1H), 3.59-3.44 (m, 1H), 3.30-3.11 (m, 1H), 2.97 (s, 3H), 2.91 (s, 3H), 2.60-2.51 (m, 1H), 2.34 (s, 1H), 1.39 (d, J=6.0, 6H). $^{13}$C NMR (101 MHz, DMSO) δ 173.30, 167.95, 164.93, 162.54, 144.69, 139.17, 134.61, 133.83, 129.39, 128.77, 127.58, 122.86, 115.87, 115.23, 114.92, 102.47, 72.54, 61.26, 44.73, 35.77, 34.99, 31.54, 27.61, 21.45. Chiral HPLC of the free base: (S)-2-(4-(5-(3-cyano-4-isopropoxyphenyl)-1,2,4-oxadiazol-3-yl)-2,3-dihydro-1H-inden-1-ylamino)-N,N-dimethyl-acetamide was eluted using 15% isopropanol in hexanes, plus 0.3% DEA: >99.9% ee, $t_R$=34.35 min. (R)-2-(4-(5-(3-cyano-4-isopropoxyphenyl)-1,2,4-oxadiazol-3-yl)-2,3-dihydro-1H-inden-1-ylamino)-N, N-dimethyl acetamide 90 can be obtained in an analogous fashion from (R)-tert-butyl 4-cyano-2,3-dihydro-1H-inden-1-ylcarbamate. $t_R$ for (R)-enantiomer=41.19 min.

Compounds 92-101 and 252 were prepared using General Procedure 4.

Methyl 3-bromo-5-hydroxybenzoate

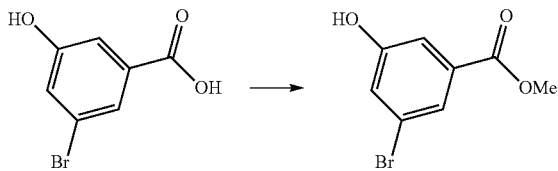 [SMILES: O=C(O)c1cc(O)cc(Br)c1 ; COC(=O)c1cc(O)cc(Br)c1]

To a flask containing 3-bromo-5-hydroxybenzoic acid (2.0 g, 9.2 mmol) in anhydrous MeOH (10 mL) at 0° C. under $N_2$ was added AcCl (912 µL, 12.9 mmol). The reaction mixture was allowed to warm to room temperature overnight. The mixture was diluted with EA and washed with $NaHCO_3$. The organic layers were dried and concentrated to provide 2.1 g (97%) of methyl 3-bromo-5-hydroxybenzoate as a white solid. LCMS-ESI (m/z) calculated for $C_8H_7BrO_3$: 231.04. found 232.9 [M+H]$^+$, $t_R$=3.06 min.

Methyl 3-bromo-5-isopropoxybenzoate

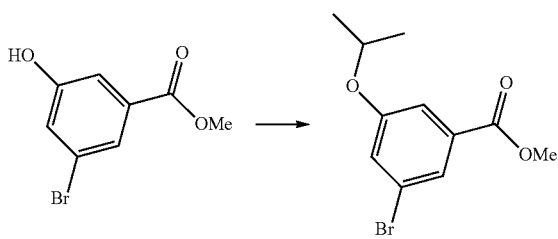

To a flask containing methyl 3-bromo-5-hydroxybenzoate (2.1 g, 8.9 mmol) in anhydrous DMF (10 mL) was added $K_2CO_3$ (2.47 g, 17.9 mmol) and 2-iodopropane (1.07 mL, 10.7 mmol). The reaction mixture was heated at 65° C. overnight then diluted with EA and washed with $NaHCO_3$. The organic layers were dried and concentrated to provide 1.81 g (75%) of methyl 3-bromo-5-isopropoxybenzoate as a white solid. LCMS-ESI (m/z) calculated for $C_{11}H_{13}BrO_3$: 273.12; no observed m/z ion, $t_R$=4.17 min.

Methyl 3-cyano-5-isopropoxybenzoate

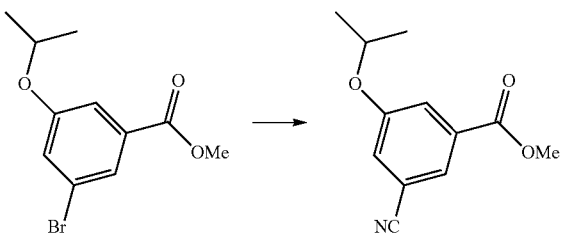 [SMILES: COC(=O)c1cc(Br)cc(OC(C)C)c1 ; COC(=O)c1cc(C#N)cc(OC(C)C)c1]

A solution of methyl 3-cyano-5-isopropoxybenzoate (1.81 g, 6.6 mmol) in anhydrous NMP (15 mL) was degassed 3 times. Zinc cyanide (1.56 g, 13.3 mmol) and Pd(PPh$_3$)$_4$ (38 mg, 0.03 mmol) were added and the reaction mixture was degassed 4 more times. The mixture was stirred under $N_2$ at 65° C. overnight. Additional Pd(PPh$_3$)$_4$ (100 mg, 0.09 mmol) was added and the reaction was degassed and stirred overnight at 65° C. The reaction mixture was diluted with EA and washed with $NaHCO_3$. The organic layers were dried and concentrated to a crude oil which was diluted in DCM and purified by chromatography (EA/hexanes) to provide 1.19 g (82%) of methyl 3-cyano-5-isopropoxybenzoate as a white solid. LCMS-ESI (m/z) calculated for $C_{12}H_{13}NO_3$: 219.2. found 220.1 [M+H]$^+$, $t_R$=3.60 min.

3-cyano-5-isopropoxybenzoic acid

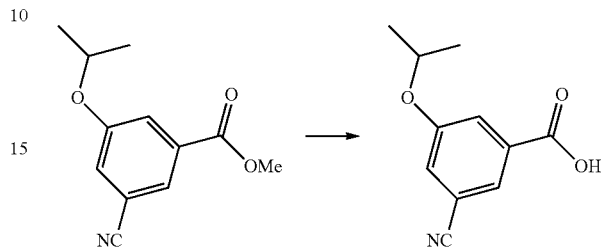

To a solution of methyl 3-cyano-5-isopropoxybenzoate (1.19 g, 5.4 mmol) in EtOH (4 mL) was added 5N NaOH (3 mL, 15 mmol). After stirring at room temperature for 4 h, the reaction mixture was diluted with 1N HCl and extracted with EA. The combined organic layers were dried over $Na_2SO_4$ and concentrated to provide 920 mg (83%) of 3-cyano-5-isopropoxybenzoic acid as a white solid. LCMS-ESI (m/z) calculated for $C_{11}H_{11}NO_3$: 205.2. found 206.1 [M+H]$^+$, $t_R$=2.97 min. $^1$H NMR (400 MHz, CDCl$_3$) δ 7.93 (t, J=1.4 Hz, 1H), 7.80 (dd, J=2.6, 1.4 Hz, 1H), 7.35 (dd, J=2.6, 1.4 Hz, 1H), 4.71-4.56 (m, 1H), 1.38 (dd, J=6.1, 2.2 Hz, 6H).

4-cyano-3-isopropoxybenzoic acid

Prepared in an analogous fashion to 3-cyano-5-isopropoxybenzoic acid starting from 4-bromo-3-hydroxybenzoic acid. LCMS-ESI (m/z) calculated for $C_{11}H_{11}NO_3$: 205.2. found 206.1 [M+H]$^+$, $t_R$=2.90 min.

5-cyano-2-isopropoxybenzoic acid

Prepared in an analogous fashion to 3-cyano-5-isopropoxybenzoic acid starting from 5-bromo-2-hydroxybenzoic acid. LCMS-ESI (m/z) calculated for $C_{11}H_{11}NO_3$: 205.2. found 206.1 [M+H]$^+$, $t_R$=2.70 min.

Methyl 3-chloro-4-isopropoxybenzoate

Prepared from methyl 3-chloro-4-hydroxybenzoate according to the procedure for methyl 3-bromo-5-isopropoxybenzoate. LCMS-ESI (m/z) calculated for $C_{11}H_{13}ClO_3$: 228.7. found 229.1 [M+H]$^+$, $t_R$=3.90 min. $^1$H NMR (400 MHz, CDCl$_3$) δ 8.05 (d, J=2.1 Hz, 1H), 7.89 (dd, J=8.7, 2.2 Hz, 1H), 6.94 (d, J=8.8 Hz, 1H), 4.67 (dt, J=12.2, 6.1 Hz, 1H), 3.89 (s, 3H), 1.37 (dd, J=34.4, 30.1 Hz, 6H).

3-chloro-4-isopropoxybenzoic acid

Prepared from methyl 3-chloro-4-isopropoxybenzoate according to the procedure for 3-cyano-5-isopropoxybenzoic acid. LCMS-ESI (m/z) calculated for $C_{10}H_{11}ClO_3$: 214.7. found 215.0 [M+H]$^+$, $t_R$=3.22 min. $^1$H NMR (400 MHz, CDCl$_3$) δ 12.94 (s, 1H), 7.98-7.74 (m, 2H), 7.26 (d, J=8.9 Hz, 1H), 4.80 (dt, J=12.1, 6.0 Hz, 1H), 1.33 (t, J=5.6 Hz, 6H).

Methyl 3-bromo-4-(cyclopropylmethoxy)benzoate

Prepared from methyl 3-bromo-4-hydroxybenzoate and cyclopropylmethylbromide according to the procedure for methyl 3-bromo-5-isopropoxybenzoate. LCMS-ESI (m/z)

calculated for C₁₂H₁₃BrO₃: 285.1; no m/z observed, $t_R$=3.96 min. ¹H NMR (400 MHz, CDCl₃) δ 8.22 (t, J=2.8 Hz, 1H), 8.02-7.88 (m, 1H), 6.91-6.81 (m, 1H), 4.02-3.91 (m, 2H), 3.88 (d, J=5.5 Hz, 3H), 1.41-1.26 (m, 1H), 0.76-0.59 (m, 2H), 0.52-0.31 (m, 2H).

Methyl 3-cyano-4-(cyclopropylmethoxy)benzoate

Prepared from methyl 3-bromo-4-(cyclopropylmethoxy)benzoate according to the procedure for methyl 3-cyano-5-isopropoxybenzoate. LCMS-ESI (m/z) calculated for C₁₃H₁₃NO₃: 231.3; no m/z observed, $t_R$=3.97 min.

3-cyano-4-(cyclopropylmethoxy)benzoic acid

Prepared from methyl 3-cyano-4-(cyclopropylmethoxy)benzoate according to the procedure for 3-cyano-5-isopropoxybenzoic acid. LCMS-ESI (m/z) calculated for C₁₂H₁₁NO₃: 217.2; no m/z observed, $t_R$=2.92 min. ¹H NMR (400 MHz, CDCl₃) δ 8.24-8.08 (m, 2H), 7.32 (d, J=8.9 Hz, 1H), 4.09 (d, J=7.1 Hz, 2H), 1.28 (s, 1H), 0.71-0.52 (m, 2H), 0.49-0.31 (m, 2H).

Methyl 3-bromo-5-(trifluoromethoxy)benzoate

Prepared from 3-bromo-5-(trifluoromethoxy)benzoic acid according to the procedure for methyl 3-bromo-5-hydroxybenzoate. LCMS-ESI (m/z) calculated for C₉H₆BrF₃O₃: 299.0; no m/z observed, $t_R$=4.08 min. ¹H NMR (400 MHz, CDCl₃) δ 8.12 (dd, J=3.9, 2.4 Hz, 1H), 7.83 (dt, J=2.2, 1.2 Hz, 1H), 7.57 (ddd, J=2.4, 1.8, 0.9 Hz, 1H), 3.99-3.87 (m, 3H).

Methyl 3-cyano-5-(trifluoromethoxy)benzoate

Prepared from methyl 3-bromo-5-(trifluoromethoxy)benzoate according to the procedure for methyl 3-cyano-5-isopropoxybenzoate. LCMS-ESI (m/z) calculated for C₁₀H₆F₃NO₃: 245.2; no m/z observed, $t_R$=4.43 min. ¹H NMR (400 MHz, CDCl₃) δ 8.27 (t, J=1.4 Hz, 1H), 8.16-8.07 (m, 1H), 7.73-7.65 (m, 1H), 3.99 (s, 3H).

3-cyano-5-(trifluoromethoxy)benzoic acid

Prepared from methyl 3-cyano-5-(trifluoromethoxy)benzoate according to the procedure for 3-cyano-5-isopropoxybenzoic acid. LCMS-ESI (m/z) calculated for C₉H₄F₃NO₃: 231.1; no m/z observed, $t_R$=2.38 min.

(R)-3-(3-(1-amino-2,3-dihydro-1H-inden-4-yl)-1,2,4-oxadiazol-5-yl)benzonitrile (Compound 92)

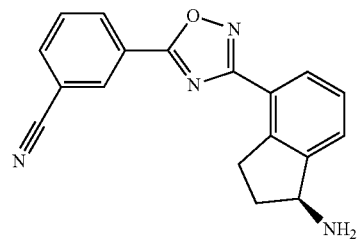 [SMILES: N#Cc1cccc(-c2nc(-c3cccc4c3CC[C@@H]4N)no2)c1]

Prepared from 3-cyanobenzoic acid using General Procedure 4. LCMS-ESI (m/z) calculated for C₁₈H₁₄N₄O: 302.3. found 286.1 [M-NH₂]⁺, $t_R$=0.78 min. ¹H NMR (400 MHz, DMSO) δ 8.67-8.60 (m, 1H), 8.54-8.47 (m, 1H), 8.25-8.17 (m, 1H), 7.97 (s, 1H), 7.89 (d, J=0.4 Hz, 1H), 7.60 (s, 1H), 7.44 (s, 1H), 4.34-4.22 (m, 1H), 3.34 (s, 1H), 3.12-2.93 (m, 1H), 2.48-2.39 (m, 1H), 2.12-1.89 (m, 1H), 1.76-1.59 (m, 1H).

(R)-3-(3-(1-amino-2,3-dihydro-1H-inden-4-yl)-1,2,4-oxadiazol-5-yl)-5-(trifluoromethoxy)benzonitrile (Compound 93)

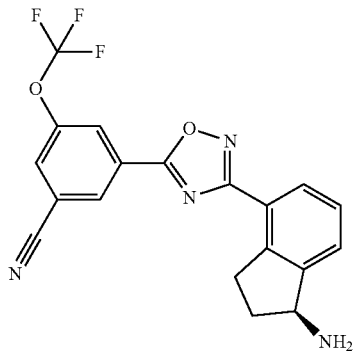 [SMILES: N#Cc1cc(OC(F)(F)F)cc(-c2nc(-c3cccc4c3CC[C@@H]4N)no2)c1]

Prepared from 3-cyano-5-(trifluoromethoxy)benzoic acid using General Procedure 4. LCMS-ESI (m/z) calculated for C₁₉H₁₃F₃N₄O₂: 386.3. found 370.0 [M-NH₂]⁺, $t_R$=2.61 min.

(R)-4-(5-(3-chloro-4-isopropoxyphenyl)-1,2,4-oxadiazol-3-yl)-2,3-dihydro-1H-inden-1-amine (Compound 95)

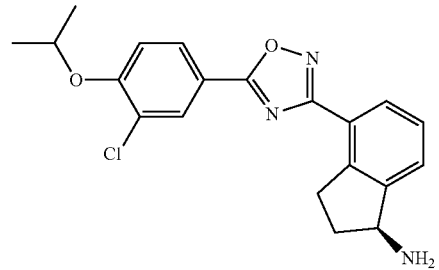 [SMILES: CC(C)Oc1ccc(-c2nc(-c3cccc4c3CC[C@@H]4N)no2)cc1Cl]

Prepared from 3-chloro-4-isopropoxybenzoic acid using General Procedure 4. LCMS-ESI (m/z) calculated for C₂₀H₂₀ClN₃O₂: 369.8. found 353.1 [M-NH₂]⁺, $t_R$=1.70 min.

(R)-4-(5-(4-isopropoxyphenyl)-1,2,4-oxadiazol-3-yl)-2,3-dihydro-1H-inden-1-amine (Compound 96)

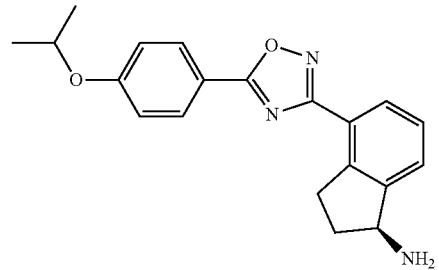 [SMILES: CC(C)Oc1ccc(-c2nc(-c3cccc4c3CC[C@@H]4N)no2)cc1]

Prepared from 4-isopropoxybenzoic acid using General Procedure 4. LCMS-ESI (m/z) calculated for $C_{20}H_{21}N_3O_2$: 335.4. found 319.1 [M-NH$_2$]$^+$, $t_R$=1.64 min. $^1$H NMR (400 MHz, CDCl$_3$) δ 8.11 (d, J=9.0 Hz, 2H), 8.02-7.89 (m, 1H), 7.65-7.54 (m, 1H), 7.50-7.36 (m, 1H), 7.17 (d, J=9.0 Hz, 2H), 4.88-4.71 (m, 1H), 4.38-4.23 (m, 1H), 3.12-2.91 (m, 2H), 2.46-2.37 (m, 1H), 1.77-1.60 (m, 1H), 1.33 (d, J=6.0 Hz, 6H).

(R)-3-(3-(1-amino-2,3-dihydro-1H-inden-4-yl)-1,2,4-oxadiazol-5-yl)-5-isopropoxy benzo-nitrile (Compound 97)

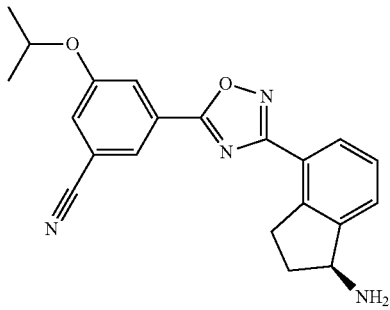 [SMILES: CC(C)Oc1cc(C#N)cc(-c2nc(-c3cccc4c3CC[C@@H]4N)no2)c1]

Prepared from 3-cyano-5-isopropoxybenzoic acid using General Procedure 4. LCMS-ESI (m/z) calculated for $C_{21}H_{20}N_4O_2$: 360.4. found 344.1 [M-NH$_2$]$^+$, $t_R$=2.59 min.

(R)-4-(3-(1-amino-2,3-dihydro-1H-inden-4-yl)-1,2,4-oxadiazol-5-yl)-2-isopropoxy benzonitrile (Compound 98)

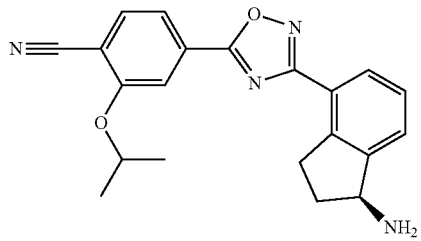 [SMILES: CC(C)Oc1cc(-c2nc(-c3cccc4c3CC[C@@H]4N)no2)ccc1C#N]

Prepared from 4-cyano-3-isopropoxybenzoic acid using General Procedure 4. LCMS-ESI (m/z) calculated for $C_{21}H_{20}N_4O_2$: 360.4. found 344.1 [M-NH$_2$]$^+$, $t_R$=2.52 min.

(R)-3-(3-(1-amino-2,3-dihydro-1H-inden-4-yl)-1,2,4-oxadiazol-5-yl)-4-isopropoxy benzonitrile (Compound 99)

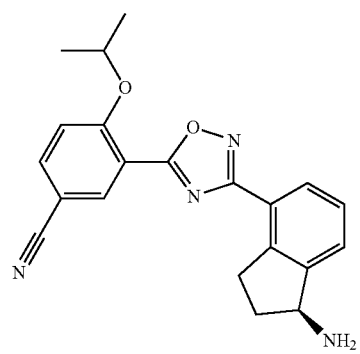 [SMILES: CC(C)Oc1ccc(C#N)cc1-c1nc(-c2cccc3c2CC[C@@H]3N)no1]

Prepared from 5-cyano-2-isopropoxybenzoic acid using General Procedure 4. LCMS-ESI (m/z) calculated for $C_{21}H_{20}N_4O_2$: 360.4. found 344.1 [M-NH$_2$]$^+$, $t_R$=1.86 min.

(R)-5-(3-(1-amino-2,3-dihydro-1H-inden-4-yl)-1,2,4-oxadiazol-5-yl)-2-(cyclopropylmethoxy)benzonitrile (Compound 100)

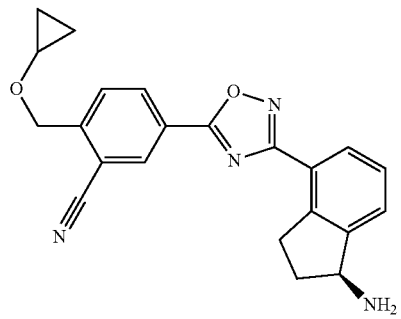 [SMILES: N#Cc1cc(-c2nc(-c3cccc4c3CC[C@@H]4N)no2)ccc1COC1CC1]

Prepared from 3-cyano-4-(cyclopropylmethoxy)benzoic acid using General Procedure 4. LCMS-ESI (m/z) calculated for $C_{22}H_{20}N_4O_2$: 372.4. found 356.1 [M-NH$_2$]$^+$, $t_R$=1.61 min.

2-hydroxy-5-(3-(1-((2-hydroxyethyl)amino)-2,3-dihydro-1H-inden-4-yl)-1,2,4-oxadiazol-5-yl)benzonitrile (Compound 102)

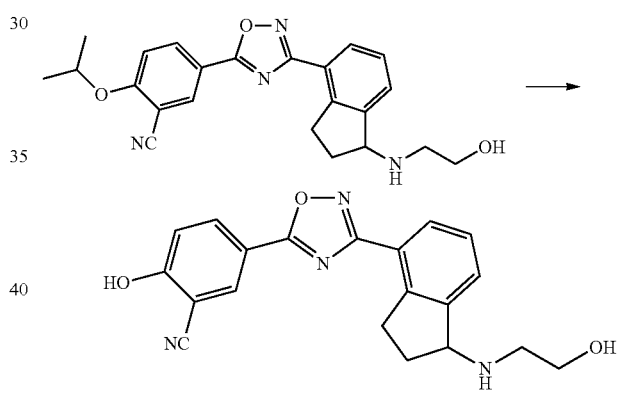

To 5-(3-(1-((2-hydroxyethyl)amino)-2,3-dihydro-1H-inden-4-yl)-1,2,4-oxadiazol-5-yl)-2-isopropoxybenzonitrile (15.0 mg, 0.37 mmol) in DCE (3 mL) was added BCl$_3$ (1.85 mL of 1M DCM solution). The reaction mixture was stirred at room temperature for 18 hrs. The solvent was evaporated, and the residue purified by chromatography (DCM/MeOH) to give 900.0 mg (67%) of 2-hydroxy-5-(3-(1-((2-hydroxyethyl)amino)-2,3-dihydro-1H-inden-4-yl)-1,2,4-oxadiazol-5-yl)benzonitrile 102 as white solid. LCMS-ESI (m/z) calculated for $C_{20}H_{18}N_4O_3$: 362.4. found 363.1 [M+H]$^+$, $t_R$=2.13 min. Enantiomerically pure materials can be obtained in an analogous fashion from (R)- or (S)-5-(3-(1-(2-hydroxyethylamino)-2,3-dihydro-1H-inden-4-yl)-1,2,4-oxadiazol-5-yl)-2-isopropoxybenzonitrile.

General Procedure 11. Alkylation of Phenols.

To a solution of the indane phenol (1 eq) in DMA (0.75 M) was added the appropriate alkyl halide (2 eq) and potassium carbonate (3 eq). The mixture was stirred 6 h at 75° C. until no starting phenol was observed by TLC. The solvent was evaporated and the mixture was extracted with EA and brine. The organic phase was dried over MgSO$_4$, filtered, and concentrated. The final compound was purified by preparative HPLC.

Compounds 103, 104, 106, 108 and 109 were prepared using General Procedure 11.

5-(3-(1-((2-hydroxyethyl)amino)-2,3-dihydro-1H-inden-4-yl)-1,2,4-oxadiazol-5-yl)-2-isobutoxybenzonitrile (Compound 103)

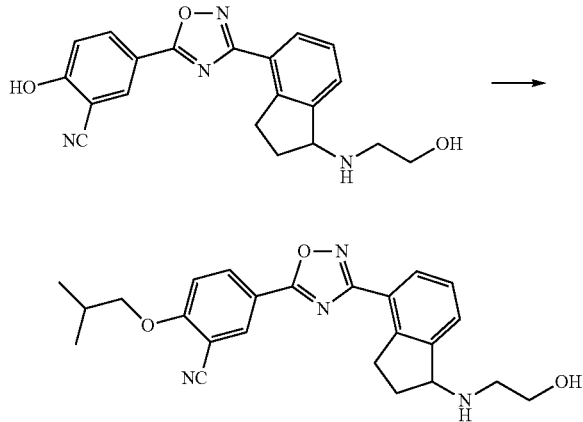 [SMILES: N#Cc1cc(-c2nc(-c3cccc4c3CCC4NCCO)no2)ccc1O ; CC(C)COc1ccc(-c2nc(-c3cccc4c3CCC4NCCO)no2)cc1C#N]

Prepared using General Procedure 11. To a solution of 2-hydroxy-5-(3-(1-(2-hydroxyethylamino)-2,3-dihydro-1H-inden-4-yl)-1,2,4-oxadiazol-5-yl)benzonitrile 102 (15.0 mg, 0.041 mmol) in DMA (2 mL) was added $K_2CO_3$ (16.9 mg, 0.12 mmol) and 1-bromo-2-methylpropane (11.3 mg, 0.08 mmol). The mixture was stirred 6 h at 75° C. The solvent was evaporated and the mixture was partitioned between EA and brine. The organic layer was dried over $MgSO_4$, filtered, and the solvent evaporated. The final compound was purified by preparative HPLC to give 6.31 mg (37%) of 5-(3-(1-((2-hydroxyethyl)amino)-2,3-dihydro-1H-inden-4-yl)-1,2,4-oxadiazol-5-yl)-2-isobutoxybenzonitrile 103 as a white solid. LCMS-ESI (m/z) calculated for $C_{24}H_{16}N_4O_3$: 418.5. found 419.2 $[M+H]^+$, $t_R$=2.61 min.

General Procedure 12. Alkylation, Acylation, and Sulfonylation of Secondary Amines.

To a stirred solution of the secondary (R)- or (S)-indane amine (1 eq) at 0° C. in DCM (0.04M) was added the appropriate alkyl halide, acid chloride, or sulfonyl chloride (1.5 eq). Triethylamine (2 eq) was added and the reaction mixture was stirred at room temperature until all the indane amine was consumed. The reaction mixtures were quenched with water, concentrated under high vacuum, and purified by preparative HPLC. For the acetyl protected derivatives, products were purified after removal of the acetyl group.

Compounds 110-117 were prepared using General Procedure 12.

(R)-N-(4-(5-(3 cyano-4-isopropoxyphenyl)-1,2,4-oxadiazol-3-yl)-2,3-dihydro-1H-inden-1-yl)-N-(2-hydroxyethyl)methanesulfonamide (Compound 112)

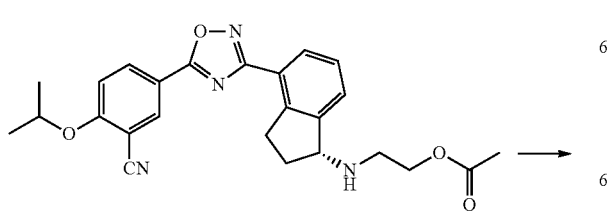

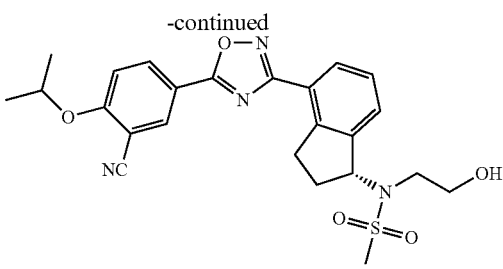

Prepared using General Procedure 12. To a stirred solution of (R)-2-((4-(5-(3-cyano-4-isopropoxyphenyl)-1,2,4-oxadiazol-3-yl)-2,3-dihydro-1H-inden-1-yl)amino)ethyl acetate (20 mg, 0.04 mmol) in DCM (1 mL) was added methanesulfonyl chloride (10.2 mg, 0.08 mmol) followed by triethylamine (9.08 mg, 0.08 mmol)) at 0° C. The reaction mixture was stirred at room temperature for 16 h. The reaction was quenched with water (1 mL), extracted with DCM (2×1 mL), and the combined extracts were dried over $MgSO_4$. The organic layers were concentrated to give 23 mg (50%) of (R)-2-(N-(4-(5-(3-cyano-4-isopropoxyphenyl)-1,2,4-oxadiazol-3-yl)-2,3-dihydro-1H-inden-1-yl)methylsulfonamido)ethyl acetate which was used in the next step without purification. LCMS-ESI (m/z) calculated for $C_{26}H_{28}N_4O_6S$: 524.2. found 547.1 $[M+Na]^+$, $t_R$=3.82 min.

To a solution of (R)-2-(N-(4-(5-(3-cyano-4-isopropoxyphenyl)-1,2,4-oxadiazol-3-yl)-2,3-dihydro-1H-inden-1-yl)methylsulfonamido)ethyl acetate (12 mg, 0.22 mmol) in a 1:1 mixture of $MeOH/H_2O$ was added $K_2CO_3$ (9.48 mg, 0.06 mmol). The reaction mixture was stirred at room temperature for 2 h and concentrated to dryness. The crude reaction mixture purified by preparative HPLC to afford (R)-N-(4-(5-(3-cyano-4-isopropoxyphenyl)-1,2,4-oxadiazol-3-yl)-2,3-dihydro-1H-inden-1-yl)-N-(2-hydroxyethyl) methanesulfonamide 112. LCMS-ESI (m/z) calculated for $C_{24}H_{26}N_4O_5S$: 482.2. found 505.1 $[M+Na]^+$, $t_R$=3.55 min.

General Procedure 13. Reductive Amination of Indane Amines.

To a solution of the primary or optionally substituted secondary (R)- or (S)-indane amine (1 eq) in MeOH (0.01 M) was added acetic acid (0.01 eq) and the appropriate aldehyde (1 eq). The reaction was stirred at 25-50° C. until imine formation was complete (2-18 h). Sodium borohydride or sodium triacetoxyborohydride (10 eq) was added and the reaction was stirred at room temperature until reduction was complete (2-8 h). The solvent was evaporated and to the residue was added $NaHCO_3$ and then extracted with EA. The organic layer was collected and dried over $Mg_2SO_4$. The final product was purified by preparative HPLC.

Compounds 119, 156-162, and 208-210 were prepared using General Procedure 13.

(S)-5-(3-(1-(((1H-imidazol-2-yl)methyl)amino)-2,3-dihydro-1H-inden-4-yl)-1,2,4-oxadiazol-5-yl)-2-isobutoxybenzonitrile (Compound 158)

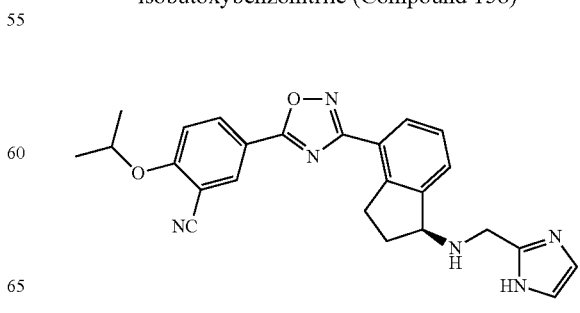

125

Prepared using General Procedure 13 from 1H-imidazole-2-carbaldehyde and heating at 50° C. for 2 h, reduction with NaBH$_4$ for 2 h. LCMS-ESI (m/z) calculated for C$_{26}$H$_{26}$N$_6$O$_2$: 440.5. found 441.2 [M+H]$^+$, t$_R$=2.49 min.

2-isopropoxy-5-(3-((S)-1-(((2R,3S,4R)-2,3,4,5-tetrahydroxypentyl)amino)-2,3-dihydro-1H-inden-4-yl)-1,2,4-oxadiazol-5-yl)benzonitrile (Compound 119)

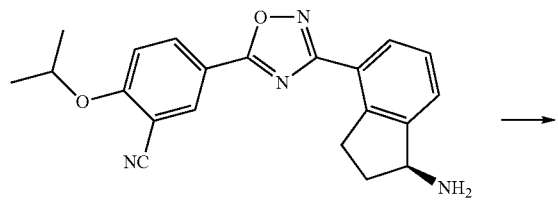

Prepared using General Procedure 13. To a solution of (S)-5-(3-(1-amino-2,3-dihydro-1H-inden-4-yl)-1,2,4-oxadiazol-5-yl)-2-isopropoxybenzonitrile 50 (50.mg, 0.14 mmol) in MeOH (10 mL) was added (2S,3R,4R)-2,3,4,5-tetrahydroxypentanal (20.71 mg, 0.14 mmol) and acetic acid (2 drops) with stirring at 50° C. for 18 h. The reaction was cooled to room temperature and sodium borohydride (52.2 mg, 1.38 mmol) was added slowly with stirring for 2 hours at room temperature. The reaction mixture was quenched with saturated NaHCO$_3$ aqueous (10 mL) and extracted with EA (3×10 mL). The organic layers were washed with brine and dried over Mg$_2$SO$_4$. The product was purified by preparative HPLC to give 8.68 mg (25%) of 2-isopropoxy-5-(3-((S)-1-(((2S,3R,4R)-2,3,4,5-tetrahydroxypentyl)amino)-2,3-dihydro-1H-inden-4-yl)-1,2,4-oxadiazol-5-yl)benzonitrile 119 as a solid. LCMS-ESI (m/z) calculated for C$_{26}$H$_{30}$N$_4$O$_6$: 494.5. found 495.2 [M+H]$^+$, t$_R$=2.42 min.

(R)-2-isopropoxy-5-(3-(1-((2-(methylsulfonyl)ethyl)amino)-2,3-dihydro-1H-inden-4-yl)-1,2,4-oxadiazol-5-yl)benzonitrile (Compound 125)

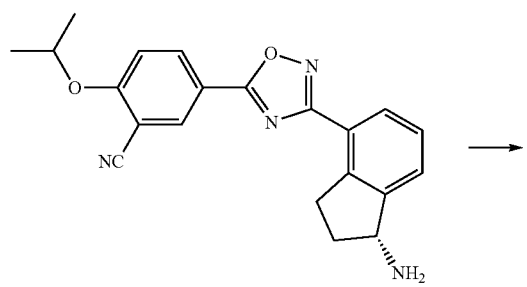

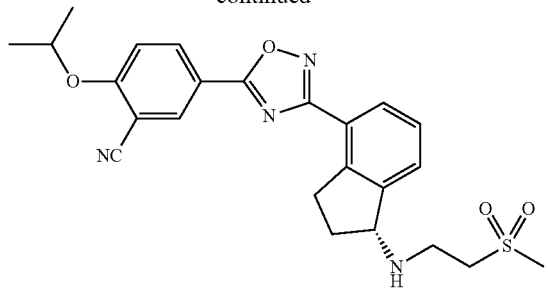

To a solution of (R)-5-(3-(1-amino-2,3-dihydro-1H-inden-4-yl)-1,2,4-oxadiazol-5-yl)-2-isopropoxybenzonitrile 49 (18 mg, 0.05 mmol) in DMA (0.5 mL) was added DIEA (87 µL, 0.5 mmol) and methylvinylsulfone (53 mg, 0.5 mmol). The reaction was heated to 80° C. for 24 h. The crude reaction mixture was purified by preparative HPLC to give (R)-2-isopropoxy-5-(3-(1-((2-(methylsulfonyl)ethyl)amino)-2,3-dihydro-1H-inden-4-yl)-1,2,4-oxadiazol-5-yl)benzonitrile 125. LCMS-ESI (m/z) calculated for C$_{24}$H$_{26}$N$_4$O$_4$S: 466.2. found 467.1 [M+H]$^+$, t$_R$=2.58 min. $^1$H NMR (400 MHz, CDCl$_3$) δ 8.41 (d, J=2.1 Hz, 1H), 8.32 (dd, J=8.9, 2.2 Hz, 1H), 8.07 (d, J=7.6 Hz, 1H), 7.47 (d, J=7.5 Hz, 1H), 7.37 (t, J=7.6 Hz, 1H), 7.10 (d, J=9.0 Hz, 1H), 4.77 (hept, J=6.1 Hz, 1H), 4.33 (t, J=6.7 Hz, 1H), 3.44 (ddd, J=17.5, 8.7, 4.8 Hz, 1H), 3.36-3.10 (m, 5H), 3.03 (s, 3H), 2.57-2.43 (m, 1H), 1.98-1.83 (m, 1H), 1.46 (d, J=6.1 Hz, 6H). $^{13}$C NMR (101 MHz, CDCl$_3$) δ 173.04, 168.94, 162.76, 146.05, 143.49, 134.11, 133.92, 128.24, 127.03, 126.83, 123.28, 116.84, 115.33, 113.58, 103.88, 72.76, 63.05, 55.41, 42.42, 40.86, 32.98, 31.86, 21.75. Compound 126 was made in an analogous fashion.

General Procedure 14. Preparation of Indane Amides via Acid Chlorides

To a stirred solution of (R)- or (S)-indane amine (1 eq) in DCM (0.25 M) was added TEA (3 eq) and the appropriate acid chloride (1.5 eq) at 0° C. The reaction mixture was stirred at room temperature for 18 h. The solvent was evaporated and the crude product isolated after partitioning between saturated NH$_4$Cl and DCM, followed by saturated NaHCO$_3$ and DCM. Pure product can be obtained by recrystallization from alcoholic solvents.

Compounds 122, 138, and 139 were prepared using General Procedure 14.

(S)-N-(4-(5-(3 cyano-4-isopropoxyphenyl)-1,2,4-oxadiazol-3-yl)-2,3-dihydro-1H-inden-1-yl)acetamide (Compound 139)

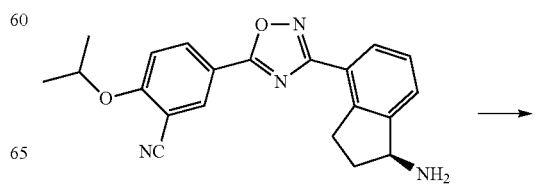

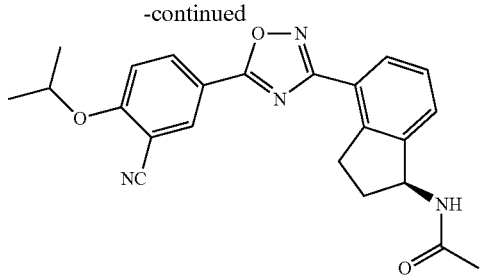

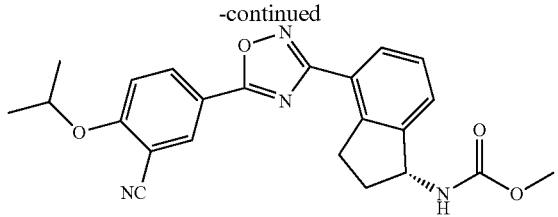

Prepared using General Procedure 14: To a stirred solution of (S)-5-(3-(1-amino-2,3-dihydro-1H-inden-4-yl)-1,2,4-oxadiazol-5-yl)-2-isopropoxybenzonitrile hydrochloride 50 (500 mg, 1.26 mmol) in DCM (5 mL) was added TEA (527 μL, 378 mmol). The reaction was cooled to 0° C. and acetyl chloride (135 μL, 1.89 mmol) was added. The reaction was stirred at room temperature for 18 h. The solvent was removed under reduced pressure. The residue was diluted with DCM (100 mL) and washed successively with saturated $NH_4Cl$ and $NaHCO_3$. The organic layers were dried over $MgSO_4$, filtered and concentrated to crude product. The crude product was recrystallized from hot ethanol (75 mL) to afford 420 mg (83%) of (S)-N-(4-(5-(3-cyano-4-isopropoxyphenyl)-1,2,4-oxadiazol-3-yl)-2,3-dihydro-1H-inden-1-yl)acetamide 139 as off-white crystals. LCMS-ESI (m/z) calculated for $C_{23}H_{22}N_4O_3$: 402.2. found 403.1 [M+H]$^+$, $t_R$=8.77 min (Method 2). Elemental Analysis determined for $C_{23}H_{22}N_4O_3$; C calculated=68.64%. found=68.54%. H calculated=5.51%. found=5.36%. N calculated=13.92%. found=13.85%. $^1$H NMR (400 MHz, DMSO) δ 8.58 (d, J=2.2 Hz, 1H), 8.47 (dd, J=9.0, 2.3 Hz, 1H), 8.39 (d, J=8.2 Hz, 1H), 8.08 (t, J=4.2 Hz, 1H), 7.62 (d, J=9.2 Hz, 1H), 7.57-7.47 (m, 2H), 5.45-5.39 (m, 1H), 5.20-4.97 (m, 1H), 3.51-3.42 (m, 1H), 3.25-3.00 (m, 1H), 2.55-2.50 (m, 1H), 1.96 (s, 3H), 1.94-1.87 (m, 1H), 1.45 (d, J=6.0 Hz, 6H). $^{13}$C NMR (101 MHz, CDCl$_3$) δ 173.14, 169.85, 168.85, 162.79, 144.91, 143.26, 134.16, 133.89, 128.49, 127.40, 126.86, 123.29, 116.82, 115.29, 113.56, 103.97, 72.77, 54.56, 33.67, 31.70, 23.50, 21.75. Chiral HPLC: (S)-N-(4-(5-(3-cyano-4-isopropoxyphenyl)-1,2,4-oxadiazol-3-yl)-2,3-dihydro-1H-inden-1-yl)acetamide was eluted using 10% i-PrOH in hexanes plus 0.3% DEA: >99.9% ee, $t_R$=15.09 min. (R)-N-(4-(5-(3-cyano-4-isopropoxyphenyl)-1,2,4-oxadiazol-3-yl)-2,3-dihydro-1H-inden-1-yl)acetamide 138 was prepared in an analogous fashion from (R)-5-(3-(1-amino-2,3-dihydro-1H-inden-4-yl)-1,2,4-oxadiazol-5-yl)-2-isopropoxybenzonitrile 49: >99.9% ee, $t_R$ for (R)-enantiomer=16.44 min.

General Procedure 15. Preparation of Indane Carbamates

To a stirred solution of (R)- or (S)-indane amine (1 eq) in DMF (0.05M) was added DIEA (3 eq) and the appropriate chloroformate (2 eq) at room temperature. The reaction mixture was stirred at room temperature for 4 h. The solvent was evaporated and the pure product isolated after preparative HPLC purification.

Compounds 149-153 were prepared using General Procedure 15.

(R)-methyl (4-(5-(3-cyano-4-isopropoxyphenyl)-1,2,4-oxadiazol-3-yl)-2,3-dihydro-1H-inden-1-yl)carbamate (Compound 149)

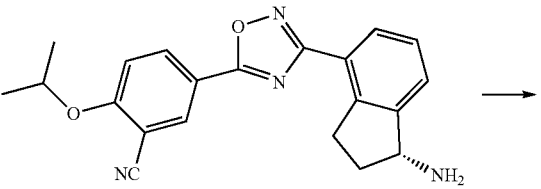

Prepared using General Procedure 15: To a stirred solution of (R)-5-(3-(1-amino-2,3-dihydro-1H-inden-4-yl)-1,2,4-oxadiazol-5-yl)-2-isopropoxybenzonitrile 49 (20.0 mg, 0.05 mmol) in DMF (1 mL) was added DIEA (19.4 mg, 0.15 mmol) and methyl chloroformate (9.5 mg, 0.1 mmol) for 4 h at room temperature. The solvent was evaporated and the residue was dissolved in DMSO (1 mL) and purified by preparative HPLC to afford 2.35 mg (11%) of (R)-methyl (4-(5-(3-cyano-4-isopropoxyphenyl)-1,2,4-oxadiazol-3-yl)-2,3-dihydro-1H-inden-1-yl)carbamate 149. LCMS-ESI (m/z) calculated for $C_{23}H_{22}N_4O_4$: 418.2. found 419.1 [M+H]$^+$, $t_R$=3.85 min. $^1$H NMR (400 MHz, CDCl$_3$) δ 8.39 (d, J=2.1 Hz, 1H), 8.32 (dd, J=8.9, 2.2 Hz, 1H), 8.07 (d, J=7.6 Hz, 1H), 7.54-7.44 (m, 1H), 7.38 (t, J=7.6 Hz, 1H), 7.12 (d, J=9.0 Hz, 1H), 5.43-5.18 (m, 1H), 5.03 (d, J=8.6 Hz, 1H), 4.90-4.63 (m, 1H), 3.77 (d, J=27.4 Hz, 3H), 3.59-3.35 (m, 1H), 3.27-3.01 (m, 1H), 2.68 (ddd, J=12.7, 8.2, 4.7 Hz, 1H), 2.05-1.75 (m, 1H), 1.47 (t, J=5.6 Hz, 6H). $^{13}$C NMR (101 MHz, DMSO) δ 167.82, 163.56, 157.51, 151.63, 139.77, 137.77, 128.85, 128.63, 123.19, 122.08, 121.53, 117.97, 111.55, 110.03, 108.32, 98.67, 51.00, 46.99, 28.68, 26.28, 24.46, 16.50.

(R)-2-isopropoxy-5-(3-(1-(2-oxooxazolidin-3-yl)-2,3-dihydro-1H-inden-4-yl)-1,2,4-oxadiazol-5-yl)benzonitrile (Compound 154)

To a stirred solution of (R)-tert-butyl (4-(5-(3-cyano-4-isopropoxyphenyl)-1,2,4-oxadiazol-3-yl)-2,3-dihydro-1H-inden-1-yl)(2-hydroxyethyl)carbamate INT-22 in DMF (1 mL) was added NaH (6 mg, 0.15 mmol, of a 60% solution in mineral oil). After stirring for 20 h, the reaction mixture was diluted with EA and washed with NaHCO₃. The combined aqueous extracts were back-extracted with EA. The combined organic extracts were dried over Na₂SO₄, concentrated, and purified by column chromatography (EA/hexanes) to provide 11.9 mg (29%) of (R)-2-isopropoxy-5-(3-(1-(2-oxooxazolidin-3-yl)-2,3-dihydro-1H-inden-4-yl)-1,2,4-oxadiazol-5-yl)benzonitrile 154. LCMS-ESI (m/z) calculated for $C_{22}H_{22}N_4O_4$: 430.5. found 431.1 [M+H]⁺, $t_R$=3.72 min. ¹H NMR (400 MHz, CDCl₃) δ 8.43 (d, J=2.2 Hz, 1H), 8.34 (dd, J=8.9, 2.2 Hz, 1H), 8.14 (t, J=4.4 Hz, 1H), 7.42 (m, 2H), 7.13 (d, J=9.0 Hz, 1H), 5.72-5.57 (m, 1H), 4.80 (dt, J=12.2, 6.1 Hz, 1H), 4.35 (qt, J=15.7, 7.8 Hz, 2H), 3.56-3.39 (m, 2H), 3.25 (dtd, J=24.4, 8.6, 7.1 Hz, 2H), 2.65-2.48 (m, 1H), 2.10 (ddt, J=13.7, 9.0, 7.1 Hz, 1H), 1.48 (d, J=6.1 Hz, 6H). Compound 155 was made in an analogous fashion.

(R)-N-(4-(5-(3 cyano-4-isopropoxyphenyl)-1,2,4-oxadiazol-3-yl)-2,3-dihydro-1H-inden-1-yl)-2-methoxyethanesulfonamide (Compound 163)

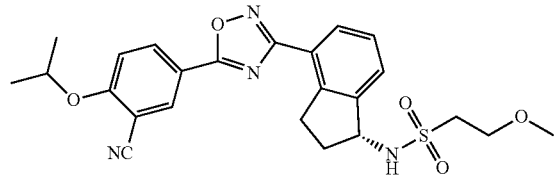 [SMILES: COCCS(=O)(=O)N[C@@H]1CCc2c(-c3noc(-c4ccc(OC(C)C)c(C#N)c4)n3)cccc21]

Prepared using General Procedure 8A. LCMS-ESI (m/z) calculated for $C_{24}H_{26}N_4O_5S$: 482.2. found 505.1 [M+Na]⁺, $t_R$=9.57 min (Method 2). Elemental Analysis determined for $C_{24}H_{26}N_4O_5S$; C calculated=59.74%. found=59.34%; H calculated=5.43%. found=5.37%; N calculated=11.61%. found=11.46%. ¹H NMR (400 MHz, CDCl₃) δ 8.42 (d, J=2.1 Hz, 1H), 8.34 (dd, J=8.9, 2.2 Hz, 1H), 8.12 (d, J=7.7 Hz, 1H), 7.66 (d, J=7.6 Hz, 1H), 7.43 (t, J=7.7 Hz, 1H), 7.13 (d, J=9.0 Hz, 1H), 5.06 (q, J=7.8 Hz, 1H), 4.80 (hept, J=6.0 Hz, 1H), 4.67 (d, J=8.6 Hz, 1H), 3.97-3.78 (m, 2H), 3.50 (ddd, J=17.4, 8.9, 3.4 Hz, 1H), 3.40 (t, J=5.7 Hz, 1H), 3.39 (s, 3H), 3.26-3.13 (m, 1H), 2.71 (dtd, J=12.9, 8.1, 3.5 Hz, 1H), 2.07 (ddd, J=16.4, 13.0, 8.6 Hz, 1H), 1.48 (d, J=6.1 Hz, 6H). ¹³C NMR (101 MHz, CDCl₃) δ 172.90, 168.49, 162.70, 144.03, 142.51, 133.89, 133.84, 128.52, 127.31, 127.12, 123.02, 116.53, 115.28, 113.65, 103.61, 72.79, 66.92, 59.02, 58.70, 52.98, 34.29, 31.49, 21.72. Chiral HPLC: (R)-N-(4-(5-(3-cyano-4-isopropoxyphenyl)-1,2,4-oxadiazol-3-yl)-2,3-dihydro-1H-inden-1-yl)-2-methoxyethanesulfonamide was eluted using methanol (Chiral Method 2): >99.9% ee, $t_R$=11.26 min. (S)-N-(4-(5-(3-cyano-4-isopropoxyphenyl)-1,2,4-oxadiazol-3-yl)-2,3-dihydro-1H-inden-1-yl)-2-methoxyethanesulfonamide 164 was prepared in an analogous fashion: >99.9% ee, $t_R$ for (S)-enantiomer=9.11 min (Chiral Method 2).

General Procedure 16. Preparation of Indane Sulfonamide Esters

To a stirred solution of (R)- or (S)-indane amine (1 eq) in DCM (0.2 M) was added the sulfonyl chloride (1 eq) at room temperature. The reaction mixture was stirred at room temperature for 18 h. The crude reaction was partitioned between DCM and saturated NaHCO₃. The organic layer was dried over MgSO₄, concentrated, and purified by column chromatography.

Compounds 72, 182 and 183 were prepared using General Procedure 16.

(S)-methyl 2 (N (4-(5-(3 cyano-4-isopropoxyphenyl)-1,2,4-oxadiazol-3-yl)-2,3-dihydro-1H-inden-1-yl)sulfamoyl)acetate (Compound 72)

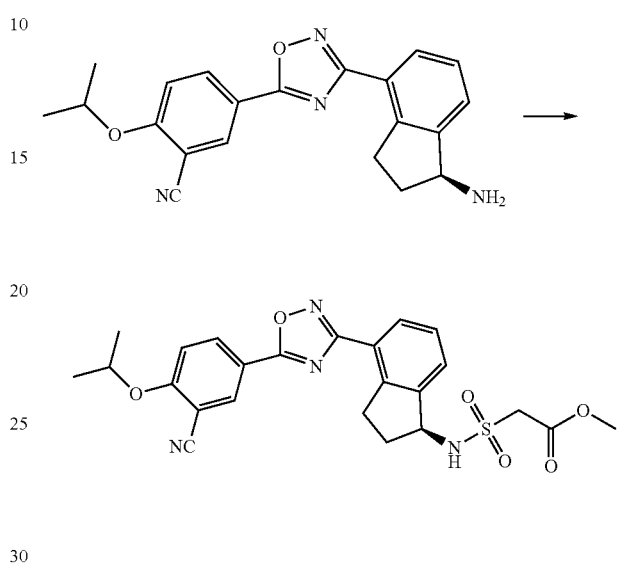

Prepared using General Procedure 16: To a stirred solution of (S)-5-(3-(1-amino-2,3-dihydro-1H-inden-4-yl)-1,2,4-oxadiazol-5-yl)-2-isopropoxybenzonitrile 50 (0.36 g, 1.0 mmol) in DCM (5 mL) was added methyl-2-(chlorosulfonyl)acetate (112 mg, 0.6 mmol). After 0.5 h, the crude reaction was partitioned between DCM and saturated NaHCO₃. The organic layer was dried over MgSO₄, concentrated, and purified by column chromatography (EA/hexanes) to give 0.21 g (42%) of (S)-methyl 2-(N-(4-(5-(3-cyano-4-isopropoxyphenyl)-1,2,4-oxadiazol-3-yl)-2,3-dihydro-1H-inden-1-yl)sulfamoyl)acetate 72. LCMS-ESI (m/z) calculated for $C_{24}H_{24}N_4O_6S$: 496.1. found 519.1 [M+Na]⁺, $t_R$=3.71 min. ¹H NMR (400 MHz, CDCl₃) δ 8.41 (d, J=2.1 Hz, 1H), 8.32 (dd, J=8.9, 2.2 Hz, 1H), 8.13 (d, J=7.7 Hz, 1H), 7.66 (d, J=7.6 Hz, 1H), 7.43 (t, J=7.7 Hz, 1H), 7.11 (d, J=9.0 Hz, 1H), 5.20-5.00 (m, 2H), 4.78 (hept, J=6.2 Hz, 1H), 4.16 (d, J=14.9 Hz, 1H), 4.08 (d, J=14.9 Hz, 1H), 3.82 (s, 3H), 3.51 (ddd, J=17.4, 8.9, 3.5 Hz, 1H), 3.28-3.11 (m, 1H), 2.71 (dtd, J=11.3, 8.1, 3.6 Hz, 1H), 2.16-2.02 (m, 1H), 1.46 (d, J=6.1 Hz, 6H). (R)-methyl 2-(N-(4-(5-(3-cyano-4-isopropoxyphenyl)-1,2,4-oxadiazol-3-yl)-2,3-dihydro-1H-inden-1-yl)sulfamoyl)acetate was synthesized in an analogous fashion from (R)-5-(3-(1-amino-2,3-dihydro-1H-inden-4-yl)-1,2,4-oxadiazol-5-yl)-2-isopropoxybenzonitrile 49.

General Procedure 17. Preparation of Indane Sulfonamide Acids

To a stirred solution of (R)- or (S)-indane sulfonamide ester (1 eq) in MeOH (0.2 M) was added 6N NaOH (2 eq) at room temperature. The reaction was stirred at room temperature for 24 h. The crude reaction was concentrated then partitioned between DCM/IPA and 1N HCl. The organic layer was dried over MgSO₄, concentrated, and isolated after preparative HPLC purification.

Compounds 71, 184, and 185 were prepared using General Procedure 17.

(R)-2 (N (4-(5-(3 cyano-4-isopropoxyphenyl)-1,2,4-oxadiazol-3-yl)-2,3-dihydro-1H-inden-1-yl)sulfamoyl)acetic acid (Compound 184)

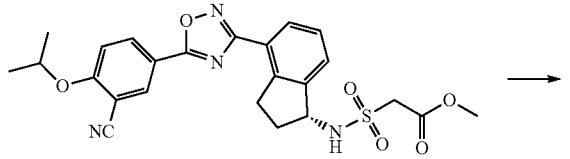

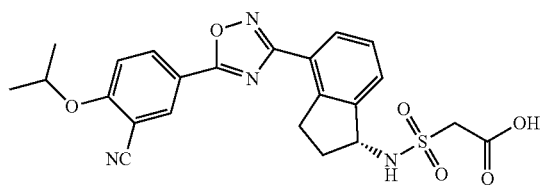

Prepared using General Procedure 17: To a stirred solution of (R)-methyl 2-(N-(4-(5-(3-cyano-4-isopropoxyphenyl)-1,2,4-oxadiazol-3-yl)-2,3-dihydro-1H-inden-1-yl)sulfamoyl)acetate (0.40 g, 0.8 mmol) in MeOH (4 mL) was added 6N NaOH (0.27 mL). After 24 h, the crude reaction was concentrated then partitioned between DCM/IPA and 1N HCl. The organic layer was dried over $MgSO_4$ and concentrated to give 0.35 g (91%) of (R)-2-(N-(4-(5-(3-cyano-4-isopropoxyphenyl)-1,2,4-oxadiazol-3-yl)-2,3-dihydro-1H-inden-1-yl)sulfamoyl)acetic acid 184. An analytically pure sample was prepared by preparative HPLC purification. LCMS-ESI (m/z) calculated for $C_{23}H_{22}N_4O_6S$: 482.1. found 505.1 $[M+Na]^+$, $t_R$=8.72 min (Method 2). (S)-2-(N-(4-(5-(3-cyano-4-isopropoxyphenyl)-1,2,4-oxadiazol-3-yl)-2,3-dihydro-1H-inden-1-yl)sulfamoyl)acetic acid was synthesized in an analogous fashion from (S)-methyl 2-(N-(4-(5-(3-cyano-4-isopropoxyphenyl)-1,2,4-oxadiazol-3-yl)-2,3-dihydro-1H-inden-1-yl)sulfamoyl)acetate.

General Procedure 18. Preparation of Indane Sulfonamide Alcohols

To a stirred solution of (R)- or (S)-indane sulfonamide ester (1 eq) in THF (0.06 M) was added sodium borohydride (4 eq) at room temperature. The reaction was heated to 75° C. and methanol (1 eq) was added dropwise. After 1 h, the reaction was cooled and concentrated. The residue was partitioned between DCM and 0.5N HCl. The organic layer was dried over $MgSO_4$, concentrated, and purified by recrystallization.

Compounds 186-188 were prepared using General Procedure 18.

(R)-N-(4-(5-(3 cyano-4-isopropoxyphenyl)-1,2,4-oxadiazol-3-yl)-2,3-dihydro-1H-inden-1-yl)-2-hydroxyethanesulfonamide (Compound 186)

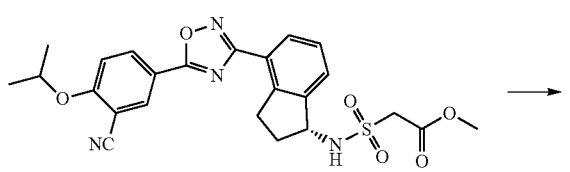

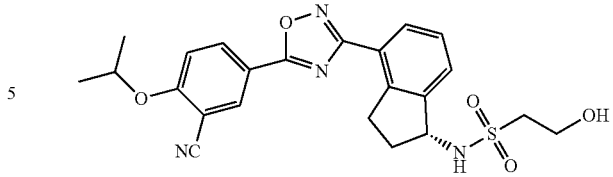

Prepared using General Procedure 18: To a stirred solution of (R)-methyl 2-(N-(4-(5-(3-cyano-4-isopropoxyphenyl)-1,2,4-oxadiazol-3-yl)-2,3-dihydro-1H-inden-1-yl)sulfamoyl)acetate (0.72 g, 1.5 mmol) in THF (25 mL) was added sodium borohydride (0.24 g, 6.2 mmol) at room temperature. The reaction was heated to 75° C. and methanol (0.06 mL, 1.5 mmol) was added dropwise. After 1 h, the reaction was cooled and concentrated. The residue was partitioned between DCM and 0.5N HCl. The organic layer was dried over $MgSO_4$, concentrated, and recrystallized from methanol to give 0.40 g (60%) of (R)-N-(4-(5-(3-cyano-4-isopropoxyphenyl)-1,2,4-oxadiazol-3-yl)-2,3-dihydro-1H-inden-1-yl)-2-hydroxyethanesulfonamide 186. LCMS-ESI (m/z) calculated for $C_{23}H_{24}N_4O_5S$: 468.2. found 491.1 $[M+Na]^+$, $t_R$=8.64 min (Method 2). Elemental Analysis determined for $C_{23}H_{24}N_4O_5S$; C calculated=58.96%. found=58.86%; H calculated=5.16%. found=5.08%; N calculated=11.96%. found=11.78%. $^1$H NMR (400 MHz, $CDCl_3$) δ 8.38 (d, J=2.2 Hz, 1H), 8.32 (dd, J=8.9, 2.2 Hz, 1H), 8.10 (d, J=7.7 Hz, 1H), 7.62 (d, J=7.6 Hz, 1H), 7.42 (t, J=7.7 Hz, 1H), 7.12 (d, J=9.1 Hz, 1H), 5.05 (q, J=7.9 Hz, 1H), 4.94-4.69 (m, 2H), 4.30-3.91 (m, 2H), 3.49 (ddd, J=17.4, 8.8, 3.5 Hz, 1H), 3.39 (td, J=4.8, 1.6 Hz, 2H), 3.25-3.07 (m, 1H), 2.71 (dtd, J=11.5, 8.0, 3.6 Hz, 1H), 2.11-1.95 (m, 1H), 1.48 (d, J=6.1 Hz, 6H). $^{13}$C NMR (101 MHz, $CDCl_3$) δ 173.30, 168.79, 162.95, 143.72, 142.80, 134.25, 134.04, 129.06, 127.76, 127.23, 123.52, 116.84, 115.41, 113.72, 104.06, 72.94, 59.01, 57.56, 55.84, 34.85, 31.61, 21.88. Chiral HPLC: (R)-N-(4-(5-(3-cyano-4-isopropoxyphenyl)-1,2,4-oxadiazol-3-yl)-2,3-dihydro-1H-inden-1-yl)-2-hydroxyethanesulfonamide was eluted with methanol (Chiral Method 2): 99.9% ee, $t_R$=8.59 min. (S)-N-(4-(5-(3-cyano-4-isopropoxyphenyl)-1,2,4-oxadiazol-3-yl)-2,3-dihydro-1H-inden-1-yl)-2-hydroxyethanesulfonamide 187 was synthesized in an analogous fashion from (S)-methyl 2-(N-(4-(5-(3-cyano-4-isopropoxyphenyl)-1,2,4-oxadiazol-3-yl)-2,3-dihydro-1H-inden-1-yl)sulfamoyl)acetate: >99.9% ee, $t_R$ for (S)-enantiomer=6.62 min (Chiral Method 2).

General Procedure 19. Preparation of Indane Sulfonamide Amide

To a stirred solution of (R)- or (S)-indane sulfonamide acid (1 eq) in DMF (0.25 M) was added EDC and N-hydroxybenzotriazole. After 5 min, the amine was added and the reaction mixture was stirred 18 h at room temperature. The crude reaction was added dropwise to water and the solid was filtered. The crude material was purified by column chromatography.

Compounds 189-201 were prepared using General Procedure 19.

(S)-2 (N (4-(5-(3 cyano-4-isopropoxyphenyl)-1,2,4-oxadiazol-3-yl)-2,3-dihydro-1H-inden-1-yl)sulfamoyl)-N,N-dimethylacetamide (Compound 195)

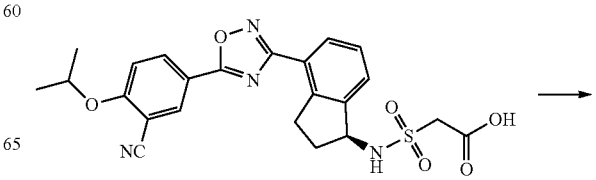

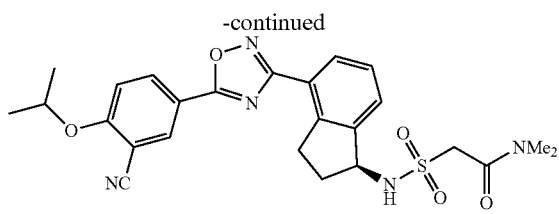

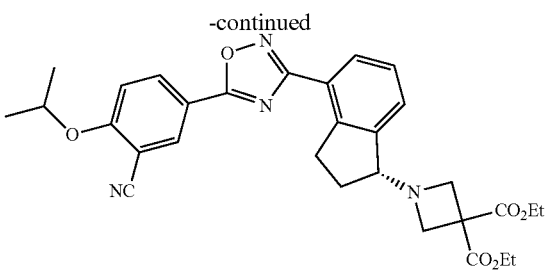

Prepared using General Procedure 19: To a stirred solution of (S)-2-(N-(4-(5-(3-cyano-4-isopropoxyphenyl)-1,2,4-oxadiazol-3-yl)-2,3-dihydro-1H-inden-1-yl)sulfamoyl)acetic acid 71 (48 mg, 0.1 mmol) in DMF (0.4 mL) was added N-hydroxybenzotriazole (46 mg, 0.3 mmol) and EDC (57 mg, 0.3 mmol). After 5 min, dimethylamine (40 wt % solution in water, 34 μL, 0.3 mmol) was added and the reaction mixture was stirred 18 h at room temperature. The reaction was added dropwise to water (20 mL) and the solid was filtered. The crude material was purified by column chromatography (MeOH/DCM) to give 36 mg (70%) of (S)-2-(N-(4-(5-(3-cyano-4-isopropoxyphenyl)-1,2,4-oxadiazol-3-yl)-2,3-dihydro-1H-inden-1-yl)sulfamoyl)-N,N-dimethylacetamide 195. LCMS-ESI (m/z) calculated for $C_{25}H_{27}N_5O_5S$: 509.2. found 532.2 [M+Na]$^+$, $t_R$=8.99 min (Method 2). (R)-2-(N-(4-(5-(3-cyano-4-isopropoxyphenyl)-1,2,4-oxadiazol-3-yl)-2,3-dihydro-1H-inden-1-yl)sulfamoyl)-N,N-dimethylacetamide 194 was synthesized in an analogous fashion from (R)-2-(N-(4-(5-(3-cyano-4-isopropoxyphenyl)-1,2,4-oxadiazol-3-yl)-2,3-dihydro-1H-inden-1-yl)sulfamoyl)acetic acid.

Diethyl 2,2-bis((((trifluoromethyl)sulfonyloxy)methyl)malonate (INT-26)

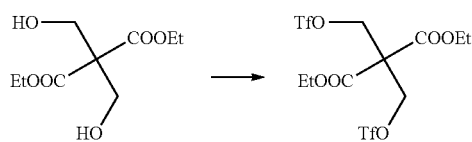 [SMILES: CCOC(=O)C(CO)(CO)C(=O)OCC ; CCOC(=O)C(COS(=O)(=O)C(F)(F)F)(COS(=O)(=O)C(F)(F)F)C(=O)OCC]

To a stirred solution of diethyl 2,2-bis(hydroxymethyl)malonate (330 μL, 1.5 mmol) in CH$_3$CN (6 mL) at −15° C., under an atmosphere of N$_2$, was added Tf$_2$O (324 μL, 1.92 mmol) dropwise over 20 min. After stirring for 5 min, DIEA (653 μL, 3.75 mmol) was added slowly over 15 min. After 2 h, additional DIEA (653 μL, 3.75 mmol) was added. The resulting solution of diethyl 2,2-bis((((trifluoromethyl)sulfonyl)oxy)methyl)malonate INT-26 was used directly in the next step.

(R)-diethyl 1-(4-(5-(3-cyano-4-isopropoxyphenyl)-1,2,4-oxadiazol-3-yl)-2,3-dihydro-1H-inden-1-yl)azetidine-3,3-dicarboxylate (INT-27)

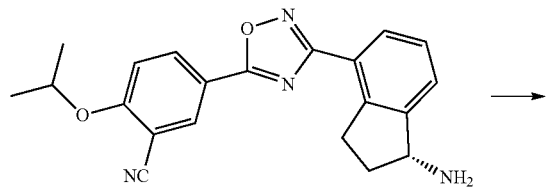

To a solution of (R)-5-(3-(1-amino-2,3-dihydro-1H-inden-4-yl)-1,2,4-oxadiazol-5-yl)-2-isopropoxybenzonitrile 49 (247 mg, 0.62 mmol) in CH$_3$CN (2 mL) at −10° C., under N$_2$, was added diethyl 2,2-bis((((trifluoromethyl)sulfonyl)oxy)methyl)malonate INT-26 (3 mL of 0.25 mmol solution in CH$_3$CN). The resulting mixture was warmed to room temperature over 30 min, then heated to 70° C. for 18 h. The mixture was concentrated, dissolved in DCM, and washed with water. The organic layer was dried over Na$_2$SO$_4$ and concentrated to provide 93 mg (28%) of crude (R)-diethyl 1-(4-(5-(3-cyano-4-isopropoxyphenyl)-1,2,4-oxadiazol-3-yl)-2,3-dihydro-1H-inden-1-yl)azetidine-3,3-dicarboxylate INT-27, which was used in the next step without further purification. LCMS-ESI (m/z) calculated for $C_{30}H_{32}N_4O_6$: 544.6. found 545.2 [M+H]$^+$, $t_R$=3.03 min.

(R)-1-(4-(5-(3-cyano-4-isopropoxyphenyl)-1,2,4-oxadiazol-3-yl)-2,3-dihydro-1H-inden-1-yl)azetidine-3-carboxylic acid (Compound 202)

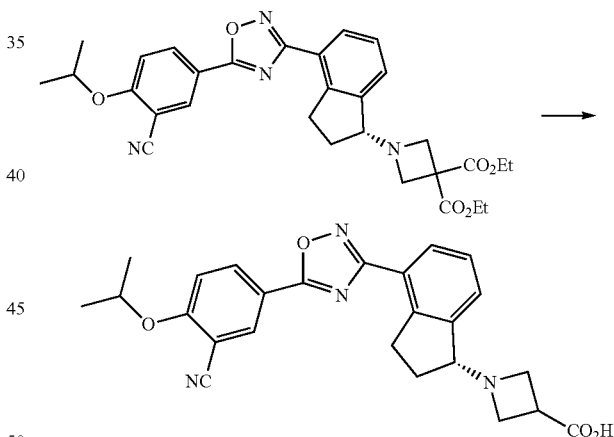

To a stirred solution of crude (R)-diethyl 1-(4-(5-(3-cyano-4-isopropoxyphenyl)-1,2,4-oxadiazol-3-yl)-2,3-dihydro-1H-inden-1-yl)azetidine-3,3-dicarboxylate (93 mg, 0.17 mmol) in MeOH (2 mL) was added 6 N NaOH (5 drops). The resulting solution was heated to 50° C. in a closed vial. After 24 h the solution was concentrated, dissolved in water, neutralized with 1N HCl, and heated at 100° C. After 15 h, additional 1N HCl was added, and the mixture was stirred at 105° C. for 24 h. The mixture was diluted with water and extracted with DCM and EA. The organic layers were combined, dried over Na$_2$SO$_4$, and purified by preparative HPLC to provide 25 mg (33%) of (R)-1-(4-(5-(3-cyano-4-isopropoxyphenyl)-1,2,4-oxadiazol-3-yl)-2,3-dihydro-1H-inden-1-yl)azetidine-3-carboxylic acid 202. LCMS-ESI (m/z) calculated for $C_{25}H_{24}N_4O_4$: 444.5. found 445.2 [M+H]$^+$, $t_R$=2.55 min. Compound 203 was made in an analogous fashion.

General Procedure 20. Preparation of Indane Azetidine Amide.

To a solution of (R)- or (S)-indane azetidine acid in DMF (0.03 mM) were added hydroxybenzotriazole (1.3 eq) and 1-ethyl-3-(3-dimethylaminopropyl) carbodiimide (1.3 eq). After 2 h, the activated acid solution is transferred to a flask containing amine (2 eq). Any amines used as salt forms were free-based by addition of DIEA (1.1 eq). After 16 h, the reaction mixture is diluted with EA and washed with NaHCO$_3$. The organic layers are dried over Na$_2$SO$_4$, concentrated, and purified by column chromatography (MeOH/DCM).

Compounds 204-207 were prepared using General Procedure 20.

(S)-N-(4-(5-(3 cyano-4-isopropoxyphenyl)-1,2,4-oxadiazol-3-yl)-2,3-dihydro-1H-inden-1-yl)methanesulfonamide (Compound 207)

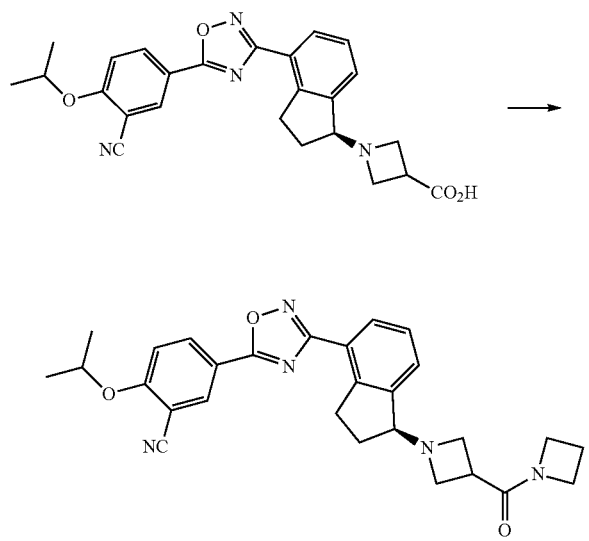

Prepared using General Procedure 20. LCMS-ESI (m/z) calculated for C$_{28}$H$_{29}$N$_5$O$_3$: 483.6. found 484.2 [M+H]$^+$, t$_R$=2.55 min. $^1$H NMR (400 MHz, CDCl$_3$) δ 8.42 (d, J=2.2 Hz, 1H), 8.33 (dd, J=8.9, 2.2 Hz, 1H), 8.08 (dd, J=7.7, 0.8 Hz, 1H), 7.44 (d, J=7.3 Hz, 1H), 7.32 (dd, J=16.8, 9.3 Hz, 1H), 7.11 (d, J=9.0 Hz, 1H), 4.85-4.70 (m, 1H), 4.05 (ddd, J=22.6, 15.0, 7.3 Hz, 4H), 3.98 (dd, J=6.8, 3.1 Hz, 1H), 3.64-3.55 (m, 1H), 3.57-3.48 (m, 2H), 3.47-3.34 (m, 2H), 3.34-3.20 (m, 2H), 2.34-2.21 (m, 2H), 2.23-2.10 (m, 1H), 2.03 (ddd, J=13.0, 7.7, 3.7 Hz, 1H), 1.51-1.42 (m, 6H). $^{13}$C NMR (101 MHz, CDCl$_3$) δ 172.92, 171.71, 169.02, 162.69, 144.54, 144.30, 134.12, 133.86, 128.22, 127.18, 126.66, 123.40, 116.96, 115.30, 113.51, 103.91, 72.69, 70.79, 55.05, 54.53, 49.77, 48.05, 32.13, 31.04, 28.64, 21.73, 15.34.

General Procedure 21. Preparation of Indane Ureas

To a stirred solution of CDI (2 eq) and Et$_3$N (3 eq) in DCM (0.16M) was added the solution of (R)- or (S)-indane amine (1 eq) and Et$_3$N (3 eq) in DCM (0.01M) for 1 h and then this solution was added to the preparative solution of amine (3 eq) and Et$_3$N (3 eq) in DCM (0.4M) at room temperature. The reaction was stirred at room temperature for 4 h until all of starting material was consumed. The solvent was evaporated and the pure product isolated after silica gel column chromatography (DCM/MeOH).

Compounds 120, 211-247 were prepared using General Procedure 21.

(R)-N-(4-(5-(3 cyano-4-isopropoxyphenyl)-1,2,4-oxadiazol-3-yl)-2,3-dihydro-1H-inden-1-yl)-3-hydroxyazetidine-1-carboxamide (Compound 234)

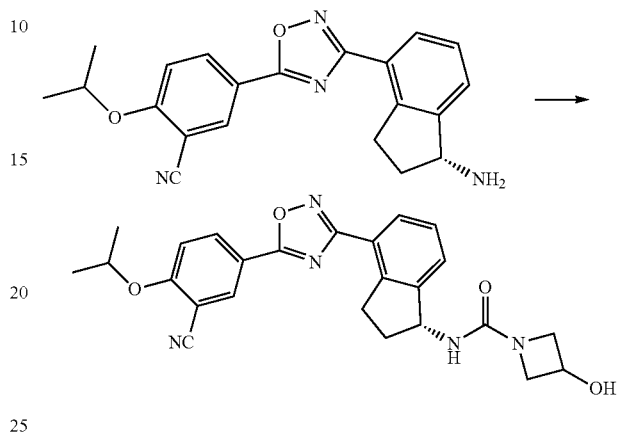

Prepared using General Procedure 21: To a stirred solution of CDI ((268.5 mg, 1.66 mmol) and Et$_3$N (279.0 mg, 2.76 mmol) in DCM (10 mL) was added the solution of (R)-5-(3-(1-amino-2,3-dihydro-1H-inden-4-yl)-1,2,4-oxadiazol-5-yl)-2-isopropoxybenzonitrile 49 (500.0 mg, 1.38 mmol) and Et$_3$N (279.0 mg, 2.76 mmol) in DCM (10 mL) for 1 h at room temperature and then this solution was added to the preparative solution of azetidin-3-ol hydrochloride (453.54 mg, 4.14 mmol)) and Et$_3$N (418.55 mg, 4.14 mmol) in DCM (10 mL) at room temperature. The reaction was stirred at room temperature for 4 h. The solvent was evaporated and the pure product was isolated after silica gel column chromatography (DCM/MeOH) to afford 474.32 mg (74.8%) of (R)-N-(4-(5-(3-cyano-4-isopropoxyphenyl)-1,2,4-oxadiazol-3-yl)-2,3-dihydro-1H-inden-1-yl)-3-hydroxyazetidine-1-carboxamide 234. LCMS-ESI (m/z) calculated for C$_{25}$H$_{25}$N$_5$O$_4$: 459.5. found 460.2 [M+H]$^+$, t$_R$=3.20 min. Elemental analysis: C calc.=65.35%. found=65.07%; H calc.=5.48%. found=5.47%; N calc.=15.24%. found=15.14%. $^1$H NMR (400 MHz, DMSO$_3$) δ 8.50 (d, J=2.3 Hz, 1H), 8.40 (dd, J=9.0, 2.3 Hz, 1H), 8.08-7.89 (m, 1H), 7.55 (d, J=9.2 Hz, 1H), 7.44 (dd, J=7.0, 5.9 Hz, 2H), 6.72 (d, J=8.7 Hz, 1H), 5.57 (d, J=6.5 Hz, 1H), 5.23 (q, J=8.3 Hz, 1H), 4.98 (hept, J=6.1 Hz, 1H), 4.39 (ddd, J=11.3, 6.6, 1.9 Hz, 1H), 4.10-3.91 (m, 2H), 3.60 (dt, J=8.6, 4.3 Hz, 2H), 3.39 (ddd, J=9.4, 7.8, 2.3 Hz, 1H), 3.05 (dt, J=8.4, 5.2 Hz, 1H), 2.47-2.35 (m, 1H), 1.95-1.74 (m, 1H), 1.37 (d, J=6.0 Hz, 6H). $^{13}$C NMR (101 MHz, DMSO) δ 173.10, 168.25, 162.48, 159.59, 147.03, 142.45, 134.57, 133.78, 127.32, 127.13, 126.97, 122.25, 115.98, 115.26, 114.86, 102.45, 72.52, 59.93, 59.08, 54.48, 32.86, 31.08, 21.48. Chiral HPLC: (R)-N-(4-(5-(3-cyano-4-isopropoxyphenyl)-1,2,4-oxadiazol-3-yl)-2,3-dihydro-1H-inden-1-yl)-3-hydroxyazetidine-1-carboxamide 234 was eluted in 15% EtOH in hexane: >99.9% ee, t$_R$=20.30 min (Chiral Method 1). Compound 235 was prepared in an analogous fashion from 50: >99.9% ee, t$_R$ for the (S)-enantiomer=23.61 min (Chiral Method 1).

General Procedure 22. Preparation of Indane Sulfamides

To a stirred solution of indane amine (1 eq) in dioxane was added sulfamide (5 eq) the reaction was stirred at 110° C. for 18 h. The solvent was evaporated and mixture was purified by column chromatography (MeOH/DCM) and the resulting isolated material was recrystallized from MeOH.

Compounds 248-249 were prepared using General Procedure 22.

137

(R)-N-(4-(5-(3 cyano-4-isopropoxyphenyl)-1,2,4-oxadiazol-3-yl)-2,3-dihydro-1H-inden-1-yl)sulfamide (Compound 248)

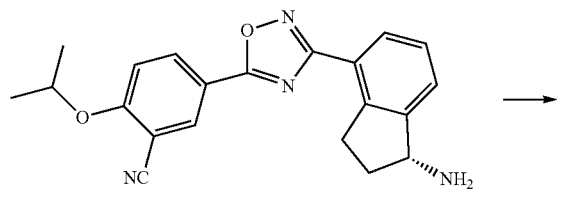

138

Prepared using General Procedure 22: To a stirred solution of (R)-5-(3-(1-amino-2,3-dihydro-1H-inden-4-yl)-1,2,4-oxadiazol-5-yl)-2-isopropoxybenzonitrile 49 (50 mg, 0.14 mmol) in dioxane (1.5 mL) was added sulfamide (66 mg, 0.69 mmol) and the mixture was heated to 110° C. After 14 h of stirring, the solvent was evaporated and the residue was purified by column chromatography. Additional purification by recrystallization from MeOH provided 15.9 mg (26%) of (R)-N-(4-(5-(3-cyano-4-isopropoxyphenyl)-1,2,4-oxadiazol-3-yl)-2,3-dihydro-1H-inden-1-yl)sulfamide 248. LCMS-ESI (m/z) calculated for $C_{21}H_{21}N_5O_4S$: 439.5. found 440.1 $[M+H]^+$, $t_R$=3.42 min. $^1$H NMR (400 MHz, $CDCl_3$) δ 8.41 (d, J=2.1 Hz, 1H), 8.33 (dd, J=8.9, 2.2 Hz, 1H), 8.13 (d, J=7.6 Hz, 1H), 7.65 (d, J=7.6 Hz, 1H), 7.43 (t, J=7.7 Hz, 1H), 7.12 (d, J=9.0 Hz, 1H), 5.08 (dd, J=16.1, 7.9 Hz, 1H), 4.80 (dt, J=12.1, 6.1 Hz, 1H), 4.65 (s, 1H), 4.59 (d, J=8.4 Hz, 1H), 3.50 (ddd, J=17.5, 8.8, 3.7 Hz, 1H), 3.30-3.09 (m, 1H), 2.87-2.67 (m, 1H), 2.07 (dt, J=21.3, 8.2 Hz, 1H), 1.47 (t, J=6.3 Hz, 6H).

Selected compounds and their corresponding analytical data is shown in Table 1, where the LCMS data was collected using Method 2 (see General Methods). The enantiomeric purity was determined for key intermediates and selected final compounds and is presumed from the synthesis for the remaining compounds.

TABLE 1

| STRUCTURE | COMPOUND NUMBER | LCMS RETENTION TIME (min) | CHIRALITY OF INDANE CARBON |
|---|---|---|---|
| 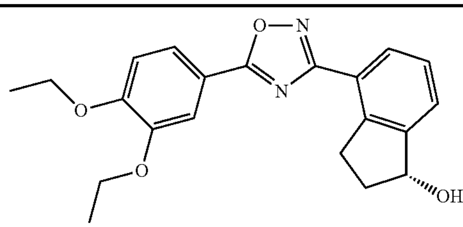 | 1 | 9.23 | R |
| 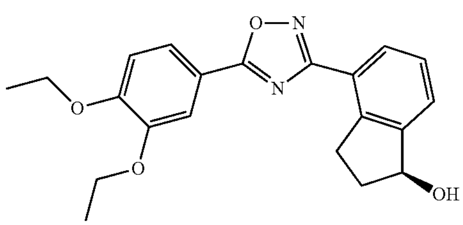 [SMILES: CCOc1ccc(-c2nc(-c3cccc4c3CC[C@@H]4O)no2)cc1OCC] | 2 | 9.25 | S |
| 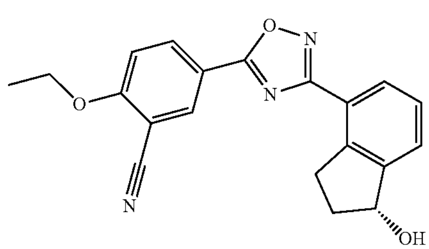 [SMILES: CCOc1ccc(-c2nc(-c3cccc4c3CC[C@H]4O)no2)cc1C#N] | 3 | 8.69 | R |
| 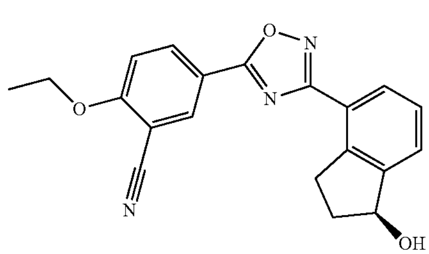 [SMILES: CCOc1ccc(-c2nc(-c3cccc4c3CC[C@@H]4O)no2)cc1C#N] | 4 | 8.68 | S |

TABLE 1-continued

| STRUCTURE | COMPOUND NUMBER | LCMS RETENTION TIME (min) | CHIRALITY OF INDANE CARBON |
|---|---|---|---|
| 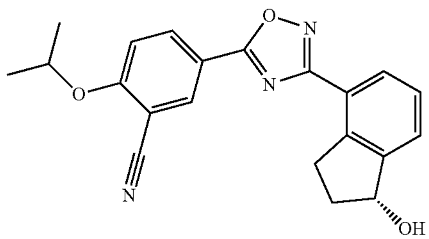 [SMILES: CC(C)Oc1ccc(-c2nc(-c3cccc4c3CC[C@H]4O)no2)cc1C#N] | 5 | 9.12 | R |
| 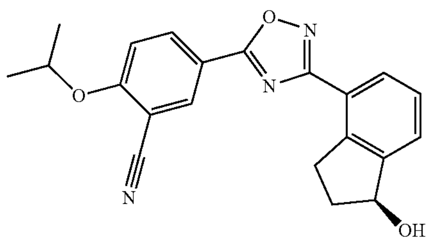 [SMILES: CC(C)Oc1ccc(-c2nc(-c3cccc4c3CC[C@@H]4O)no2)cc1C#N] | 6 | 9.08 | S |
| 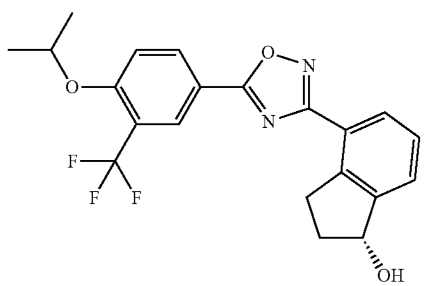 [SMILES: CC(C)Oc1ccc(-c2nc(-c3cccc4c3CC[C@H]4O)no2)cc1C(F)(F)F] | 7 | 10.54 | R |
| 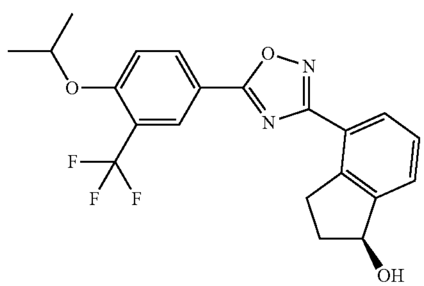 [SMILES: CC(C)Oc1ccc(-c2nc(-c3cccc4c3CC[C@@H]4O)no2)cc1C(F)(F)F] | 8 | 10.54 | S |
| 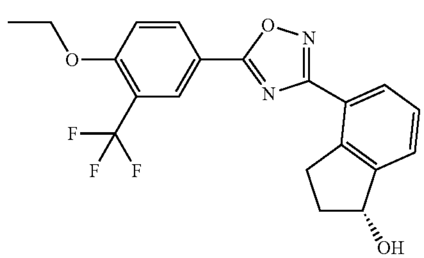 [SMILES: CCOc1ccc(-c2nc(-c3cccc4c3CC[C@H]4O)no2)cc1C(F)(F)F] | 9 | 10.13 | R |
| 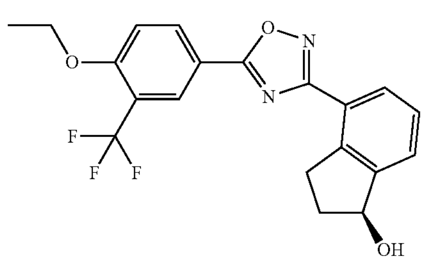 [SMILES: CCOc1ccc(-c2nc(-c3cccc4c3CC[C@@H]4O)no2)cc1C(F)(F)F] | 10 | 10.09 | S |

TABLE 1-continued

| STRUCTURE | COMPOUND NUMBER | LCMS RETENTION TIME (min) | CHIRALITY OF INDANE CARBON |
|---|---|---|---|
| 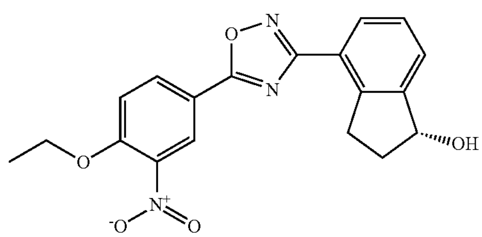 | 11 | 8.91 | R |
| 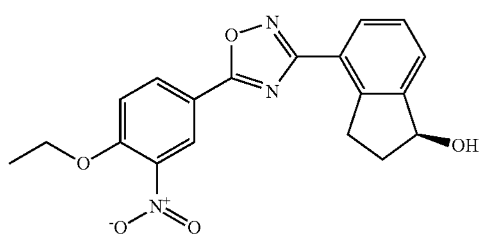 | 12 | 8.91 | S |
| 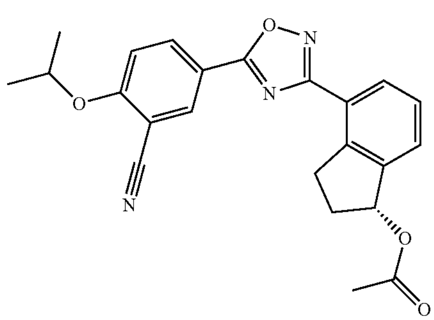 [SMILES: CC(=O)O[C@@H]1CCc2c(-c3noc(-c4ccc(OC(C)C)c(C#N)c4)n3)cccc21] | 13 | 10.72 | R |
| 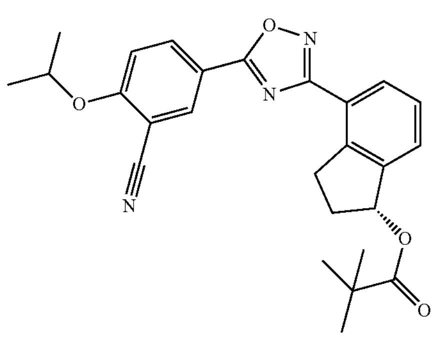 [SMILES: CC(C)Oc1ccc(-c2nc(-c3cccc4c3CC[C@H]4OC(=O)C(C)(C)C)no2)cc1C#N] | 14 | 11.96 | R |
| 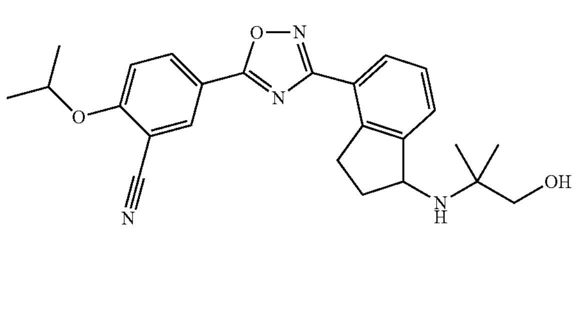 [SMILES: CC(C)Oc1ccc(-c2nc(-c3cccc4c3CCC4NC(C)(C)CO)no2)cc1C#N] | 15 | 6.58 | Racemic mixture |

TABLE 1-continued

| STRUCTURE | COMPOUND NUMBER | LCMS RETENTION TIME (min) | CHIRALITY OF INDANE CARBON |
|---|---|---|---|
| 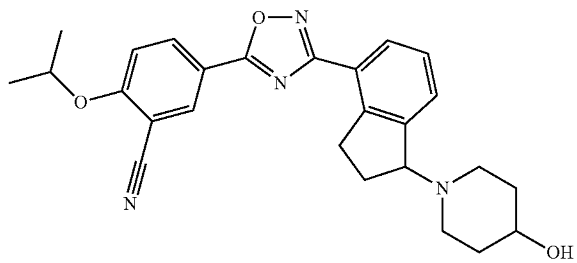 [SMILES: CC(C)Oc1ccc(-c2nc(-c3cccc4c3CCC4N3CCC(O)CC3)no2)cc1C#N] | 16 | 6.42 | Racemic mixture |
| 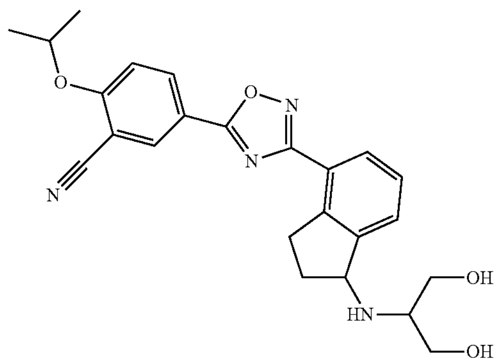 [SMILES: CC(C)Oc1ccc(-c2nc(-c3cccc4c3CCC4NC(CO)CO)no2)cc1C#N] | 17 | 6.24 | Racemic mixture |
| 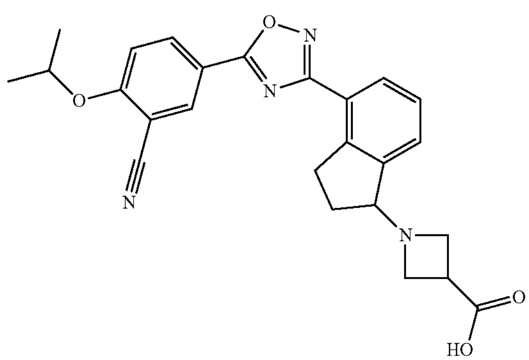 [SMILES: CC(C)Oc1ccc(-c2nc(-c3cccc4c3CCC4N3CC(C(=O)O)C3)no2)cc1C#N] | 18 | 6.52 | Racemic mixture |
| 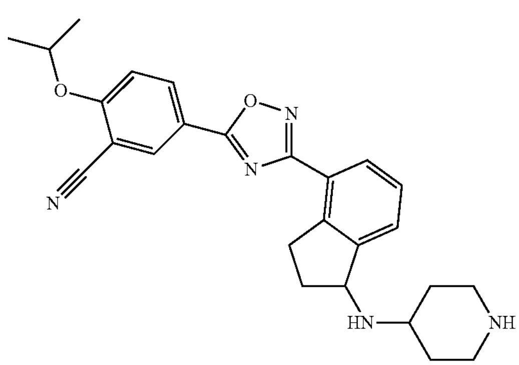 [SMILES: CC(C)Oc1ccc(-c2nc(-c3cccc4c3CCC4NC3CCNCC3)no2)cc1C#N] | 19 | 5.31 | Racemic mixture |

TABLE 1-continued

| STRUCTURE | COMPOUND NUMBER | LCMS RETENTION TIME (min) | CHIRALITY OF INDANE CARBON |
|---|---|---|---|
| 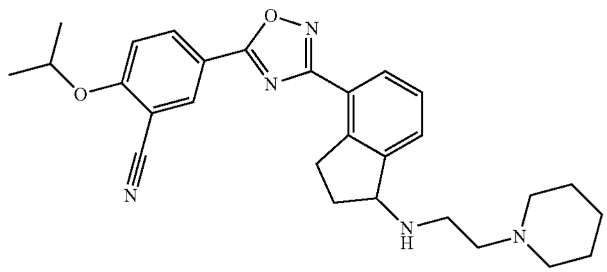 [SMILES: CC(C)Oc1ccc(-c2nc(-c3cccc4c3CCC4NCCN3CCCCC3)no2)cc1C#N] | 20 | 5.63 | Racemic mixture |
| 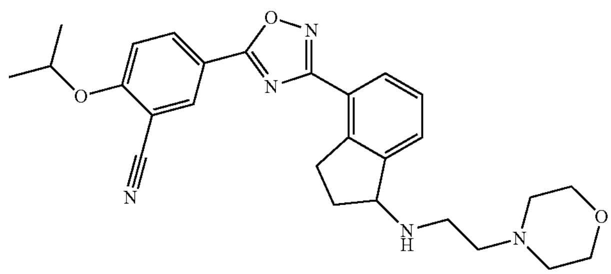 [SMILES: CC(C)Oc1ccc(-c2nc(-c3cccc4c3CCC4NCCN3CCOCC3)no2)cc1C#N] | 21 | 5.81 | Racemic mixture |
| 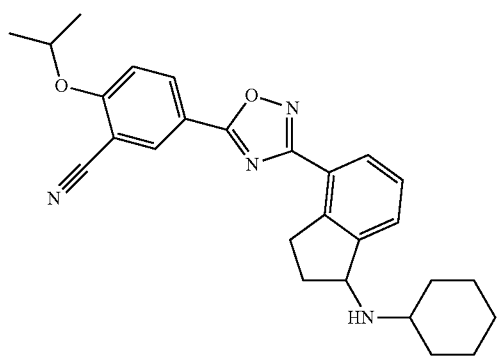 [SMILES: CC(C)Oc1ccc(-c2nc(-c3cccc4c3CCC4NC3CCCCC3)no2)cc1C#N] | 22 | 7.36 | Racemic mixture |
| 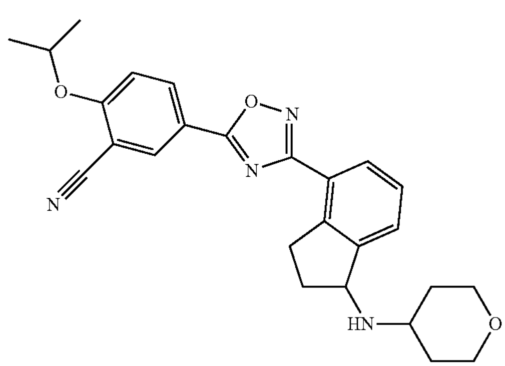 [SMILES: CC(C)Oc1ccc(-c2nc(-c3cccc4c3CCC4NC3CCOCC3)no2)cc1C#N] | 23 | 6.65 | Racemic mixture |

TABLE 1-continued

| STRUCTURE | COMPOUND NUMBER | LCMS RETENTION TIME (min) | CHIRALITY OF INDANE CARBON |
|---|---|---|---|
| 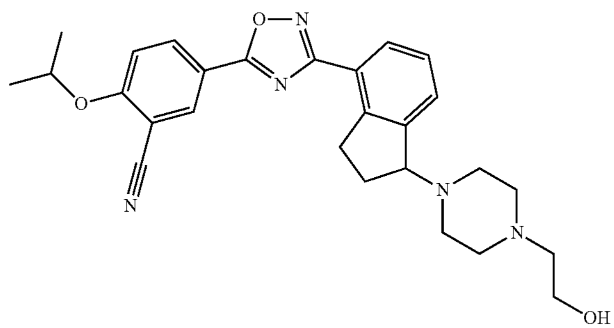 [SMILES: CC(C)Oc1ccc(-c2nc(-c3cccc4c3CCC4N3CCN(CCO)CC3)no2)cc1C#N] | 24 | 6.40 | Racemic mixture |
| 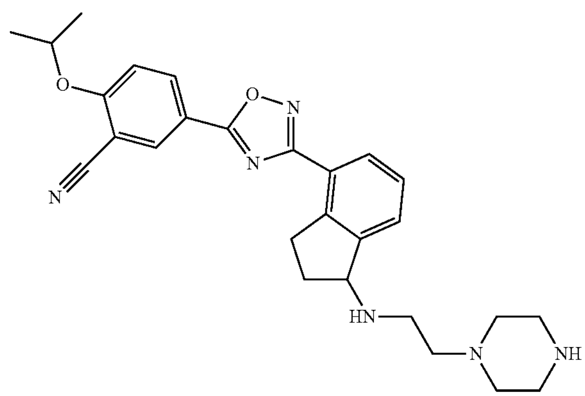 [SMILES: CC(C)Oc1ccc(-c2nc(-c3cccc4c3CCC4NCCN3CCNCC3)no2)cc1C#N] | 25 | 5.51 | Racemic mixture |
| 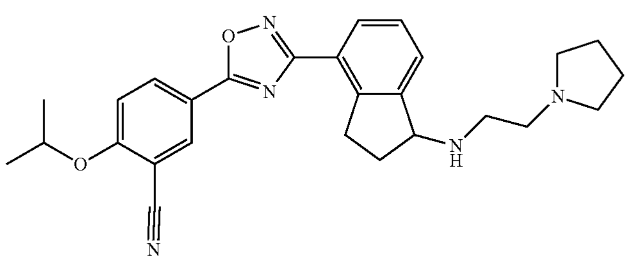 [SMILES: CC(C)Oc1ccc(-c2nc(-c3cccc4c3CCC4NCCN3CCCC3)no2)cc1C#N] | 26 | 5.77 | Racemic mixture |
| 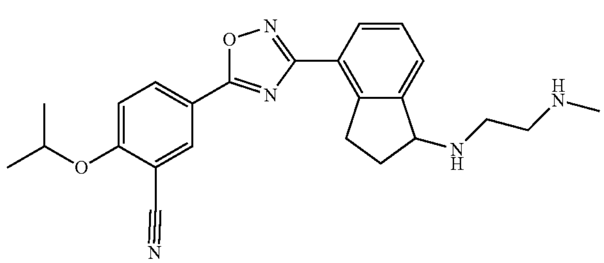 [SMILES: CNCCNC1CCc2c(-c3noc(-c4ccc(OC(C)C)c(C#N)c4)n3)cccc21] | 27 | 5.43 | Racemic mixture |
| 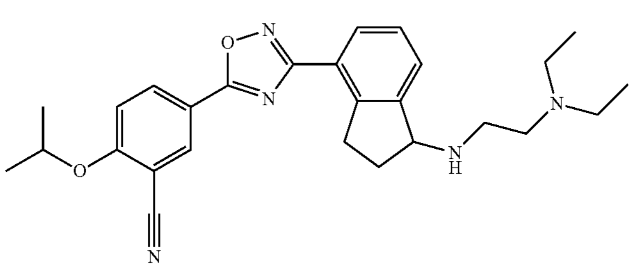 [SMILES: CCN(CC)CCNC1CCc2c(-c3noc(-c4ccc(OC(C)C)c(C#N)c4)n3)cccc21] | 28 | 5.62 | Racemic mixture |

TABLE 1-continued

| STRUCTURE | COMPOUND NUMBER | LCMS RETENTION TIME (min) | CHIRALITY OF INDANE CARBON |
|---|---|---|---|
| 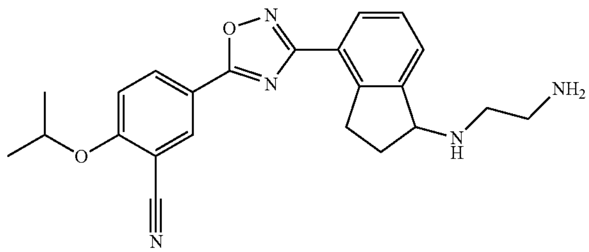 [SMILES: CC(C)Oc1ccc(-c2nc(-c3cccc4c3CCC4NCCN)no2)cc1C#N] | 29 | 5.47 | Racemic mixture |
| 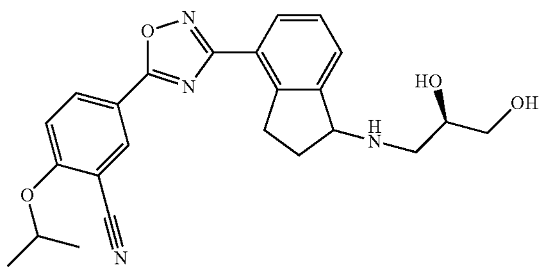 [SMILES: CC(C)Oc1ccc(-c2nc(-c3cccc4c3CCC4NC[C@@H](O)CO)no2)cc1C#N] | 30 | 6.21 | Diastereomeric mixture |
| 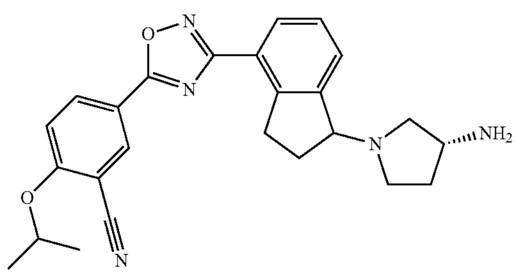 [SMILES: CC(C)Oc1ccc(-c2nc(-c3cccc4c3CCC4N3CC[C@@H](N)C3)no2)cc1C#N] | 31 | 5.69 | Diastereomeric mixture |
| 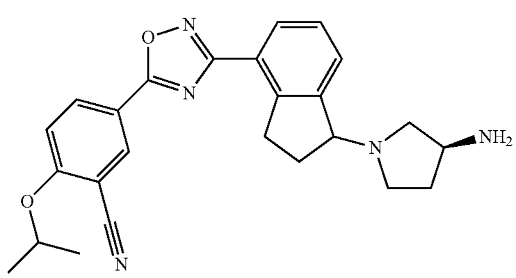 [SMILES: CC(C)Oc1ccc(-c2nc(-c3cccc4c3CCC4N3CC[C@H](N)C3)no2)cc1C#N] | 32 | 5.66 | Diastereomeric mixture |
| 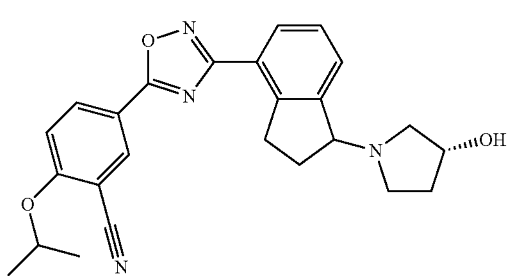 [SMILES: CC(C)Oc1ccc(-c2nc(-c3cccc4c3CCC4N3CC[C@@H](O)C3)no2)cc1C#N] | 33 | 6.39 | Diastereomeric mixture |

TABLE 1-continued

| STRUCTURE | COMPOUND NUMBER | LCMS RETENTION TIME (min) | CHIRALITY OF INDANE CARBON |
|---|---|---|---|
| 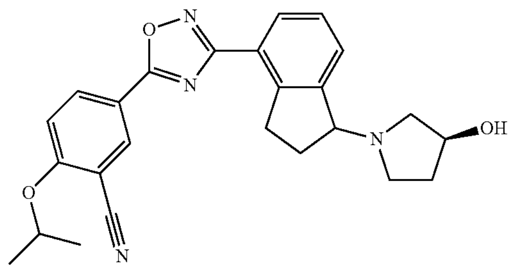 [SMILES: CC(C)Oc1ccc(-c2nc(-c3cccc4c3CCC4N3CC[C@H](O)C3)no2)cc1C#N] | 34 | 6.37 | Diastereomeric mixture |
| 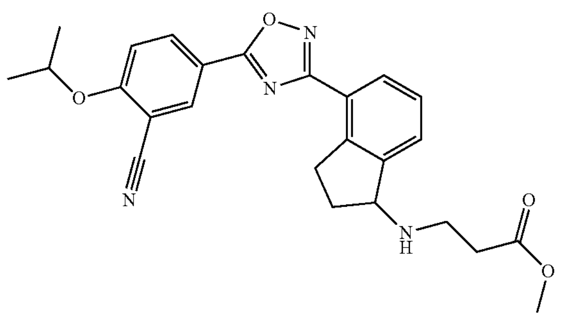 [SMILES: COC(=O)CCNC1CCc2c(-c3noc(-c4ccc(OC(C)C)c(C#N)c4)n3)cccc21] | 35 | 6.70 | Racemic |
| 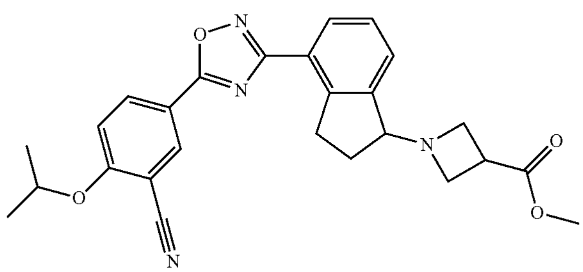 [SMILES: COC(=O)C1CN(C2CCc3c(-c4noc(-c5ccc(OC(C)C)c(C#N)c5)n4)cccc32)C1] | 36 | 6.83 | Racemic mixture |
| 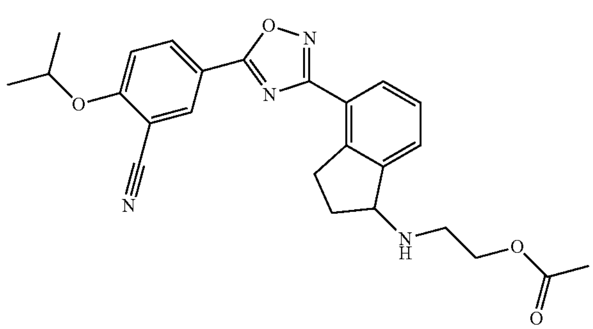 [SMILES: CC(=O)OCCNC1CCc2c(-c3noc(-c4ccc(OC(C)C)c(C#N)c4)n3)cccc21] | 37 | 6.70 | Racemic mixture |
| 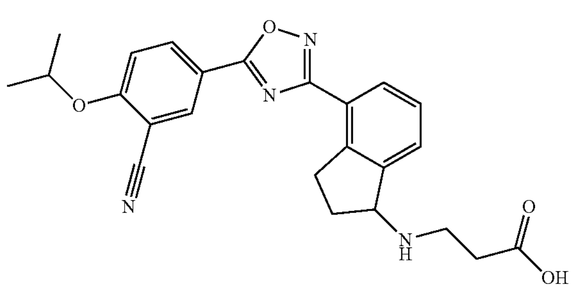 [SMILES: CC(C)Oc1ccc(-c2nc(-c3cccc4c3CCC4NCCC(=O)O)no2)cc1C#N] | 38 | 6.51 | Racemic mixture |

TABLE 1-continued

| STRUCTURE | COMPOUND NUMBER | LCMS RETENTION TIME (min) | CHIRALITY OF INDANE CARBON |
|---|---|---|---|
| 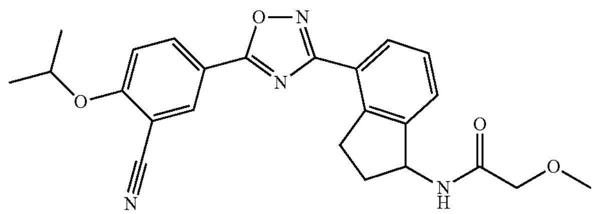 [SMILES: COCC(=O)NC1CCc2c(-c3noc(-c4ccc(OC(C)C)c(C#N)c4)n3)cccc21] | 39 | 9.22 | Racemic mixture |
| 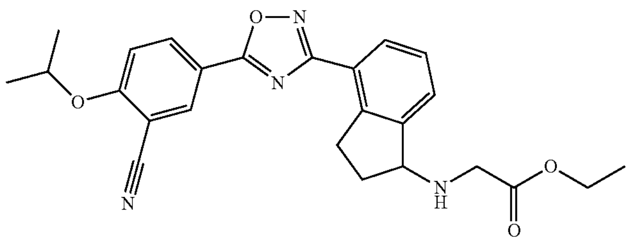 [SMILES: CCOC(=O)CNC1CCc2c(-c3noc(-c4ccc(OC(C)C)c(C#N)c4)n3)cccc21] | 40 | 6.86 | Racemic mixture |
| 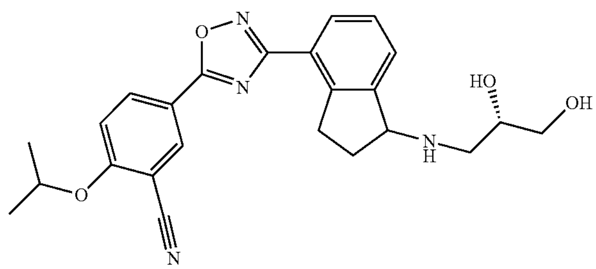 [SMILES: CC(C)Oc1ccc(-c2nc(-c3cccc4c3CCC4NC[C@H](O)CO)no2)cc1C#N] | 41 | 6.02 | Diastereomeric mixture |
| 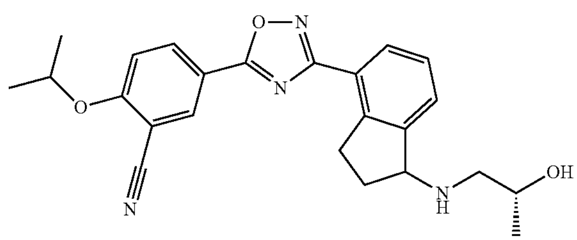 [SMILES: CC(C)Oc1ccc(-c2nc(-c3cccc4c3CCC4NC[C@@H](C)O)no2)cc1C#N] | 42 | 6.26 | Diastereomeric mixture |
| 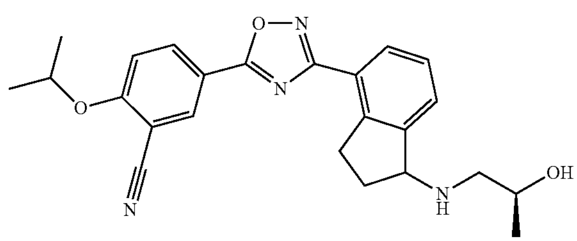 [SMILES: CC(C)Oc1ccc(-c2nc(-c3cccc4c3CCC4NC[C@H](C)O)no2)cc1C#N] | 43 | 6.35 | Diastereomeric mixture |
| 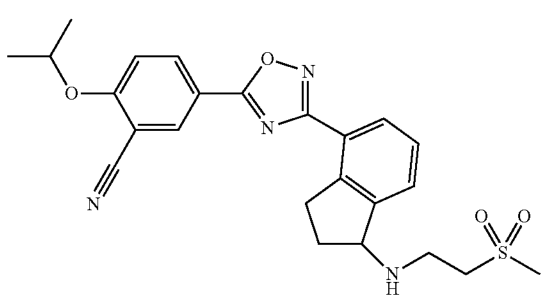 [SMILES: CC(C)Oc1ccc(-c2nc(-c3cccc4c3CCC4NCCS(C)(=O)=O)no2)cc1C#N] | 44 | 6.61 | Racemic mixture |

TABLE 1-continued

| STRUCTURE | COMPOUND NUMBER | LCMS RETENTION TIME (min) | CHIRALITY OF INDANE CARBON |
|---|---|---|---|
| 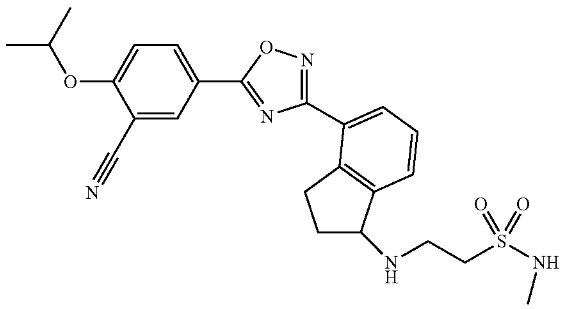 [SMILES: CNS(=O)(=O)CCNC1CCc2c(-c3noc(-c4ccc(OC(C)C)c(C#N)c4)n3)cccc21] | 45 | 6.66 | Racemic mixture |
| 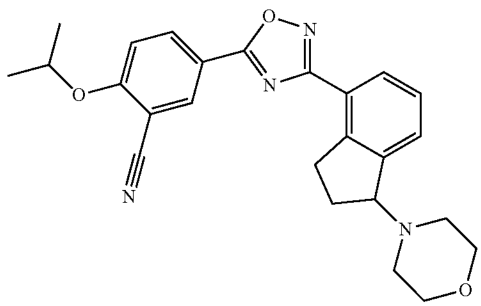 [SMILES: CC(C)Oc1ccc(-c2nc(-c3cccc4c3CCC4N3CCOCC3)no2)cc1C#N] | 46 | 6.47 | Racemic mixture |
| 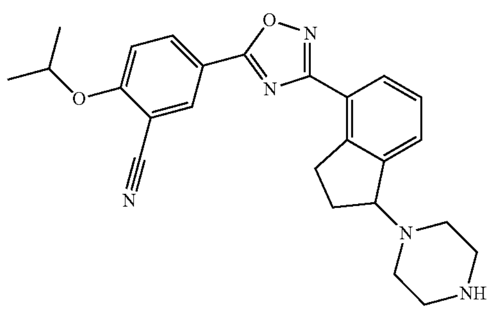 [SMILES: CC(C)Oc1ccc(-c2nc(-c3cccc4c3CCC4N3CCNCC3)no2)cc1C#N] | 47 | 6.23 | Racemic mixture |
| 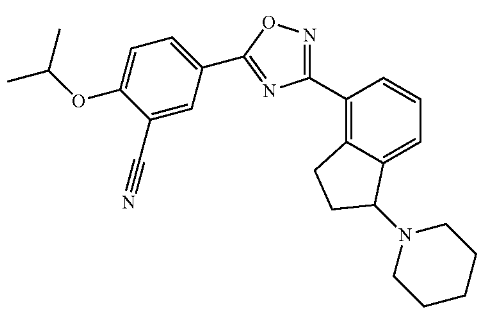 | 48 | 6.81 | Racemic mixture |
| 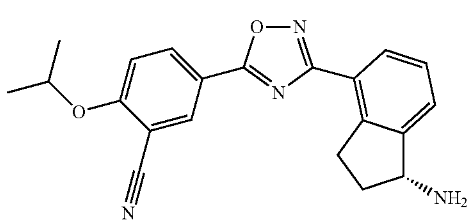 [SMILES: CC(C)Oc1ccc(-c2nc(-c3cccc4c3CC[C@H]4N)no2)cc1C#N] | 49 | 6.29 | R |

TABLE 1-continued
| STRUCTURE | COMPOUND NUMBER | LCMS RETENTION TIME (min) | CHIRALITY OF INDANE CARBON |
|---|---|---|---|
| 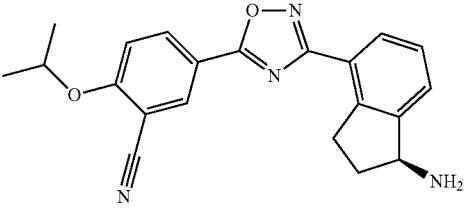 [SMILES: CC(C)Oc1ccc(-c2nc(-c3cccc4c3CC[C@@H]4N)no2)cc1C#N] | 50 | 6.42 | S |
| 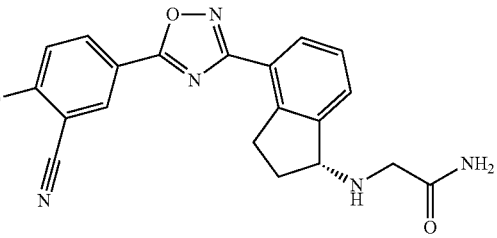 | 51 | 6.44 | R |
| 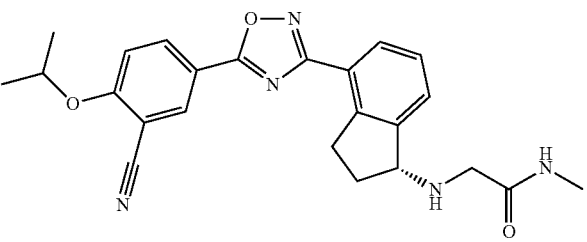 [SMILES: CNC(=O)CN[C@@H]1CCc2c(-c3noc(-c4ccc(OC(C)C)c(C#N)c4)n3)cccc21] | 52 | 6.33 | R |
| 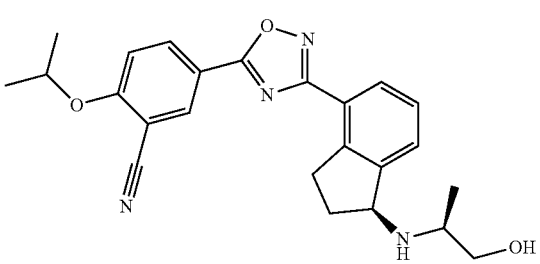 [SMILES: CC(C)Oc1ccc(-c2nc(-c3cccc4c3CC[C@@H]4N[C@@H](C)CO)no2)cc1C#N] | 53 | 6.42 | S, S |
| 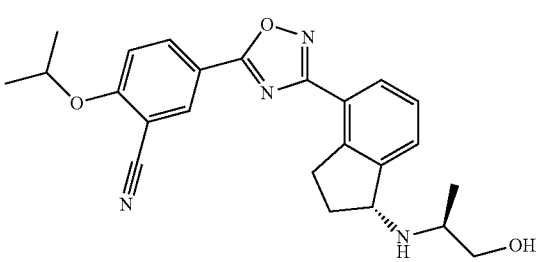 [SMILES: CC(C)Oc1ccc(-c2nc(-c3cccc4c3CC[C@H]4N[C@@H](C)CO)no2)cc1C#N] | 54 | 6.46 | R, S |
| 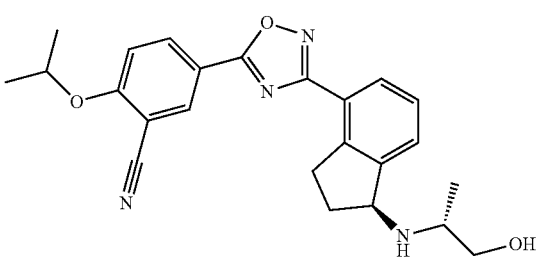 [SMILES: CC(C)Oc1ccc(-c2nc(-c3cccc4c3CC[C@@H]4N[C@H](C)CO)no2)cc1C#N] | 55 | 6.30 | S, R |

TABLE 1-continued

| STRUCTURE | COMPOUND NUMBER | LCMS RETENTION TIME (min) | CHIRALITY OF INDANE CARBON |
|---|---|---|---|
| 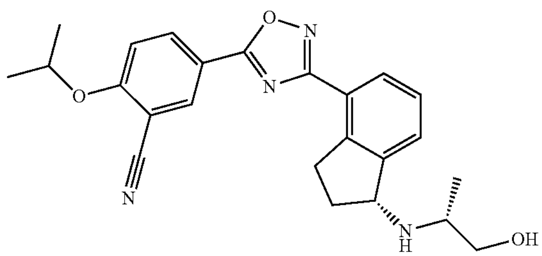 [SMILES: CC(C)Oc1ccc(-c2nc(-c3cccc4c3CC[C@H]4N[C@H](C)CO)no2)cc1C#N] | 56 | 6.36 | R, R |
| 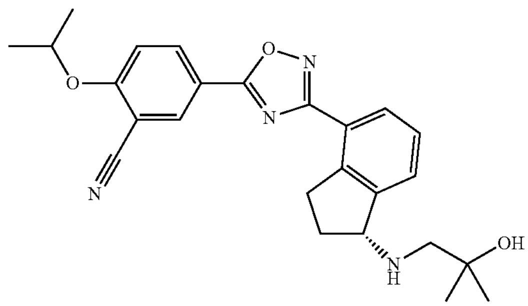 [SMILES: CC(C)Oc1ccc(-c2nc(-c3cccc4c3CC[C@H]4NCC(C)(C)O)no2)cc1C#N] | 57 | 6.50 | R |
| 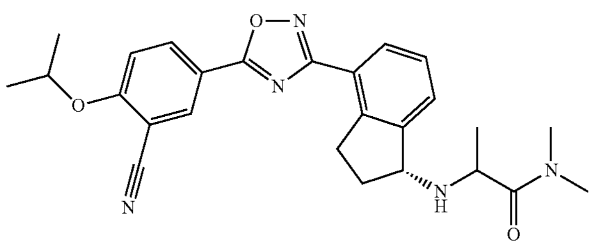 [SMILES: CC(C)Oc1ccc(-c2nc(-c3cccc4c3CC[C@H]4NC(C)C(=O)N(C)C)no2)cc1C#N] | 58 | 6.61 | Diastereomeric mixture |
| 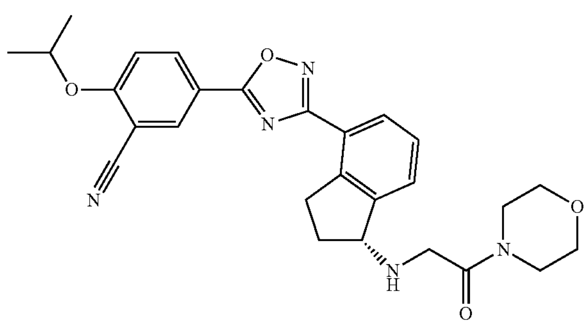 [SMILES: CC(C)Oc1ccc(-c2nc(-c3cccc4c3CC[C@H]4NCC(=O)N3CCOCC3)no2)cc1C#N] | 59 | 6.58 | R |
| 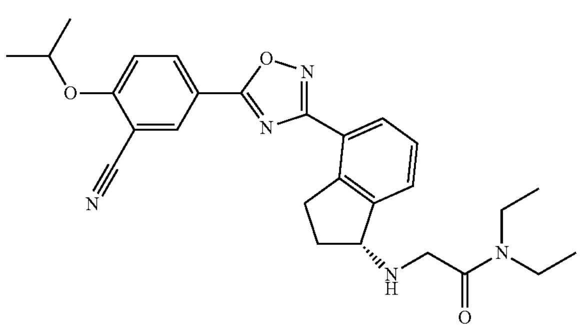 [SMILES: CCN(CC)C(=O)CN[C@@H]1CCc2c(-c3noc(-c4ccc(OC(C)C)c(C#N)c4)n3)cccc21] | 60 | 7.03 | R |

TABLE 1-continued

| STRUCTURE | COMPOUND NUMBER | LCMS RETENTION TIME (min) | CHIRALITY OF INDANE CARBON |
|---|---|---|---|
| 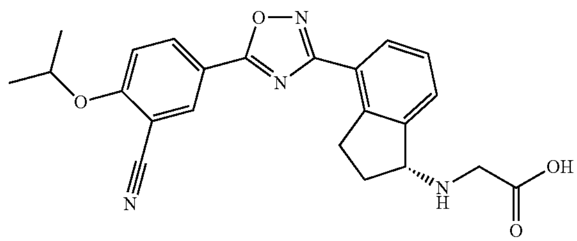 [SMILES: CC(C)Oc1ccc(-c2nc(-c3cccc4c3CC[C@H]4NCC(=O)O)no2)cc1C#N] | 61 | 6.63 | R |
| 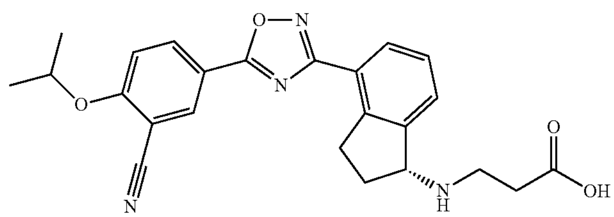 [SMILES: CC(C)Oc1ccc(-c2nc(-c3cccc4c3CC[C@H]4NCCC(=O)O)no2)cc1C#N] | 62 | 6.56 | R |
| 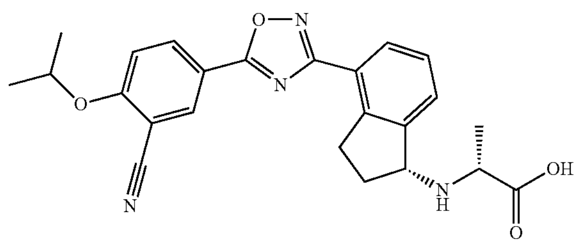 [SMILES: CC(C)Oc1ccc(-c2nc(-c3cccc4c3CC[C@H]4N[C@H](C)C(=O)O)no2)cc1C#N] | 63 | 6.70 | R, R |
| 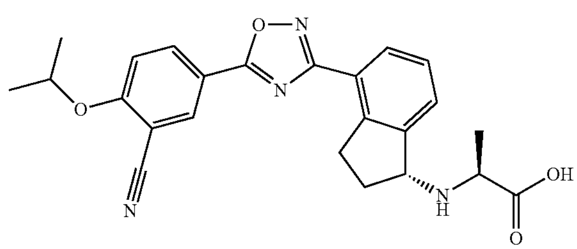 [SMILES: CC(C)Oc1ccc(-c2nc(-c3cccc4c3CC[C@H]4N[C@@H](C)C(=O)O)no2)cc1C#N] | 64 | 6.71 | R, S |
| 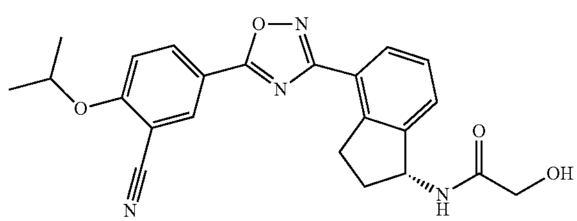 [SMILES: CC(C)Oc1ccc(-c2nc(-c3cccc4c3CC[C@H]4NC(=O)CO)no2)cc1C#N] | 65 | 8.23 | R |
| 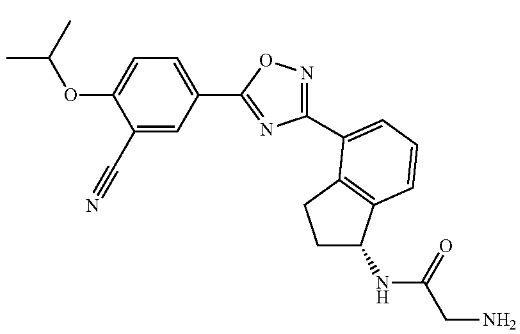 [SMILES: CC(C)Oc1ccc(-c2nc(-c3cccc4c3CC[C@H]4NC(=O)CN)no2)cc1C#N] | 66 | 6.44 | R |

TABLE 1-continued

| STRUCTURE | COMPOUND NUMBER | LCMS RETENTION TIME (min) | CHIRALITY OF INDANE CARBON |
|---|---|---|---|
| 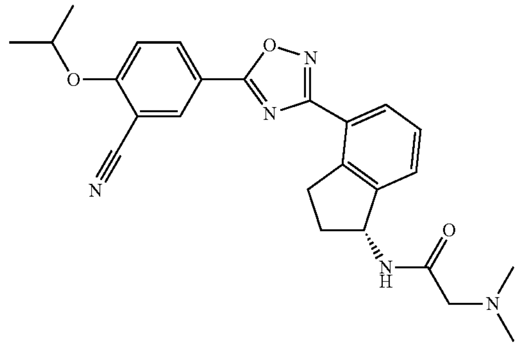 [SMILES: CC(C)Oc1ccc(-c2nc(-c3cccc4c3CC[C@H]4NC(=O)CN(C)C)no2)cc1C#N] | 67 | 6.64 | R |
| 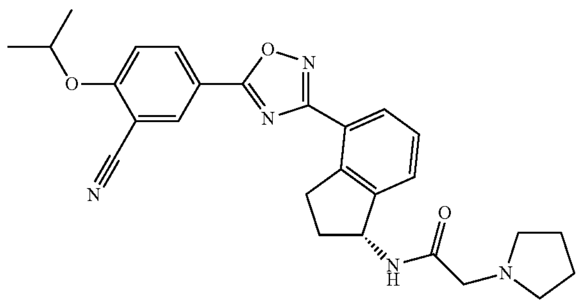 [SMILES: CC(C)Oc1ccc(-c2nc(-c3cccc4c3CC[C@H]4NC(=O)CN3CCCC3)no2)cc1C#N] | 68 | 6.71 | R |
| 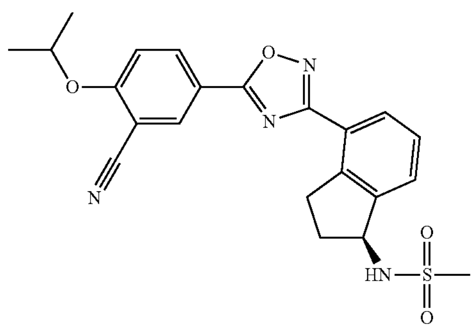 [SMILES: CC(C)Oc1ccc(-c2nc(-c3cccc4c3CC[C@@H]4NS(C)(=O)=O)no2)cc1C#N] | 69 | 9.30 | S |
| 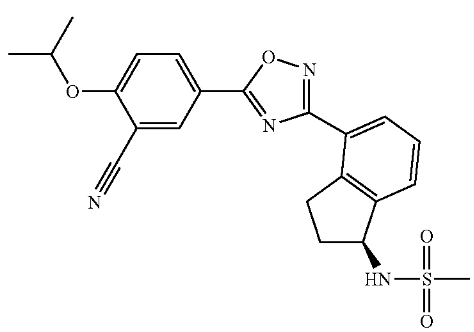 [SMILES: CC(C)Oc1ccc(-c2nc(-c3cccc4c3CC[C@@H]4NS(C)(=O)=O)no2)cc1C#N] | 70 | 9.24 | R |
| 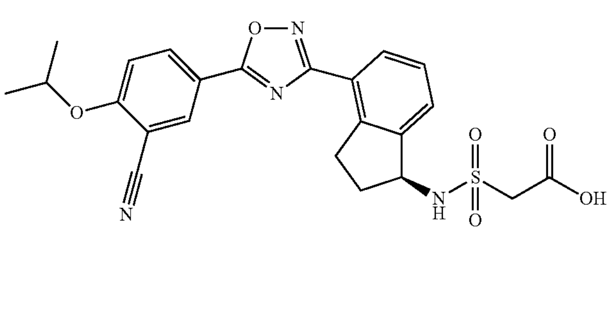 [SMILES: CC(C)Oc1ccc(-c2nc(-c3cccc4c3CC[C@@H]4NS(=O)(=O)CC(=O)O)no2)cc1C#N] | 71 | 8.72 | S |

TABLE 1-continued

| STRUCTURE | COMPOUND NUMBER | LCMS RETENTION TIME (min) | CHIRALITY OF INDANE CARBON |
|---|---|---|---|
| 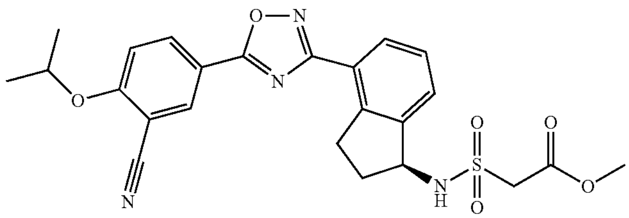 [SMILES: COC(=O)CS(=O)(=O)N[C@H]1CCc2c(-c3noc(-c4ccc(OC(C)C)c(C#N)c4)n3)cccc21] | 72 | 9.51 | S |
| 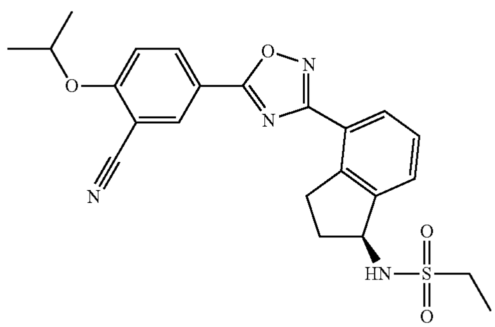 [SMILES: CCS(=O)(=O)N[C@H]1CCc2c(-c3noc(-c4ccc(OC(C)C)c(C#N)c4)n3)cccc21] | 73 | 9.63 | S |
| 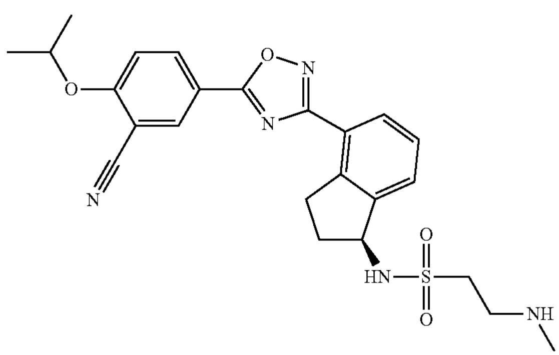 [SMILES: CNCCS(=O)(=O)N[C@H]1CCc2c(-c3noc(-c4ccc(OC(C)C)c(C#N)c4)n3)cccc21] | 74 | 6.75 | R |
| 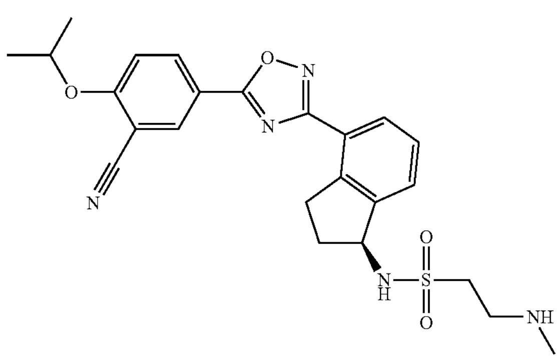 [SMILES: CNCCS(=O)(=O)N[C@H]1CCc2c(-c3noc(-c4ccc(OC(C)C)c(C#N)c4)n3)cccc21] | 75 | 6.66 | S |

TABLE 1-continued

| STRUCTURE | COMPOUND NUMBER | LCMS RETENTION TIME (min) | CHIRALITY OF INDANE CARBON |
|---|---|---|---|
| 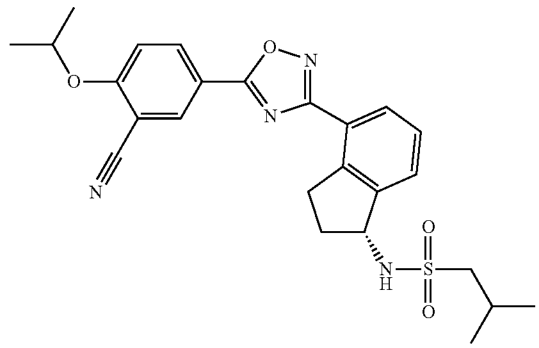 [SMILES: CC(C)CS(=O)(=O)N[C@@H]1CCc2c(-c3noc(-c4ccc(OC(C)C)c(C#N)c4)n3)cccc21] | 76 | 10.35 | R |
| 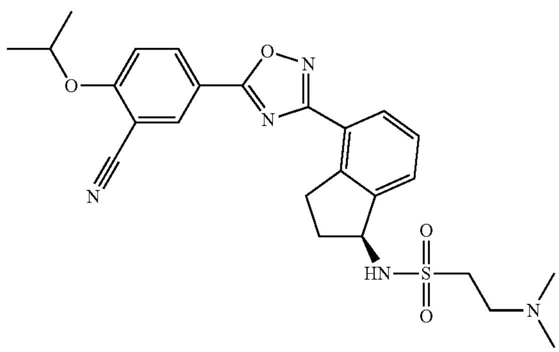 [SMILES: CC(C)Oc1ccc(-c2nc(-c3cccc4c3CC[C@@H]4NS(=O)(=O)CCN(C)C)no2)cc1C#N] | 77 | 6.96 | R |
| 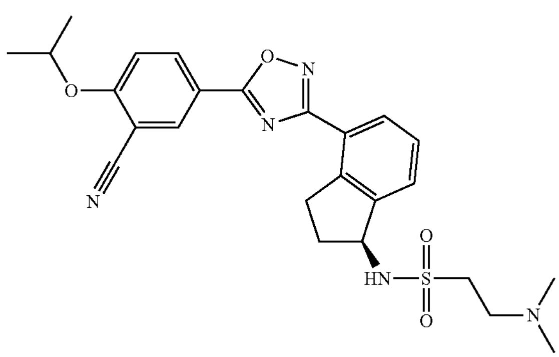 [SMILES: CC(C)Oc1ccc(-c2nc(-c3cccc4c3CC[C@@H]4NS(=O)(=O)CCN(C)C)no2)cc1C#N] | 78 | 6.69 | S |
| 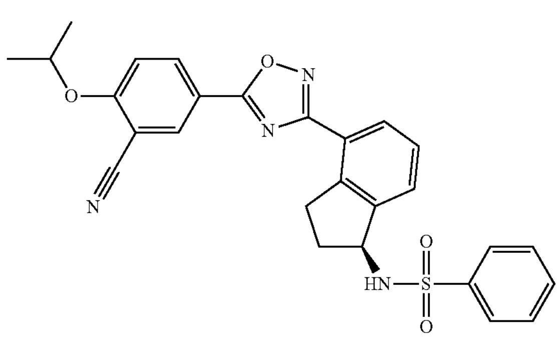 [SMILES: CC(C)Oc1ccc(-c2nc(-c3cccc4c3CC[C@@H]4NS(=O)(=O)c3ccccc3)no2)cc1C#N] | 79 | 10.37 | R |

TABLE 1-continued

| STRUCTURE | COMPOUND NUMBER | LCMS RETENTION TIME (min) | CHIRALITY OF INDANE CARBON |
|---|---|---|---|
| 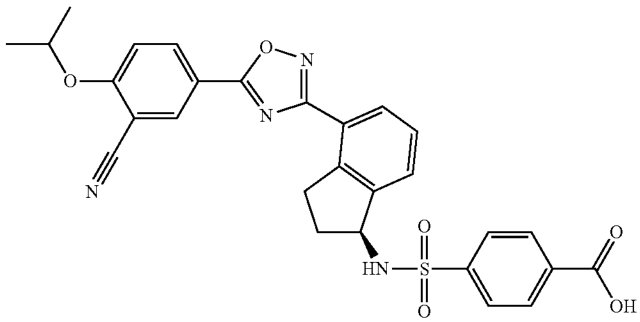 [SMILES: CC(C)Oc1ccc(-c2nc(-c3cccc4c3CC[C@@H]4NS(=O)(=O)c3ccc(C(=O)O)cc3)no2)cc1C#N] | 80 | 9.36 | R |
| 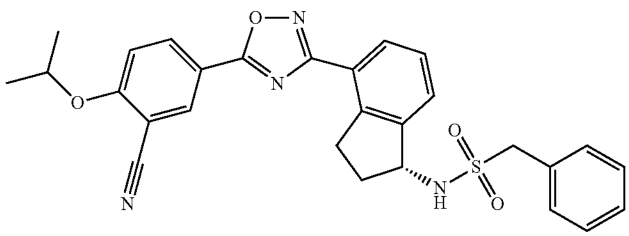 [SMILES: CC(C)Oc1ccc(-c2nc(-c3cccc4c3CC[C@H]4NS(=O)(=O)Cc3ccccc3)no2)cc1C#N] | 81 | 10.33 | R |
| 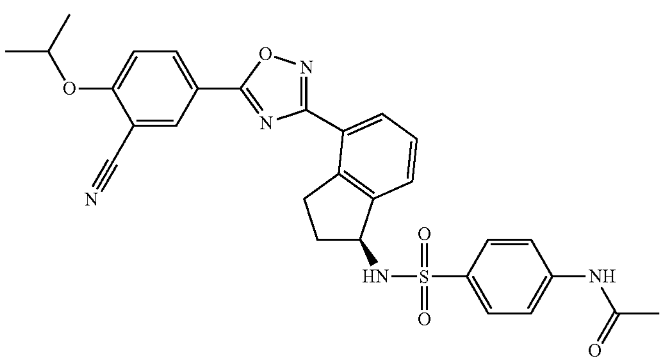 [SMILES: CC(=O)Nc1ccc(S(=O)(=O)N[C@H]2CCc3c(-c4noc(-c5ccc(OC(C)C)c(C#N)c5)n4)cccc32)cc1] | 82 | 9.27 | R |
| 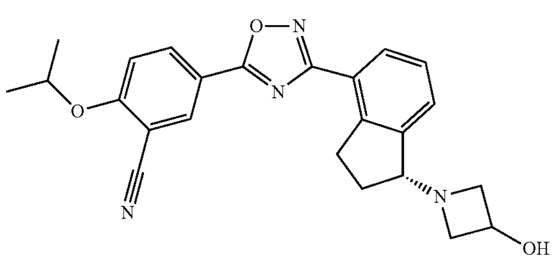 [SMILES: CC(C)Oc1ccc(-c2nc(-c3cccc4c3CC[C@H]4N3CC(O)C3)no2)cc1C#N] | 83 | 6.19 | R |
| 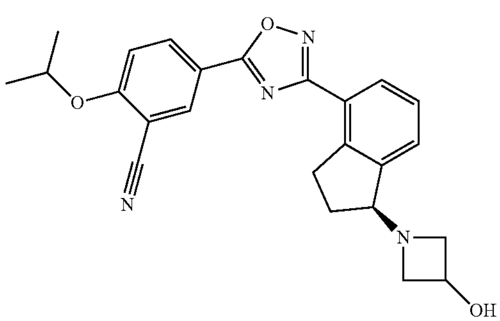 [SMILES: CC(C)Oc1ccc(-c2nc(-c3cccc4c3CC[C@@H]4N3CC(O)C3)no2)cc1C#N] | 84 | 6.46 | S |

TABLE 1-continued

| STRUCTURE | COMPOUND NUMBER | LCMS RETENTION TIME (min) | CHIRALITY OF INDANE CARBON |
|---|---|---|---|
| 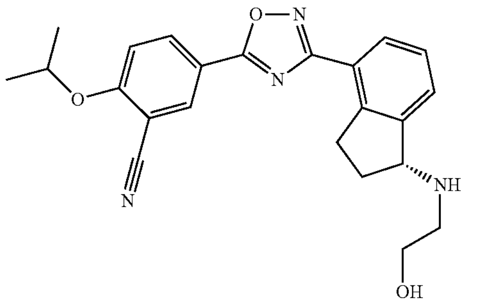 [SMILES: CC(C)Oc1ccc(-c2nc(-c3cccc4c3CC[C@H]4NCCO)no2)cc1C#N] | 85 | 6.30 | R |
| 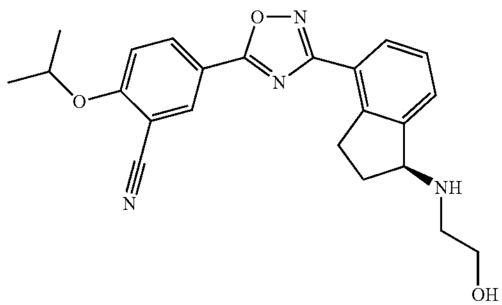 [SMILES: CC(C)Oc1ccc(-c2nc(-c3cccc4c3CC[C@@H]4NCCO)no2)cc1C#N] | 86 | 6.41 | S |
| 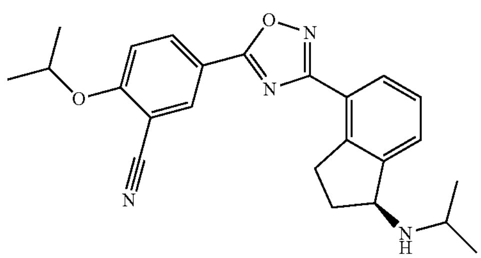 [SMILES: CC(C)N[C@H]1CCc2c(-c3noc(-c4ccc(OC(C)C)c(C#N)c4)n3)cccc21] | 87 | 6.80 | S |
| 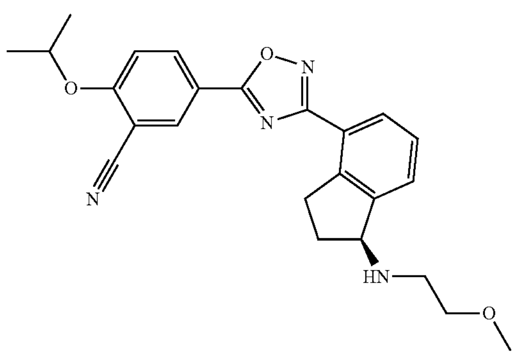 [SMILES: COCCN[C@H]1CCc2c(-c3noc(-c4ccc(OC(C)C)c(C#N)c4)n3)cccc21] | 88 | 6.61 | R |
| 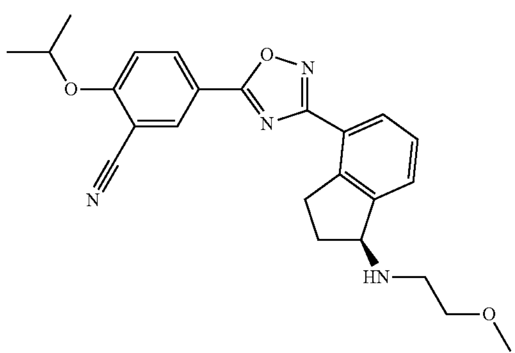 [SMILES: COCCN[C@H]1CCc2c(-c3noc(-c4ccc(OC(C)C)c(C#N)c4)n3)cccc21] | 89 | 6.66 | S |

TABLE 1-continued
| STRUCTURE | COMPOUND NUMBER | LCMS RETENTION TIME (min) | CHIRALITY OF INDANE CARBON |
|---|---|---|---|
| 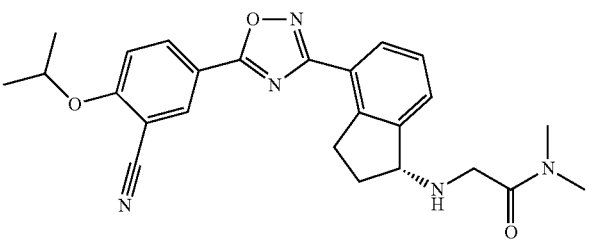 | 90 | 6.58 | R |
| 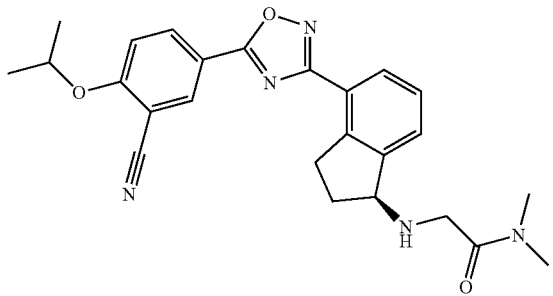 [SMILES: CC(C)Oc1ccc(-c2nc(-c3cccc4c3CC[C@@H]4NCC(=O)N(C)C)no2)cc1C#N] | 91 | 6.56 | S |
| 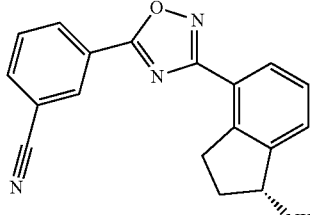 | 92 | 5.46 | R |
| 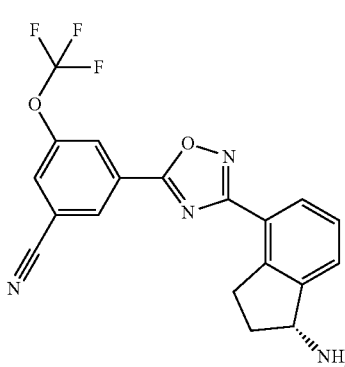 | 93 | 6.57 | R |
| 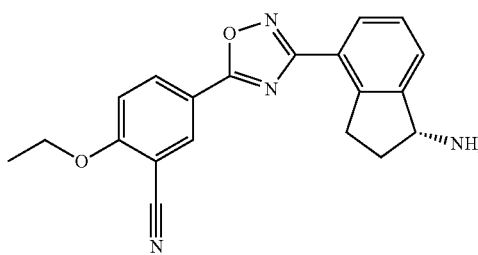 | 94 | 8.30 | R |

TABLE 1-continued
| STRUCTURE | COMPOUND NUMBER | LCMS RETENTION TIME (min) | CHIRALITY OF INDANE CARBON |
|---|---|---|---|
| 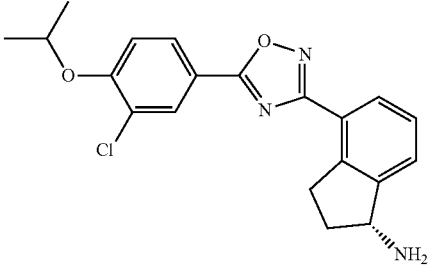 [SMILES: CC(C)Oc1ccc(-c2nc(-c3cccc4c3CC[C@H]4N)no2)cc1Cl] | 95 | 7.11 | R |
| 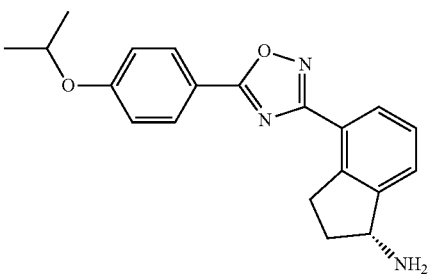 [SMILES: CC(C)Oc1ccc(-c2nc(-c3cccc4c3CC[C@H]4N)no2)cc1] | 96 | 6.55 | R |
| 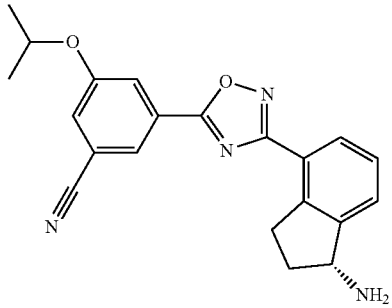 [SMILES: CC(C)Oc1cc(C#N)cc(-c2nc(-c3cccc4c3CC[C@H]4N)no2)c1] | 97 | 6.41 | R |
| 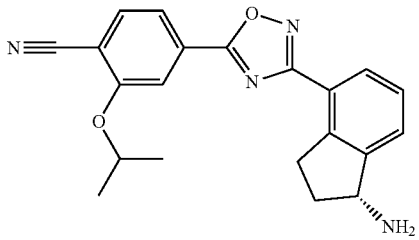 [SMILES: CC(C)Oc1cc(-c2nc(-c3cccc4c3CC[C@H]4N)no2)ccc1C#N] | 98 | 6.39 | R |
| 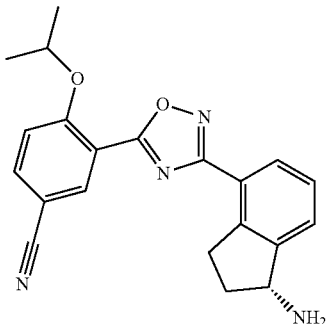 | 99 | 6.26 | R |

TABLE 1-continued

| STRUCTURE | COMPOUND NUMBER | LCMS RETENTION TIME (min) | CHIRALITY OF INDANE CARBON |
|---|---|---|---|
| 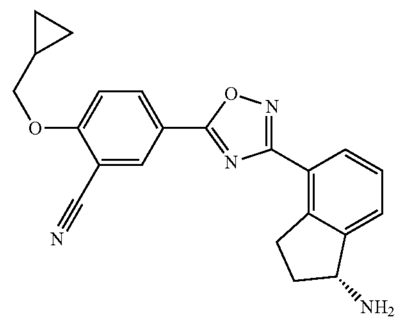 [SMILES: N#Cc1cc(-c2nc(-c3cccc4c3CC[C@H]4N)no2)ccc1OCC1CC1] | 100 | 6.47 | R |
| 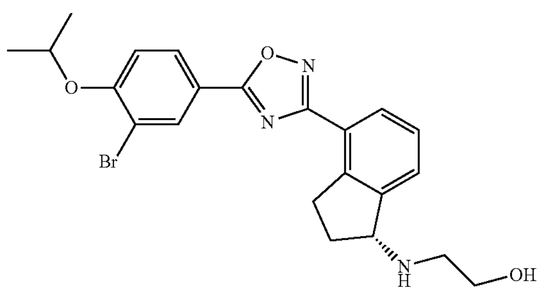 [SMILES: CC(C)Oc1ccc(-c2nc(-c3cccc4c3CC[C@H]4NCCO)no2)cc1Br] | 101 | 7.06 | R |
| 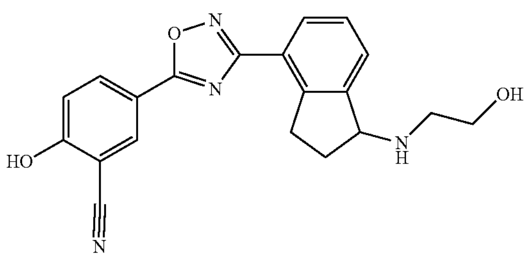 [SMILES: N#Cc1cc(-c2nc(-c3cccc4c3CCC4NCCO)no2)ccc1O] | 102 | 5.37 | Racemic mixture |
| 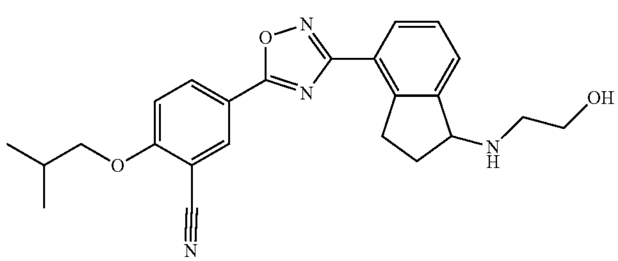 [SMILES: CC(C)COc1ccc(-c2nc(-c3cccc4c3CCC4NCCO)no2)cc1C#N] | 103 | 6.80 | Racemic mixture |
| 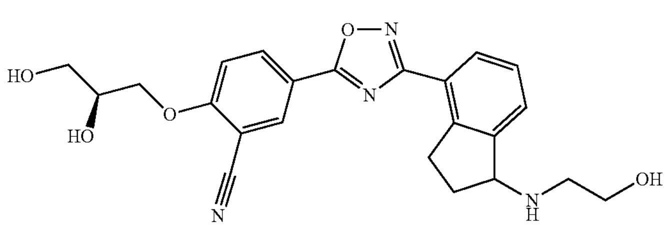 [SMILES: N#Cc1cc(-c2nc(-c3cccc4c3CCC4NCCO)no2)ccc1OC[C@@H](O)CO] | 104 | 5.16 | Diastereomeric Mixture |

TABLE 1-continued
| STRUCTURE | COMPOUND NUMBER | LCMS RETENTION TIME (min) | CHIRALITY OF INDANE CARBON |
|---|---|---|---|
| 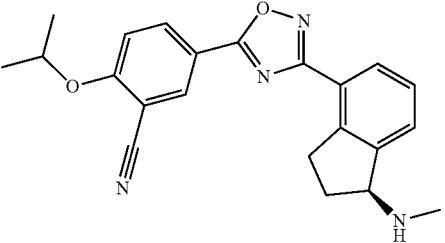 [SMILES: CN[C@H]1CCc2c(-c3noc(-c4ccc(OC(C)C)c(C#N)c4)n3)cccc21] | 105 | 6.44 | S |
| 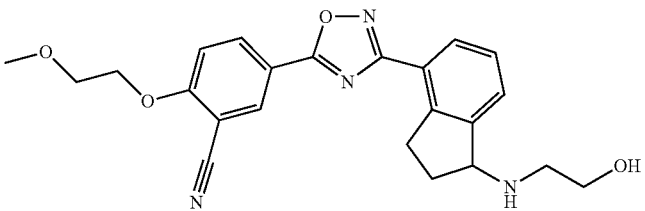 [SMILES: COCCOc1ccc(-c2nc(-c3cccc4c3CCC4NCCO)no2)cc1C#N] | 106 | 5.76 | Racemic |
| 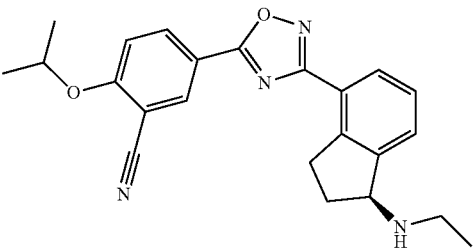 [SMILES: CCN[C@H]1CCc2c(-c3noc(-c4ccc(OC(C)C)c(C#N)c4)n3)cccc21] | 107 | 6.70 | S |
| 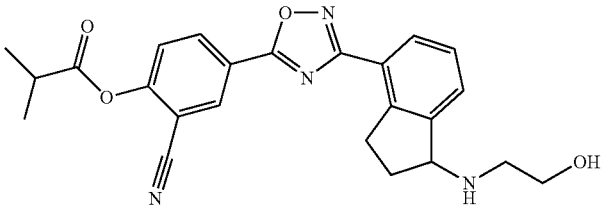 [SMILES: CC(C)C(=O)Oc1ccc(-c2nc(-c3cccc4c3CCC4NCCO)no2)cc1C#N] | 108 | 6.56 | Racemic mixture |
| 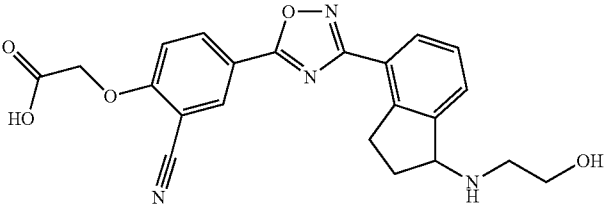 [SMILES: N#Cc1cc(-c2nc(-c3cccc4c3CCC4NCCO)no2)ccc1OCC(=O)O] | 109 | 6.45 | Racemic mixture |
| 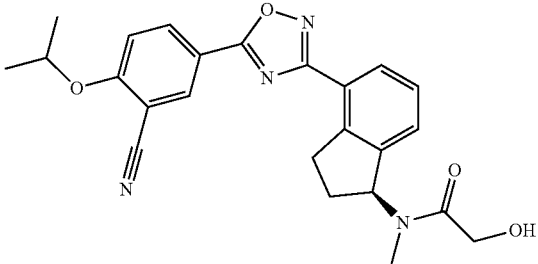 [SMILES: CC(C)Oc1ccc(-c2nc(-c3cccc4c3CC[C@@H]4N(C)C(=O)CO)no2)cc1C#N] | 110 | 9.08 | S |

TABLE 1-continued

| STRUCTURE | COMPOUND NUMBER | LCMS RETENTION TIME (min) | CHIRALITY OF INDANE CARBON |
|---|---|---|---|
| 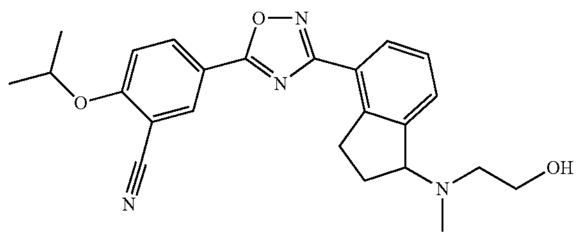 [SMILES: CC(C)Oc1ccc(-c2nc(-c3cccc4c3CCC4N(C)CCO)no2)cc1C#N] | 111 | 6.42 | R |
| 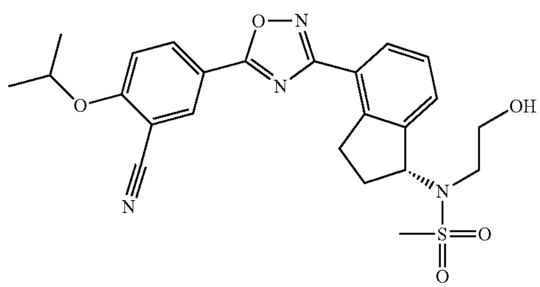 [SMILES: CC(C)Oc1ccc(-c2nc(-c3cccc4c3CC[C@H]4N(CCO)S(C)(=O)=O)no2)cc1C#N] | 112 | 8.98 | R |
| 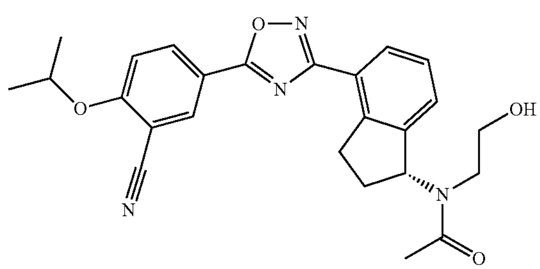 [SMILES: CC(=O)N(CCO)[C@@H]1CCc2c(-c3noc(-c4ccc(OC(C)C)c(C#N)c4)n3)cccc21] | 113 | 8.45 | R |
| 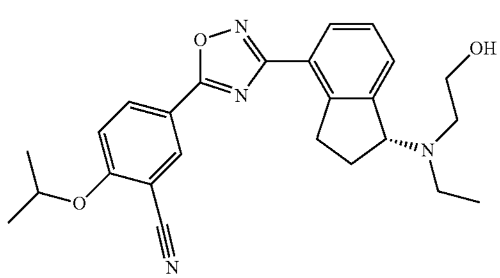 [SMILES: CCN(CCO)[C@@H]1CCc2c(-c3noc(-c4ccc(OC(C)C)c(C#N)c4)n3)cccc21] | 114 | 6.64 | R |
| 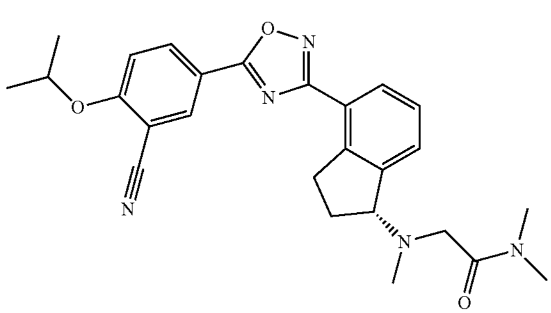 [SMILES: CC(C)Oc1ccc(-c2nc(-c3cccc4c3CC[C@H]4N(C)CC(=O)N(C)C)no2)cc1C#N] | 115 | 6.77 | R |

TABLE 1-continued

| STRUCTURE | COMPOUND NUMBER | LCMS RETENTION TIME (min) | CHIRALITY OF INDANE CARBON |
|---|---|---|---|
| 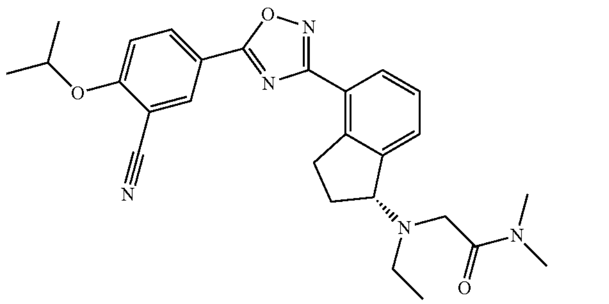 [SMILES: CCN(CC(=O)N(C)C)[C@@H]1CCc2c(-c3noc(-c4ccc(OC(C)C)c(C#N)c4)n3)cccc21] | 116 | 6.92 | R |
| 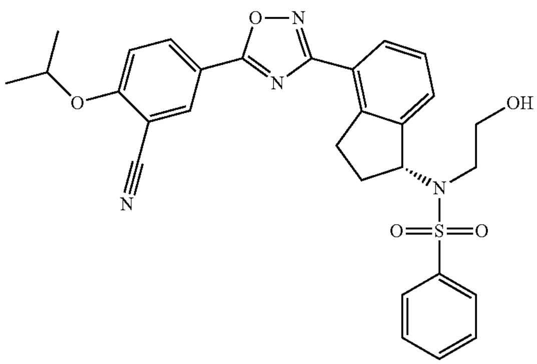 [SMILES: CC(C)Oc1ccc(-c2nc(-c3cccc4c3CC[C@H]4N(CCO)S(=O)(=O)c3ccccc3)no2)cc1C#N] | 117 | 10.17 | S |
| 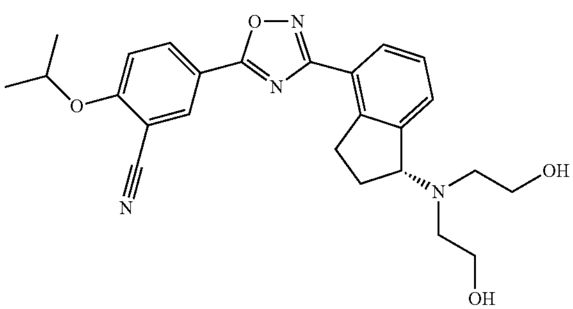 [SMILES: CC(C)Oc1ccc(-c2nc(-c3cccc4c3CC[C@H]4N(CCO)CCO)no2)cc1C#N] | 118 | 6.09 | R |
| 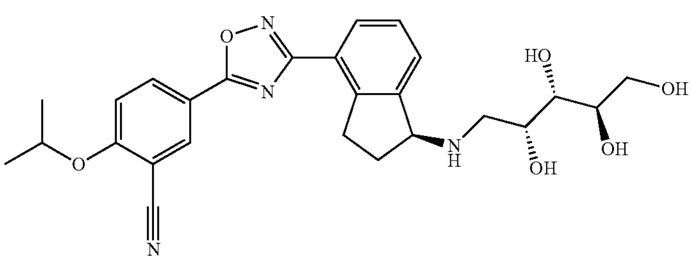 [SMILES: CC(C)Oc1ccc(-c2nc(-c3cccc4c3CC[C@@H]4NC[C@@H](O)[C@H](O)[C@H](O)CO)no2)cc1C#N] | 119 | 6.15 | S, R, S, R |
| 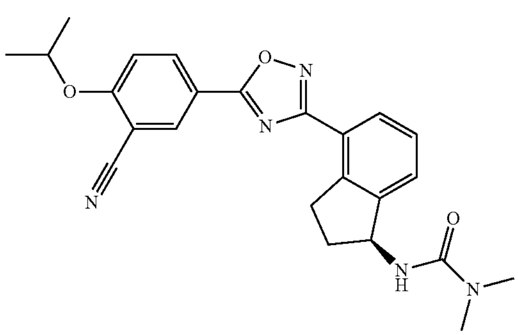 [SMILES: CC(C)Oc1ccc(-c2nc(-c3cccc4c3CC[C@@H]4NC(=O)N(C)C)no2)cc1C#N] | 120 | 9.09 | S |

TABLE 1-continued

| STRUCTURE | COMPOUND NUMBER | LCMS RETENTION TIME (min) | CHIRALITY OF INDANE CARBON |
|---|---|---|---|
| 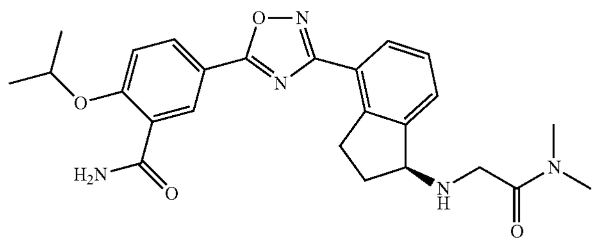 [SMILES: CC(C)Oc1ccc(-c2nc(-c3cccc4c3CC[C@@H]4NCC(=O)N(C)C)no2)cc1C(N)=O] | 121 | 5.87 | S |
| 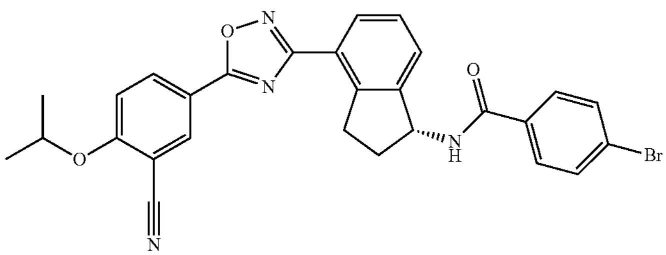 [SMILES: CC(C)Oc1ccc(-c2nc(-c3cccc4c3CC[C@H]4NC(=O)c3ccc(Br)cc3)no2)cc1C#N] | 122 | 10.80 | R |
| 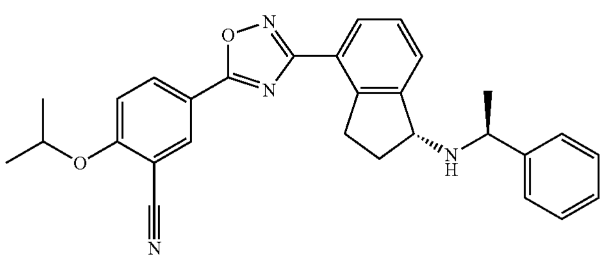 [SMILES: CC(C)Oc1ccc(-c2nc(-c3cccc4c3CC[C@H]4N[C@@H](C)c3ccccc3)no2)cc1C#N] | 123 | 7.38 | S, S |
| 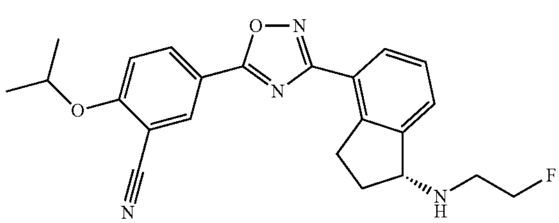 [SMILES: CC(C)Oc1ccc(-c2nc(-c3cccc4c3CC[C@H]4NCCF)no2)cc1C#N] | 124 | 6.89 | R |
| 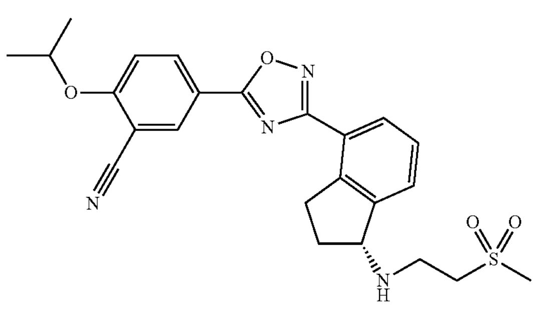 [SMILES: CC(C)Oc1ccc(-c2nc(-c3cccc4c3CC[C@H]4NCCS(C)(=O)=O)no2)cc1C#N] | 125 | 6.50 | R |

TABLE 1-continued

| STRUCTURE | COMPOUND NUMBER | LCMS RETENTION TIME (min) | CHIRALITY OF INDANE CARBON |
|---|---|---|---|
| 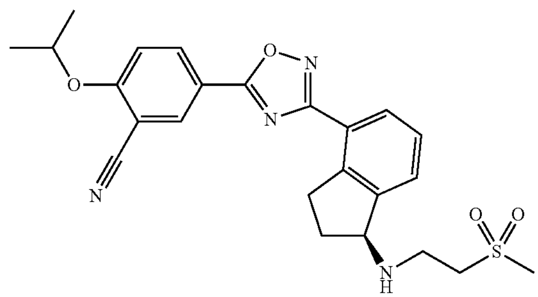 [SMILES: CC(C)Oc1ccc(-c2nc(-c3cccc4c3CC[C@@H]4NCCS(C)(=O)=O)no2)cc1C#N] | 126 | 6.67 | S |
| 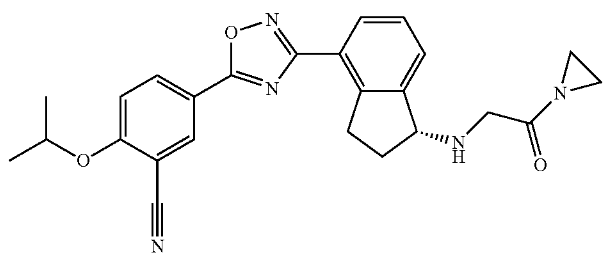 [SMILES: CC(C)Oc1ccc(-c2nc(-c3cccc4c3CC[C@H]4NCC(=O)N3CC3)no2)cc1C#N] | 127 | 5.35 | R |
| 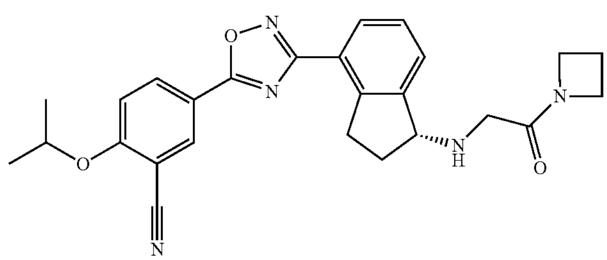 [SMILES: CC(C)Oc1ccc(-c2nc(-c3cccc4c3CC[C@H]4NCC(=O)N3CCC3)no2)cc1C#N] | 128 | 6.47 | R |
| 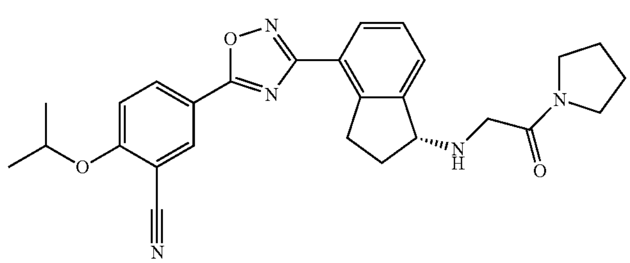 [SMILES: CC(C)Oc1ccc(-c2nc(-c3cccc4c3CC[C@H]4NCC(=O)N3CCCC3)no2)cc1C#N] | 129 | 6.48 | R |
| 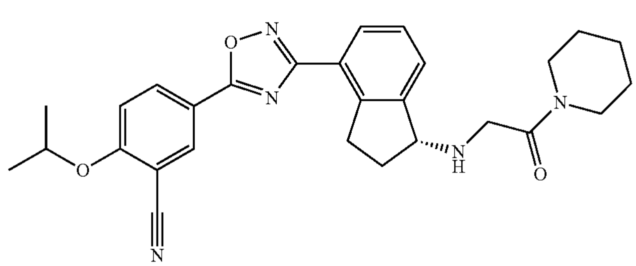 [SMILES: CC(C)Oc1ccc(-c2nc(-c3cccc4c3CC[C@H]4NCC(=O)N3CCCCC3)no2)cc1C#N] | 130 | 6.95 | R |

TABLE 1-continued

| STRUCTURE | COMPOUND NUMBER | LCMS RETENTION TIME (min) | CHIRALITY OF INDANE CARBON |
|---|---|---|---|
| 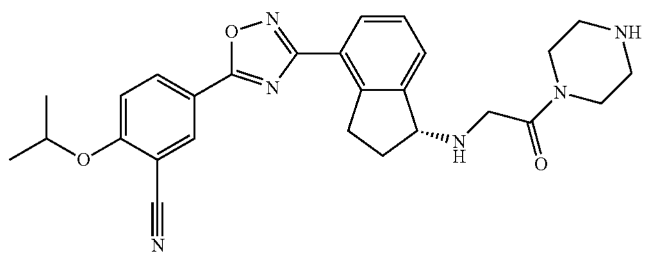 [SMILES: CC(C)Oc1ccc(-c2nc(-c3cccc4c3CC[C@H]4NCC(=O)N3CCNCC3)no2)cc1C#N] | 131 | 5.44 | R |
| 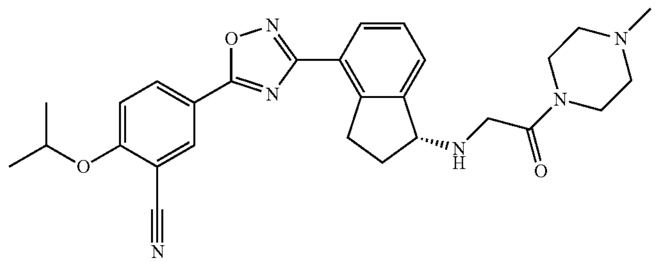 [SMILES: CC(C)Oc1ccc(-c2nc(-c3cccc4c3CC[C@H]4NCC(=O)N3CCN(C)CC3)no2)cc1C#N] | 132 | 5.64 | R |
| 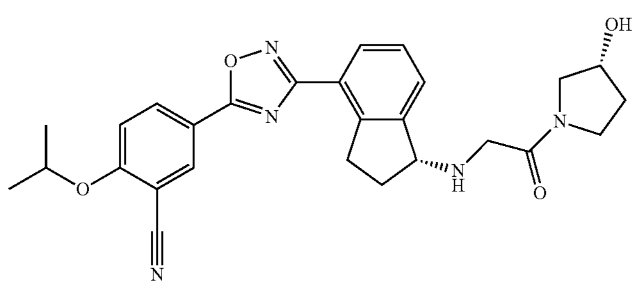 [SMILES: CC(C)Oc1ccc(-c2nc(-c3cccc4c3CC[C@H]4NCC(=O)N3CC[C@@H](O)C3)no2)cc1C#N] | 133 | 6.34 | R, R |
| 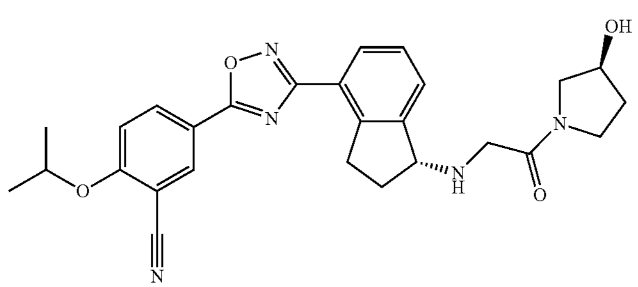 [SMILES: CC(C)Oc1ccc(-c2nc(-c3cccc4c3CC[C@H]4NCC(=O)N3CC[C@H](O)C3)no2)cc1C#N] | 134 | 632 | R, S |
| 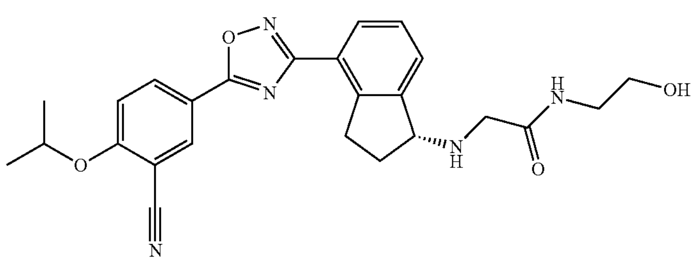 [SMILES: CC(C)Oc1ccc(-c2nc(-c3cccc4c3CC[C@H]4NCC(=O)NCCO)no2)cc1C#N] | 135 | 6.24 | R |

TABLE 1-continued

| STRUCTURE | COMPOUND NUMBER | LCMS RETENTION TIME (min) | CHIRALITY OF INDANE CARBON |
|---|---|---|---|
| 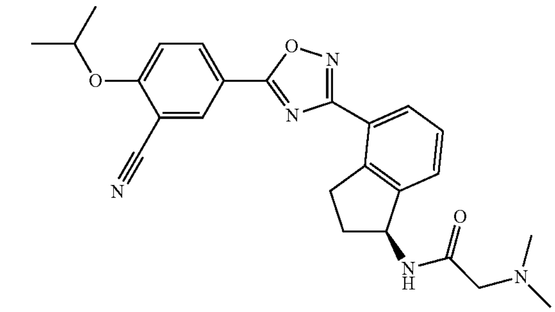 [SMILES: CC(C)Oc1ccc(-c2nc(-c3cccc4c3CC[C@@H]4NC(=O)CN(C)C)no2)cc1C#N] | 136 | 6.82 | S |
| 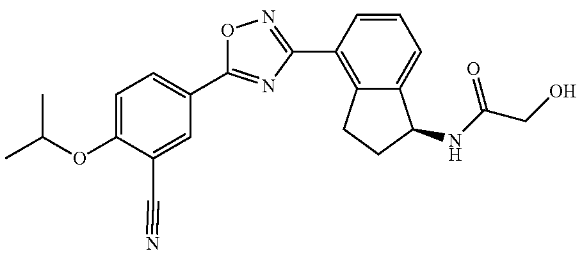 [SMILES: CC(C)Oc1ccc(-c2nc(-c3cccc4c3CC[C@@H]4NC(=O)CO)no2)cc1C#N] | 137 | 8.21 | S |
| 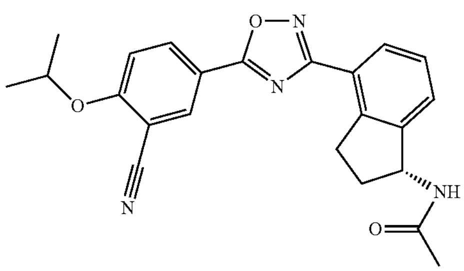 [SMILES: CC(=O)N[C@@H]1CCc2c(-c3noc(-c4ccc(OC(C)C)c(C#N)c4)n3)cccc21] | 138 | 8.76 | R |
| 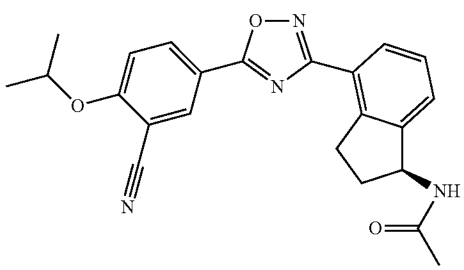 [SMILES: CC(=O)N[C@H]1CCc2c(-c3noc(-c4ccc(OC(C)C)c(C#N)c4)n3)cccc21] | 139 | 8.76 | S |
| 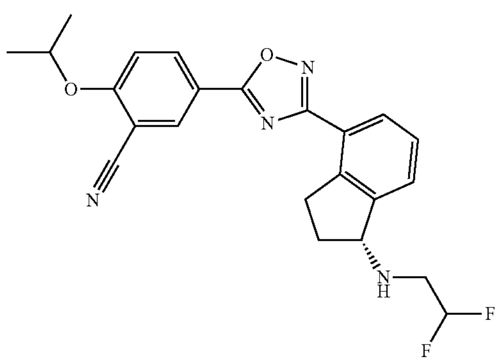 [SMILES: CC(C)Oc1ccc(-c2nc(-c3cccc4c3CC[C@H]4NCC(F)F)no2)cc1C#N] | 140 | 7.01 | R |

TABLE 1-continued

| STRUCTURE | COMPOUND NUMBER | LCMS RETENTION TIME (min) | CHIRALITY OF INDANE CARBON |
|---|---|---|---|
| 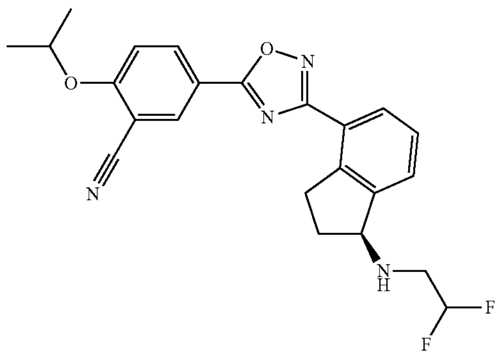 [SMILES: CC(C)Oc1ccc(-c2nc(-c3cccc4c3CC[C@@H]4NCC(F)F)no2)cc1C#N] | 141 | 9.83 | S |
| 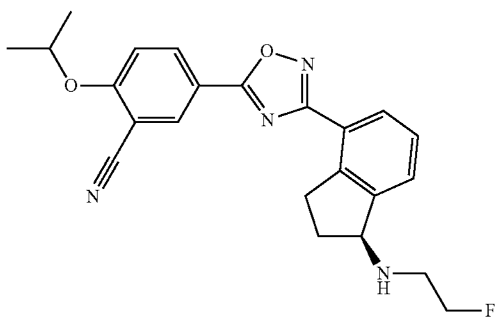 [SMILES: CC(C)Oc1ccc(-c2nc(-c3cccc4c3CC[C@@H]4NCCF)no2)cc1C#N] | 142 | 7.11 | S |
| 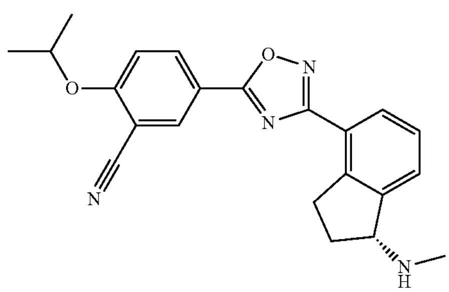 [SMILES: CN[C@@H]1CCc2c(-c3noc(-c4ccc(OC(C)C)c(C#N)c4)n3)cccc21] | 143 | 6.33 | R |
| 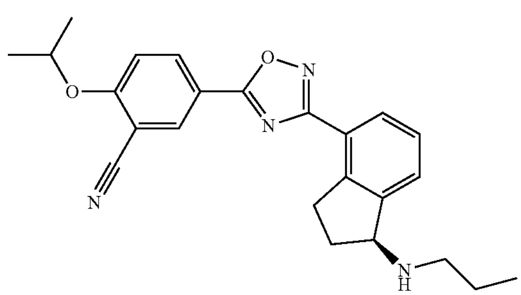 [SMILES: CCCN[C@H]1CCc2c(-c3noc(-c4ccc(OC(C)C)c(C#N)c4)n3)cccc21] | 144 | 6.71 | S |
| 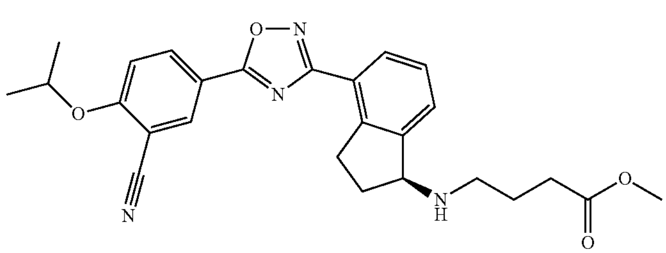 [SMILES: COC(=O)CCCN[C@H]1CCc2c(-c3noc(-c4ccc(OC(C)C)c(C#N)c4)n3)cccc21] | 145 | 7.01 | S |

TABLE 1-continued

| STRUCTURE | COMPOUND NUMBER | LCMS RETENTION TIME (min) | CHIRALITY OF INDANE CARBON |
|---|---|---|---|
| 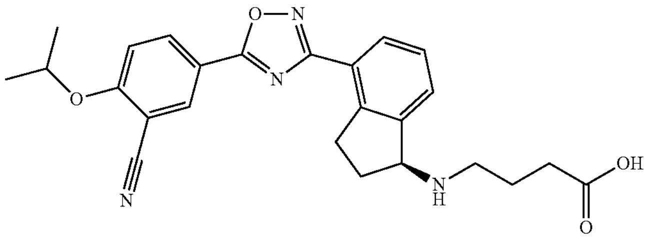 [SMILES: CC(C)Oc1ccc(-c2nc(-c3cccc4c3CC[C@@H]4NCCCC(=O)O)no2)cc1C#N] | 146 | 6.65 | S |
| 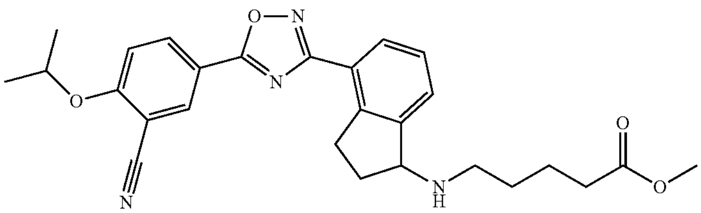 [SMILES: COC(=O)CCCCNC1CCc2c(-c3noc(-c4ccc(OC(C)C)c(C#N)c4)n3)cccc21] | 147 | 7.18 | Racemic mixture |
| 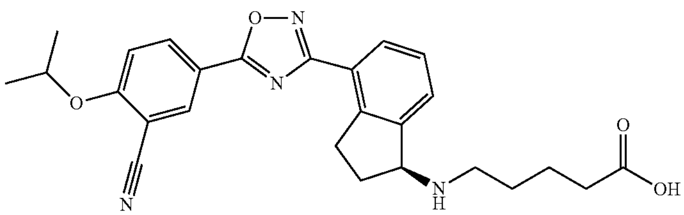 [SMILES: CC(C)Oc1ccc(-c2nc(-c3cccc4c3CC[C@@H]4NCCCCC(=O)O)no2)cc1C#N] | 148 | 6.78 | S |
| 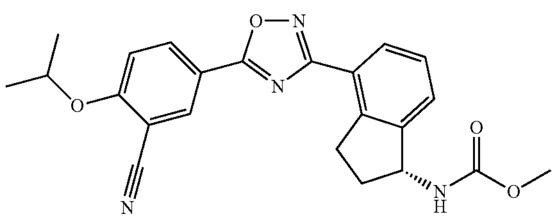 [SMILES: COC(=O)N[C@@H]1CCc2c(-c3noc(-c4ccc(OC(C)C)c(C#N)c4)n3)cccc21] | 149 | 9.74 | R |
| 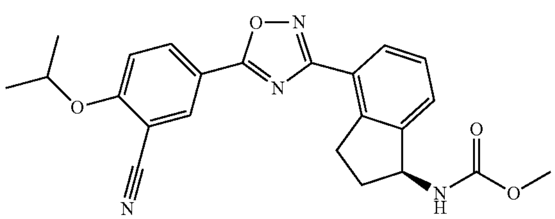 [SMILES: COC(=O)N[C@H]1CCc2c(-c3noc(-c4ccc(OC(C)C)c(C#N)c4)n3)cccc21] | 150 | 9.75 | S |
| 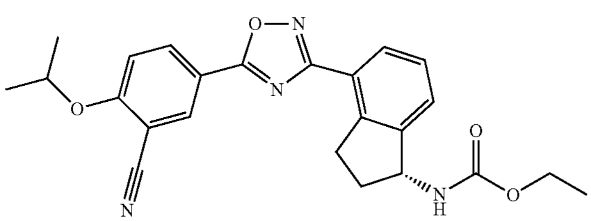 [SMILES: CCOC(=O)N[C@@H]1CCc2c(-c3noc(-c4ccc(OC(C)C)c(C#N)c4)n3)cccc21] | 151 | 10.14 | R |
| 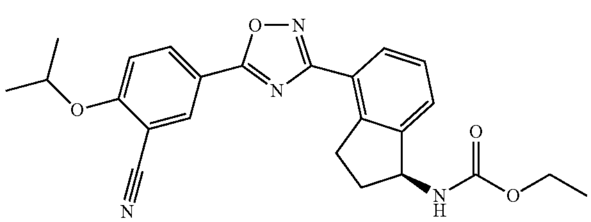 [SMILES: CCOC(=O)N[C@H]1CCc2c(-c3noc(-c4ccc(OC(C)C)c(C#N)c4)n3)cccc21] | 152 | 10.15 | S |

TABLE 1-continued

| STRUCTURE | COMPOUND NUMBER | LCMS RETENTION TIME (min) | CHIRALITY OF INDANE CARBON |
|---|---|---|---|
| 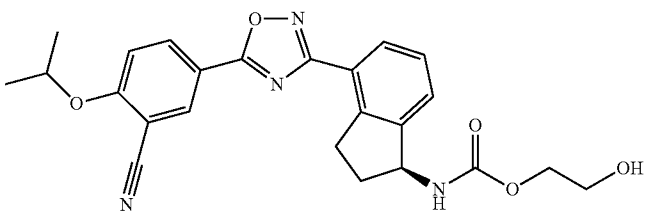 [SMILES: CC(C)Oc1ccc(-c2nc(-c3cccc4c3CC[C@@H]4NC(=O)OCCO)no2)cc1C#N] | 153 | 8.60 | S |
| 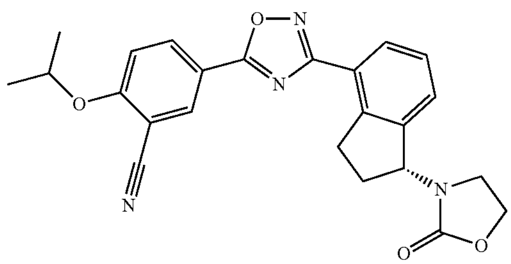 [SMILES: CC(C)Oc1ccc(-c2nc(-c3cccc4c3CC[C@H]4N3CCOC3=O)no2)cc1C#N] | 154 | 9.40 | R |
| 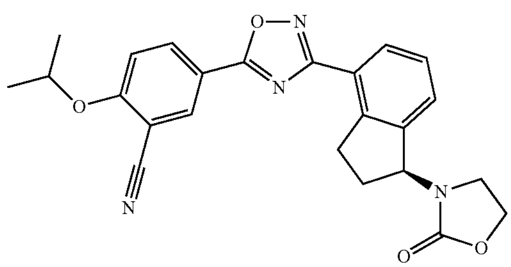 [SMILES: CC(C)Oc1ccc(-c2nc(-c3cccc4c3CC[C@@H]4N3CCOC3=O)no2)cc1C#N] | 155 | 9.41 | S |
| 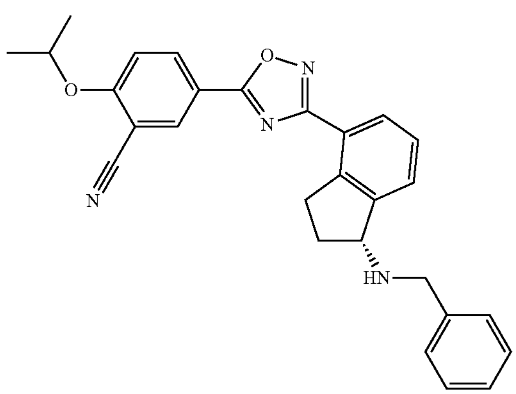 [SMILES: CC(C)Oc1ccc(-c2nc(-c3cccc4c3CC[C@H]4NCc3ccccc3)no2)cc1C#N] | 156 | 7.39 | R |
| 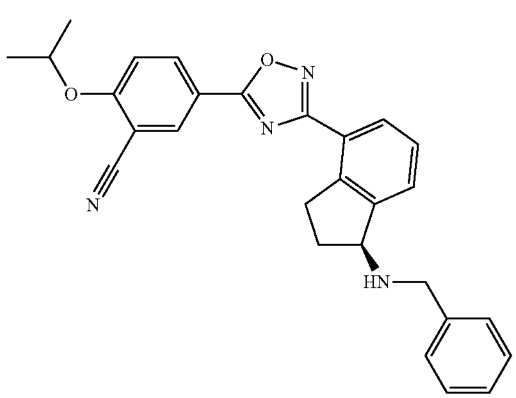 [SMILES: CC(C)Oc1ccc(-c2nc(-c3cccc4c3CC[C@@H]4NCc3ccccc3)no2)cc1C#N] | 157 | 7.39 | S |

TABLE 1-continued

| STRUCTURE | COMPOUND NUMBER | LCMS RETENTION TIME (min) | CHIRALITY OF INDANE CARBON |
|---|---|---|---|
| 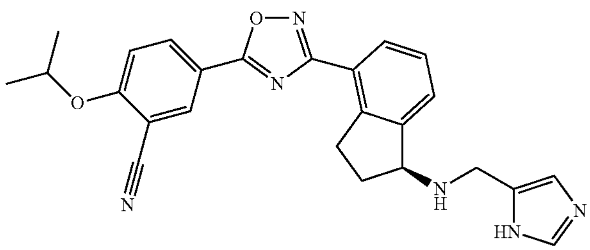 [SMILES: CC(C)Oc1ccc(-c2nc(-c3cccc4c3CC[C@@H]4NCc3cnc[nH]3)no2)cc1C#N] | 158 | 5.86 | S |
| 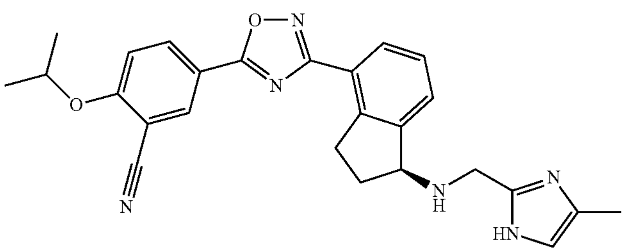 [SMILES: Cc1c[nH]c(CN[C@H]2CCc3c(-c4noc(-c5ccc(OC(C)C)c(C#N)c5)n4)cccc32)n1] | 159 | 6.29 | S |
| 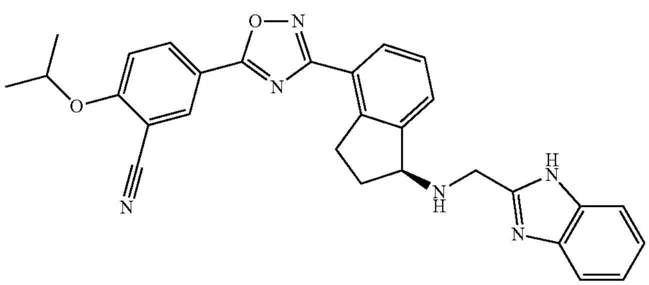 [SMILES: CC(C)Oc1ccc(-c2nc(-c3cccc4c3CC[C@@H]4NCc3nc4ccccc4[nH]3)no2)cc1C#N] | 160 | 7.13 | S |
| 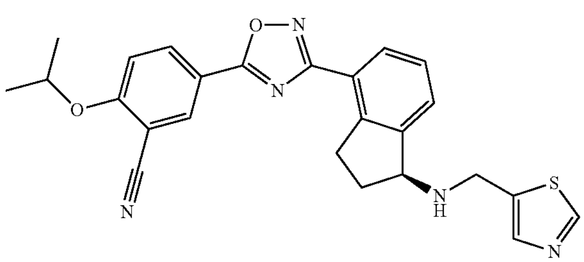 [SMILES: CC(C)Oc1ccc(-c2nc(-c3cccc4c3CC[C@@H]4NCc3cncs3)no2)cc1C#N] | 161 | 6.64 | S |
| 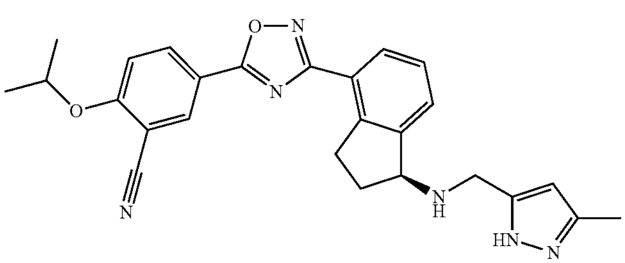 [SMILES: Cc1cc(CN[C@H]2CCc3c(-c4noc(-c5ccc(OC(C)C)c(C#N)c5)n4)cccc32)[nH]n1] | 162 | 6.95 | S |

TABLE 1-continued

| STRUCTURE | COMPOUND NUMBER | LCMS RETENTION TIME (min) | CHIRALITY OF INDANE CARBON |
|---|---|---|---|
| 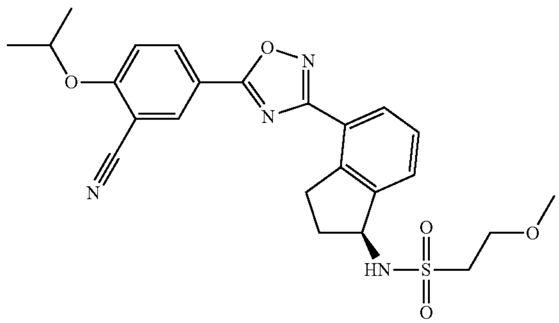 [SMILES: COCCS(=O)(=O)N[C@H]1CCc2c(-c3noc(-c4ccc(OC(C)C)c(C#N)c4)n3)cccc21] | 163 | 9.55 | R |
| 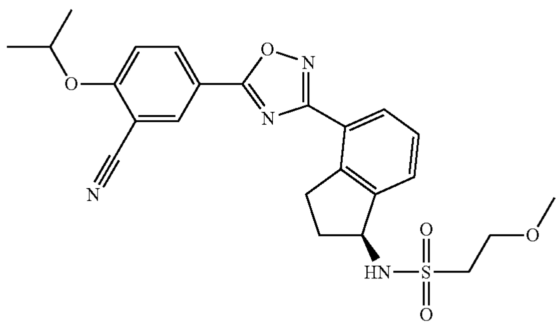 [SMILES: COCCS(=O)(=O)N[C@H]1CCc2c(-c3noc(-c4ccc(OC(C)C)c(C#N)c4)n3)cccc21] | 164 | 9.56 | S |
| 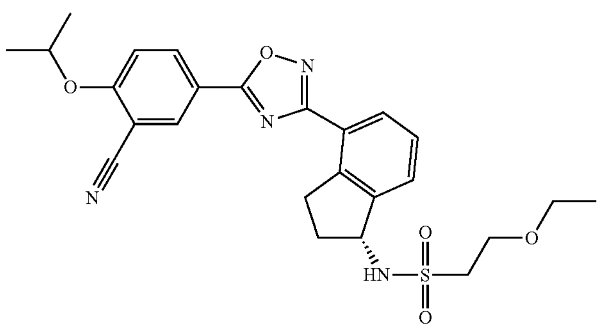 [SMILES: CCOCCS(=O)(=O)N[C@@H]1CCc2c(-c3noc(-c4ccc(OC(C)C)c(C#N)c4)n3)cccc21] | 165 | 9.95 | R |
| 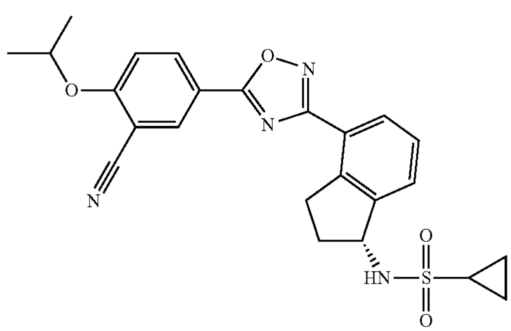 [SMILES: CC(C)Oc1ccc(-c2nc(-c3cccc4c3CC[C@H]4NS(=O)(=O)C3CC3)no2)cc1C#N] | 166 | 9.75 | R |

TABLE 1-continued

| STRUCTURE | COMPOUND NUMBER | LCMS RETENTION TIME (min) | CHIRALITY OF INDANE CARBON |
|---|---|---|---|
| 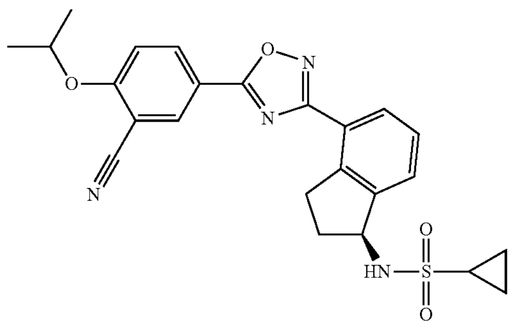 [SMILES: CC(C)Oc1ccc(-c2nc(-c3cccc4c3CC[C@@H]4NS(=O)(=O)C3CC3)no2)cc1C#N] | 167 | 9.73 | S |
| 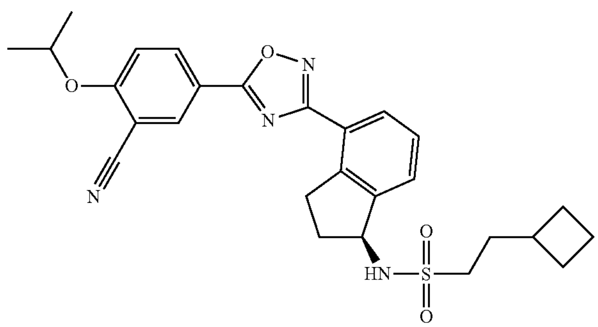 [SMILES: CC(C)Oc1ccc(-c2nc(-c3cccc4c3CC[C@@H]4NS(=O)(=O)CCC3CCC3)no2)cc1C#N] | 168 | 6.92 | R |
| 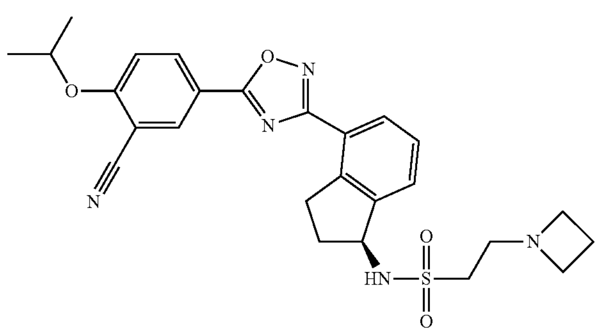 [SMILES: CC(C)Oc1ccc(-c2nc(-c3cccc4c3CC[C@@H]4NS(=O)(=O)CCN3CCC3)no2)cc1C#N] | 169 | 7.05 | S |
| 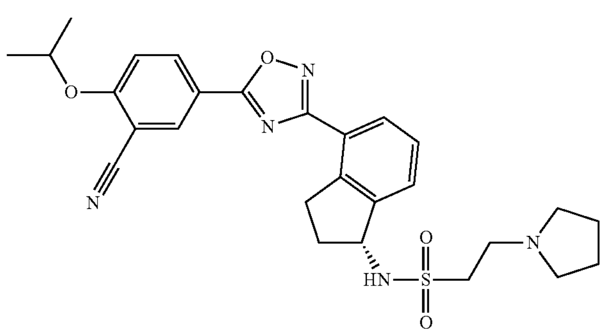 [SMILES: CC(C)Oc1ccc(-c2nc(-c3cccc4c3CC[C@H]4NS(=O)(=O)CCN3CCCC3)no2)cc1C#N] | 170 | 6.96 | R |

TABLE 1-continued

| STRUCTURE | COMPOUND NUMBER | LCMS RETENTION TIME (min) | CHIRALITY OF INDANE CARBON |
|---|---|---|---|
| 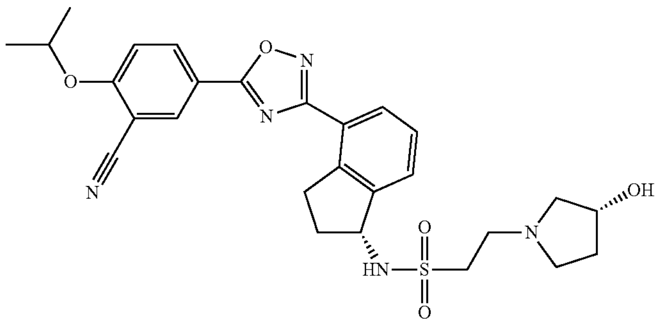 [SMILES: CC(C)Oc1ccc(-c2nc(-c3cccc4c3CC[C@H]4NS(=O)(=O)CCN3CC[C@@H](O)C3)no2)cc1C#N] | 171 | 6.78 | R, R |
| 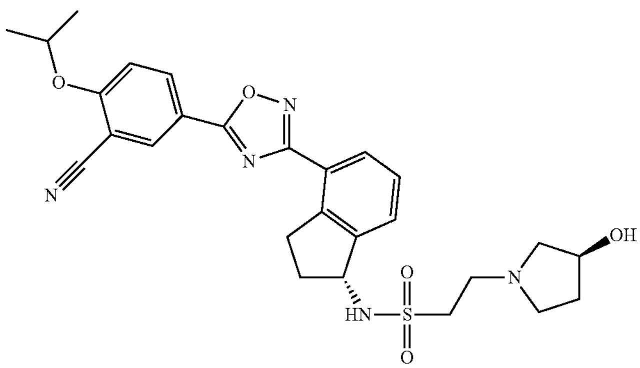 [SMILES: CC(C)Oc1ccc(-c2nc(-c3cccc4c3CC[C@H]4NS(=O)(=O)CCN3CC[C@H](O)C3)no2)cc1C#N] | 172 | 6.76 | R, S |
| 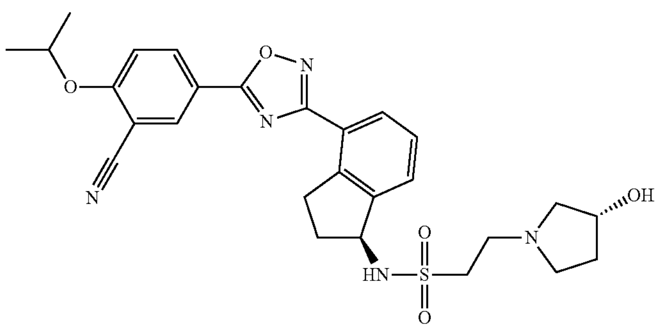 [SMILES: CC(C)Oc1ccc(-c2nc(-c3cccc4c3CC[C@@H]4NS(=O)(=O)CCN3CC[C@@H](O)C3)no2)cc1C#N] | 173 | 6.91 | S, R |
| 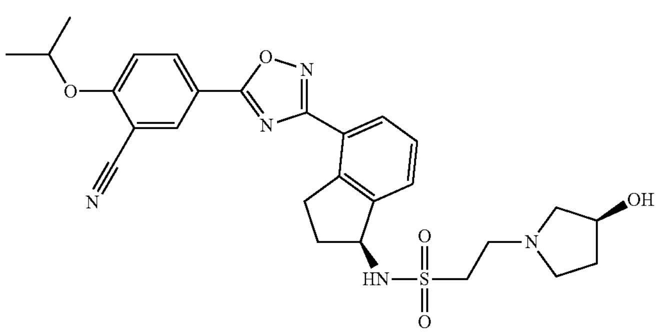 [SMILES: CC(C)Oc1ccc(-c2nc(-c3cccc4c3CC[C@@H]4NS(=O)(=O)CCN3CC[C@H](O)C3)no2)cc1C#N] | 174 | 6.81 | S, S |

TABLE 1-continued

| STRUCTURE | COMPOUND NUMBER | LCMS RETENTION TIME (min) | CHIRALITY OF INDANE CARBON |
|---|---|---|---|
| 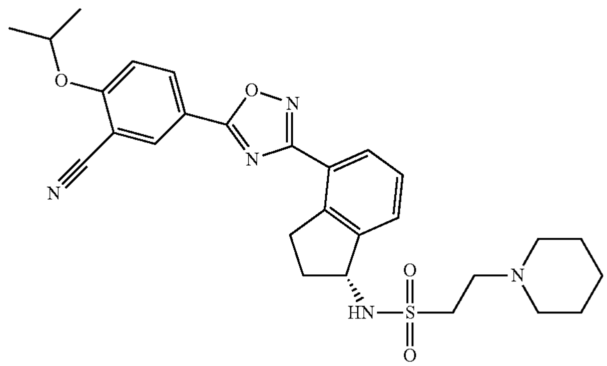 [SMILES: CC(C)Oc1ccc(-c2nc(-c3cccc4c3CC[C@H]4NS(=O)(=O)CCN3CCCCC3)no2)cc1C#N] | 175 | 7.12 | R |
| 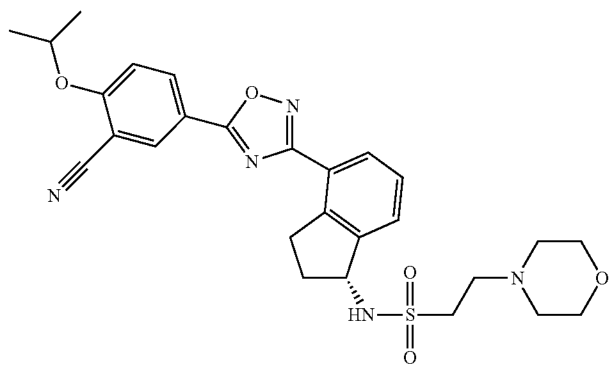 [SMILES: CC(C)Oc1ccc(-c2nc(-c3cccc4c3CC[C@H]4NS(=O)(=O)CCN3CCOCC3)no2)cc1C#N] | 176 | 6.94 | R |
| 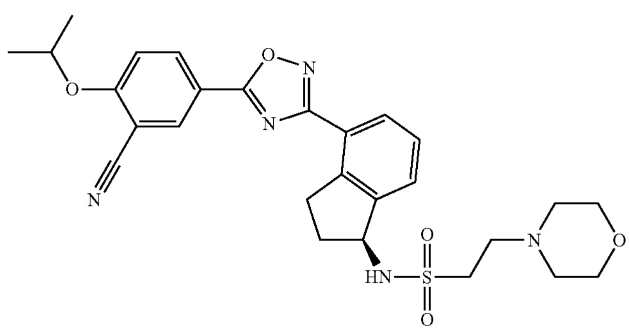 [SMILES: CC(C)Oc1ccc(-c2nc(-c3cccc4c3CC[C@@H]4NS(=O)(=O)CCN3CCOCC3)no2)cc1C#N] | 177 | 7.06 | S |
| 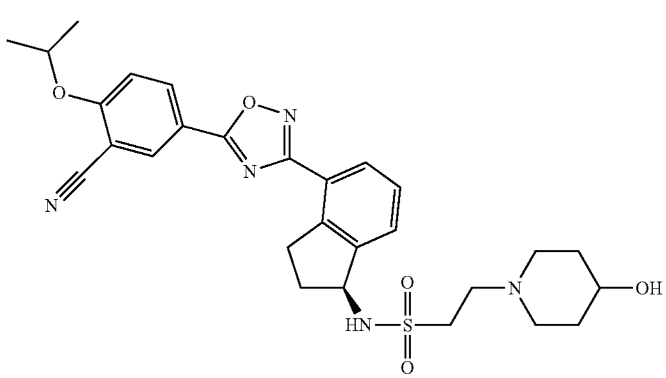 [SMILES: CC(C)Oc1ccc(-c2nc(-c3cccc4c3CC[C@@H]4NS(=O)(=O)CCN3CCC(O)CC3)no2)cc1C#N] | 178 | 6.81 | R |

TABLE 1-continued
| STRUCTURE | COMPOUND NUMBER | LCMS RETENTION TIME (min) | CHIRALITY OF INDANE CARBON |
|---|---|---|---|
| 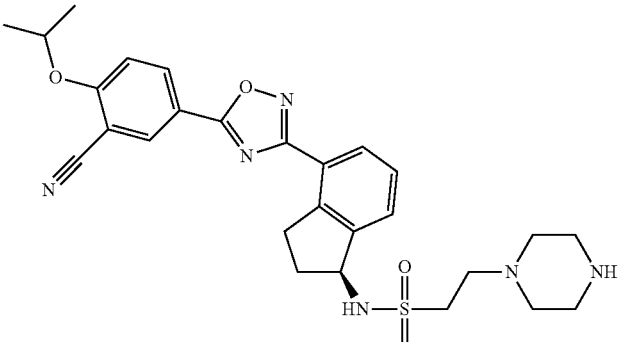 | 179 | 6.70 | R |
| 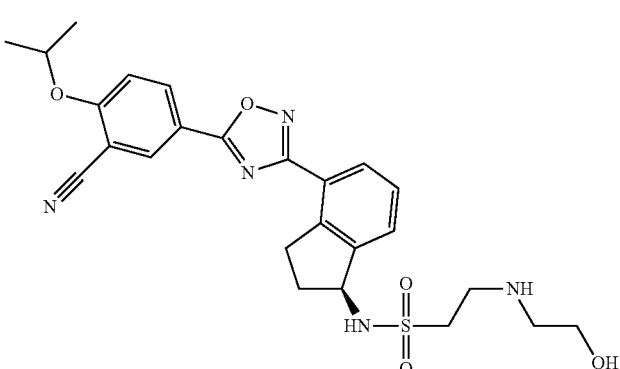 | 180 | 6.75 | R |
| 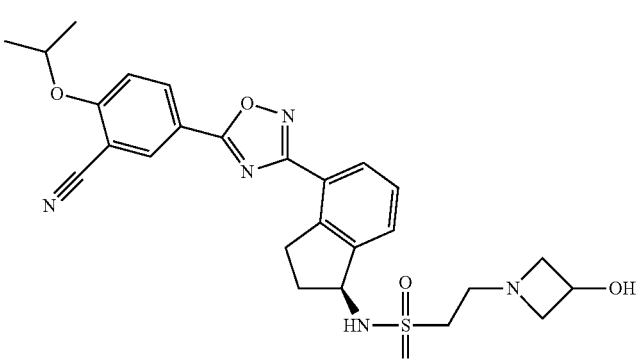 | 181 | 6.80 | R |
| 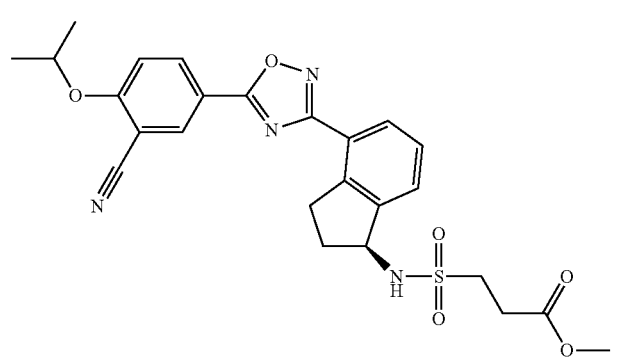 [SMILES: COC(=O)CCS(=O)(=O)N[C@H]1CCc2c(-c3noc(-c4ccc(OC(C)C)c(C#N)c4)n3)cccc21] | 182 | 9.54 | S |

TABLE 1-continued

| STRUCTURE | COMPOUND NUMBER | LCMS RETENTION TIME (min) | CHIRALITY OF INDANE CARBON |
|---|---|---|---|
| 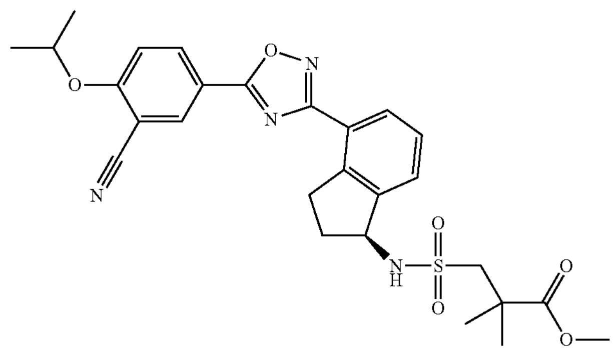 [SMILES: COC(=O)C(C)(C)CS(=O)(=O)N[C@H]1CCc2c(-c3noc(-c4ccc(OC(C)C)c(C#N)c4)n3)cccc21] | 183 | 10.05 | S |
| 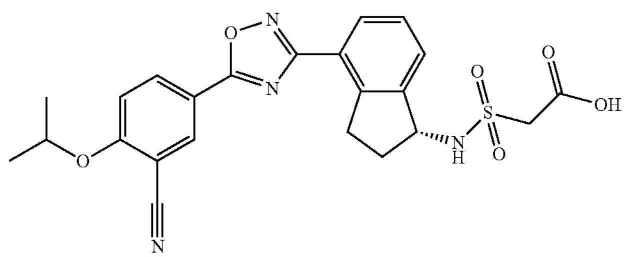 [SMILES: CC(C)Oc1ccc(-c2nc(-c3cccc4c3CC[C@H]4NS(=O)(=O)CC(=O)O)no2)cc1C#N] | 184 | 8.73 | R |
| 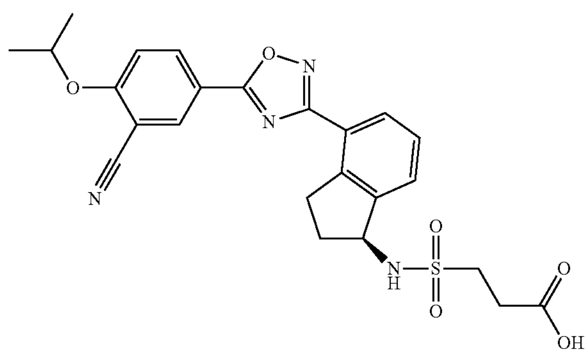 [SMILES: CC(C)Oc1ccc(-c2nc(-c3cccc4c3CC[C@@H]4NS(=O)(=O)CCC(=O)O)no2)cc1C#N] | 185 | 8.71 | S |
| 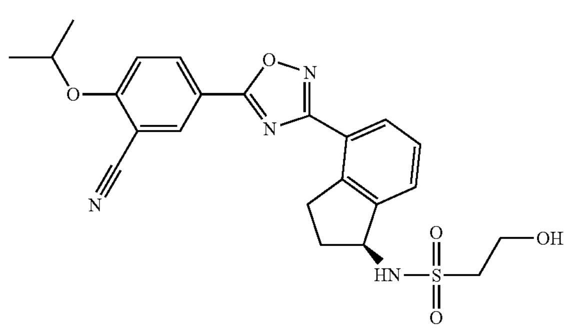 [SMILES: CC(C)Oc1ccc(-c2nc(-c3cccc4c3CC[C@@H]4NS(=O)(=O)CCO)no2)cc1C#N] | 186 | 8.58 | R |

TABLE 1-continued
| STRUCTURE | COMPOUND NUMBER | LCMS RETENTION TIME (min) | CHIRALITY OF INDANE CARBON |
|---|---|---|---|
| 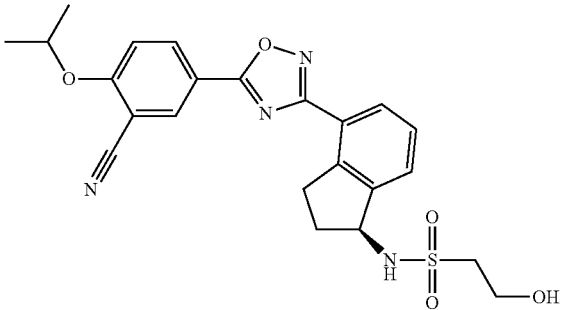 [SMILES: CC(C)Oc1ccc(-c2nc(-c3cccc4c3CC[C@@H]4NS(=O)(=O)CCO)no2)cc1C#N] | 187 | 8.62 | S |
| 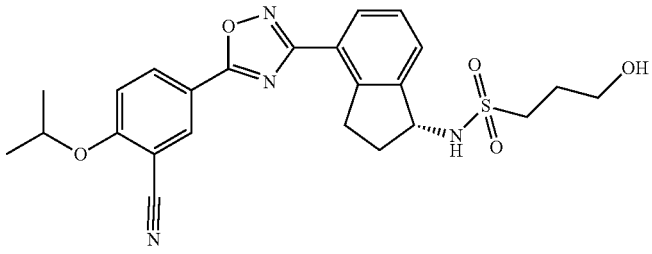 [SMILES: CC(C)Oc1ccc(-c2nc(-c3cccc4c3CC[C@H]4NS(=O)(=O)CCCO)no2)cc1C#N] | 188 | 8.60 | R |
| 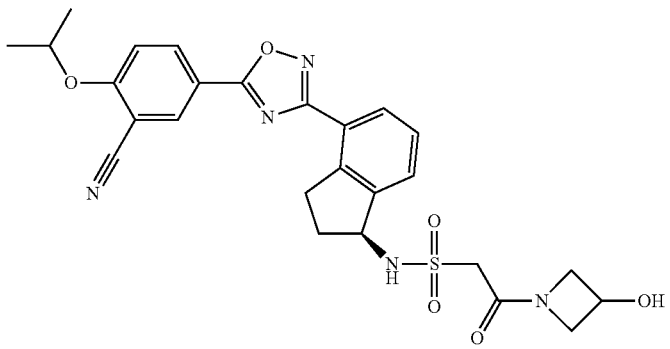 [SMILES: CC(C)Oc1ccc(-c2nc(-c3cccc4c3CC[C@@H]4NS(=O)(=O)CC(=O)N3CC(O)C3)no2)cc1C#N] | 189 | 8.16 | S |
| 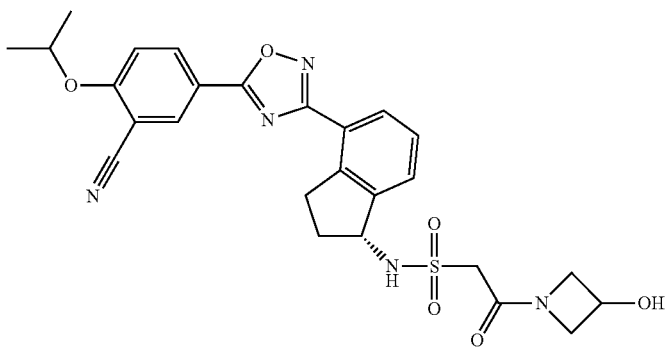 [SMILES: CC(C)Oc1ccc(-c2nc(-c3cccc4c3CC[C@H]4NS(=O)(=O)CC(=O)N3CC(O)C3)no2)cc1C#N] | 190 | 8.15 | R |

TABLE 1-continued

| STRUCTURE | COMPOUND NUMBER | LCMS RETENTION TIME (min) | CHIRALITY OF INDANE CARBON |
|---|---|---|---|
| 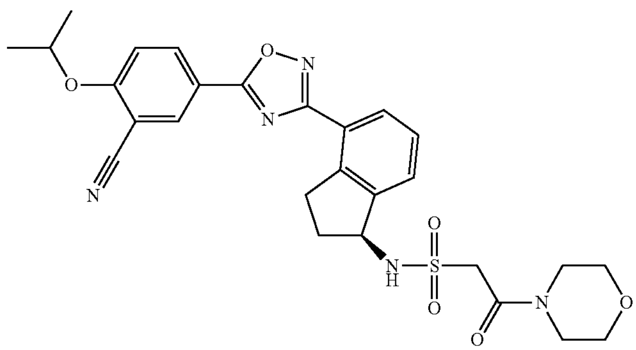 [SMILES: CC(C)Oc1ccc(-c2nc(-c3cccc4c3CC[C@@H]4NS(=O)(=O)CC(=O)N3CCOCC3)no2)cc1C#N] | 191 | 8.92 | S |
| 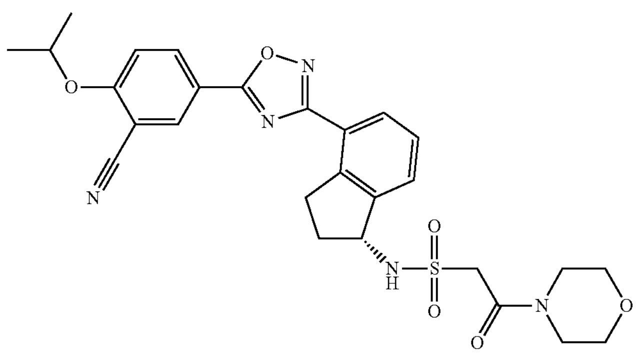 [SMILES: CC(C)Oc1ccc(-c2nc(-c3cccc4c3CC[C@H]4NS(=O)(=O)CC(=O)N3CCOCC3)no2)cc1C#N] | 192 | 8.92 | R |
| 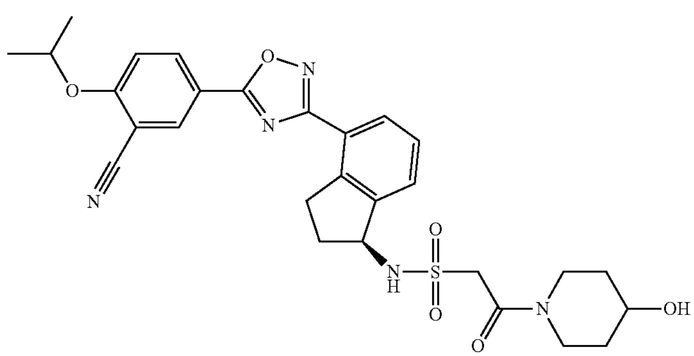 [SMILES: CC(C)Oc1ccc(-c2nc(-c3cccc4c3CC[C@@H]4NS(=O)(=O)CC(=O)N3CCC(O)CC3)no2)cc1C#N] | 193 | 8.32 | S |
| 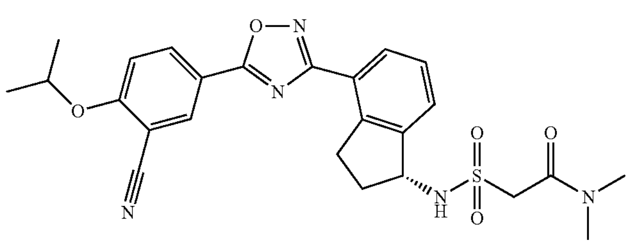 [SMILES: CC(C)Oc1ccc(-c2nc(-c3cccc4c3CC[C@H]4NS(=O)(=O)CC(=O)N(C)C)no2)cc1C#N] | 194 | 8.98 | R |

TABLE 1-continued

| STRUCTURE | COMPOUND NUMBER | LCMS RETENTION TIME (min) | CHIRALITY OF INDANE CARBON |
|---|---|---|---|
| 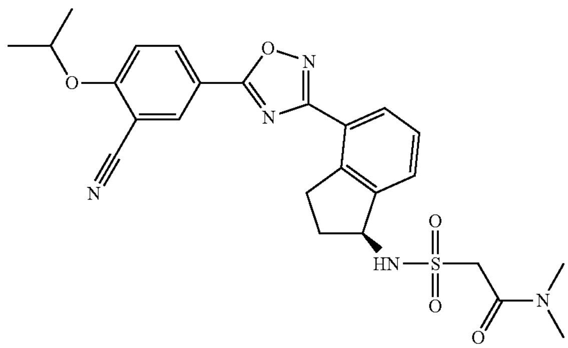 [SMILES: CC(C)Oc1ccc(-c2nc(-c3cccc4c3CC[C@@H]4NS(=O)(=O)CC(=O)N(C)C)no2)cc1C#N] | 195 | 8.96 | S |
| 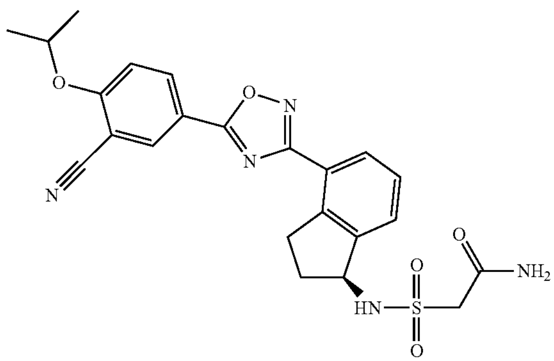 [SMILES: CC(C)Oc1ccc(-c2nc(-c3cccc4c3CC[C@@H]4NS(=O)(=O)CC(N)=O)no2)cc1C#N] | 196 | 8.37 | S |
| 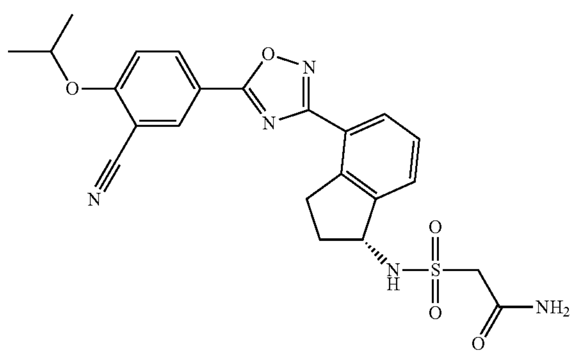 [SMILES: CC(C)Oc1ccc(-c2nc(-c3cccc4c3CC[C@H]4NS(=O)(=O)CC(N)=O)no2)cc1C#N] | 197 | 8.36 | R |
| 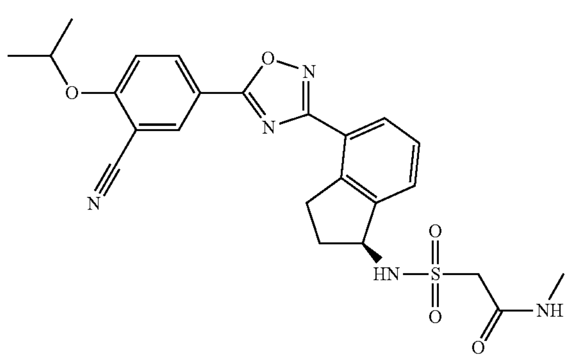 [SMILES: CNC(=O)CS(=O)(=O)N[C@H]1CCc2c(-c3noc(-c4ccc(OC(C)C)c(C#N)c4)n3)cccc21] | 198 | 8.61 | S |

TABLE 1-continued

| STRUCTURE | COMPOUND NUMBER | LCMS RETENTION TIME (min) | CHIRALITY OF INDANE CARBON |
|---|---|---|---|
| 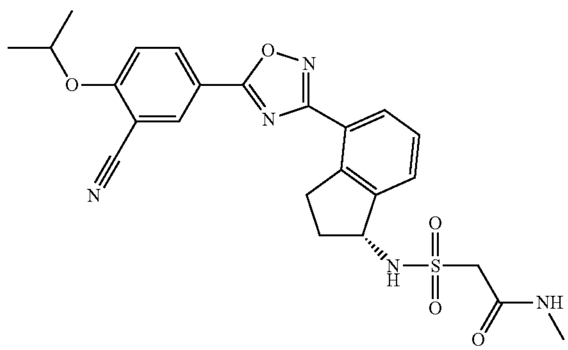 [SMILES: CNC(=O)CS(=O)(=O)N[C@@H]1CCc2c(-c3noc(-c4ccc(OC(C)C)c(C#N)c4)n3)cccc21] | 199 | 8.60 | R |
| 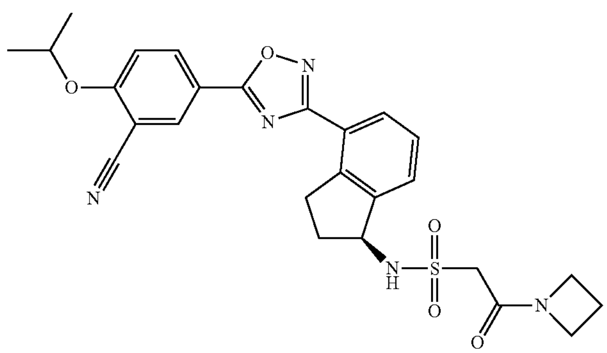 [SMILES: CC(C)Oc1ccc(-c2nc(-c3cccc4c3CC[C@@H]4NS(=O)(=O)CC(=O)N3CCC3)no2)cc1C#N] | 200 | 8.90 | S |
| 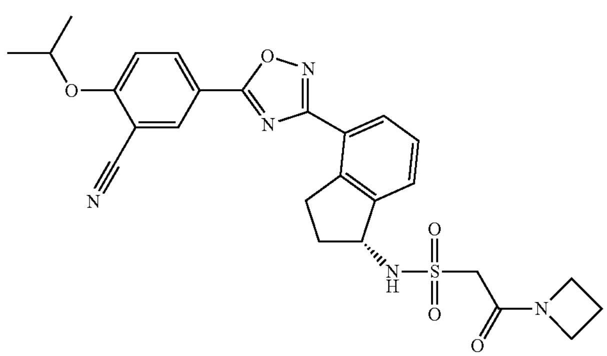 [SMILES: CC(C)Oc1ccc(-c2nc(-c3cccc4c3CC[C@H]4NS(=O)(=O)CC(=O)N3CCC3)no2)cc1C#N] | 201 | 8.91 | R |
| 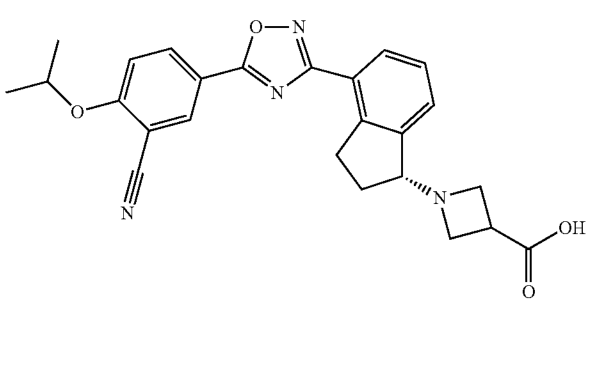 [SMILES: CC(C)Oc1ccc(-c2nc(-c3cccc4c3CC[C@H]4N3CC(C(=O)O)C3)no2)cc1C#N] | 202 | 6.60 | R |

TABLE 1-continued

| STRUCTURE | COMPOUND NUMBER | LCMS RETENTION TIME (min) | CHIRALITY OF INDANE CARBON |
|---|---|---|---|
| 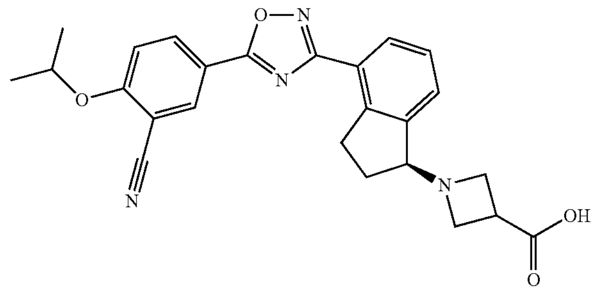 [SMILES: CC(C)Oc1ccc(-c2nc(-c3cccc4c3CC[C@@H]4N3CC(C(=O)O)C3)no2)cc1C#N] | 203 | 6.54 | S |
| 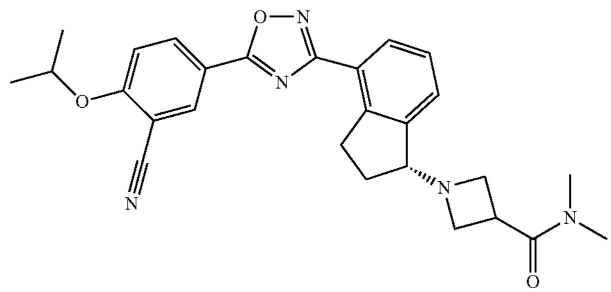 [SMILES: CC(C)Oc1ccc(-c2nc(-c3cccc4c3CC[C@H]4N3CC(C(=O)N(C)C)C3)no2)cc1C#N] | 204 | 6.59 | R |
| 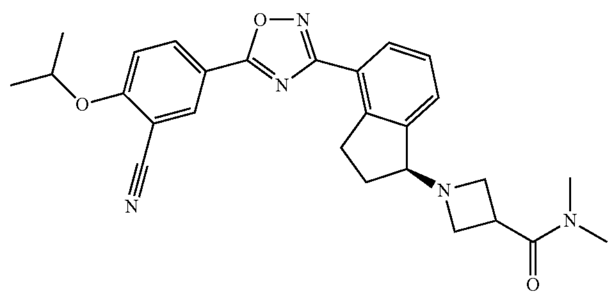 [SMILES: CC(C)Oc1ccc(-c2nc(-c3cccc4c3CC[C@@H]4N3CC(C(=O)N(C)C)C3)no2)cc1C#N] | 205 | 6.55 | S |
| 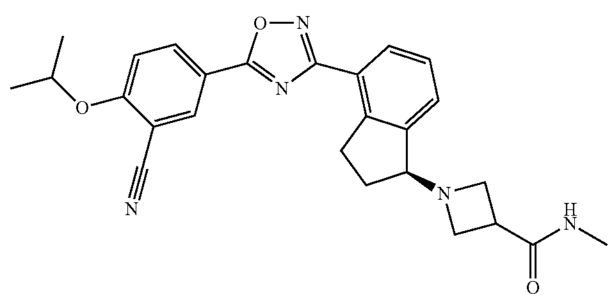 [SMILES: CNC(=O)C1CN([C@H]2CCc3c(-c4noc(-c5ccc(OC(C)C)c(C#N)c5)n4)cccc32)C1] | 206 | 6.52 | S |
| 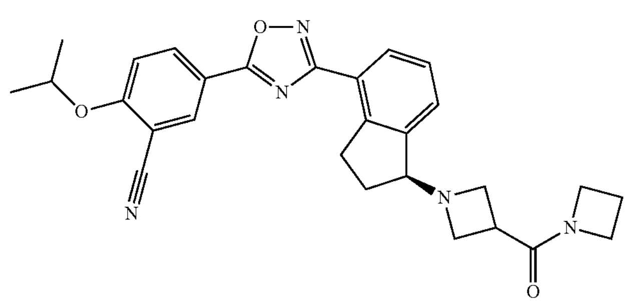 [SMILES: CC(C)Oc1ccc(-c2nc(-c3cccc4c3CC[C@@H]4N3CC(C(=O)N4CCC4)C3)no2)cc1C#N] | 207 | 6.52 | S |

TABLE 1-continued

| STRUCTURE | COMPOUND NUMBER | LCMS RETENTION TIME (min) | CHIRALITY OF INDANE CARBON |
|---|---|---|---|
| 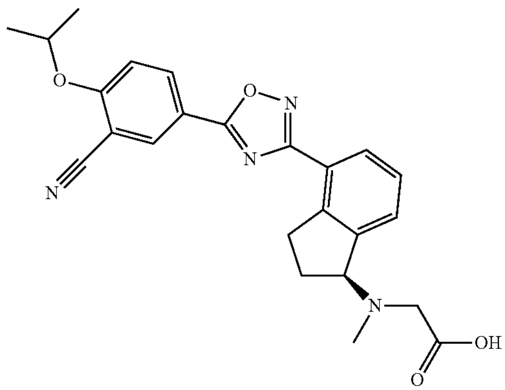 [SMILES: CC(C)Oc1ccc(-c2nc(-c3cccc4c3CC[C@@H]4N(C)CC(=O)O)no2)cc1C#N] | 208 | 6.80 | S |
| 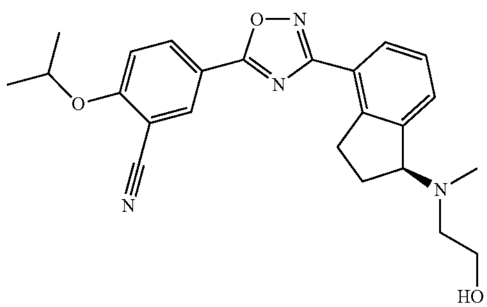 [SMILES: CC(C)Oc1ccc(-c2nc(-c3cccc4c3CC[C@@H]4N(C)CCO)no2)cc1C#N] | 209 | 6.42 | S |
| 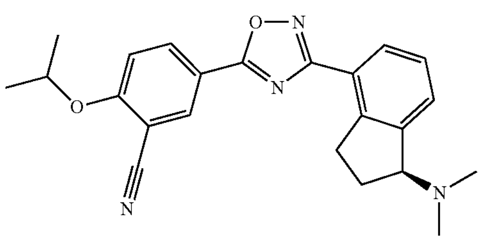 [SMILES: CC(C)Oc1ccc(-c2nc(-c3cccc4c3CC[C@@H]4N(C)C)no2)cc1C#N] | 210 | 6.63 | S |
| 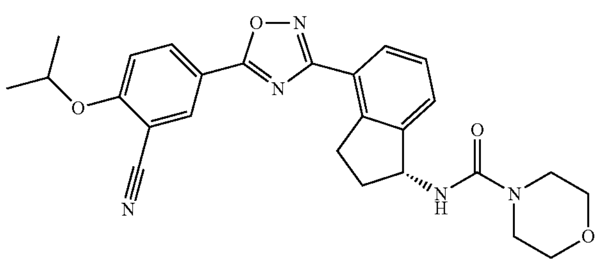 [SMILES: CC(C)Oc1ccc(-c2nc(-c3cccc4c3CC[C@H]4NC(=O)N3CCOCC3)no2)cc1C#N] | 211 | 8.86 | R |
| 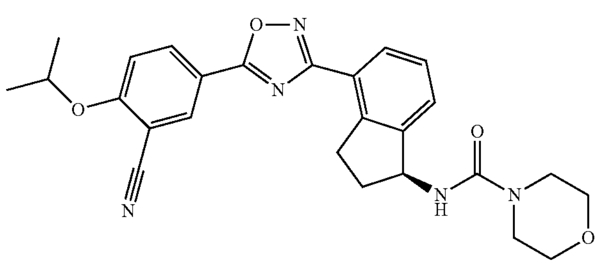 [SMILES: CC(C)Oc1ccc(-c2nc(-c3cccc4c3CC[C@@H]4NC(=O)N3CCOCC3)no2)cc1C#N] | 212 | 8.84 | S |

TABLE 1-continued

| STRUCTURE | COMPOUND NUMBER | LCMS RETENTION TIME (min) | CHIRALITY OF INDANE CARBON |
|---|---|---|---|
| 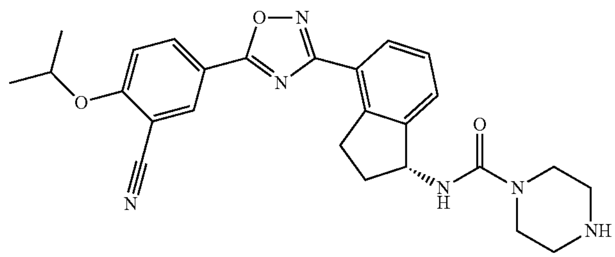 [SMILES: CC(C)Oc1ccc(-c2nc(-c3cccc4c3CC[C@H]4NC(=O)N3CCNCC3)no2)cc1C#N] | 213 | 6.52 | R |
| 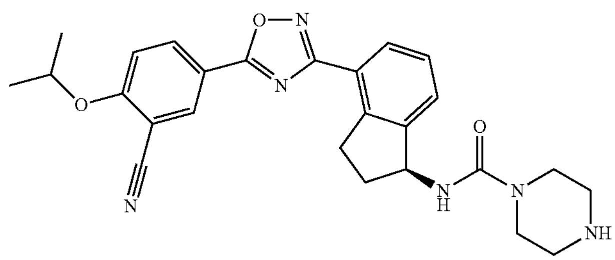 [SMILES: CC(C)Oc1ccc(-c2nc(-c3cccc4c3CC[C@@H]4NC(=O)N3CCNCC3)no2)cc1C#N] | 214 | 6.43 | S |
| 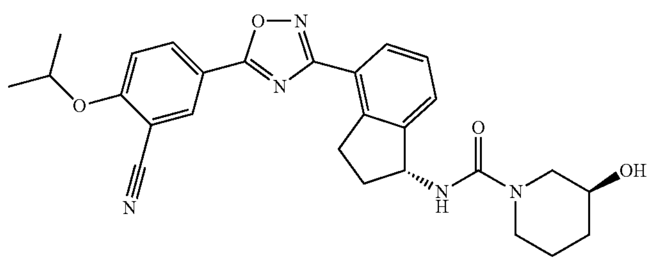 [SMILES: CC(C)Oc1ccc(-c2nc(-c3cccc4c3CC[C@H]4NC(=O)N3CCC[C@H](O)C3)no2)cc1C#N] | 215 | 8.40 | R, S |
| 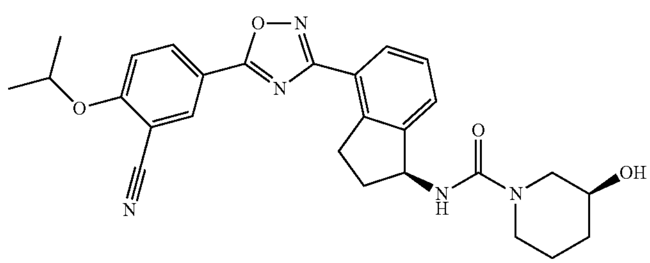 [SMILES: CC(C)Oc1ccc(-c2nc(-c3cccc4c3CC[C@@H]4NC(=O)N3CCC[C@H](O)C3)no2)cc1C#N] | 216 | 8.41 | S, S |
| 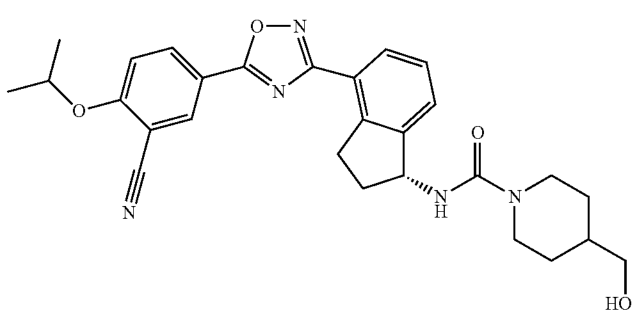 [SMILES: CC(C)Oc1ccc(-c2nc(-c3cccc4c3CC[C@H]4NC(=O)N3CCC(CO)CC3)no2)cc1C#N] | 217 | 8.39 | R |

TABLE 1-continued

| STRUCTURE | COMPOUND NUMBER | LCMS RETENTION TIME (min) | CHIRALITY OF INDANE CARBON |
|---|---|---|---|
| 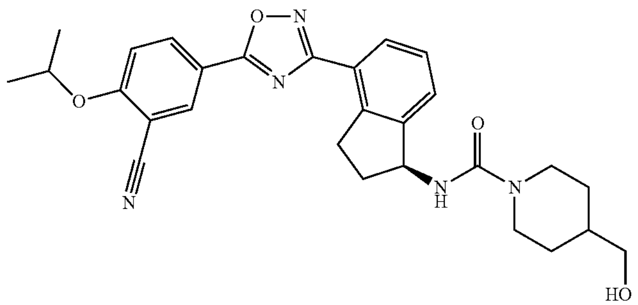 [SMILES: CC(C)Oc1ccc(-c2nc(-c3cccc4c3CC[C@@H]4NC(=O)N3CCC(CO)CC3)no2)cc1C#N] | 218 | 8.43 | S |
| 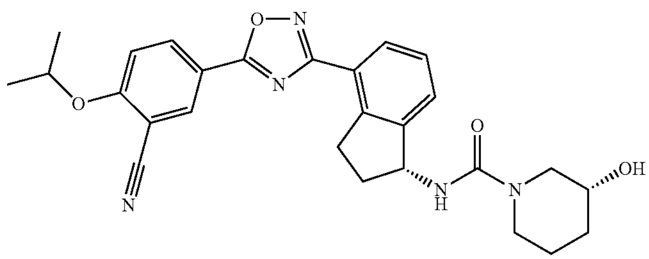 [SMILES: CC(C)Oc1ccc(-c2nc(-c3cccc4c3CC[C@H]4NC(=O)N3CCC[C@@H](O)C3)no2)cc1C#N] | 219 | 8.40 | R, R |
| 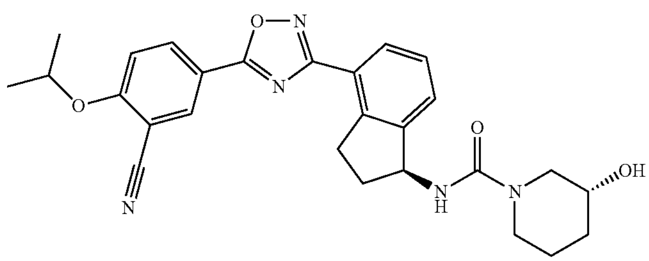 [SMILES: CC(C)Oc1ccc(-c2nc(-c3cccc4c3CC[C@@H]4NC(=O)N3CCC[C@@H](O)C3)no2)cc1C#N] | 220 | 8.41 | S, R |
| 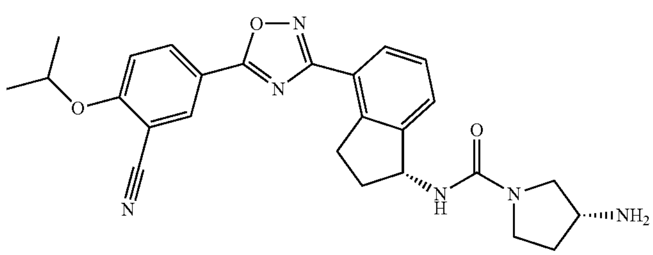 [SMILES: CC(C)Oc1ccc(-c2nc(-c3cccc4c3CC[C@H]4NC(=O)N3CC[C@@H](N)C3)no2)cc1C#N] | 221 | 6.36 | R, R |
| 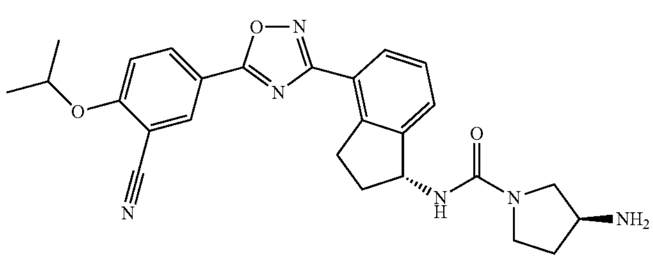 [SMILES: CC(C)Oc1ccc(-c2nc(-c3cccc4c3CC[C@H]4NC(=O)N3CC[C@H](N)C3)no2)cc1C#N] | 222 | 6.28 | R, S |

TABLE 1-continued

| STRUCTURE | COMPOUND NUMBER | LCMS RETENTION TIME (min) | CHIRALITY OF INDANE CARBON |
|---|---|---|---|
| 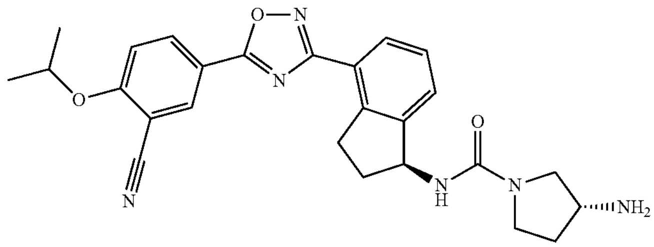 [SMILES: CC(C)Oc1ccc(-c2nc(-c3cccc4c3CC[C@@H]4NC(=O)N3CC[C@@H](N)C3)no2)cc1C#N] | 223 | 6.35 | S, R |
| 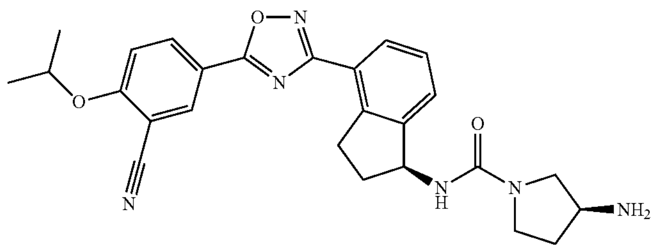 [SMILES: CC(C)Oc1ccc(-c2nc(-c3cccc4c3CC[C@@H]4NC(=O)N3CC[C@H](N)C3)no2)cc1C#N] | 224 | 6.39 | S, S |
| 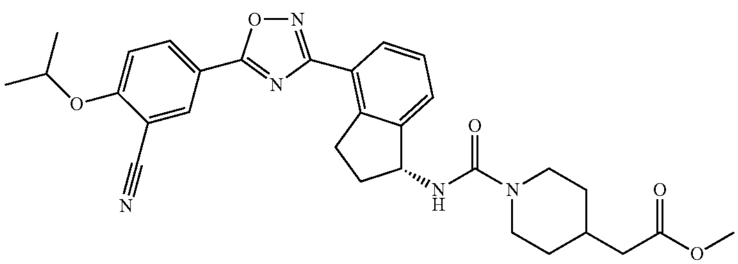 [SMILES: COC(=O)CC1CCN(C(=O)N[C@@H]2CCc3c(-c4noc(-c5ccc(OC(C)C)c(C#N)c5)n4)cccc32)CC1] | 225 | 9.57 | R |
| 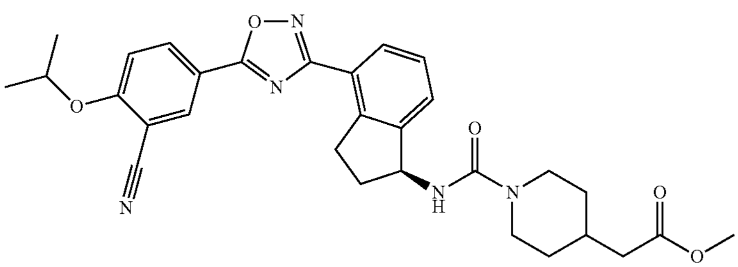 [SMILES: COC(=O)CC1CCN(C(=O)N[C@H]2CCc3c(-c4noc(-c5ccc(OC(C)C)c(C#N)c5)n4)cccc32)CC1] | 226 | 9.61 | S |
| 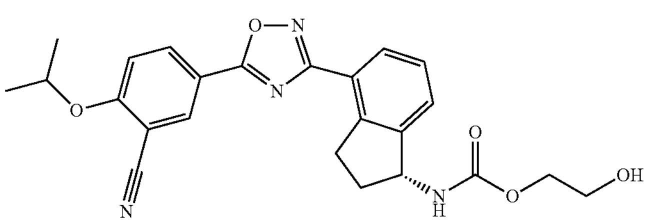 [SMILES: CC(C)Oc1ccc(-c2nc(-c3cccc4c3CC[C@H]4NC(=O)OCCO)no2)cc1C#N] | 227 | 8.61 | R |
| 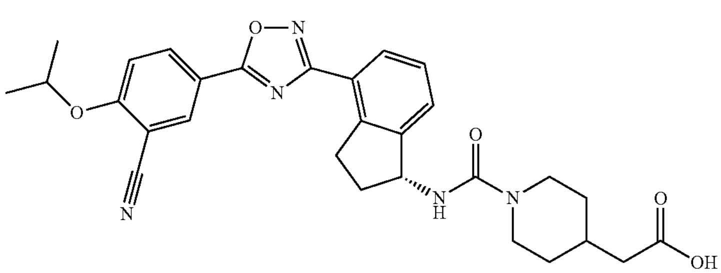 [SMILES: CC(C)Oc1ccc(-c2nc(-c3cccc4c3CC[C@H]4NC(=O)N3CCC(CC(=O)O)CC3)no2)cc1C#N] | 228 | 8.57 | R |

TABLE 1-continued

| STRUCTURE | COMPOUND NUMBER | LCMS RETENTION TIME (min) | CHIRALITY OF INDANE CARBON |
|---|---|---|---|
| 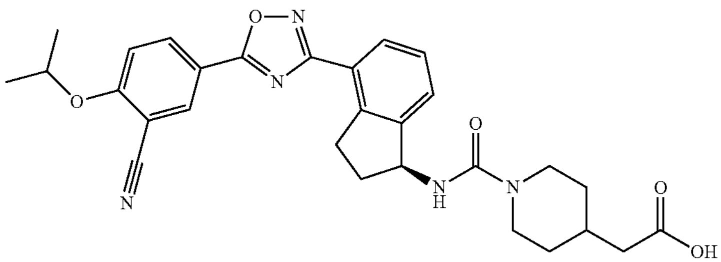 [SMILES: CC(C)Oc1ccc(-c2nc(-c3cccc4c3CC[C@@H]4NC(=O)N3CCC(CC(=O)O)CC3)no2)cc1C#N] | 229 | 8.60 | S |
| 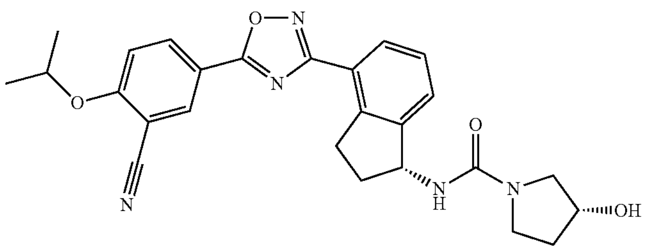 [SMILES: CC(C)Oc1ccc(-c2nc(-c3cccc4c3CC[C@H]4NC(=O)N3CC[C@@H](O)C3)no2)cc1C#N] | 230 | 8.01 | R, R |
| 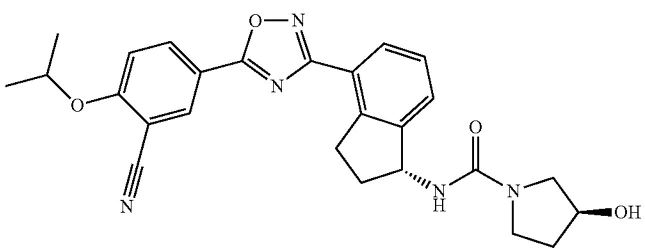 [SMILES: CC(C)Oc1ccc(-c2nc(-c3cccc4c3CC[C@H]4NC(=O)N3CC[C@H](O)C3)no2)cc1C#N] | 231 | 8.03 | R, S |
| 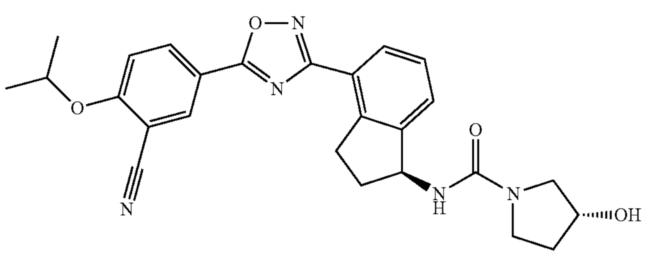 [SMILES: CC(C)Oc1ccc(-c2nc(-c3cccc4c3CC[C@@H]4NC(=O)N3CC[C@@H](O)C3)no2)cc1C#N] | 232 | 8.01 | S, R |
| 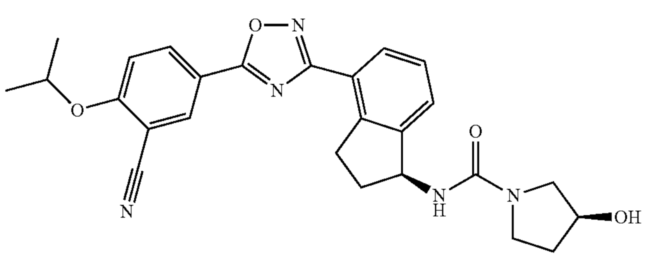 [SMILES: CC(C)Oc1ccc(-c2nc(-c3cccc4c3CC[C@@H]4NC(=O)N3CC[C@H](O)C3)no2)cc1C#N] | 233 | 8.02 | S, S |
| 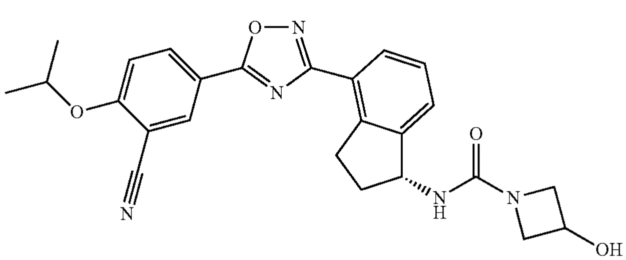 [SMILES: CC(C)Oc1ccc(-c2nc(-c3cccc4c3CC[C@H]4NC(=O)N3CC(O)C3)no2)cc1C#N] | 234 | 7.96 | R |

TABLE 1-continued

| STRUCTURE | COMPOUND NUMBER | LCMS RETENTION TIME (min) | CHIRALITY OF INDANE CARBON |
|---|---|---|---|
| 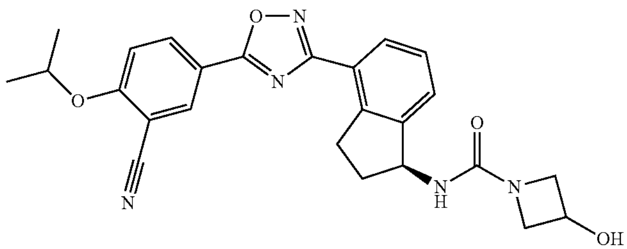 [SMILES: CC(C)Oc1ccc(-c2nc(-c3cccc4c3CC[C@@H]4NC(=O)N3CC(O)C3)no2)cc1C#N] | 235 | 7.95 | S |
| 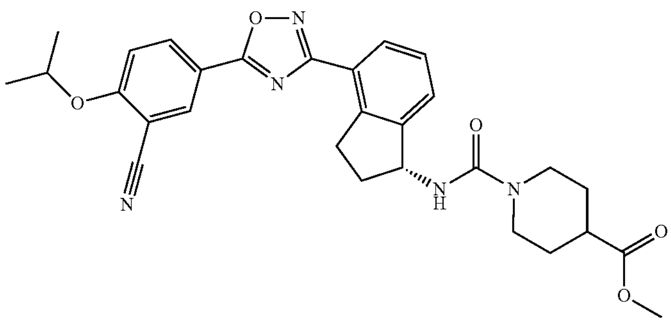 [SMILES: COC(=O)C1CCN(C(=O)N[C@@H]2CCc3c(-c4noc(-c5ccc(OC(C)C)c(C#N)c5)n4)cccc32)CC1] | 236 | 9.41 | R |
| 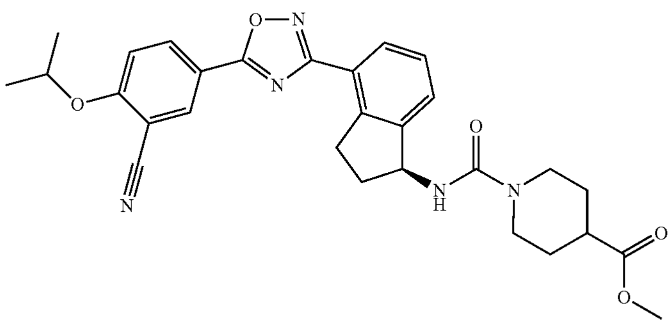 [SMILES: COC(=O)C1CCN(C(=O)N[C@H]2CCc3c(-c4noc(-c5ccc(OC(C)C)c(C#N)c5)n4)cccc32)CC1] | 237 | 9.40 | S |
| 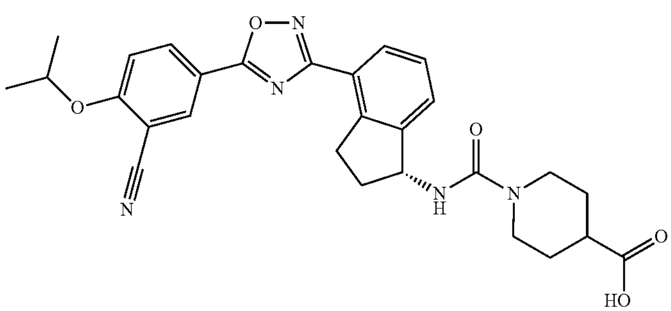 [SMILES: CC(C)Oc1ccc(-c2nc(-c3cccc4c3CC[C@H]4NC(=O)N3CCC(C(=O)O)CC3)no2)cc1C#N] | 238 | 8.45 | R |
| 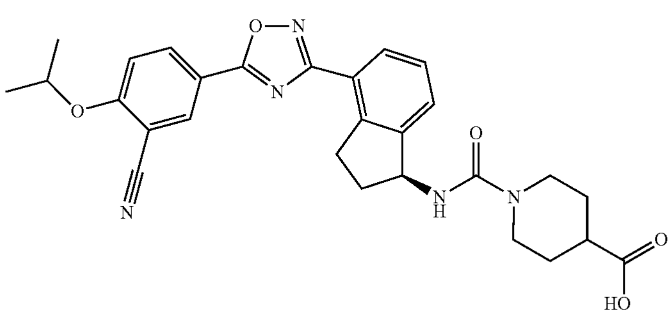 [SMILES: CC(C)Oc1ccc(-c2nc(-c3cccc4c3CC[C@@H]4NC(=O)N3CCC(C(=O)O)CC3)no2)cc1C#N] | 239 | 8.46 | S |

TABLE 1-continued

| STRUCTURE | COMPOUND NUMBER | LCMS RETENTION TIME (min) | CHIRALITY OF INDANE CARBON |
|---|---|---|---|
| 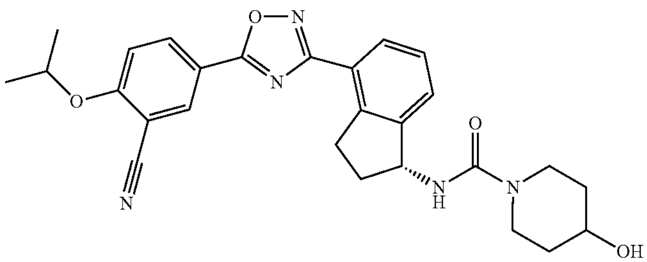 [SMILES: CC(C)Oc1ccc(-c2nc(-c3cccc4c3CC[C@H]4NC(=O)N3CCC(O)CC3)no2)cc1C#N] | 240 | 8.17 | R |
| 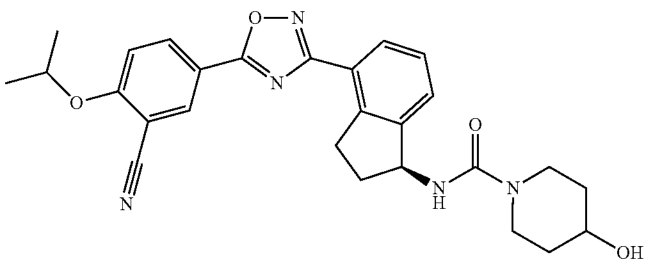 [SMILES: CC(C)Oc1ccc(-c2nc(-c3cccc4c3CC[C@@H]4NC(=O)N3CCC(O)CC3)no2)cc1C#N] | 241 | 8.19 | S |
| 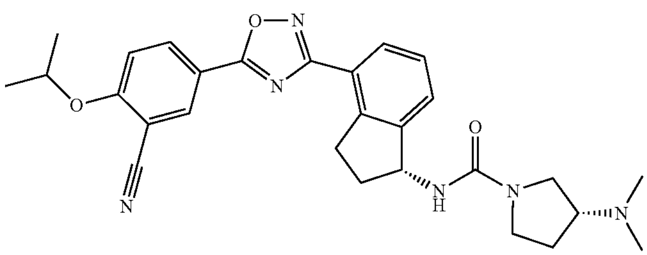 [SMILES: CC(C)Oc1ccc(-c2nc(-c3cccc4c3CC[C@H]4NC(=O)N3CC[C@@H](N(C)C)C3)no2)cc1C#N] | 242 | 6.39 | R, R |
| 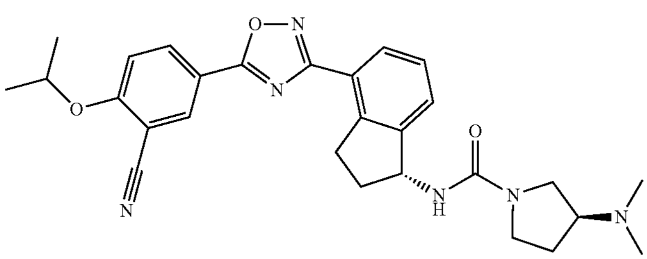 [SMILES: CC(C)Oc1ccc(-c2nc(-c3cccc4c3CC[C@H]4NC(=O)N3CC[C@H](N(C)C)C3)no2)cc1C#N] | 243 | 6.65 | R, S |
| 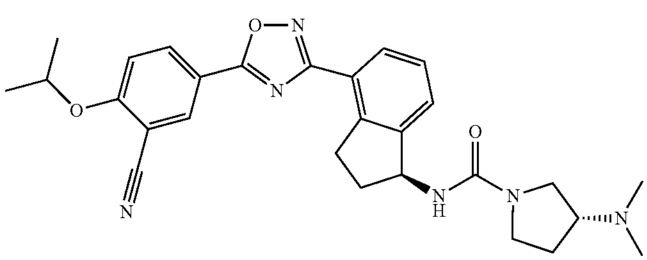 [SMILES: CC(C)Oc1ccc(-c2nc(-c3cccc4c3CC[C@@H]4NC(=O)N3CC[C@@H](N(C)C)C3)no2)cc1C#N] | 244 | 6.51 | S, R |
| 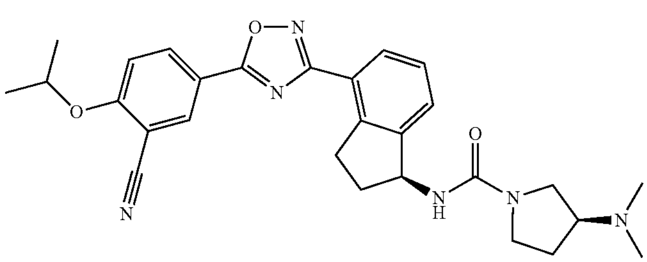 [SMILES: CC(C)Oc1ccc(-c2nc(-c3cccc4c3CC[C@@H]4NC(=O)N3CC[C@H](N(C)C)C3)no2)cc1C#N] | 245 | 6.45 | S, S |

TABLE 1-continued

| STRUCTURE | COMPOUND NUMBER | LCMS RETENTION TIME (min) | CHIRALITY OF INDANE CARBON |
|---|---|---|---|
| 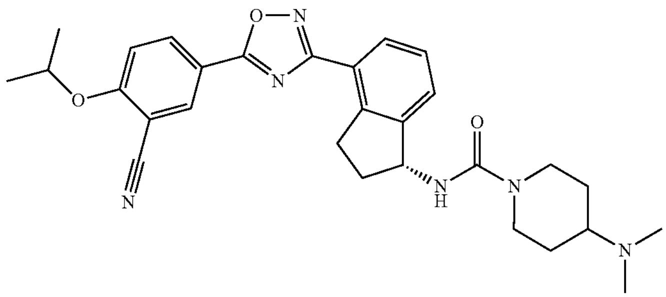 [SMILES: CC(C)Oc1ccc(-c2nc(-c3cccc4c3CC[C@H]4NC(=O)N3CCC(N(C)C)CC3)no2)cc1C#N] | 246 | 6.34 | R |
| 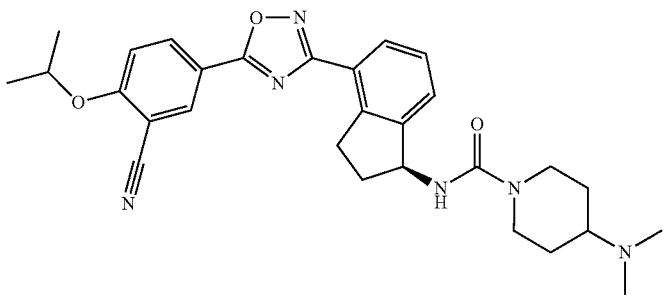 [SMILES: CC(C)Oc1ccc(-c2nc(-c3cccc4c3CC[C@@H]4NC(=O)N3CCC(N(C)C)CC3)no2)cc1C#N] | 247 | 6.47 | S |
| 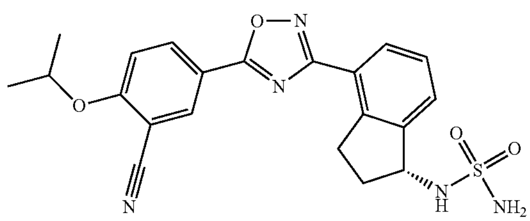 [SMILES: CC(C)Oc1ccc(-c2nc(-c3cccc4c3CC[C@H]4NS(N)(=O)=O)no2)cc1C#N] | 248 | 8.67 | R |
| 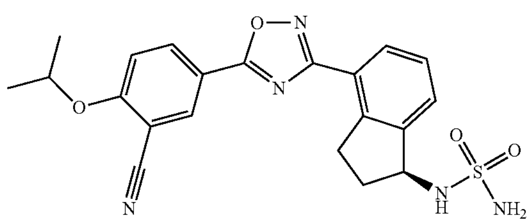 [SMILES: CC(C)Oc1ccc(-c2nc(-c3cccc4c3CC[C@@H]4NS(N)(=O)=O)no2)cc1C#N] | 249 | 8.67 | S |
| 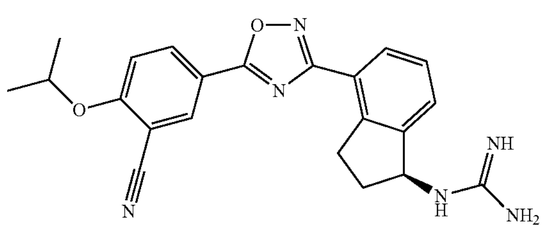 [SMILES: CC(C)Oc1ccc(-c2nc(-c3cccc4c3CC[C@@H]4NC(=N)N)no2)cc1C#N] | 250 | 6.54 | S |
| 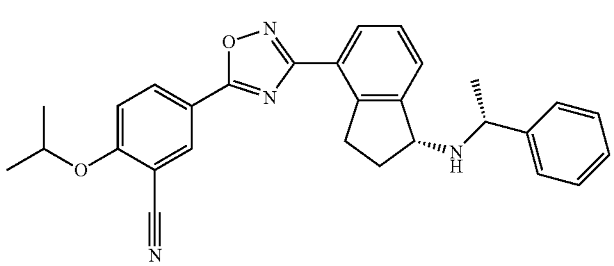 [SMILES: CC(C)Oc1ccc(-c2nc(-c3cccc4c3CC[C@H]4N[C@H](C)c3ccccc3)no2)cc1C#N] | 251 | 7.61 | R, R |

TABLE 1-continued

| STRUCTURE | COMPOUND NUMBER | LCMS RETENTION TIME (min) | CHIRALITY OF INDANE CARBON |
|---|---|---|---|
| 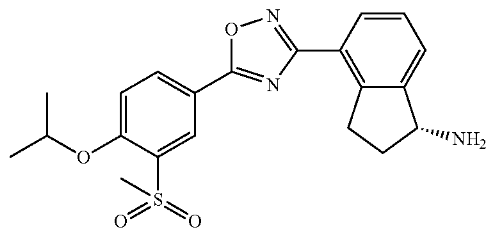 [SMILES: CC(C)Oc1ccc(-c2nc(-c3cccc4c3CC[C@H]4N)no2)cc1S(C)(=O)=O] | 252 | 5.85 | R |

Comparative Examples

Compounds 253 (CYM5442) and 254 are included for comparative purposes.

(+/−)-2-((4-(5-(3,4,diethoxyphenyl)-1,2,4-oxadiazol-3-yl)-2,3-dihydro-1H-inden-1-yl)amino)ethanol (Compound 253)

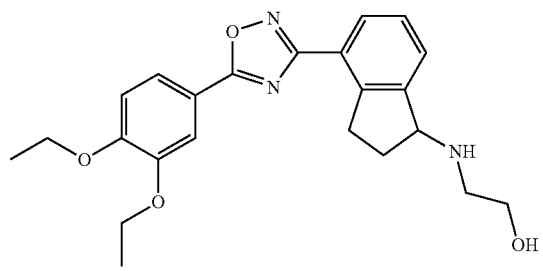 [SMILES: CCOc1ccc(-c2nc(-c3cccc4c3CCC4NCCO)no2)cc1OCC]

(+/−)-4-(5-(3,4,diethoxyphenyl)-1,2,4-oxadiazol-3-yl)-2,3-dihydro-1H-inden-1-ol (Compound 254)

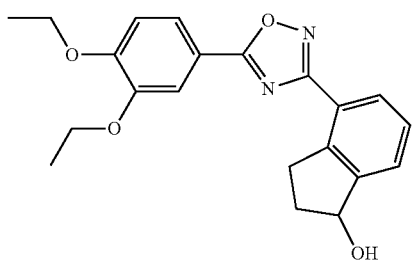 [SMILES: CCOc1ccc(-c2nc(-c3cccc4c3CCC4O)no2)cc1OCC]

Biological Assays

Assay Procedures

Generation of $S1P_1$-Mediated Inhibition of cAMP Reporter Assay

A mammalian expression plasmid containing $S1P_1$/EDG1 cloned into pcDNA3.1 was purchased from Missouri S&T cDNA Resource Centre. The nucleotide and amino acid sequence of human $S1P_1$/EDG1 are published in Hla and Maciag (J Biol Chem, 265(1990), 9308-9313). $S1P_1$/pcDNA3.1 was transfected into the CRE-bla CHO K1 (Invitrogen) cell line, and stable single cell clones were selected using standard techniques. Expression of functional $S1P_1$/EDG1 receptor was confirmed by cell surface FACS with a $S1P_1$ antibody (R&D Systems, clone 218713) and S1P-mediated inhibition of Forskolin induced cAMP.

$S1P_1$ CRE-Bla CHOK1 Reporter Assay—Characterization of $S1P_1$ Agonists

Cells were seeded into 384-well black wall/clear bottom plates at $10^4$ cells/well/19.5 µl assay media (DMEM-phenol free, 0.5% charcoal/dextran stripped serum, 2 mM glutamine, 0.1 mM NEAA, 1 mM Na-Pyruvate, 25 mM Hepes) and incubated for 18 hrs at 37° C. in 5% $CO_2$. Dose response curves (10-point) were generated in 10 mM Hepes, 0.1% Pluronic F127, in the presence of Forskolin. Cells were treated with 0.5 µl compound in the presence of 2 µM Forskolin for 4 hrs at 37° C. The FRET-based β-lactamase fluorescent substrate (LiveBLAzer™-FRET B/G Loading Kit CC4-AM; Invitrogen) was prepared according to manufacturer's directions, and incubated with cells for 2 hrs at room temperature. Plates were read at Ex:410/Em:458 and Ex:410/Em:522, and the response ratio determined. Data was analyzed by non-linear regression to determine the EC50 for inhibition of Forskolin induced cAMP.

Specificity Over Other S1P Receptors

To assess compound specificity on other S1P receptors the following cell lines were used: $S1P_2$ CRE-bla CHOK1, $S1P_3$-Gα15 NFAT-bla HEK293T (Invitrogen), $S1P_4$-bla TANGO U2OS (Invitrogen), $S1P_5$-bla TANGO U2OS (Invitrogen). The same assay set up for $S1P_1$ was used but without Forskolin. $S1P_4$ and $S1P_5$ assays were performed in FreeStyle Expression medium (Invitrogen). $S1P_5$ cells were incubated for 48 hrs in prior to treatment with compound.

Reported $S1P_1$ Activity

Activity data for selected $S1P_1$ agonists is displayed in Table 2. The activity range is denoted as follows: ++++ denotes agonist activity <0.05 nM. +++ denotes agonist activity between 0.05 to 0.50 nM, and ++ denotes agonist activity between 0.50-5.00 nM, and + denotes agonist activity >5.00 nM. N/A denotes not available.

TABLE 2

| COMPOUND NUMBER | $S1P_1$ ACTIVITY |
|---|---|
| 1 | +++ |
| 2 | +++ |
| 3 | +++ |
| 4 | +++ |
| 5 | ++++ |
| 6 | ++++ |
| 7 | ++ |
| 8 | +++ |
| 9 | ++ |
| 10 | +++ |
| 11 | ++ |

TABLE 2-continued

| COMPOUND NUMBER | S1P$_1$ ACTIVITY |
|---|---|
| 12 | ++ |
| 13 | ++ |
| 14 | + |
| 15 | ++ |
| 16 | +++ |
| 17 | +++ |
| 18 | ++++ |
| 19 | + |
| 20 | + |
| 21 | ++ |
| 22 | + |
| 23 | ++ |
| 24 | +++ |
| 25 | + |
| 26 | ++ |
| 27 | ++ |
| 28 | ++ |
| 29 | +++ |
| 30 | +++ |
| 31 | + |
| 32 | ++ |
| 33 | ++ |
| 34 | ++ |
| 35 | +++ |
| 36 | +++ |
| 37 | +++ |
| 38 | ++++ |
| 39 | +++ |
| 40 | +++ |
| 41 | +++ |
| 42 | ++ |
| 43 | +++ |
| 44 | +++ |
| 45 | +++ |
| 46 | ++ |
| 47 | +++ |
| 48 | + |
| 49 | +++ |
| 50 | +++ |
| 51 | ++++ |
| 52 | +++ |
| 53 | ++ |
| 54 | +++ |
| 55 | +++ |
| 56 | +++ |
| 57 | ++ |
| 58 | ++ |
| 59 | +++ |
| 60 | ++ |
| 61 | ++++ |
| 62 | ++++ |
| 63 | ++++ |
| 64 | ++++ |
| 65 | ++++ |
| 66 | +++ |
| 67 | +++ |
| 68 | ++ |
| 69 | ++++ |
| 70 | +++ |
| 71 | +++ |
| 72 | N/A |
| 73 | ++ |
| 74 | +++ |
| 75 | ++ |
| 76 | ++ |
| 77 | +++ |
| 78 | ++ |
| 79 | ++ |
| 80 | + |
| 81 | ++ |
| 82 | + |
| 83 | +++ |
| 84 | +++ |
| 85 | +++ |
| 86 | +++ |
| 87 | ++ |
| 88 | ++ |
| 89 | +++ |
| 90 | +++ |
| 91 | +++ |
| 92 | + |
| 93 | + |
| 94 | ++ |
| 95 | + |
| 96 | + |
| 97 | + |
| 98 | + |
| 99 | + |
| 100 | ++ |
| 101 | ++ |
| 102 | + |
| 103 | ++ |
| 104 | + |
| 105 | +++ |
| 106 | + |
| 107 | +++ |
| 108 | + |
| 109 | + |
| 110 | +++ |
| 111 | ++ |
| 112 | ++ |
| 113 | ++ |
| 114 | +++ |
| 115 | ++ |
| 116 | ++ |
| 117 | + |
| 118 | +++ |
| 119 | ++ |
| 120 | +++ |
| 121 | + |
| 122 | + |
| 123 | + |
| 124 | +++ |
| 125 | +++ |
| 126 | +++ |
| 127 | ++ |
| 128 | +++ |
| 129 | +++ |
| 130 | ++ |
| 131 | + |
| 132 | ++ |
| 133 | +++ |
| 134 | +++ |
| 135 | +++ |
| 136 | +++ |
| 137 | ++++ |
| 138 | ++++ |
| 139 | +++ |
| 140 | ++ |
| 141 | +++ |
| 142 | +++ |
| 143 | +++ |
| 144 | +++ |
| 145 | ++++ |
| 146 | ++++ |
| 147 | ++++ |
| 148 | ++++ |
| 149 | +++ |
| 150 | +++ |
| 151 | ++ |
| 152 | ++ |
| 153 | +++ |
| 154 | +++ |
| 155 | +++ |
| 156 | ++ |
| 157 | ++ |
| 158 | ++ |
| 159 | ++ |
| 160 | ++ |
| 161 | +++ |
| 162 | ++ |
| 163 | +++ |
| 164 | +++ |
| 165 | +++ |

TABLE 2-continued

| COMPOUND NUMBER | S1P$_1$ ACTIVITY |
|---|---|
| 166 | +++ |
| 167 | +++ |
| 168 | +++ |
| 169 | ++ |
| 170 | ++ |
| 171 | +++ |
| 172 | ++ |
| 173 | ++ |
| 174 | ++ |
| 175 | ++ |
| 176 | ++ |
| 177 | ++ |
| 178 | ++ |
| 179 | ++ |
| 180 | +++ |
| 181 | +++ |
| 182 | +++ |
| 183 | ++ |
| 184 | ++++ |
| 185 | ++++ |
| 186 | +++ |
| 187 | +++ |
| 188 | ++++ |
| 189 | +++ |
| 190 | ++++ |
| 191 | +++ |
| 192 | ++++ |
| 193 | +++ |
| 194 | ++++ |
| 195 | +++ |
| 196 | ++++ |
| 197 | ++++ |
| 198 | +++ |
| 199 | ++++ |
| 200 | ++++ |
| 201 | ++++ |
| 202 | ++++ |
| 203 | +++ |
| 204 | +++ |
| 205 | +++ |
| 206 | +++ |
| 207 | +++ |
| 208 | +++ |
| 209 | +++ |
| 210 | ++ |
| 211 | +++ |
| 212 | +++ |
| 213 | ++ |
| 214 | +++ |
| 215 | ++ |
| 216 | +++ |
| 217 | ++ |
| 218 | +++ |
| 219 | ++ |
| 220 | +++ |
| 221 | +++ |
| 222 | ++ |
| 223 | ++ |
| 224 | ++ |
| 225 | ++ |
| 226 | +++ |
| 227 | +++ |
| 228 | ++ |
| 229 | +++ |
| 230 | +++ |
| 231 | +++ |
| 232 | +++ |
| 233 | +++ |
| 234 | +++ |
| 235 | +++ |
| 236 | +++ |
| 237 | +++ |
| 238 | +++ |
| 239 | +++ |
| 240 | ++ |
| 241 | +++ |
| 242 | ++ |
| 243 | ++ |
| 244 | ++ |
| 245 | ++ |
| 246 | + |
| 247 | ++ |
| 248 | ++++ |
| 249 | ++++ |
| 250 | +++ |
| 251 | + |
| 252 | ++ |
| 253 | ++ |
| 254 | +++ |

S1P$_1$ Mutagenesis

A. Quick-change mutagenesis with PfuTurbo DNA polymerase (Stratagene) was conducted using S1P$_1$/pcDNA3.1 (Missouri S&T cDNA Resource Centre) as the template. Primers were as follows:

```
                Primer sequence

R120A/E121A     CCAGTGGTTTCTGGCGGCAGGGAGTATGTTTGTGGCC
Forward         (SEQ ID NO: 1)

R120A/E121A     GGCCACAAACATACTCCCTGCCGCCAGAAACCACT
Reverse         GG (SEQ ID NO: 2)

N101A Forward   CTACACAGCTGCCCTGCTCTTGTCTGGGGC (SEQ
                ID NO: 3)

N101A Reverse   GCCCCAGACAAGAGCAGGGCAGCTGTGTAG (SEQ
                ID NO: 4)
```

PCR conditions were 15 cycles with the following parameters: 95° C. 30 sec, 58° C. 30 sec, 68° C. for 60 sec. All constructs were sequence verified.

Phosphorylated-ERK1/2 In Cell Western

CHOK1 cells were transfected using Fugene (Roche). Stably expressing mixed pools were selected with 2 mg/ml G418. Expression of functional S1P$_1$/EDG1 receptor was confirmed by cell surface FACS with a S1P$_1$ antibody (R&D Systems, clone 218713). Stable pools were seeded at 40,000 cells/well in a clear bottom 96-well tray, and incubated at 37° C. in 5% CO$_2$ for 18 hrs. Cells were serum-starved in FreeStyle 293 medium (Invitrogen) for 4-6 h, then incubated for 5 min with a dose response of compound, in duplicate. Cells were fixed with 4% paraformaldehyde for 20 min, permeabilized with 0.1% Triton X-100 in PBS (4×5 min washes) and blocked for 1 h in Odyssey Blocking Buffer (LI-COR). All incubations were at room temperature. Cells were incubated for 18 h at 4° C. in Rabbit anti-Phospho-ERK1/2 (Cell Signaling #4377) and Mouse anti-ERK1/2 (Cell Signaling #9107) both diluted 1:800 in Odyssey Blocking Buffer. Plates were washed with 0.1% Tween-20 in PBS and then incubated with Odyssey Blocking Buffer containing IRDye 680-labeled goat anti-rabbit antibody (#926-32221; diluted 1/500) and IRDye 800CW-labeled goat anti-mouse antibody (#926-32210; diluted 1/1000). Plates were washed with 0.1% Tween-20 in PBS, all liquid was removed from the wells and the plates were scanned using a LICOR Odyssey scanner. The phospho-ERK1/2 signal was normalized to the ERK1/2 signal. Data was analyzed by non-linear regression using GraphPad Prism to determine the $EC_{50}$ of binding.

Results of the mutagenesis analysis are shown in Table 3.

TABLE 3

| | Fold change in $EC_{50}$ compared to wild type $S1P_1$ | |
|---|---|---|
| $S1P_1$ Variant | Compound 50 | Compound 38 |
| R120A/E121A | 2 | 11 |
| N101A | 32 | 2 |

Conclusions from $S1P_1$ Mutagenesis Analysis

Included in this invention are $S1P_1$ agonists that potentially bind to the $S1P_1$ receptor at different sites. For example, compounds 50 and 38 are both $S1P_1$ agonists that induce phosphorylation of ERK1/2 (Table 3). Mutation of $S1P_1$ to produce $S1P_1$ R120A/E121A has no influence on the binding of compound 50, but diminishes binding of compound 38. In contrast, mutation of $S1P_1$ to produce N101A had no effect on binding of compound 38 but reduces the binding of compound 50. Finally, mutation of W269L abolishes binding of both compounds.

In Vivo Assays

Determination of Absolute Oral Bioavailability in Rats.

All pharmacokinetic studies were conducted in non-fasted female Sprague-Dawely rats (Simonsen Laboratories or Harlan Laboratories). Rats were housed in an ALAAC accredited facility and the research was approved by the facilities Institutional Animal Care and Use Committee (IACUC). The animals were acclimated to the laboratory for at least 48 h prior to initiation of experiments.

Compounds were formulated in 5% DMSO/5% Tween20 and 90% purified water (intravenous infusion) or 5% DMSO/5% Tween20 and 90% 0.1N HCL (oral gavage). The concentration of the dosing solutions was verified by HPLC-UV. For intravenous dosing, compounds were administered by an infusion pump into the jugular vein over one minute to manually restrained animals (n=4 rats/compound). The intravenous doses were 0.8 for a 1:1 mixture (racemic) of 85 and 86, and 0.3 and 0.3 mg/kg for compounds 49 and 50, respectively. Oral dosing was by gavage using a standard stainless steel gavage needle (n=2-4 rats/compound). The oral solution doses were 0.3, 2 and 2 mg/kg for compounds 85, 49 and 50, respectively. For both routes of administration, blood was collected at eight time-points after dosing with the final sample drawn 24 h post dose. Aliquots of the blood samples were transferred to polypropylene 96-well plate and frozen at −20° C. until analysis.

After thawing the blood samples at room temperature, 5 µL of DMSO was added to each well. Proteins were precipitated by adding 150 µL acetonitrile containing 200 nM internal standard (4-hydroxy-3-(alpha-iminobenzyl)-1-methyl-6-phenylpyrindin-2-(1H)-one) and 0.1% formic acid. Plates were mixed for 1 min on a plate shaker to facilitate protein precipitation and then centrifuged at 3,000 rpm for 10 min to pellet protein. The supernatant was transferred to a clean plate and centrifuged at 3,000 rpm for 10 min to pellet any remaining solid material prior to LC/MS/MS analysis. Calibration curve standards were prepared by spiking 54 compound stock in DMSO into freshly collected EDTA rat blood. An eight point standard curve spanning a range of 5 nM to 10,000 nM was included with each bio-analytical run. The standards were processed identically to the rat pharmacokinetic samples.

Concentrations in the rat pharmacokinetic samples were determined using a standardized HPLC-LC/MS/MS method relative to the eight point standard curve. The system consisted of a Leap CTC Pal injector, Agilent 1200 HPLC with binary pump coupled with an Applied Biosystems 3200 QTrap. Compounds were chromatographed on a Phenomenex Synergy Fusion RP 20×2 mm 2 um Mercury Cartridge with Security Guard. A gradient method was used with mobile phase A consisting of 0.1% formic acid in water and mobile phase B consisting of 0.1% formic acid in acetonitrile at flow rates varying from 0.7 to 0.8 mL/min. Ions were generated in positive ionization mode using an electrospray ionization (ESI) interface. Multiple reaction monitoring (MRM) methods were developed specific to each compound. The heated nebulizer was set at 325° C. with a nebulizer current of 4.8 µA. Collision energies used to generate daughter ions ranged between 29 and 39 V. Peak area ratios obtained from MRM of the mass transitions specific for each compound were used for quantification. The limit of quantification of the method was typically 5 nM. Data were collected and analyzed using Analyst software version 1.4.2.

Blood concentration versus time data were analyzed using non-compartmental methods (WinNonlin version 5.2; model 200 for oral dosing and model 202 for intravenous infusion). Absolute oral bioavailability (%) was calculated using the following expression: (Oral AUC×IV Dose)/(IV AUC×Oral Dose)×100.

The rat absolute oral bioavailability data for compound 253 was obtained from the literature (Gonzalez-Cabrera et al. 2008, Molecular Pharmacology 74(5):1308-1318). Briefly, a racemic mixture of compounds 253 and 254 was formulated in 10% DMSO/10% Tween 80 in 80% water and dosed orally to Sprague-Dawley rats by gavage at a dose level of 2 mg/kg or intravenously at a dose level 1 mg/kg. Blood was collected at intervals into EDTA and compound concentrations were determined using standardized HPLC-LC/MS/MS method.

Lymphopenia

In mice: Female C57BL6 mice (Simonsen Laboratories, Gilroy Calif.) were housed in an ALAAC accredited facility and the research was approved by the facilities Institutional Animal Care and Use Committee (IACUC). The animals were acclimated to the laboratory for at least 5 days prior to initiation of experiments. Mice (n=3/compound/time-point) were dosed by oral gavage with 1 mg/kg compound formulated in a vehicle consisting of 5% DMSO/5% Tween 20 and 90% 0.1N HCl. Control mice were dosed PO with the vehicle. Terminal whole blood samples were collected from isoflurane anesthetized mice by cardiac puncture into EDTA. Whole blood was incubated with rat anti-mouse CD16/CD32 (Mouse BD Fc Block, #553141), PE-Rat anti-mouse CD45R/B220 (BD #553089), APC-Cy7-Rat anti-mouse CD8a (BD #557654), and Alexa Fluor647-Rat anti-mouse CD4 (BD #557681) for 30 min on ice. Red blood cells were lysed using BD Pharm Lyse Lysing buffer (#555899) and white blood cells were analyzed by FACS. Lymphopenia was expressed as the % of white blood cells that were CD4 or CD8 positive T cells. The overall lymphopenia response over 24 h was estimated by calculating the area under the effect curve (AUEC) using the linear trapezoidal rule.

In rats: Female rats (Simonsen Laboratories, Gilroy Calif.) were housed in an ALAAC accredited facility and the research was approved by the facilities Institutional Animal Care and Use Committee (IACUC). The animals were acclimated to the laboratory for at least 5 days prior to initiation of experiments. Rats (n=3/compound/time-point) were dosed by oral gavage with 1 mg/kg compound formulated in a vehicle consisting of 5% DMS0/5% Tween 20 and 90% 0.1N HCL. Control rats were dosed PO with the vehicle. Whole blood was collected from isoflurane anesthetized rats via the retro-orbital sinus and terminal samples were collected by cardiac puncture into EDTA. Whole blood was incubated with mouse anti-rat CD32 (BD #550271), PE-mouse anti-rat CD45R/B220 (BD #554881), PECy5-mouse anti-rat CD4 (BD #554839), and APC-mouse anti-rat CD8a (eBioscience #17-0084) for 30 minutes on ice. Red blood cells were lysed using BD Pharm Lyse Lysing buffer (#555899) and white blood cells were analyzed with a BD FACSArray. Lymphopenia was expressed as the % of white blood cells that were CD4 or CD8 positive T cells. The overall lymphopenia response over 24 h was estimated by calculating the area under the effect curve (AUEC) using the linear trapezoidal rule.

Evaluation of Therapeutic Index in Rats

All studies were conducted in non-fasted male and female Sprague-Dawely rats (Simonsen Laboratories). Rats were housed in an AAALAC accredited facility and the research was approved by the facilities Institutional Animal Care and Use Committee (IACUC). The animals were acclimated to the laboratory for at least 5 days prior to initiation of experiments.

The compounds listed in Table 6 were formulated as suspensions in a vehicle consisting of 0.5% carboxymethyl cellulose (Acros Organics) in purified water (pH adjusted to ~2.2 with hydrochloric acid). The same formulation was used in the rat lymphopenia and toxicology studies described below. The concentration of each compound in suspension was verified to be within ±10% of the target concentration by HPLC-UV.

Prior to the conduct of toxicology studies, the effect of three to five daily doses of each compound on peripheral T-cell counts of female rats was determined (see lymphopenia measurements in rats above). In these lymphopenia studies, blood samples were collected onto EDTA at intervals after the final study dose. The collection times were not identical for each study, however, all studies included a sample collected 24 hours after the final dose. The lymphopenia data was used as a biomarker to select equally pharmacologically active doses for the subsequent toxicology study. The low dose for the toxicology study was the dose of each compound that resulted in a 50% reduction of T-cell count 24 h after the final dose in the lymphopenia study relative to vehicle treated rats. The high dose in the toxicology study represented a ≥20-fold increment over the low dose.

In the toxicology studies, three male and three female rats per group were assigned to dosing groups using body weight based randomization. A control group in each study received vehicle. All animals were dosed orally by gavage on 5 or 14-consecutive days at a dose volume of 5 mL/kg/day. The animals were observed daily for any manifestations of adverse effect. Twenty-four hours after the final study dose, the rats were anesthetized with isoflurane and a terminal blood sample was taken by intra-cardiac puncture for hematology and clinical chemistry evaluation (IDEXX Laboratories, Sacramento, Calif.). The lungs with trachea were collected, weighed, and then prepared for histology by perfusion with 10% neutral buffered formalin via the trachea. The internally fixed lungs were then preserved in 10% neutral buffered formalin and submitted for histological examination (IDEXX).

The dose of each compound resulting in a 10% increase in the lung to terminal body weight ratio was estimated for each compound by linear interpolation. The therapeutic index was estimated as the ratio of the dose producing 10% lung weight increase to the dose producing 50% T-Cell depletion.

Description of the TNBS Crohn's Colitis Model in Rats

Male Sprague-Dawley rats (180-200 g) were acclimatized for seven days and then assigned to 8 rats per group so that each group had approximately the same mean weight. Twenty-four hours prior to disease initiation, rats are deprived of food. Rats were anaesthetized and weighed, then 80 mg/kg TNBS solution (50% TNBS: 50% 200 proof ethanol) was instilled into colon via a 20 g feeding needle inserted into the anus. The rats were maintained in head down position until recovery from anesthesia. Daily oral dosing was initiated 2 h post TNBS-instillation for six days. Prednisolone served as a positive control and was administered orally daily at 10 mg/kg. Body weights were monitored daily and 24 h after the last dose, all groups are terminated. The colon was removed, flushed of fecal matter and examined for gross changes including strictures, adhesions and ulcers. The colon length, weight of the distal 2 cm, and wall thickness was recorded. Oral delivery of 1 mg/kg of Compound 85 reduced TNBS induced colon shortening from 31% in the diseased rats to 15%.

Description of Influenza A H1N1 Model in Mice

Male C57B1/6 (6-8 weeks of age) were acclimatized for seven days and then assigned to 5-8 mice per group so that each group has approximately the same mean weight. Mice were infected with $10^4$ PFUs mouse-adapted influenza A virus (A/WSN/33) via the intra-tracheal route. Mice were then treated with 0.2-1.5 mg/kg compound p.o. 1 hr post-infection. Forty eight hours after infection mice were euthanized by cervical dislocation and bronchoalveolar lavage fluid was collected. Quantitative cytokine analysis was performed via ELISA. In some experiments whole body perfusion was performed and lungs were collected for cellular enumeration of inflammatory cells. Longevity studies were performed by infection with $3\text{-}10 \times 10^4$ PFUs mouse-adapted influenza A virus over 14 days. Intratracheal delivery of 0.5 mg/kg of Compound 85, 1 hr after virus infection suppressed cellular infiltrate into the lungs by 40%.

Comparative Data

Comparative potency data for $S1P_1$—$S1P_5$ is shown in Table 4. The agonist values ($EC_{50}$) are reported in nM.

TABLE 4

| COMPOUND NUMBER | $S1P_1$ | $S1P_2$ | $S1P_3$ | $S1P_4$ | $S1P_5$ |
| --- | --- | --- | --- | --- | --- |
| 253 | 2.88 | >1000 | 4300 | 3250 | 135.94 |
| 254 | 0.16 | 5500 | 5274 | 5500 | 56.81 |
| 49 | 0.17 | 1080 | 8945 | 9034 | 20.11 |
| 50 | 0.19 | 7717 | 8914 | 7866 | 44.55 |
| 85 | 0.16 | 5690 | 4501 | 1610 | 15.06 |
| 86 | 0.16 | 9559 | 9938 | 4192 | 55.20 |
| 90 | 0.13 | 6662 | 8816 | >10000 | 12.90 |
| 91 | 0.09 | >10000 | >10000 | >10000 | 15.23 |
| 163 | 0.09 | >10000 | >10000 | >10000 | 49.98 |
| 164 | 0.36 | >10000 | >10000 | >10000 | 173.55 |
| 186 | 0.05 | 1569 | >10000 | 1210 | 32.28 |
| 187 | 0.10 | >10000 | >10000 | >10000 | 57.11 |
| 234 | 0.10 | >10000 | >10000 | 739 | 76.11 |
| 235 | 0.10 | >10000 | >10000 | >10000 | 39.80 |

Comparative PK and lymphopenia data is shown in Table 5. Data for racemic compound 253 was reported by Gonazalez-Cabrera et al., 2008, Molecular Pharmacology Vol. 74 No. 5.

TABLE 5

| Compound Number | Rat -Oral bioavailability Solution | Mouse Lymphopenia (AUEC) |
| --- | --- | --- |
| 253 | 21% | 116 |
| 254 | N/A | 84 |
| 49 | 93% | 1762 |
| 50 | 91% | 1632 |
| 85 | 69% | 1425 |
| 86 | N/A | 1342 |
| 90 | N/A | 1486 |
| 91 | N/A | 1408 |

Table 6 shows the therapeutic index (TI) obtained after 5 or 14 day toxicology studies in rats for selected compounds. The dose producing a 10% increase in lung to body weight ratio was interpolated from a plot of dose versus lung to body weight. The lymphopenia response was measured 24 hours following the final dose of a 3-5 day multiple dose regimen.

TABLE 6

| Compound Number | Dose Resulting in 10% increase in lung weight (mg/kg) | Dose Producing 50% lymphopenia (mg/kg) | TI 5 days | TI 14 days |
|---|---|---|---|---|
| 49 | 0.2 | 0.10 | N/A | 2 |
| 50 | 2.0 | 0.10 | N/A | 20 |
| 85 | 2.8 | 0.15 | N/A | 14 |
| 86 | 2.7 | 0.15 | N/A | 18 |
| 90 | 5.5 | 0.40 | N/A | 14 |
| 91 | 0.3 | 0.30 | N/A | 1 |
| 163 | 2.1 | 0.07 | N/A | 30 |
| 164 | 5.0 | 0.25 | 20 | N/A |
| 186 | 1.1 | 0.07 | 16 | N/A |
| 187 | 5.0 | 0.50 | 10 | N/A |
| 234 | 21.3 | 0.90 | 24 | N/A |
| 235 | 11.3 | 2.00 | 6 | N/A |

We claim:

1. A method for the synthesis of a compound comprising an indane moiety having a chiral carbon in the five-membered ring of the indane moiety where the compound is enantiomerically enriched with respect to the chiral carbon, wherein the compound is

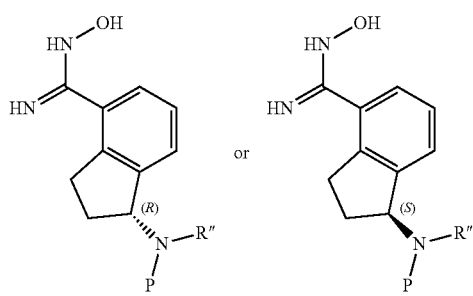

the method comprising the steps of:

(i) providing an indane moiety where the ring carbon of the five-membered ring of the indane moiety where chiral substitution is desired is oxo substituted at such carbon, the compound having the following structure:

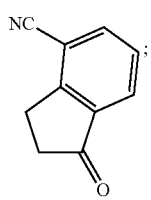 [SMILES: N#Cc1cccc2c1CCC2=O]

(ii) reacting the compound of step (i) with a chiral reagent, wherein the chiral agent is a chiral sulfinamide of the form RS(=O)NH$_2$ where R is selected from the group consisting of t-butyl, branched C$_{2-6}$ alkyl and C$_{3-8}$ cycloalkyl, thereby forming a compound of one of the following structures:

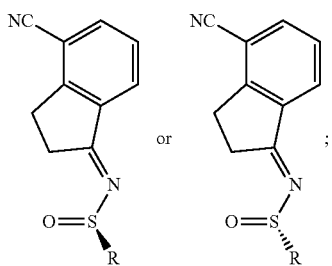

(iii) forming a chiral center at the indane moiety carbon previously bound to the oxo group by reacting the compound of step (ii) with a reducing agent, thereby forming a compound of one of the following structures:

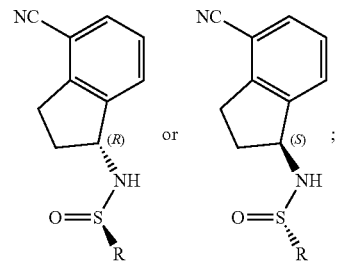

(iv) converting the compound of step (iii) to a chiral amine, thereby forming a compound of one of the following structures:

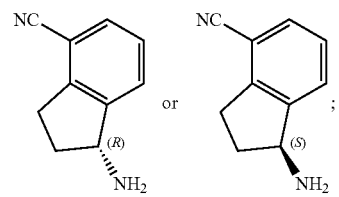

(v) reacting the compound of step (v) with an activated substituted alkyl group, a compound of one of the following structures where P is a protecting group;

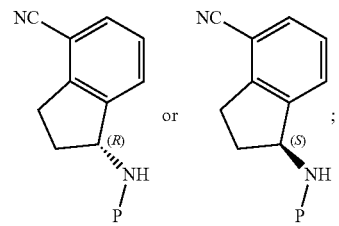

(vi) reacting the compound of step (v) with an activated substituted alkyl group, thereby forming a compound of one of the following structures where R" is a substituted alkyl group;

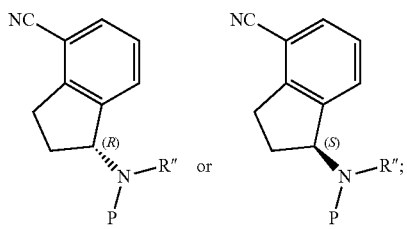

and (vii) treating the compound of step (vi) with a hydroxylamine or a hydroxylamine hydrochloride to convert the cyano substituent to a hydroxyamidine at the 4-position of the indane moiety, thereby forming a compound of one of the following structures:

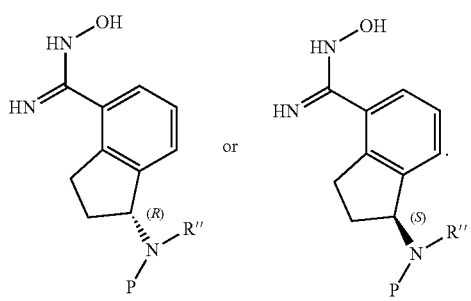
2. The method of claim 1, wherein:
the compound formed in step (ii) is:
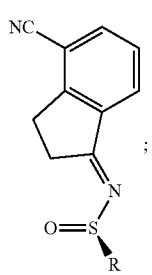
the compound formed in step (iii) is:
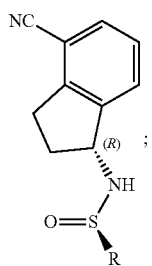
the compound formed in step (iv) is:
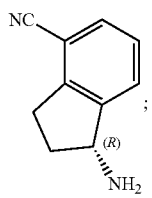
the compound formed in step (v) is:
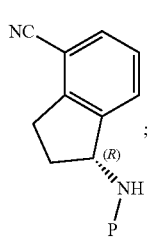
the compound formed in step (vi) is:
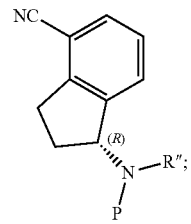
and
the compound formed in step (vii) is:
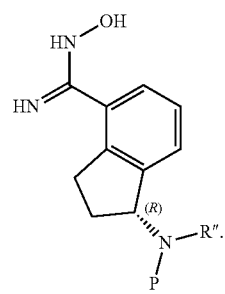
3. The method of claim 1 wherein
the compound formed in step (ii) is:
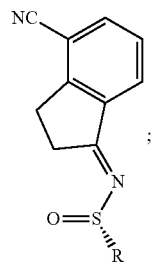
the compound formed in step (iii) is:
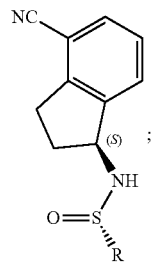
the compound formed in step (iv) is:
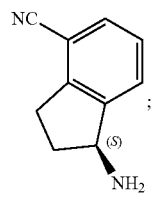

the compound formed in step (v) is:

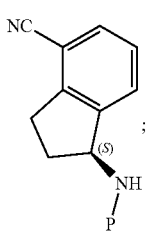

the compound formed in step (vi) is:

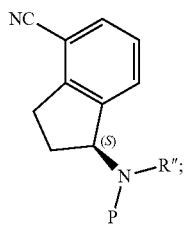

and
the compound formed in step (vii) is:

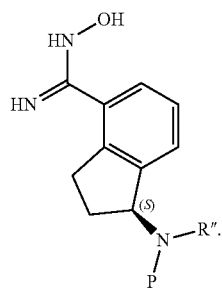

4. The method of claim 1 wherein the chiral reagent is t-Bu-S(=O)NH$_2$.

5. The method of claim 4 wherein the compound formed in step (ii) has one of the following structures:

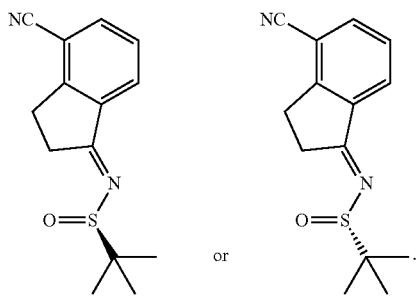 [SMILES: CC(C)(C)[S@@](=O)/N=C1\CCc2c(C#N)cccc21 ; CC(C)(C)[S@](=O)/N=C1\CCc2c(C#N)cccc21]

6. The method of claim 4 wherein the compound formed in step (iii) has one of the following structures:

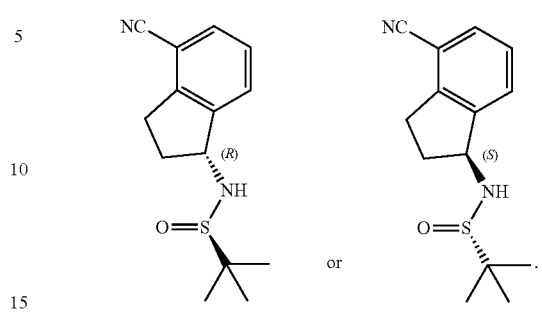

7. The method of claim 1 wherein step (vii) is carried out in the presence of a base.

8. The method of claim 1 wherein the method further comprises the step of:
(viii) contacting the compound of step (vii) with a substituted benzoic acid and a coupling reagent to form a compound of one of the following structures:

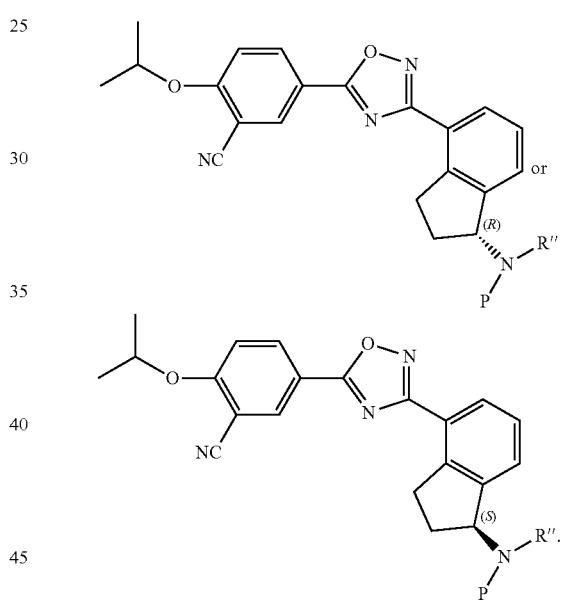

9. The method of claim 8 wherein the coupling reagent is a mixture comprising hydroxybenzotriazole (HOBt) and 1-ethyl-3-(3-dimethylaminopropyl)-carbodiimide (EDC).

10. The method of claim 8 wherein P is Boc and R" is —CH$_2$CH$_2$—OTBS and the compound of step (viii) is one of the following structures:

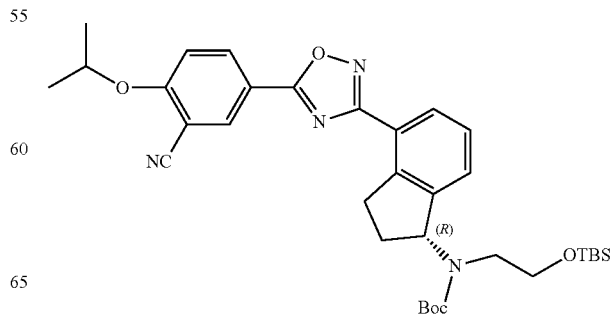

-continued

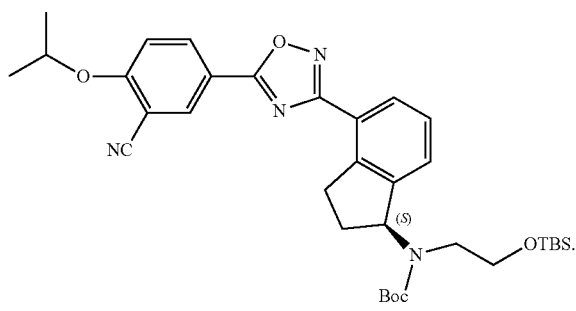

11. The method of claim 8 wherein the formation of the compound of step (viii) proceeds through one of the following intermediate structures,

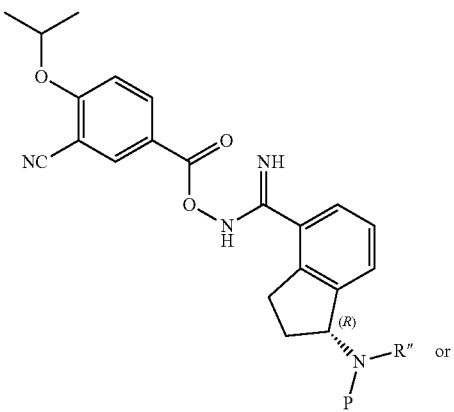

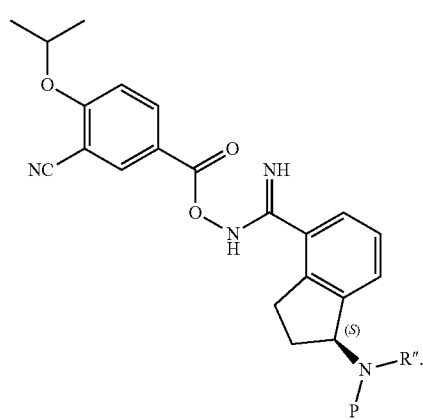

12. The method of claim 10 wherein the formation of the compound of step (viii) proceeds through one of the following intermediate structures:

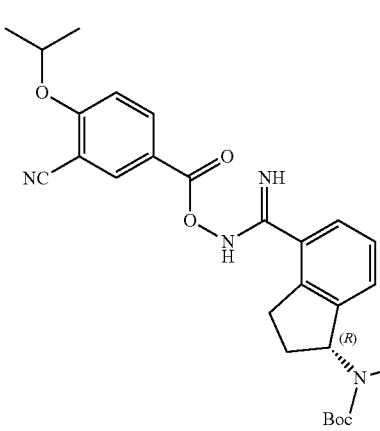

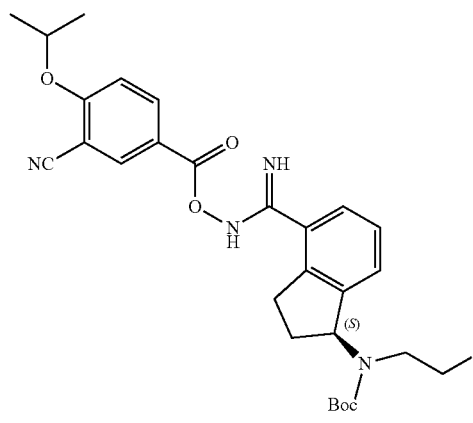

13. The method of claim 1 wherein the compound of step (vii) is enantiomerically enriched at least 90%.

14. The method of claim 13 wherein the compound of step (vii) is enantiomerically enriched at least 95%.

15. The method of claim 14 wherein the compound of step (vii) is enantiomerically enriched at least 98%.

16. The method of claim 15 wherein the compound of step (vii) is enantiomerically enriched at least 99%.

17. The method of claim 10 wherein the method further comprises the step of:

(ix) deprotecting the compound of step (viii) to form a compound of one of the following structures:

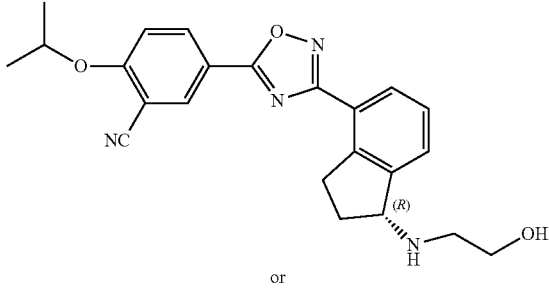

or

-continued

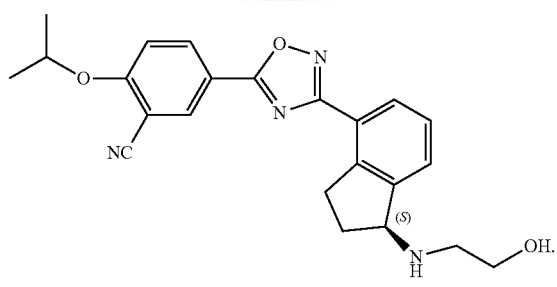

18. The method of claim 17 wherein the compound of step (ix) is:

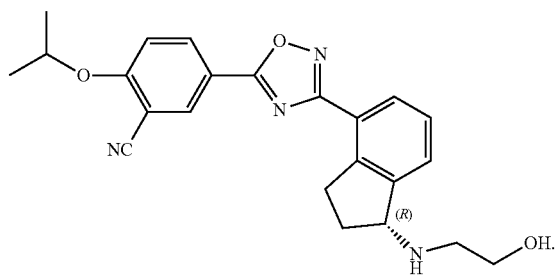

19. The method of claim 17 wherein the compound of step (ix) is:

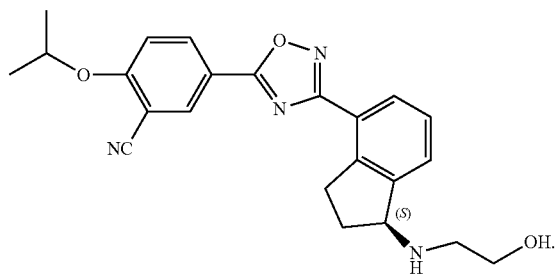

20. A method for the synthesis of a compound comprising an indane moiety having a chiral carbon in the five-membered ring of the indane moiety where the compound is enantiomerically enriched with respect to the chiral carbon, wherein the compound is

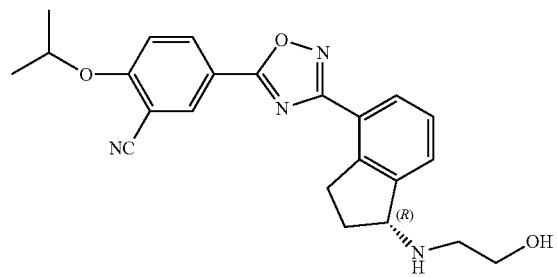

the method comprising the steps of:

(i) providing an indane moiety having the following structure:

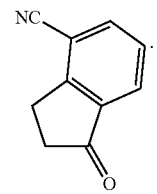 [SMILES: N#Cc1cccc2c1CCC2=O]

(ii) reacting the compound of step (i) with a chiral reagent, wherein the chiral agent is t-Bu-S(=O)NH$_2$, thereby forming a compound having the following structure:

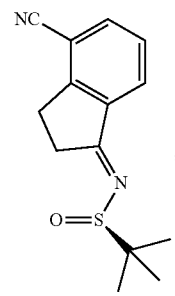

(iii) reacting the compound of step (ii) with a reducing agent, thereby forming a compound having the following structure:

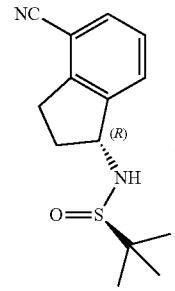

(iv) converting the compound of step (iii) to a chiral amine, thereby forming a compound having the following structure:

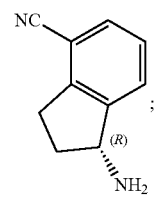

(v) converting the compound of step (iv) to a protected chiral amine, thereby forming a compound having the following structure where P is a protecting group:

261

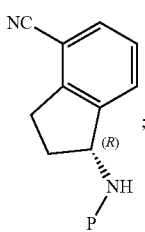

(vi) reacting the compound of step (v) with an activated substituted alkyl group, wherein the activated substituted alkyl group is (2-bromoethoxy)(tert-butyl)dimethylsilane, thereby forming a compound of the following structure:

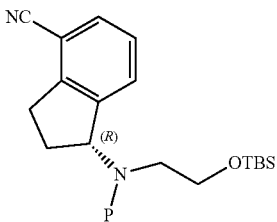

(vii) treating the compound of step (vi) with a hydroxylamine or a hydroxylamine hydrochloride, thereby forming a compound of the following structure:

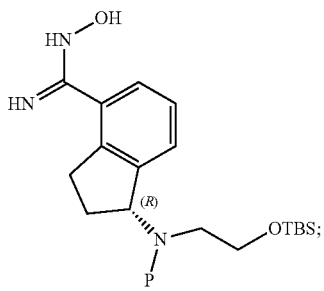

(viii) contacting the compound of step (vii) with a substituted benzoic acid and a coupling reagent to form a compound of the following structure:

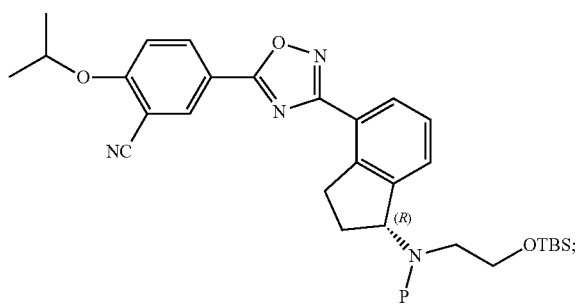

262 and
(ix) deprotecting the compound of step (viii) to form a compound of the following structure:

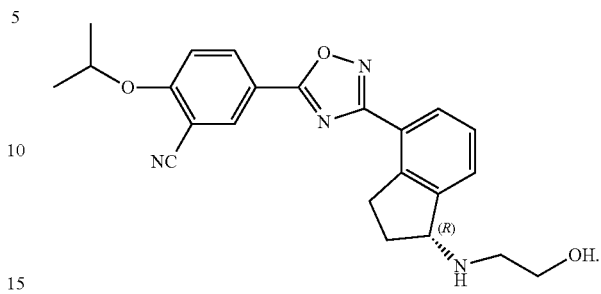

21. A method for the synthesis of a compound comprising an indane moiety having a chiral carbon in the five-membered ring of the indane moiety where the compound is enantiomerically enriched with respect to the chiral carbon, wherein the compound is

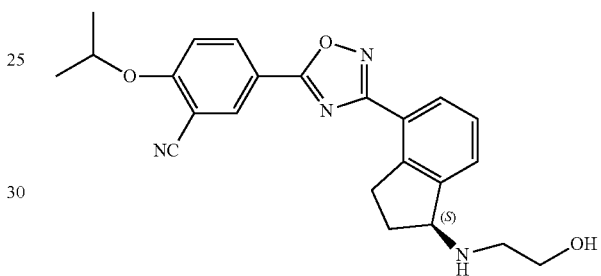

the method comprising the steps of:
(i) providing an indane moiety having the following structure:

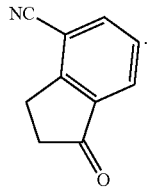 [SMILES: N#Cc1cccc2c1CCC2=O]

(ii) reacting the compound of step (i) with a chiral reagent, wherein the chiral agent is t-Bu-S(=O)NH$_2$, thereby forming a compound having the following structure:

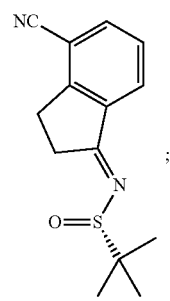 [SMILES: CC(C)(C)[S@](=O)/N=C1\CCc2c(C#N)cccc21]

(iii) reacting the compound of step (ii) with a reducing agent, thereby forming a compound having the following structure:

263

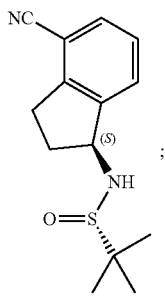

(iv) converting the compound of step (iii) to a chiral amine, thereby forming a compound having the following structure:

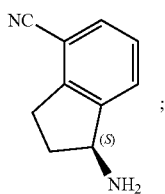

(v) converting the compound of step (iv) to a protected chiral amine, thereby forming a compound having the following structure where P is a protecting group:

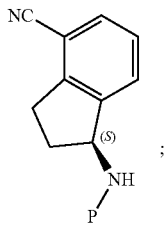

(vi) reacting the compound of step (v) with an activated substituted alkyl group, wherein the activated substituted alkyl group is (2-bromoethoxy)(tert-butyl)dimethylsilane, thereby forming a compound of the following structure:

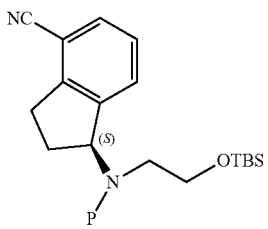

(vii) treating the compound of step (vi) with a hydroxylamine or a hydroxylamine hydrochloride, thereby forming a compound of the following structure:

264

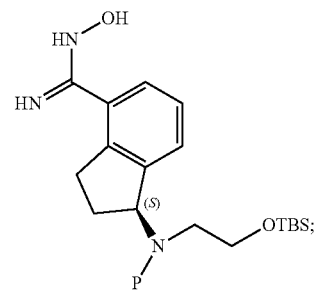

(viii) contacting the compound of step (vii) with a substituted benzoic acid and a coupling reagent to form a compound of the following structure:

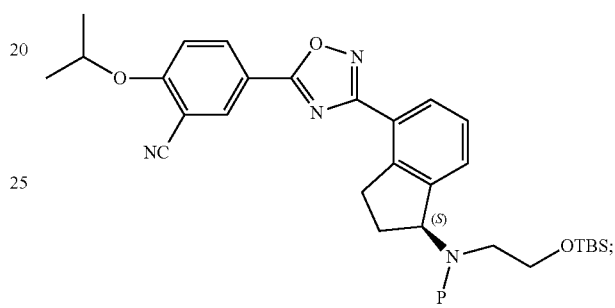

and (ix) deprotecting the compound of step (viii) to form a compound of the following structure:

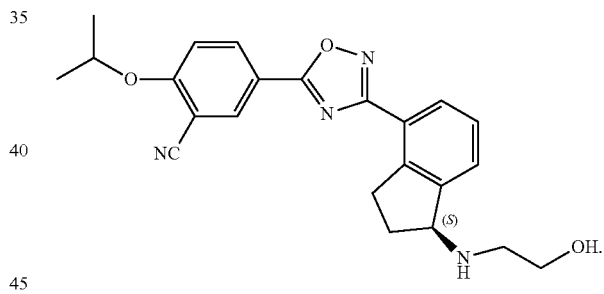

22. The method of claim 20 wherein the formation of the compound of step (viii) proceeds through the following intermediate structure:

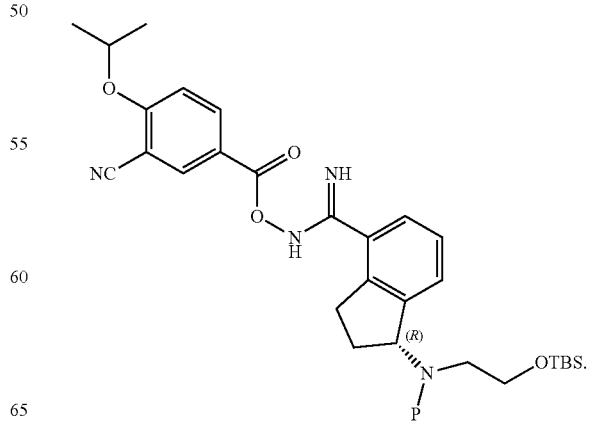

23. The method of claim 22 wherein the formation of the compound of step (viii) proceeds through the following intermediate structure:

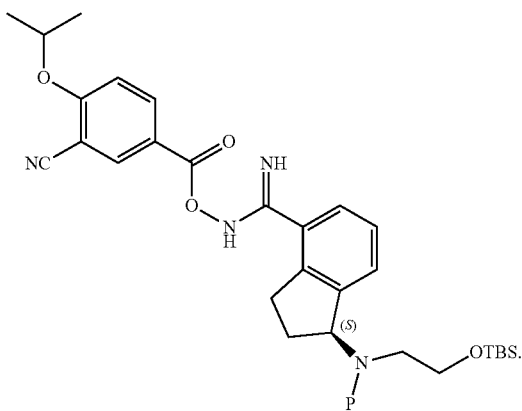

24. The method of any one of claims 21 and 22 wherein step (ii) is performed in the presence of Ti(OEt)$_4$.

25. The method of any one of claims 21 and 22 wherein the reducing agent of step (iii) is sodium borohydride.

26. The method of any one of claims 21 and 22 wherein step (iv) is accomplished in the presence of hydrochloric acid.

27. The method of any one of claims 21 and 22 wherein step (v) is accomplished by addition of di-tert-butyl dicarbonate (Boc$_2$O) and P is Boc.

28. The method of any one of claims 21 and 22 wherein step (vi) is accomplished in the presence of sodium hydride.

29. The method of any one of claims 21 and 22 wherein step (vii) is accomplished in the presence of hydroxylamine hydrochloride and trimethylamine.

30. The method of any one of claims 21 and 22 wherein the coupling reagent of step (viii) is a mixture comprising hydroxybenzotriazole (HOBt) and 1-ethyl-3-(3-dimethylaminopropyl)-carbodiimide (EDC).

31. The method of claim 30 wherein heat is applied following the addition of the coupling agent.

32. The method of any one of claims 21 and 22 wherein step (ix) is accomplished in the presence of hydrochloric acid.

33. The method of any one of claims 18-22 wherein the compound of step (viii) is enantiomerically enriched at least 90%.

34. The method of any one of claims 18-22 wherein the compound of step (viii) is enantiomerically enriched at least 95%.

35. The method of any one of claims 18-22 wherein the compound of step (viii) is enantiomerically enriched at least 98%.

36. The method of any one of claims 18-22 wherein the compound of step (viii) is enantiomerically enriched at least 99%.

* * * * *